(12) United States Patent
Roy et al.

(10) Patent No.: US 11,684,584 B2
(45) Date of Patent: *Jun. 27, 2023

(54) BRANCHED PEG MOLECULES AND RELATED COMPOSITIONS AND METHODS

(71) Applicant: Genevant Sciences GmbH, Basel (CH)

(72) Inventors: Debashish Roy, Seattle, WA (US); Jean-Rene E. Ella-Menye, Seattle, WA (US); Sean D. Monahan, Middleton, WI (US); Pierrot Harvie, Vancouver (CA); Anna Galperin, Seattle, WA (US); Michael E. Houston, Kirkland, WA (US); Mary G. Prieve, Lake Forest Park, WA (US)

(73) Assignee: Genevant Sciences GmbH, Basel (CH)

( * ) Notice: Subject to any disclaimer, the term of this patent is extended or adjusted under 35 U.S.C. 154(b) by 265 days.

This patent is subject to a terminal disclaimer.

(21) Appl. No.: 16/475,006

(22) PCT Filed: Dec. 29, 2017

(86) PCT No.: PCT/US2017/068841
§ 371 (c)(1),
(2) Date: Jun. 28, 2019

(87) PCT Pub. No.: WO2018/126084
PCT Pub. Date: Jul. 5, 2018

(65) Prior Publication Data
US 2020/0078313 A1    Mar. 12, 2020

Related U.S. Application Data

(60) Provisional application No. 62/446,186, filed on Jan. 13, 2017, provisional application No. 62/440,941, filed on Dec. 30, 2016.

(51) Int. Cl.
*A61K 9/00* (2006.01)
*A61K 9/51* (2006.01)
(Continued)

(52) U.S. Cl.
CPC ........ *A61K 9/5123* (2013.01); *A61K 38/1816* (2013.01); *A61K 47/34* (2013.01); *A61K 48/0041* (2013.01); *A61K 49/0093* (2013.01)

(58) Field of Classification Search
CPC .................. A61K 9/5123; A61K 41/0066
See application file for complete search history.

(56) References Cited

U.S. PATENT DOCUMENTS

| 4,699,784 A | 10/1987 | Shih et al. |
| 5,057,313 A | 10/1991 | Shih et al. |

(Continued)

FOREIGN PATENT DOCUMENTS

| EP | 0321233 A1 | 3/1989 |
| EP | 2180004 A1 | 4/2010 |

(Continued)

OTHER PUBLICATIONS

Agarwal, A., et al., "Dual-Role Self-Assembling Nanoplexes for Efficient Gene Transfection and Sustained Gene Delivery," Biomaterials 29(5):607-617, Feb. 2008.

(Continued)

*Primary Examiner* — Paul W Dickinson
(74) *Attorney, Agent, or Firm* — Sterne, Kessler, Goldstein & Fox

(57) ABSTRACT

Disclosed are branched PEG molecules, including branched PEG-lipids and branched-PEG proteins, as well as related compositions and methods for making branched PEG molecules. Also disclosed are related compositions, systems, (Continued)

and methods for in vivo delivery of therapeutic and diagnostic agents.

10 Claims, 1 Drawing Sheet

Specification includes a Sequence Listing.

(51) Int. Cl.
*A61K 38/18* (2006.01)
*A61K 47/34* (2017.01)
*A61K 48/00* (2006.01)
*A61K 49/00* (2006.01)

(56) References Cited

U.S. PATENT DOCUMENTS

| | | |
|---|---|---|
| 6,306,994 B1 | 10/2001 | Donald et al. |
| 6,359,054 B1 | 3/2002 | Lemieux et al. |
| 6,383,811 B2 | 5/2002 | Wolff et al. |
| 6,410,057 B1 | 6/2002 | Kweon-Choi et al. |
| 6,780,428 B2 | 8/2004 | Ranger et al. |
| 6,835,393 B2 | 12/2004 | Hoffman et al. |
| 6,939,564 B2 | 6/2005 | Ranger et al. |
| 6,916,488 B1 | 7/2005 | Meier et al. |
| 6,919,091 B2 | 7/2005 | Trubetskoy et al. |
| 7,033,607 B2 | 4/2006 | Trubetskoy et al. |
| 7,094,810 B2 | 8/2006 | Sant et al. |
| 7,098,032 B2 | 8/2006 | Trubetskoy et al. |
| 7,217,776 B1 | 5/2007 | Mallapragada et al. |
| 7,374,778 B2 | 5/2008 | Hoffman et al. |
| 7,510,731 B2 | 3/2009 | Ranger et al. |
| 7,524,680 B2 | 4/2009 | Wolff et al. |
| 7,718,193 B2 | 5/2010 | Stayton et al. |
| 7,737,108 B1 | 6/2010 | Hoffman et al. |
| 7,976,834 B2 | 7/2011 | Zhao et al. |
| 8,367,113 B2 | 2/2013 | Gu et al. |
| 8,822,213 B2 | 9/2014 | Stayton et al. |
| 8,962,757 B2 | 2/2015 | Devore et al. |
| 9,006,193 B2 | 4/2015 | Stayton et al. |
| 9,211,250 B2 | 12/2015 | Johnson et al. |
| 9,220,791 B2 | 12/2015 | Stayton et al. |
| 9,339,558 B2 | 5/2016 | Stayton et al. |
| 9,464,300 B2 | 10/2016 | Prieve et al. |
| 9,476,063 B2 | 10/2016 | Stayton et al. |
| 9,662,403 B2 | 5/2017 | Stayton et al. |
| 9,862,792 B2 | 1/2018 | Stayton et al. |
| 9,867,885 B2 | 1/2018 | Monahan et al. |
| 10,420,790 B2 | 9/2019 | Stayton et al. |
| 10,646,582 B2 | 5/2020 | Monahan et al. |
| 10,660,970 B2 | 5/2020 | Monahan et al. |
| 11,219,634 B2 | 1/2022 | Prieve et al. |
| 2001/0007666 A1 | 7/2001 | Hoffman et al. |
| 2003/0017206 A1 | 1/2003 | Seo et al. |
| 2003/0134420 A1 | 7/2003 | Lollo et al. |
| 2003/0191081 A1 | 10/2003 | Lemieux et al. |
| 2003/0211167 A1 | 11/2003 | Gustavsson et al. |
| 2004/0054127 A1 | 3/2004 | Uin et al. |
| 2004/0072784 A1 | 4/2004 | Sant et al. |
| 2004/0016223 A1 | 8/2004 | Trubetskoy et al. |
| 2004/0151775 A1 | 8/2004 | Rozema et al. |
| 2005/0070721 A1 | 3/2005 | Bae et al. |
| 2005/0154165 A1 | 7/2005 | Petereit et al. |
| 2005/0220880 A1 | 10/2005 | Lewis et al. |
| 2005/0260276 A1 | 11/2005 | Yang et al. |
| 2006/0030685 A1 | 2/2006 | Boupat et al. |
| 2006/0134221 A1 | 6/2006 | Geall |
| 2006/0165810 A1 | 7/2006 | Discher et al. |
| 2006/0171980 A1 | 8/2006 | Helmus et al. |
| 2006/0217285 A1 | 9/2006 | Destarac |
| 2006/0235161 A1 | 10/2006 | Heller et al. |
| 2007/0003609 A1 | 1/2007 | Collin-Djangone et al. |
| 2007/0010632 A1 | 1/2007 | Kaplan et al. |
| 2007/0037891 A1 | 2/2007 | Esfand et al. |
| 2007/0059271 A1 | 3/2007 | Kataoka et al. |
| 2007/0110709 A1 | 5/2007 | Ranger et al. |
| 2007/0134188 A1 | 6/2007 | Collin-Djangone et al. |
| 2007/0224241 A1 | 9/2007 | Stayton et al. |
| 2008/0069902 A1 | 3/2008 | Zhao et al. |
| 2008/0081075 A1 | 4/2008 | Hsiue et al. |
| 2008/0171067 A1 | 7/2008 | Govindan et al. |
| 2008/0243049 A1 | 10/2008 | Hardy |
| 2009/0036625 A1 | 2/2009 | Chang et al. |
| 2010/0150952 A1 | 6/2010 | Stayton et al. |
| 2010/0159019 A1 | 6/2010 | Yang et al. |
| 2011/0123636 A1 | 5/2011 | Stayton et al. |
| 2011/0143434 A1 | 6/2011 | Stayton et al. |
| 2011/0143435 A1 | 6/2011 | Stayton et al. |
| 2011/0281934 A1 | 11/2011 | Johnson et al. |
| 2011/0286957 A1 | 11/2011 | Prieve et al. |
| 2012/0021514 A1 | 1/2012 | Johnson et al. |
| 2012/0232169 A1 | 9/2012 | Wu et al. |
| 2012/0251618 A1 | 10/2012 | Schrum et al. |
| 2013/0011362 A1 | 1/2013 | Monahan et al. |
| 2013/0344160 A1 | 12/2013 | Moine et al. |
| 2014/0155472 A1 | 6/2014 | Bancel et al. |
| 2014/0228516 A1 | 8/2014 | Stayton et al. |
| 2015/0238619 A1 | 8/2015 | Stayton et al. |
| 2015/0283254 A1 | 10/2015 | Duvall et al. |
| 2016/0082121 A1 | 3/2016 | Stayton et al. |
| 2016/0206750 A1 | 7/2016 | Monahan et al. |
| 2017/0049801 A1 | 2/2017 | Prieve et al. |
| 2018/0221402 A1 | 8/2018 | Prieve et al. |
| 2018/0243433 A1 | 8/2018 | Monahan et al. |
| 2018/0311381 A1 | 11/2018 | Bancel et al. |
| 2019/0030129 A1 | 1/2019 | Schrum et al. |
| 2020/0147121 A1 | 5/2020 | Stayton et al. |
| 2021/0023235 A1 | 1/2021 | Monahan et al. |

FOREIGN PATENT DOCUMENTS

| | | |
|---|---|---|
| EP | 2922554 A1 | 9/2015 |
| FR | 2767829 A1 | 3/1999 |
| WO | WO 99/19303 A1 | 6/1999 |
| WO | WO-9929303 A1 | 6/1999 |
| WO | WO 01/87227 A1 | 11/2001 |
| WO | WO 03/87188 A1 | 10/2003 |
| WO | WO 2005/108614 A2 | 11/2005 |
| WO | WO 2006/016166 A1 | 2/2006 |
| WO | WO 2007/008300 A2 | 1/2007 |
| WO | WO 2007/109584 A1 | 9/2007 |
| WO | WO 2008/004978 A1 | 1/2008 |
| WO | WO 2008/022309 A2 | 2/2008 |
| WO | WO 2008/071009 A1 | 6/2008 |
| WO | WO 2008/085556 A2 | 7/2008 |
| WO | WO 2008/148174 A1 | 12/2008 |
| WO | WO 2008/153940 A1 | 12/2008 |
| WO | WO 2009/009025 A1 | 1/2009 |
| WO | WO 2009/021728 A2 | 2/2009 |
| WO | WO-2009016166 A1 | 2/2009 |
| WO | WO 2009/140421 A2 | 11/2009 |
| WO | WO 2009/140423 A2 | 11/2009 |
| WO | WO 2009/140427 A2 | 11/2009 |
| WO | WO-2009140429 A2 | 11/2009 |
| WO | WO-2009140432 A2 | 11/2009 |
| WO | WO 2010/021770 A1 | 2/2010 |
| WO | WO 2010/053596 A1 | 5/2010 |
| WO | WO 2010/053597 A2 | 5/2010 |
| WO | WO 2010/054266 A2 | 5/2010 |
| WO | WO 2010/077678 A2 | 7/2010 |
| WO | WO-2011060281 A1 | 5/2011 |
| WO | WO-2011062965 A2 | 5/2011 |
| WO | WO-2012019168 A2 | 2/2012 |
| WO | WO-2013071047 A1 | 5/2013 |
| WO | WO-2015138348 A1 | 9/2015 |
| WO | WO-2015138357 A2 | 9/2015 |
| WO | WO 2016/077625 A1 | 5/2016 |
| WO | WO 2016/118697 A1 | 7/2016 |
| WO | WO-2017201349 A1 | 11/2017 |
| WO | WO-2018129586 A1 | 7/2018 |
| WO | WO-2018183808 A1 | 10/2018 |
| WO | WO-2019089818 A1 | 5/2019 |

(56) References Cited

FOREIGN PATENT DOCUMENTS

| WO | WO-2019104152 A1 | 5/2019 |
|---|---|---|
| WO | WO-2019104195 A1 | 5/2019 |

OTHER PUBLICATIONS

Alvarez-Lorenzo, C., et al., "Biophysical Characterization of Complexation of DNA With Block Copolymers of Poly(2-dimethylaminoethyl) Methacrylate, Poly(ethylene oxide), and Poly-(propylene oxide)," Langmuir 21(11):5142-5148, May 2005.
Benoit, D.SW., et al., "Resensitizing Multidrug Resistant Cells to Doxorubicin Through Plk1 Knockdown Using a Novel pH-Responsive Micelle siRNA Delivery System," Abstracts of Society for Biomaterials Meeting, Apr. 22, 2009, 1 page.
Boeckle, S., et al., "Purification of Polyethylenimine Polyplexes Highlights the Role of Free Polycations in Gene Transfer," Journal of Gene Medicine 6(10):1102-1111, Oct. 2004.
Bulmus, V., et al., "A New pH-Responsive and Glutathione-Reactive, Endosomal Membrane-Disruptive Polymeric Carrier for Intracellular Delivery of Biomolecular Drugs," Journal of Controlled Release 93(2): 105-120, Dec. 2003.
Cai, Y., et al., "A Zwitterionic ABC Triblock Copolymer That Forms a 'Trinity' of Micellar Aggregates in Aqueous Solution," Macromolecules 37(19):7116-7122, Sep. 2004.
Cheng, Z., et al., "Brush-Type Amphiphilic Diblock Copolymers From 'Living'/Controlled Radical Polymerizations and Their Aggregation Behavior," Langmuir 21(16):7180-7185, Jul. 2005.
Chiefari, Y. K., et al. "Living Free-Radical Polymerization by Reversible Addition-Fragmentation Chain Transfer: The RAFT Process," Macromolecules, vol. 31, pp. 5559-5562, 1998.
Chiu, H.-C., et al., "Synthesis and Characterization of Amphiphilic Poly( ethylene glycol) Graft Copolymers and their Potential Application as Drug Carriers," Polymer 39(8-9):1609-1616, 1998.
Cho, Y.W., et al., "Polycation Gene Delivery Systems: Escape From Endosomes to Cytosol," Journal of Pharmacy and Pharmacology 55(6):721-734, Jun. 2003.
Convertine, A.J., et al., "Development of a Novel Endosomolytic Diblock Copolymer for siRNA Delivery," Journal of Controlled Release 133(3):221-229, Feb. 2009.
Dufresne, M.-H., et al., "Characterization of Polyion Complex Micelles Designed to Address the Challenges of oligonucleotide Delivery," Pharmaceutical Research 25(9):2083-2093, Sep. 2008.
Duvall, C.L., et al., "Polymer Enhanced Intracellular Delivery of a Pro-Apoptotic Peptide for Cancer Therapy," abstracts of Society for Biomaterials Meeting, Apr. 22, 2009, 1 page.
Eliyahu, H., et al., "Novel Dextran-Spermine Conjugates as Transfecting Agents: Comparing Water-Soluble and Micellar Polymers," Gene Therapy 12(6):494-503, Mar. 2005.
El-Sayed, M.E.H., et al., "Rational Design of Composition and Activity Correlations for pH-Sensitive and Glutathione-Reactive Polymer Therapeutics," Journal of Controlled Release 101 (1-3):47-58, Jan. 2005.
El-Sayed, M.E.H., et al., "Smart Polymeric Carriers for Enhanced Intracellular Delivery of Therapeutic Macromolecules," Expert Opinion on Biological Therapy 5(1):23-32, Jan. 2005.
Finne-Wistrand, A., and A.-C. Albertson, "The Use of Polymer Design in Resorbable Colloids," Annual Review of Materials Research 36:369-395, Aug. 2006.
Fishbein, I., et al., "Local Delivery of Gene Vectors From Bare-Metal Stents by Use of a Biodegradable Synthetic complex Inhibits In-Stent Restenosis in Rat Carotid Arteries," Circulation 117(16):2096-2103, Apr. 2008.
Funhoff, A.M., et al., "Endosomal Escape of Polymeric Gene Delivery Complexes Is Not Always Enhanced by Polymers Buffering at Low pH," Biomacromolecules 5(1):32-39, Jan.-Feb. 2004.
Gary, D.J., et al., "Polymer-Based siRNA Delivery: Perspectives on the Fundamental and Phenomenological Distinctions From Polymer-Based DNA Delivery," Journal of Controlled Release 121(1-2):64-73, Aug. 2007.
Gaucher, G., et al., "Block Copolymer Micelles: Preparation, Characterization and Application in Drug Delivery," Journal of Controlled Release 109(1-3):169-188, Dec. 2005.
Georgiou, T.K., and C.S. Patrickios, "Synthesis, Characterization, and DNA Adsorption Studies of Ampholytic Model Conetworks Based on Cross-Linked Star Copolymers," Biomacromolecules 9(2):574-582, Feb. 2008.
Germershaus, O., et al., "Gene Delivery Using Chitosan, Trimethyl Chitosan or Polyethylenglycol-grafl-trimethyl Chitosan Block Copolymers: Establishment of Structure-Activity Relationships In Vitro," Journal of Controlled Release 125(2):145-154, Jan. 2008.
Guo, Y., et al., "Capillary Electrophoresis Analysis of Poly( ethylene glycol) and Ligand-Modified Polylysine Gene Delivery Vectors," Analytical Biochemistry 363(2):204-209, Apr. 2007.
Gyda, et al. (2012) "The Tumor Suppressor Gene retinoblastoma-1 Is Required for Retinotectal Development and Visual Function in Zebrafish", PLoS Genetics, 8(11) article e11003106, 11 pages.
Henry, S.M., et al., "pH-Responsive Poly(styrene-alt-maleic anhydride) Alkylamide Copolymers for Intracellular Drag Delivery," Biomacromolecules 7(8):2407-2414, Aug. 2006.
Heredia, K.L., et al., "Reversible siRNA-Polymer Conjugates by RAFT Polymerization," Chemical Communications 28(28):3245-3247, Jul. 2008.
Hood, J.D., et al., "Tumor Regression by Targeted Gene Delivery to the Neovasculature," Science 296(5577):2404-2407, Jun. 2002.
Inoue, T., et al., "An AB Block Copolymer of Oligo(methyl methacrylate) and Poly(acrylic acid) for Micellar Delivery of Hydrophobic Drags," Journal of Controlled Release 51(2-3):221-229, Feb. 1998.
Jensen, K.D., et al., "Antisense Oligonucleotides Delivered to the Lysosome Escape and Actively Inhibit the Hepatitis B Virus," Bioconjugate Chemistry 13{5}:975-984, Sep.-Oct. 2002.
Jeong, J.H., et al., "siRNA Conjugate Delivery Systems," Bioconjugate Chemistry 20(1):5-14, Jan. 2009.
Jeong, Y.-l., et al., "Cellular Recognition of Paclitaxei-Loaded Polymeric Nanoparticles Composed of Poly{y-benzyl 40-glutamate) and Poly{ ethylene glycol) Diblock Copolymer Endcapped With Galactose Moiety," International Journal of Pharmaceutics 296{1-2):151-161, May 2005.
Jiang, T., et al., "Adsorption of Plasmid DNA Onto N,N'-{Dimethylamino)ethyl-methacrylate Graft-Polymerized Poly-L-Lactic Acid Film Surface for Promotion of In-Situ Gene Delivery," Biomacromolecules 8{6}: 1951-1957, Jun. 2007.
Joralemon, M.J., et al., "Synthesis, Characterization, and Bioavailability of Mannosylated Shell Cross-Linked Nanoparticles," Biomacromolecules 5{3}:903-913, May-Jun. 2004.
Kabanov, A.V., et al., "Piuronic Micelles as a Tool for Low-Molecular Compound Vector Delivery Into a Cell: Effect of *Staphylococcus aureus* Enterotoxin Bon Cell Loading With Micelle Incorporated Fluorescent Dye," Biochemistry International 26{6}: 1035-1042, May 1992.
Kariko, et al. (2012) "Increased Erythropoiesis in Mice Injected With Submicrogram Quantities of Pseudouridine-Containing rnRNA Encoding Erythropoietin", Molecular Therapy, 20(5): 948-53.
Kataoka, K., et al., "Smart Polymeric Micelles as Nanocarriers for Oligonucleotides and siRNA Delivery," Nucleic Acids Symposium Series 49{1 ): Sep. 17-18, 2005.
Kim et al., "Asialoglycoprotein receptor targeted gene delivery using galactosylated polyethylenimine-graft-poly(ethylene glycol): in vitro and in vivo studies," Journal of Controlled Release 108:557-67 (2005).
Kim, E.-M., et al., "Monitoring the Effect of PEGylation on Polyethylenimine In Vivo Using Nuclear Imaging Technique," Nuclear Medicine and Biology 31 (6):781-784, Aug. 2004.
Kono, K., et al., "Transfection Activity of Polyamidoamine Dendrimers Having Hydrophobic Amino Acid Residues in the Periphery," Bioconjugate Chemistry 16(1):208-214, Jan. 2005.
Kulkarni, S., et al., "Controlling the Aggregation of Conjugates of Streptavidin With Smart Block Copolymers Prepared via the RAFT Copolymerization Technique," Biomacromolecules 7(10):2736-2741, Oct. 2006.

(56) References Cited

OTHER PUBLICATIONS

Kurisawa, M., et al., "Transfection Efficiency Increases by Incorporating Hydrophobic Monomer Units Into Polymeric Gene Carriers," Journal of Controlled Release 68(1): Jul. 1-8, 2000.
Lam, J.K.W., et al., "Phosphocoline-Polycation Diblock Copolymers as Synthetic Vectors for Gene Delivery," Journal of Controlled Release 100(2):293-312, Nov. 2004.
Le Garrec, D., et al., "Micelles in Anticancer Drug Delivery," American Journal of Drug Delivery 2(1):15-42, Mar. 2004.
Lee, E.S., et al., "Poly{L-histidine)-PEG Block Copolymer Micelles and pH-Induced Destabilization," Journal of Controlled Release 90(3):363-374, Jul. 2003.
Lee, E.S., et al., "Super pH-Sensitive Multifunctional Polymeric Micelle," Nano Letters 5(2):325-329, Feb. 2005.
Lomas, H., et al., "Biomimetic pH Sensitive Polymersomes for Efficient DNA Encapsulation and Delivery," Advanced Materials 19(23):4238-4243( 2007).
Lowe, A.B., and C.L. McCormick, "Stimuli Responsive Water-Soluble and Amphiphilic {Co)polymers," Chap. 1, in C.L. McCormick {ed.), "Stimuli-Responsive Water Soluble and Amphiphilic Polymers," ACS Symposium Series, American Chemical Society, Washington, D.C., 2000, vol. 780, pp. 1-13.
Meyer, M., et al., "Synthesis and Biological Evaluation of a Bioresponsive and Endosomolytic siRNA-Polymer conjugate," Molecular Pharmaceutics 6{3):752-762, May-Jun. 2009.
Meyer, O., et al., "Copolymers of N-lsopropylacrylamide Can Trigger pH Sensitivity to Stable Liposomes," EBS Letters 421 {1 ):61-64, Jan. 1998.
Mian, et al. (2004) "Long-term correction of ornithine transcarbarnylase deficiency by WPRE-rnediated overexpression using a helper-dependent adenovirus", Molecular Therapy, 1 0(3): 492-99.
Mountrichas, G., and S. Pispas, "Synthesis and pH Responsive Self-Assembly of New Double Hydrophilic Block Copolymers," Macromolecules 39{14):4767-4774, Jul. 2006.
Murthy, N., et al., "Bioinspired pH-Responsive Polymers for the Intracellular Delivery of Biomolecular Drugs," Bioconjugate Chemistry 14{2):412-419, Mar.-Apr. 2003.
Murthy, N., et al., "The Design and Synthesis of Polymers for Eukaryotic Membrane Disruption," Journal of Controlled Release 61{1-2):137-143, Aug. 1999.
Nagasaki, Y., et al., "Sugar-Installed Block Copolymer Micelles: Their Preparation and Specific Interaction with Lectin Molecules," Biomacromolecules 2{4):1067-1070, Winter 2001.
Neu, M., et al., "Recent Advances in Rational Gene Transfer Vector Design Based on Poly (ethylene imine) and Its Derivatives," Journal of Gene Medicine 7(8):992-1009, Aug. 2005.
Ogris, M., et al., "PEGylated DNA/Transferrin-PEl Complexes: Reduced Interaction With Blood Components, extended Circulation in Blood and Potential for Systemic Gene Delivery," Gene Therapy 6(4):595-605, Apr. 1999.
Oishi, M., et al., "Lactosylated Poly( ethylene glycol)-siRNA Conjugate Through Acid-Labile Jl-Thiopropionate 19 linkage to Construct pH-Sensitive Polyion Complex Micelles Achieving Enhanced Gene Silencing in Hepatoma Cells," Journal of the American Chemical Society 127(6):1624-1625, Feb. 2005.
Oishi, M., et al., "pH-Responsive Oligodeoxynucleotide (ODN}-Poly(Ethylene Glycol) Conjugate Through acid-Labile Jl-Thiopropionate Linkage: Preparation and Polyion Complex Micelle Formation," Biomacromolecules (5): 1426-1432, Aug. 2003.
Oupicky, D., et al., "DNA Delivery Systems Based on Complexes of DNA With Synthetic Polycations and their Copolymers," Journal of Controlled Release 65( 1-2):149-171, Mar. 2000.
Patrickios, C.S., et al., "Diblock, ABC Triblock, and Random Methacrylic Polyampholytes: Synthesis by Group Transfer Polymerization and Solution Behavior," Macromolecules 27(4):930-937, Feb. 1994.
Peppas, N.A., "Is There a Future in Glucose-Sensitive, Responsive Insulin Delivery Systems?" Drug Delivery Science and Technology 14(4):247-256, Sep. 2004.
Raso, V., "Intracellular Targeting Using Bispecific Antibodies," Methods in Molecular Medicine 25:37-49, Jan. 2000.
Read, M.L., et al., "Physicochemical and Biological Characterisation of an Antisense Oligonucleotide Targeted gains the Bcl-2 mRNA Complexed With Cationic-Hydrophilic Copolymers," European Journal of Pharmaceutical Sciences 10(3):169-177, May 2000.
Rozema, D.B., et al., "Dynamic PolyConjugates for Targeted In Vivo Delivery of siRNA to Hepatocytes," Proceedings of the National Academy of Sciences (PNAS) 104(32): 12982-12987, Aug. 2007.
Satturwar, P., et al., "pH-Responsive Polymeric Micelles of Poly( ethylene glycol)-b-poly(alkyl(meth)acrylate-co-methacrylic acid): influence of the Copolymer Composition on Self-Assembling Properties and Release of Candesartan Cilexetil," European Journal of Pharmaceutics and Biopharmaceutics 65(3):379-387, Mar. 2007.
Sawant, R.M., et al., "'SMART' Drug Delivery Systems: Double-Targeted pH-Responsive Pharmaceutical Nanocarriers," Bioconjugate Chemistry 17(4):943-949, Jul.-Aug. 2006.
Scales, C.W., et al., "Corona-Stabilized Interpolyelectrolyte Complexes of SiRNA With Nonimmunogenic, Hydrophilic/Cationic Block Copolymers Prepared by Aqueous RAFT Polymerization," Macromolecules 9(20):6871-6881, Oct. 2006.
Segura, T., and J.A. Hubbell, "Synthesis and In Vitro Characterization of an ABC Triblock Copolymer or siRNA Delivery," Bioconjugate Chemistry 18(3):736-745, May 2007.
Stayton, P.S., and A.S. Hoffman, "'Smart' pH-Responsive Camers for Intracellular Delivery of Biomolecular Drugs," in V. Torchilin (ed.), "Fundamental Biomedical Technologies: Multifunctional Pharmaceutical Nanocarriers," Springer Science+Business Media, LLC, New York, May 2008, vol. 4, pp. 143-159.
Stayton, P.S., et al., "Intelligent Biohybrid Materials for Therapeutic and Imaging Agent Delivery," Proceedings of the IEEE 93(4):726-736, Apr. 2005.
Takeda, N., et al., "Temperature-Responsive Polymeric Carriers Incorporating Hydrophobic Monomers for Effective Transfection in Small Doses," Journal of Controlled Release 95(2):343-355, Mar. 2004.
Taton, D., et al., "Direct Synthesis of Double Hydrophilic Statistical Di- and Triblock Copolymers Comprised of Acrylamide and Acrylic Acid Units via the MADIX Process," Macromolecular Rapid Communications 2(18):1497-1503, Dec. 2001.
Teoh, S.K., et al., "Self-Assembly of Stimuli-Responsive Water-Soluble [60]Fullerene End-Capped Ampholytic Block Copolymer," Journal of Physical Chemistry B 109(10):4431-4438, Feb. 2005.
Torchilin, V.P., "Micellar Nanocarriers: Pharmaceutical Perspectives," Pharmaceutical Research 24(1):Jan. 1-16, 2007.
Turk, M.J., et al., "Characterization of a Novel pH-Sensitive Peptide That Enhances Drug Release From Folate-Targeted Liposomes at Endosomal pHs," Biochimica et Biophysica Acta 1559(1):56-68, Feb. 2002.
Varghese, O.P., et al., "In Situ Cross-Linkable High Molecular Weight Hyaluronan-Bisphosphonate Conjugate or Localized Delivery and Cell-Specific Targeting: A Hydrogel Linked Prodrug Approach," Journal of the American Chemical Society 131(25):8781-8783, Jul. 2009.
Veron, L., et al., "Hydrolyzable p(DMAPEMA) Polymers for Gene Delivery," Macromolecular Bioscience 6(7):540-554, Jul. 2006.
Wakebayashi, D., et al., "Lactose-Conjugated Polyion Complex Micelles Incorporating Plasmid DNA as a Targetable Gene Vector System: Their Preparation and Gene Transfecting Efficiency Against Cultured HepG2 Cells," Journal of Controlled Release 95(3):653-664, Mar. 2004.
Wang, L., et al., "Delivery of Antisense Oligonucleotides Using HPMA Polymer: Synthesis of a Thiol Polymer and Is Conjugation to Water-Soluble Molecules," Bioconjugate Chemistry 9(6):749-757, Nov.-Dec. 1998.
Wei, J.-S., et al., "Temperature- and pH-Sensitive Core-Shell Nanoparticles Self-Assembled From Poly(N-isopropylacrylamide-co-acrylic acid-co-cholesteryl acrylate) for Intracellular Delivery of Anticancer Drugs," Frontiers in Bioscience 10:3058-3067, Sep. 2005.

(56) References Cited

OTHER PUBLICATIONS

Yamamoto, S.-I., et al., "Temperature- and pH-Responsive Dense Copolymer Brushes Prepared by ATRP," Macromolecules 41 (19): 7013-7020, Oct. 2008.

Yasugi, K., et al., "Sugar-Installed Polymer Micelles: Synthesis and Micellization of Poly( ethylene glycol)-poly(D,L-lactide) Block Copolymers Having Sugar Groups at the PEG Chain End," Macromolecules 2(24):8024-8032, Nov. 1999.

Yessine, M.-A., et al., "Proton-Actuated Membrane-Destabilizing Polyion Complex Micelles," Bioconjugate Chemistry 18(3):1010-1014, May-Jun. 2007.

Yoo, H.S., and T.G. Park, "Folate Receptor Targeted Biodegradable Polymeric Doxorubicin Micelles," Journal of Controlled Release 96(2):273-283, Apr. 2004.

York, A.W., et al., "Advances in the Synthesis of Amphiphilic Block Copolymers via RAFT Polymerization: Stimuli-Responsive Drug and Gene Delivery," Advanced Drug Delivery Reviews 60(9):1018-1036, Jun. 2008.

Yu, H., et al., "A Novel Amphiphilic Double-[60]Fullerene-Capped Triblock Copolymer," Macromolecules 38(23):9889-9893, Nov. 2005.

Zhao, X., et al.,"Nanostructure of Polyplexes Formed Between Cationic Diblock Copolymer and Antisense 4 Oligodeoxynucleotide and Its influence on Cell Transfection Efficiency," Biomacromolecules 8(11 ):3493-3502, Nov. 2007.

Cheung, CY., et al., "A pH-Sensitive Polymer That Enhances Cationic Lipid-Mediated Gene Transfer," Bioconjugate Chemistry 12(6):906-910, Oct. 2001.

Glinel, K. et al., "Responsive Polyelectrolyte Multilayers," Colloids and Surfaces A: Physiochemical and Engineering Aspects, 303:3-13, (Aug. 2007).

Kyriakides, T.R, et al., "pH-Sensitive Polymers That Enhance Intracellular Drug Delivery In Vivo," Journal of Controlled Release 78(1-3):295-303, (Jan. 2002).

Lundy, B. B. et al., "Neutral Polymeric Micelles for RNA Delivery," Bioconjugate Chemistry, 24(3):398-407, (Mar. 20, 2013).

Nelson, C.E. et al., "Balancing Cationic and Hydrophobic Content of PEGylated siRNA Polyplexes Enhances Endosome Escape, Stability, Blood Circulation Time, and Bioactivity in Vivo," ACS Nano, 7:8870-8880 (2013).

Schellinger, J.G. et al., "Melittin-Grafted HPMA-Oligolysine Based Copolymers for Gene Delivery," Biomaterials, 34(9):2318-2326 (Mar. 2013).

Shi, J. et al., "Influence of Histidine Incorporation on Buffer Capacity and Gene Transfection Efficiency of HPMA-co-oligolysine Brush Polymers," Biomacromolecules, 14(6):1961-1970 (Jun. 10, 2013).

Wilson, J.T. et al., "pH-Responsive Nanoparticle Vaccines for Dual-Delivery of Antigens and Immunostimulatory Oligonucleotides," ACS Nano, 7(5):3912-3925, (May 28, 2013).

Co-pending U.S. Appl. No. 16/543,324, inventors Monahan, S et al., filed Aug. 16, 2019 (Not Published).

Co-pending U.S. Appl. No. 16/579,662, inventors Stayton, P. et al., filed Aug. 16, 2019 (Not Published).

International Search Report and Written Opinion for International Application No. PCT/US2017/068841, International Search Authority, United States, dated May 11, 2018, 18 pages.

Li, G., et al., "Double-responsive core-shell-corona micelles from self-assembly of diblock copolymer of poly(t-butyl acrylate-co-acrylic acid)-b-poly(N-isopropylacrylamide)," Polymer 47:4581-4587, Elsevier Ltd., United Kingdom (2006).

Chen, Q.-R., et al., "Co-polymer of histidine and lysine markedly enhances transfection efficiency of liposomes", Gene Therapy 7(19):1698-1705, Nature Publishing Group, United Kingdom (2000).

Chen, Q.-R., et al., "Branched co-polymers of histidine and lysine are efficient carriers of plasmids," Nucleic Acids Research 29(6):1334-1340, Oxford University Press, United Kingdom (2001).

Wooddell, C., et al., "Hepatocyte-targeted RNAi Therapeutics for the Treatment of Chronic Hepatitis B Virus Infection," Molecular Therapy 21(5):973-985, Cell Press, United States (2013).

SEQUENCE LISTING

<160> NUMBER OF SEQ ID NOS: 6

<210> SEQ ID NO 1
<211> LENGTH: 354
<212> TYPE: PRT
<213> ORGANISM: Homo sapiens

<400> SEQUENCE: 1

Met Leu Phe Asn Leu Arg Ile Leu Leu Asn Asn Ala Ala Phe Arg Asn
1               5                   10                  15

Gly His Asn Phe Met Val Arg Asn Phe Arg Cys Gly Gln Pro Leu Gln
                20                  25                  30

Asn Lys Val Gln Leu Lys Gly Arg Asp Leu Leu Thr Leu Lys Asn Phe
            35                  40                  45

Thr Gly Glu Glu Ile Lys Tyr Met Leu Trp Leu Ser Ala Asp Leu Lys
    50                  55                  60

Phe Arg Ile Lys Gln Lys Gly Glu Tyr Leu Pro Leu Leu Gln Gly Lys
65                  70                  75                  80

Ser Leu Gly Met Ile Phe Glu Lys Arg Ser Thr Arg Thr Arg Leu Ser
                85                  90                  95

Thr Glu Thr Gly Phe Ala Leu Leu Gly Gly His Pro Cys Phe Leu Thr
            100                 105                 110

Thr Gln Asp Ile His Leu Gly Val Asn Glu Ser Leu Thr Asp Thr Ala
        115                 120                 125

Arg Val Leu Ser Ser Met Ala Asp Ala Val Leu Ala Arg Val Tyr Lys
    130                 135                 140

Gln Ser Asp Leu Asp Thr Leu Ala Lys Glu Ala Ser Ile Pro Ile Ile
145                 150                 155                 160

Asn Gly Leu Ser Asp Leu Tyr His Pro Ile Gln Ile Leu Ala Asp Tyr
                165                 170                 175

Leu Thr Leu Gln Glu His Tyr Ser Ser Leu Lys Gly Leu Thr Leu Ser
            180                 185                 190

Trp Ile Gly Asp Gly Asn Asn Ile Leu His Ser Ile Met Met Ser Ala
        195                 200                 205

Ala Lys Phe Gly Met His Leu Gln Ala Ala Thr Pro Lys Gly Tyr Glu

-continued

```
                210                 215                 220
Pro Asp Ala Ser Val Thr Lys Leu Ala Glu Gln Tyr Ala Lys Glu Asn
225                 230                 235                 240

Gly Thr Lys Leu Leu Leu Thr Asn Asp Pro Leu Glu Ala Ala His Gly
                245                 250                 255

Gly Asn Val Leu Ile Thr Asp Thr Trp Ile Ser Met Gly Gln Glu Glu
                260                 265                 270

Glu Lys Lys Lys Arg Leu Gln Ala Phe Gln Gly Tyr Gln Val Thr Met
                275                 280                 285

Lys Thr Ala Lys Val Ala Ala Ser Asp Trp Thr Phe Leu His Cys Leu
                290                 295                 300

Pro Arg Lys Pro Glu Glu Val Asp Asp Glu Val Phe Tyr Ser Pro Arg
305                 310                 315                 320

Ser Leu Val Phe Pro Glu Ala Glu Asn Arg Lys Trp Thr Ile Met Ala
                325                 330                 335

Val Met Val Ser Leu Leu Thr Asp Tyr Ser Pro Gln Leu Gln Lys Pro
                340                 345                 350

Lys Phe

<210> SEQ ID NO 2
<211> LENGTH: 464
<212> TYPE: PRT
<213> ORGANISM: Homo sapiens

<400> SEQUENCE: 2

Met Ala Ser Glu Ser Gly Lys Leu Trp Gly Gly Arg Phe Val Gly Ala
1               5                   10                  15

Val Asp Pro Ile Met Glu Lys Phe Asn Ala Ser Ile Ala Tyr Asp Arg
                20                  25                  30

His Leu Trp Glu Val Asp Val Gln Gly Ser Lys Ala Tyr Ser Arg Gly
                35                  40                  45

Leu Glu Lys Ala Gly Leu Leu Thr Lys Ala Glu Met Asp Gln Ile Leu
                50                  55                  60

His Gly Leu Asp Lys Val Ala Glu Glu Trp Ala Gln Gly Thr Phe Lys
65                  70                  75                  80

Leu Asn Ser Asn Asp Glu Asp Ile His Thr Ala Asn Glu Arg Arg Leu
                85                  90                  95

Lys Glu Leu Ile Gly Ala Thr Ala Gly Lys Leu His Thr Gly Arg Ser
                100                 105                 110

Arg Asn Asp Gln Val Val Thr Asp Leu Arg Leu Trp Met Arg Gln Thr
                115                 120                 125

Cys Ser Thr Leu Ser Gly Leu Leu Trp Glu Leu Ile Arg Thr Met Val
130                 135                 140

Asp Arg Ala Glu Ala Glu Arg Asp Val Leu Phe Pro Gly Tyr Thr His
145                 150                 155                 160

Leu Gln Arg Ala Gln Pro Ile Arg Trp Ser His Trp Ile Leu Ser His
                165                 170                 175

Ala Val Ala Leu Thr Arg Asp Ser Glu Arg Leu Leu Glu Val Arg Lys
                180                 185                 190

Arg Ile Asn Val Leu Pro Leu Gly Ser Gly Ala Ile Ala Gly Asn Pro
                195                 200                 205

Leu Gly Val Asp Arg Glu Leu Leu Arg Ala Glu Leu Asn Phe Gly Ala
                210                 215                 220

Ile Thr Leu Asn Ser Met Asp Ala Thr Ser Glu Arg Asp Phe Val Ala
```

```
               225                 230                 235                 240

Glu Phe Leu Phe Trp Ala Ser Leu Cys Met Thr His Leu Ser Arg Met
                        245                 250                 255

Ala Glu Asp Leu Ile Leu Tyr Cys Thr Lys Glu Phe Ser Phe Val Gln
                        260                 265                 270

Leu Ser Asp Ala Tyr Ser Thr Gly Ser Ser Leu Met Pro Gln Lys Lys
                        275                 280                 285

Asn Pro Asp Ser Leu Glu Leu Ile Arg Ser Lys Ala Gly Arg Val Phe
                        290                 295                 300

Gly Arg Cys Ala Gly Leu Leu Met Thr Leu Lys Gly Leu Pro Ser Thr
        305                 310                 315                 320

Tyr Asn Lys Asp Leu Gln Glu Asp Lys Glu Ala Val Phe Glu Val Ser
                        325                 330                 335

Asp Thr Met Ser Ala Val Leu Gln Val Ala Thr Gly Val Ile Ser Thr
                        340                 345                 350

Leu Gln Ile His Gln Glu Asn Met Gly Gln Ala Leu Ser Pro Asp Met
                        355                 360                 365

Leu Ala Thr Asp Leu Ala Tyr Tyr Leu Val Arg Lys Gly Met Pro Phe
                        370                 375                 380

Arg Gln Ala His Glu Ala Ser Gly Lys Ala Val Phe Met Ala Glu Thr
        385                 390                 395                 400

Lys Gly Val Ala Leu Asn Gln Leu Ser Leu Gln Glu Leu Gln Thr Ile
                        405                 410                 415

Ser Pro Leu Phe Ser Gly Asp Val Ile Cys Val Trp Asp Tyr Gly His
                        420                 425                 430

Ser Val Glu Gln Tyr Gly Ala Leu Gly Gly Thr Ala Arg Ser Ser Val
                        435                 440                 445

Asp Trp Gln Ile Arg Gln Val Arg Ala Leu Leu Gln Ala Gln Gln Ala
                        450                 455                 460

<210> SEQ ID NO 3
        <211> LENGTH: 412
        <212> TYPE: PRT
        <213> ORGANISM: Homo sapiens

<400> SEQUENCE: 3

Met Ser Ser Lys Gly Ser Val Val Leu Ala Tyr Ser Gly Gly Leu Asp
        1               5                   10                  15

Thr Ser Cys Ile Leu Val Trp Leu Lys Glu Gln Gly Tyr Asp Val Ile
                        20                  25                  30

Ala Tyr Leu Ala Asn Ile Gly Gln Lys Glu Asp Phe Glu Ala Arg
                        35                  40                  45

Lys Lys Ala Leu Lys Leu Gly Ala Lys Lys Val Phe Ile Glu Asp Val
                        50                  55                  60

Ser Arg Glu Phe Val Glu Glu Phe Ile Trp Pro Ala Ile Gln Ser Ser
        65                  70                  75                  80

Ala Leu Tyr Glu Asp Arg Tyr Leu Leu Gly Thr Ser Leu Ala Arg Pro
                        85                  90                  95

Cys Ile Ala Arg Lys Gln Val Glu Ile Ala Gln Arg Glu Gly Ala Lys
                        100                 105                 110

Tyr Val Ser His Gly Ala Thr Gly Lys Gly Asn Asp Gln Val Arg Phe
                        115                 120                 125

Glu Leu Ser Cys Tyr Ser Leu Ala Pro Gln Ile Lys Val Ile Ala Pro
                        130                 135                 140
```

```
Trp Arg Met Pro Glu Phe Tyr Asn Arg Phe Lys Gly Arg Asn Asp Leu
145                 150                 155                 160

Met Glu Tyr Ala Lys Gln His Gly Ile Pro Ile Pro Val Thr Pro Lys
                165                 170                 175

Asn Pro Trp Ser Met Asp Glu Asn Leu Met His Ile Ser Tyr Glu Ala
            180                 185                 190

Gly Ile Leu Glu Asn Pro Lys Asn Gln Ala Pro Pro Gly Leu Tyr Thr
        195                 200                 205

Lys Thr Gln Asp Pro Ala Lys Ala Pro Asn Thr Pro Asp Ile Leu Glu
    210                 215                 220

Ile Glu Phe Lys Lys Gly Val Pro Val Lys Val Thr Asn Val Lys Asp
225                 230                 235                 240

Gly Thr Thr His Gln Thr Ser Leu Glu Leu Phe Met Tyr Leu Asn Glu
                245                 250                 255

Val Ala Gly Lys His Gly Val Gly Arg Ile Asp Ile Val Glu Asn Arg
            260                 265                 270

Phe Ile Gly Met Lys Ser Arg Gly Ile Tyr Glu Thr Pro Ala Gly Thr
        275                 280                 285

Ile Leu Tyr His Ala His Leu Asp Ile Glu Ala Phe Thr Met Asp Arg
    290                 295                 300

Glu Val Arg Lys Ile Lys Gln Gly Leu Gly Leu Lys Phe Ala Glu Leu
305                 310                 315                 320

Val Tyr Thr Gly Phe Trp His Ser Pro Glu Cys Glu Phe Val Arg His
                325                 330                 335

Cys Ile Ala Lys Ser Gln Glu Arg Val Glu Gly Lys Val Gln Val Ser
            340                 345                 350

Val Leu Lys Gly Gln Val Tyr Ile Leu Gly Arg Glu Ser Pro Leu Ser
        355                 360                 365

Leu Tyr Asn Glu Glu Leu Val Ser Met Asn Val Gln Gly Asp Tyr Glu
    370                 375                 380

Pro Thr Asp Ala Thr Gly Phe Ile Asn Ile Asn Ser Leu Arg Leu Lys
385                 390                 395                 400

Glu Tyr His Arg Leu Gln Ser Lys Val Thr Ala Lys
                405                 410

<210> SEQ ID NO 4
<211> LENGTH: 750
<212> TYPE: PRT
<213> ORGANISM: Homo sapiens

<400> SEQUENCE: 4

Met Leu Arg Ala Lys Asn Gln Leu Phe Leu Leu Ser Pro His Tyr Leu
1               5                   10                  15

Arg Gln Val Lys Glu Ser Ser Gly Ser Arg Leu Ile Gln Arg Leu
                20                  25                  30

Leu His Gln Gln Pro Leu His Pro Glu Trp Ala Ala Leu Ala Lys
        35                  40                  45

Lys Gln Leu Lys Gly Lys Asn Pro Glu Asp Leu Ile Trp His Thr Pro
    50                  55                  60

Glu Gly Ile Ser Ile Lys Pro Leu Tyr Ser Lys Arg Asp Thr Met Asp
65                  70                  75                  80

Leu Pro Glu Glu Leu Pro Gly Val Lys Pro Phe Thr Arg Gly Pro Tyr
                85                  90                  95

Pro Thr Met Tyr Thr Phe Arg Pro Trp Thr Ile Arg Gln Tyr Ala Gly
                100                 105                 110
```

Phe Ser Thr Val Glu Glu Ser Asn Lys Phe Tyr Lys Asp Asn Ile Lys
            115                 120                 125

Ala Gly Gln Gln Gly Leu Ser Val Ala Phe Asp Leu Ala Thr His Arg
130                 135                 140

Gly Tyr Asp Ser Asp Asn Pro Arg Val Arg Gly Asp Val Gly Met Ala
145                 150                 155                 160

Gly Val Ala Ile Asp Thr Val Glu Asp Thr Lys Ile Leu Phe Asp Gly
            165                 170                 175

Ile Pro Leu Glu Lys Met Ser Val Ser Met Thr Met Asn Gly Ala Val
            180                 185                 190

Ile Pro Val Leu Ala Asn Phe Ile Val Thr Gly Glu Glu Gln Gly Val
            195                 200                 205

Pro Lys Glu Lys Leu Thr Gly Thr Ile Gln Asn Asp Ile Leu Lys Glu
            210                 215                 220

Phe Met Val Arg Asn Thr Tyr Ile Phe Pro Pro Glu Pro Ser Met Lys
225                 230                 235                 240

Ile Ile Ala Asp Ile Phe Glu Tyr Thr Ala Lys His Met Pro Lys Phe
            245                 250                 255

Asn Ser Ile Ser Ile Ser Gly Tyr His Met Gln Glu Ala Gly Ala Asp
            260                 265                 270

Ala Ile Leu Glu Leu Ala Tyr Thr Leu Ala Asp Gly Leu Glu Tyr Ser
            275                 280                 285

Arg Thr Gly Leu Gln Ala Gly Leu Thr Ile Asp Glu Phe Ala Pro Arg
            290                 295                 300

Leu Ser Phe Phe Trp Gly Ile Gly Met Asn Phe Tyr Met Glu Ile Ala
305                 310                 315                 320

Lys Met Arg Ala Gly Arg Arg Leu Trp Ala His Leu Ile Glu Lys Met
            325                 330                 335

Phe Gln Pro Lys Asn Ser Lys Ser Leu Leu Leu Arg Ala His Cys Gln
            340                 345                 350

Thr Ser Gly Trp Ser Leu Thr Glu Gln Asp Pro Tyr Asn Asn Ile Val
            355                 360                 365

Arg Thr Ala Ile Glu Ala Met Ala Ala Val Phe Gly Gly Thr Gln Ser
            370                 375                 380

Leu His Thr Asn Ser Phe Asp Glu Ala Leu Gly Leu Pro Thr Val Lys
385                 390                 395                 400

Ser Ala Arg Ile Ala Arg Asn Thr Gln Ile Ile Ile Gln Glu Glu Ser
            405                 410                 415

Gly Ile Pro Lys Val Ala Asp Pro Trp Gly Gly Ser Tyr Met Met Glu
            420                 425                 430

Cys Leu Thr Asn Asp Val Tyr Asp Ala Ala Leu Lys Leu Ile Asn Glu
            435                 440                 445

Ile Glu Glu Met Gly Gly Met Ala Lys Ala Val Ala Glu Gly Ile Pro
450                 455                 460

Lys Leu Arg Ile Glu Glu Cys Ala Ala Arg Gln Ala Arg Ile Asp
465                 470                 475                 480

Ser Gly Ser Glu Val Ile Val Gly Val Asn Lys Tyr Gln Leu Glu Lys
            485                 490                 495

Glu Asp Ala Val Glu Val Leu Ala Ile Asp Asn Thr Ser Val Arg Asn
            500                 505                 510

Arg Gln Ile Glu Lys Leu Lys Lys Ile Lys Ser Ser Arg Asp Gln Ala
            515                 520                 525

-continued

```
Leu Ala Glu Arg Cys Leu Ala Leu Thr Glu Cys Ala Ala Ser Gly
        530                 535                 540
Asp Gly Asn Ile Leu Ala Leu Ala Val Asp Ala Ser Arg Ala Arg Cys
545                 550                 555                 560
Thr Val Gly Glu Ile Thr Asp Ala Leu Lys Lys Val Phe Gly Glu His
                565                 570                 575
Lys Ala Asn Asp Arg Met Val Ser Gly Ala Tyr Arg Gln Glu Phe Gly
            580                 585                 590
Glu Ser Lys Glu Ile Thr Ser Ala Ile Lys Arg Val His Lys Phe Met
        595                 600                 605
Glu Arg Glu Gly Arg Arg Pro Arg Leu Leu Val Ala Lys Met Gly Gln
    610                 615                 620
Asp Gly His Asp Arg Gly Ala Lys Val Ile Ala Thr Gly Phe Ala Asp
625                 630                 635                 640
Leu Gly Phe Asp Val Asp Ile Gly Pro Leu Phe Gln Thr Pro Arg Glu
                645                 650                 655
Val Ala Gln Gln Ala Val Asp Ala Asp Val His Ala Val Gly Ile Ser
            660                 665                 670
Thr Leu Ala Ala Gly His Lys Thr Leu Val Pro Glu Leu Ile Lys Glu
        675                 680                 685
Leu Asn Ser Leu Gly Arg Pro Asp Ile Leu Val Met Cys Gly Gly Val
    690                 695                 700
Ile Pro Pro Gln Asp Tyr Glu Phe Leu Phe Glu Val Gly Val Ser Asn
705                 710                 715                 720
Val Phe Gly Pro Gly Thr Arg Ile Pro Lys Ala Ala Val Gln Val Leu
                725                 730                 735
Asp Asp Ile Glu Lys Cys Leu Glu Lys Lys Gln Gln Ser Val
            740                 745                 750

<210> SEQ ID NO 5
<211> LENGTH: 728
<212> TYPE: PRT
<213> ORGANISM: Homo sapiens

<400> SEQUENCE: 5

Met Ala Gly Phe Trp Val Gly Thr Ala Pro Leu Val Ala Ala Gly Arg
1               5                   10                  15
Arg Gly Arg Trp Pro Pro Gln Gln Leu Met Leu Ser Ala Ala Leu Arg
            20                  25                  30
Thr Leu Lys His Val Leu Tyr Tyr Ser Arg Gln Cys Leu Met Val Ser
        35                  40                  45
Arg Asn Leu Gly Ser Val Gly Tyr Asp Pro Asn Glu Lys Thr Phe Asp
    50                  55                  60
Lys Ile Leu Val Ala Asn Arg Gly Glu Ile Ala Cys Arg Val Ile Arg
65                  70                  75                  80
Thr Cys Lys Lys Met Gly Ile Lys Thr Val Ala Ile His Ser Asp Val
                85                  90                  95
Asp Ala Ser Ser Val His Val Lys Met Ala Asp Glu Ala Val Cys Val
            100                 105                 110
Gly Pro Ala Pro Thr Ser Lys Ser Tyr Leu Asn Met Asp Ala Ile Met
        115                 120                 125
Glu Ala Ile Lys Lys Thr Arg Ala Gln Ala Val His Pro Gly Tyr Gly
    130                 135                 140
Phe Leu Ser Glu Asn Lys Glu Phe Ala Arg Cys Leu Ala Ala Glu Asp
145                 150                 155                 160
```

```
Val Val Phe Ile Gly Pro Asp Thr His Ala Ile Gln Ala Met Gly Asp
                165                 170                 175

Lys Ile Glu Ser Lys Leu Leu Ala Lys Lys Ala Glu Val Asn Thr Ile
            180                 185                 190

Pro Gly Phe Asp Gly Val Val Lys Asp Ala Glu Glu Ala Val Arg Ile
        195                 200                 205

Ala Arg Glu Ile Gly Tyr Pro Val Met Ile Lys Ala Ser Ala Gly Gly
    210                 215                 220

Gly Gly Lys Gly Met Arg Ile Ala Trp Asp Asp Glu Thr Arg Asp
225                 230                 235                 240

Gly Phe Arg Leu Ser Ser Gln Glu Ala Ala Ser Ser Phe Gly Asp Asp
                245                 250                 255

Arg Leu Leu Ile Glu Lys Phe Ile Asp Asn Pro Arg His Ile Glu Ile
                260                 265                 270

Gln Val Leu Gly Asp Lys His Gly Asn Ala Leu Trp Leu Asn Glu Arg
            275                 280                 285

Glu Cys Ser Ile Gln Arg Arg Asn Gln Lys Val Val Glu Glu Ala Pro
    290                 295                 300

Ser Ile Phe Leu Asp Ala Glu Thr Arg Arg Ala Met Gly Glu Gln Ala
305                 310                 315                 320

Val Ala Leu Ala Arg Ala Val Lys Tyr Ser Ser Ala Gly Thr Val Glu
                325                 330                 335

Phe Leu Val Asp Ser Lys Lys Asn Phe Tyr Phe Leu Glu Met Asn Thr
                340                 345                 350

Arg Leu Gln Val Glu His Pro Val Thr Glu Cys Ile Thr Gly Leu Asp
            355                 360                 365

Leu Val Gln Glu Met Ile Arg Val Ala Lys Gly Tyr Pro Leu Arg His
        370                 375                 380

Lys Gln Ala Asp Ile Arg Ile Asn Gly Trp Ala Val Glu Cys Arg Val
385                 390                 395                 400

Tyr Ala Glu Asp Pro Tyr Lys Ser Phe Gly Leu Pro Ser Ile Gly Arg
                405                 410                 415

Leu Ser Gln Tyr Gln Glu Pro Leu His Leu Pro Gly Val Arg Val Asp
                420                 425                 430

Ser Gly Ile Gln Pro Gly Ser Asp Ile Ser Ile Tyr Tyr Asp Pro Met
            435                 440                 445

Ile Ser Lys Leu Ile Thr Tyr Gly Ser Asp Arg Thr Glu Ala Leu Lys
        450                 455                 460

Arg Met Ala Asp Ala Leu Asp Asn Tyr Val Ile Arg Gly Val Thr His
465                 470                 475                 480

Asn Ile Ala Leu Leu Arg Glu Val Ile Asn Ser Arg Phe Val Lys
                485                 490                 495

Gly Asp Ile Ser Thr Lys Phe Leu Ser Asp Val Tyr Pro Asp Gly Phe
            500                 505                 510

Lys Gly His Met Leu Thr Lys Ser Glu Lys Asn Gln Leu Leu Ala Ile
        515                 520                 525

Ala Ser Ser Leu Phe Val Ala Phe Gln Leu Arg Ala Gln His Phe Gln
530                 535                 540

Glu Asn Ser Arg Met Pro Val Ile Lys Pro Asp Ile Ala Asn Trp Glu
545                 550                 555                 560

Leu Ser Val Lys Leu His Asp Lys Val His Thr Val Val Ala Ser Asn
                565                 570                 575
```

```
Asn Gly Ser Val Phe Ser Val Glu Val Asp Gly Ser Lys Leu Asn Val
            580                 585                 590

Thr Ser Thr Trp Asn Leu Ala Ser Pro Leu Leu Ser Val Ser Val Asp
        595                 600                 605

Gly Thr Gln Arg Thr Val Gln Cys Leu Ser Arg Glu Ala Gly Gly Asn
        610                 615                 620

Met Ser Ile Gln Phe Leu Gly Thr Val Tyr Lys Val Asn Ile Leu Thr
625                 630                 635                 640

Arg Leu Ala Ala Glu Leu Asn Lys Phe Met Leu Glu Lys Val Thr Glu
                645                 650                 655

Asp Thr Ser Ser Val Leu Arg Ser Pro Met Pro Gly Val Val Val Ala
            660                 665                 670

Val Ser Val Lys Pro Gly Asp Ala Val Ala Glu Gly Gln Glu Ile Cys
        675                 680                 685

Val Ile Glu Ala Met Lys Met Gln Asn Ser Met Thr Ala Gly Lys Thr
690                 695                 700

Gly Thr Val Lys Ser Val His Cys Gln Ala Gly Asp Thr Val Gly Glu
705                 710                 715                 720

Gly Asp Leu Leu Val Glu Leu Glu
                725

<210> SEQ ID NO 6
<211> LENGTH: 539
<212> TYPE: PRT
<213> ORGANISM: Homo sapiens

<400> SEQUENCE: 6

Met Ala Ala Ala Leu Arg Val Ala Ala Val Gly Ala Arg Leu Ser Val
1               5                   10                  15

Leu Ala Ser Gly Leu Arg Ala Ala Val Arg Ser Leu Cys Ser Gln Ala
            20                  25                  30

Thr Ser Val Asn Glu Arg Ile Glu Asn Lys Arg Arg Thr Ala Leu Leu
        35                  40                  45

Gly Gly Gly Gln Arg Arg Ile Asp Ala Gln His Lys Arg Gly Lys Leu
    50                  55                  60

Thr Ala Arg Glu Arg Ile Ser Leu Leu Leu Asp Pro Gly Ser Phe Val
65                  70                  75                  80

Glu Ser Asp Met Phe Val Glu His Arg Cys Ala Asp Phe Gly Met Ala
                85                  90                  95

Ala Asp Lys Asn Lys Phe Pro Gly Asp Ser Val Val Thr Gly Arg Gly
            100                 105                 110

Arg Ile Asn Gly Arg Leu Val Tyr Val Phe Ser Gln Asp Phe Thr Val
        115                 120                 125

Phe Gly Gly Ser Leu Ser Gly Ala His Ala Gln Lys Ile Cys Lys Ile
    130                 135                 140

Met Asp Gln Ala Ile Thr Val Gly Ala Pro Val Ile Gly Leu Asn Asp
145                 150                 155                 160

Ser Gly Gly Ala Arg Ile Gln Glu Gly Val Glu Ser Leu Ala Gly Tyr
                165                 170                 175

Ala Asp Ile Phe Leu Arg Asn Val Thr Ala Ser Gly Val Ile Pro Gln
            180                 185                 190

Ile Ser Leu Ile Met Gly Pro Cys Ala Gly Gly Ala Val Tyr Ser Pro
        195                 200                 205

Ala Leu Thr Asp Phe Thr Phe Met Val Lys Asp Thr Ser Tyr Leu Phe
    210                 215                 220
```

```
Ile Thr Gly Pro Asp Val Val Lys Ser Val Thr Asn Glu Asp Val Thr
225                 230                 235                 240

Gln Glu Glu Leu Gly Gly Ala Lys Thr His Thr Thr Met Ser Gly Val
            245                 250                 255

Ala His Arg Ala Phe Glu Asn Asp Val Asp Ala Leu Cys Asn Leu Arg
        260                 265                 270

Asp Phe Phe Asn Tyr Leu Pro Leu Ser Ser Gln Asp Pro Ala Pro Val
        275                 280                 285

Arg Glu Cys His Asp Pro Ser Asp Arg Leu Val Pro Glu Leu Asp Thr
        290                 295                 300

Ile Val Pro Leu Glu Ser Thr Lys Ala Tyr Asn Met Val Asp Ile Ile
305                 310                 315                 320

His Ser Val Val Asp Glu Arg Glu Phe Phe Glu Ile Met Pro Asn Tyr
                325                 330                 335

Ala Lys Asn Ile Ile Val Gly Phe Ala Arg Met Asn Gly Arg Thr Val
                340                 345                 350

Gly Ile Val Gly Asn Gln Pro Lys Val Ala Ser Gly Cys Leu Asp Ile
        355                 360                 365

Asn Ser Ser Val Lys Gly Ala Arg Phe Val Arg Phe Cys Asp Ala Phe
370                 375                 380

Asn Ile Pro Leu Ile Thr Phe Val Asp Val Pro Gly Phe Leu Pro Gly
385                 390                 395                 400

Thr Ala Gln Glu Tyr Gly Gly Ile Ile Arg His Gly Ala Lys Leu Leu
            405                 410                 415

Tyr Ala Phe Ala Glu Ala Thr Val Pro Lys Val Thr Val Ile Thr Arg
        420                 425                 430

Lys Ala Tyr Gly Gly Ala Tyr Asp Val Met Ser Ser Lys His Leu Cys
        435                 440                 445

Gly Asp Thr Asn Tyr Ala Trp Pro Thr Ala Glu Ile Ala Val Met Gly
450                 455                 460

Ala Lys Gly Ala Val Glu Ile Ile Phe Lys Gly His Glu Asn Val Glu
465                 470                 475                 480

Ala Ala Gln Ala Glu Tyr Ile Glu Lys Phe Ala Asn Pro Phe Pro Ala
                485                 490                 495

Ala Val Arg Gly Phe Val Asp Asp Ile Ile Gln Pro Ser Ser Thr Arg
            500                 505                 510

Ala Arg Ile Cys Cys Asp Leu Asp Val Leu Ala Ser Lys Lys Val Gln
        515                 520                 525

Arg Pro Trp Arg Lys His Ala Asn Ile Pro Leu
        530                 535
```

BRANCHED PEG MOLECULES AND RELATED COMPOSITIONS AND METHODS

CROSS-REFERENCE TO RELATED APPLICATIONS

This application is a national stage entry of International Application No. PCT/US2017/068841, filed on Dec. 29, 2017, which claims the benefit of U.S. Provisional Application No. 62/440,941 filed on Dec. 30, 2016 and U.S. Provisional Application No. 62/446,186 filed on Jan. 13, 2017, each of which is hereby incorporated by reference in its entirety.

REFERENCE TO SEQUENCE LISTING

The instant application contains a Sequence Listing which has been submitted in ASCII format via EFS-Web and is hereby incorporated by reference in its entirety. Said ASCII copy, created on Jun. 28, 2019, is named "4170.0050002_SL_ST25.txt" and is 28,391 bytes in size, and corresponds to the Sequence Listing originally submitted in International Appl. No. PCT/US2017/068841.

BACKGROUND OF THE INVENTION

PEGylation has been used to improve circulatory stability of therapeutic peptides, proteins, and lipid nanoparticles. See. e.g., Immordino et al., *Int. J. Nanomedicine* 1:297-315, 2006; Banerjee et al., *J. Drug Deliv.* 2012, Article ID 103973, 2012; Fishbum, *J. Pharm. Sci.* 97:4167-83, 2008; Fishburn, *J. Pharm. Sci.* 2008, DOI 10.1002/jps.21278; Hamley, *Biomacromolecules* 15:1543-1559, 2014; Turecek et al., *J. Pharm. Sci.* 105:460-475, 2016; Damodaran and Fee, "Protein PEGylation: An overview of chemistry and process considerations," *European Pharmaceutical Review*, 2010 (1). PEGylation has also been used to improve formulation and formulation stability of these materials. See U.S. Pat. No. 8,304,565 to Wu et al. In these functions, long linear PEG chains have been conjugated to peptides and proteins, or have been made into lipids (such as, for example, DPSE-PEG, DSG-PEG, DMPE-PEG, or DSG-PEG) for use in lipid nanoparticle formation.

Currently known PEGylated lipids contain from one to three linear PEG chains. One example of a PEG-lipid containing three linear PEG chains is SUNBRIGHT® DSPE-PTE020 (NOF Corporation). In addition, functionalized branched PEG derivatives are available from a number of sources for modification of peptides or proteins, including 2 Arm PEG Branched PEG Derivatives (Nanocs Inc., New York, N.Y.), Activated PEGs for PEGylation (NOF Corporation, Tokyo, Japan), Multiarm PEGs for Hydrogels (Jen-Kem Technology, Plano, Tex.), 4-arm PEGs (Sigma-Aldrich, Milwaukee, Wis.), 6-arm PEGs (SINOPEG, Fujian Province, China), and 8-arm PEGs (Creative PEGWorks, Chapel Hill, N.C.). See also U.S. Pat. No. 8,703,893 to Hemandez et al.

Current PEGylation strategies can, however, result in stimulation of the immune system or binding with serum components, resulting in accelerated blood clearance (ABC) and lower delivery of materials upon repeat delivery. See. e.g., Yang and Lai, *WIREs Nanomed. Nanobiotechnol.* 7:655-677, 2015, doi: 10.1002/wnan.13392015. A recent study of PEG-specific antibody responses to PEG-liposomes suggests that ABC can be influenced by the hydrophobic linkage of the PEG to the nanoparticle. See Shiraishi et al., *Journal of Controlled Release* 2016, doi: 10.1016/j.jcon-rel.2016.05.010. Another study, using nanocarriers prepared with DSPE-PEG$_{200}$, indicates that anti-PEG IgM preferentially binds to PEGylated nanocarriers that have PEG chains in a brush conformation. See Wang et al., *Int. J. Nanomedicine* 10:3533-45, 2015.

There is a need in the art for alternative PEGylation strategies and corresponding PEG-compositions, including PEGylated lipids, lipid nanoparticles, and therapeutic proteins. There is particularly a need for improvements in terms of decreased immune system stimulation, decreased accelerated blood clearance, and/or delivery of agents upon repeat dosing.

SUMMARY OF THE INVENTION

In one aspect, the present invention provides a branched PEG-lipid of Formula I $$L-X1-P-X2-T \qquad (I)$$

where P is a polymer comprising (i) an alkylenic or heteroalkylenic backbone of chain atoms and (ii) a plurality of pendant polyethylene glycol (PEG) moieties distributed along the polymer backbone; L is a lipid attached to a first end of the polymer; X1 is absent or a first linking moiety; T is absent or a targeting moiety attached to a second end of the polymer; and X2 is absent or a second linking moiety. In some embodiments, the ratio of chain atoms to pendant PEG moieties of the polymer is less than 4:1. Particularly suitable polymers of a branched PEG-lipid as above comprise at least five pendant PEG moieties. In certain variations, the lipid is attached to the α end of the polymer.

In some embodiments of a branched PEG-lipid as above, L is selected from (i) a lipid comprising two $C_8$-$C_{24}$ hydrocarbon chains (e.g., two $C_{10}$-$C_{18}$ hydrocarbon chains), (ii) a sterol lipid (e.g., cholesterol), and (iii) a sphingolipid (e.g., N-octanoyl-sphingosine). In some such embodiments where L is the lipid comprising two $C_8$-$C_{24}$ hydrocarbon chains, L is a glycerophospholipid such as, for example, 1,2-dimyristoyl-sn-glycero-3-phosphoethanolamine (DMPE) or 1,2-distearoyl-sn-glycero-3-phosphoethanolamine (DSPE). In other embodiments where L is the lipid comprising two $C_8$-$C_{24}$ hydrocarbon chains, L is a glycerolipid such as, for example, dimyristolglycerol (DMG), distearoyl glycerol (DSG), or dipalmitoyl glycerol (DPG).

In certain embodiments of a branched PEG-lipid as above, the polymer chain atoms are carbon atoms or a combination of carbon and oxygen atoms.

In some embodiments of a branched PEG-lipid as above, each of the pendant PEG moieties comprises from 2 to 50 (e.g., from 2 to 40, from 2 to 25, or from 2 to 20) ethylene oxide units. In more specific variations, each of the pendant PEG moieties comprises from 4 to 5 ethylene oxide units. In other variations, each of the pendant PEG moieties comprises from 7 to 9 ethylene oxide units. In certain embodiments, the polymer comprising the pendant PEG moieties is a polymer comprising monomeric residues derived from polymerization of a monomer of formula A1

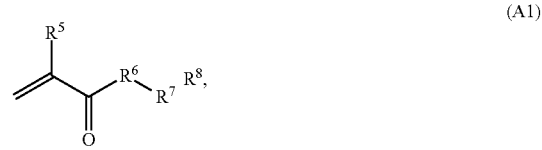

(A1)

where $R^5$ is H or C1-C6alkyl, $R^6$ is O, S, $NR^9$, OC1-C6alkyl, OC1-C6alkyl-O, OC1-C6alkyl-OC(O)C1-C6alkyl, OC1-C6alkyl-OC(O)C1-C6alkyl-O, OC1-C6alkyl-OC(O)C1-C6alkyl-NH, OC1-C6alkyl-NH, OC1-C6alkyl-NHC(O)C1-C6alkyl, OC1-C6alkyl-NHC(O)C1-C6alkyl-O, OC1-C6alkyl-NHC(O)C1-C6alkyl-NH, $NR^9$(C1-C6alkyl), $NR^9$(C1-C6alkyl)-O, $NR^9$(C1-C6alkyl)-OC(O)C1-C6alkyl, $NR^9$(C1-C6alkyl)-OC(O)C1-C6alkyl-O, $NR^9$(C1-C6alkyl)-OC(O)C1-C6alkyl-NH, $NR^9$(C1-C6alkyl)-NH, $NR^9$(C1-C6alkyl)-NHC(O)C1-C6alkyl, $NR^9$(C1-C6alkyl)-NHC(O)C1-C6alkyl-O, $NR^9$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6alkyl-O, or C1-C6alkyl-NHC(O)C1-C6alkyl-NH, $R^7$ is $(CH_2CH_2O)_{2-50}$ (e.g., $(CH_2CH_2O)_{2-40}$, $(CH_2CH_2O)_{2-20}$, or $(CH_2CH_2O)_{2-20}$), $R^8$ is H or C1-C6alkyl-$R^{10}$, $R^9$ is H or C1-C6alkyl, and $R^{10}$ is H, $CO_2H$, $NH_2$, NH(C1-C6alkyl), N(C1-C6alkyl)$_2$, or N(C1-C6alkyl)$_3$, Particularly suitable polymers comprising pendant PEG moieties are polymers comprising monomeric residues derived from polymerization of a monomer selected from a poly(ethylene glycol) methyl ether methacrylate (PEGMA), a poly(ethylene glycol) methyl ether acrylate (PEGA), a poly(ethylene glycol) methyl ether methacrylamide, and a poly(ethylene glycol) methyl ether acrylamide, where the monomer has from 2 to 50 (e.g., from 2 to 40, from 2 to 25, or from 2 to 20) ethylene oxide units; in some such variations in which the polymer comprises monomeric residues derived from polymerization of the PEGMA, the PEGMA has from 4 to 5 ethylene oxide units (PEGMA$_{300}$) or from 7 to 9 ethylene oxide units (PEGMA$_{500}$).

In some embodiments of a branched PEG-lipid as above, the polymer is a homopolymer.

In some embodiments of a branched PEG-lipid as above, the targeting moiety comprises a N-acetyl galactosamine (GalNAc) residue.

Particularly suitable branched PEG-lipids include DSPE-PEGMA, DMPE-PEGMA, DSG-PEGMA, DMG-PEGMA, and DPG-PEGMA. In some such embodiments, the branched PEG-lipid is DSPE-PEGMA$_{300}$, DSPE-PEGMA$_{500}$, DMPE-PEGMA$_{300}$, DMPE-PEGMA$_{500}$, DSG-PEGMA$_{300}$, DSG-PEGMA$_{500}$, DMG-PEGMA$_{300}$, DMG-PEGMA$_{500}$, DPG-PEGMA$_{300}$, or DPG-PEGMA$_{500}$. In more specific variations, the branched PEG-lipid is a compound of Formula IIa, IIb IIc, IId, IIe, IIf, IIg, IIh, IIi, or IIj

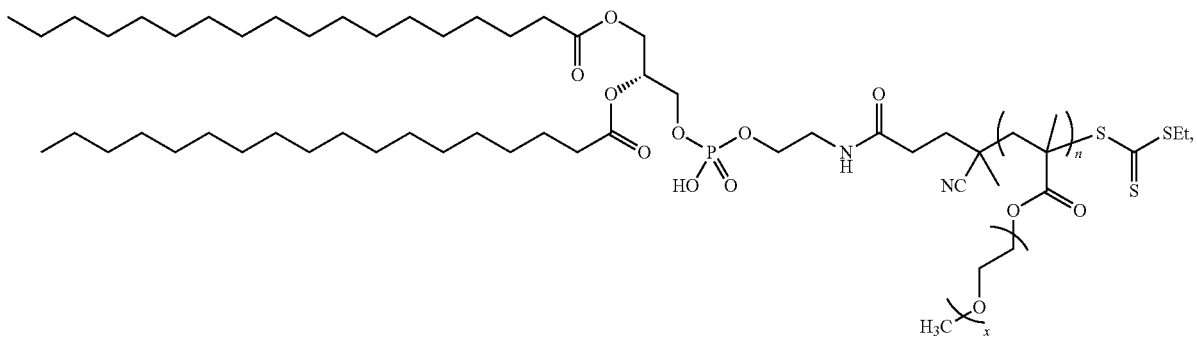

(IIa)

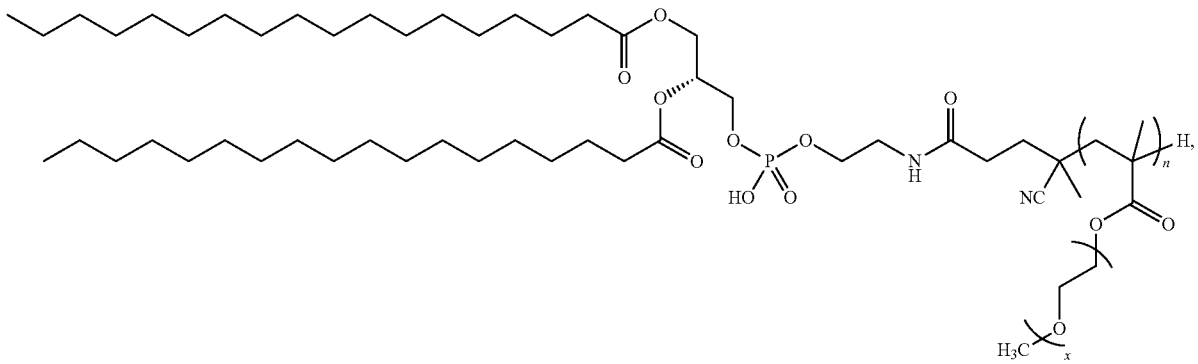

(IIb)

-continued
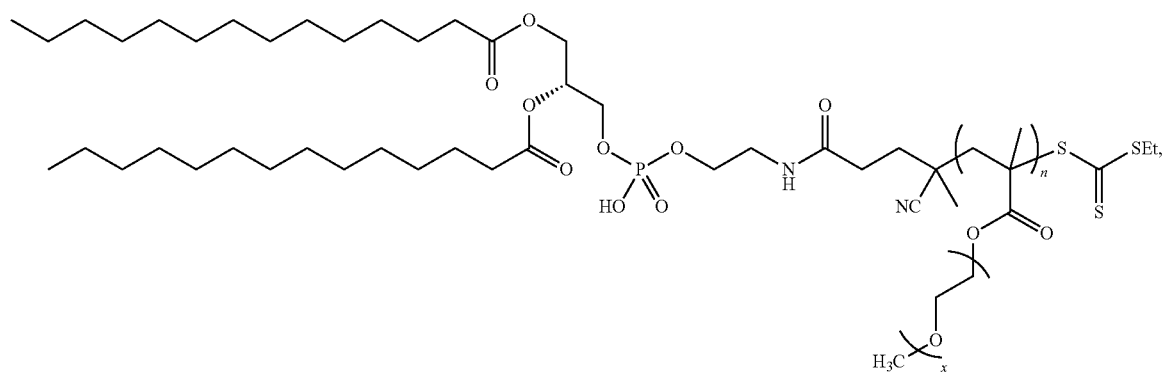
(IIc)
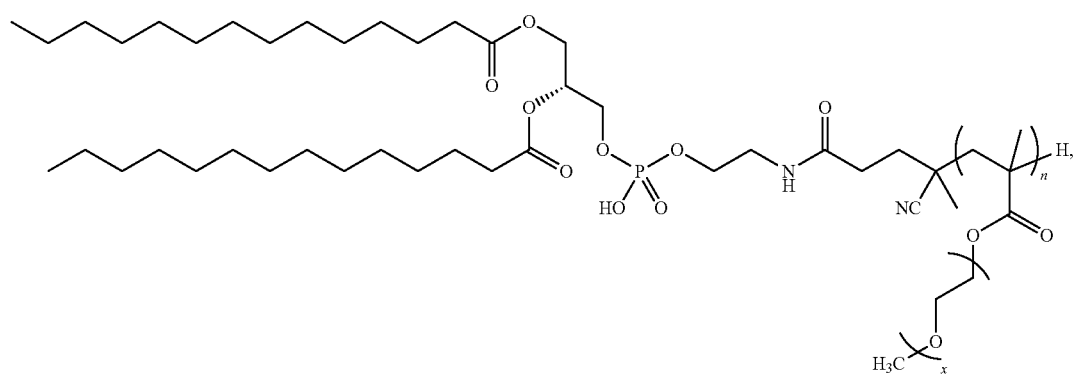
(IId)
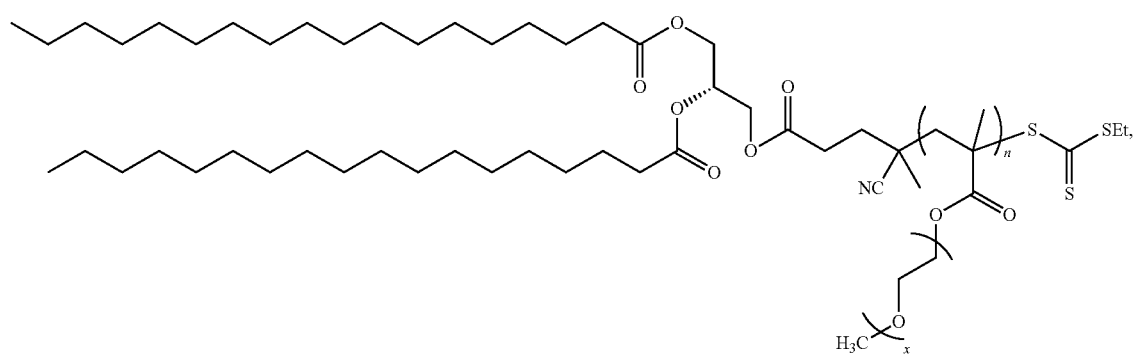
(IIe)
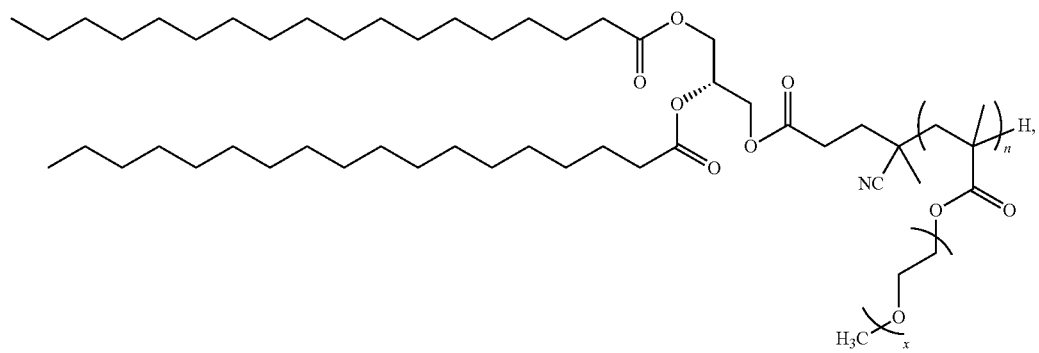
(IIf)

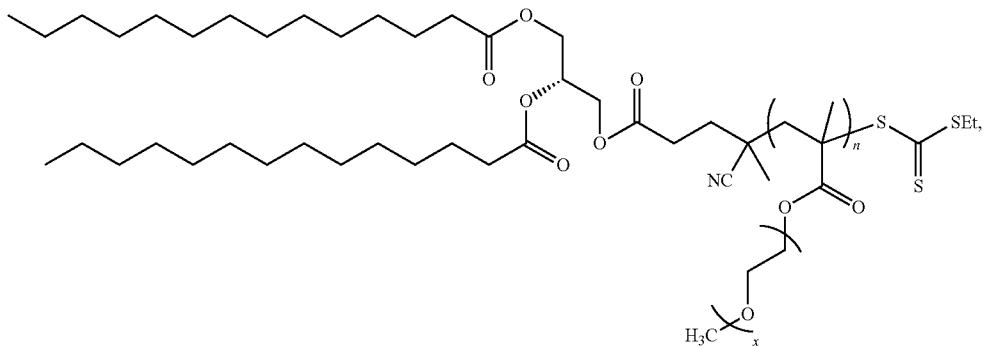

(IIg)

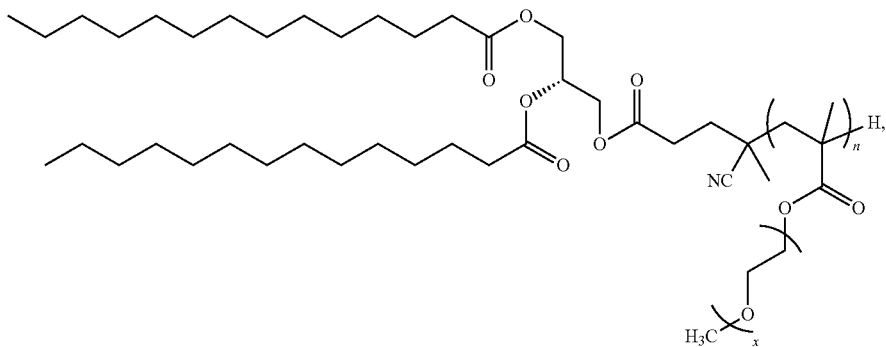

(IIh)

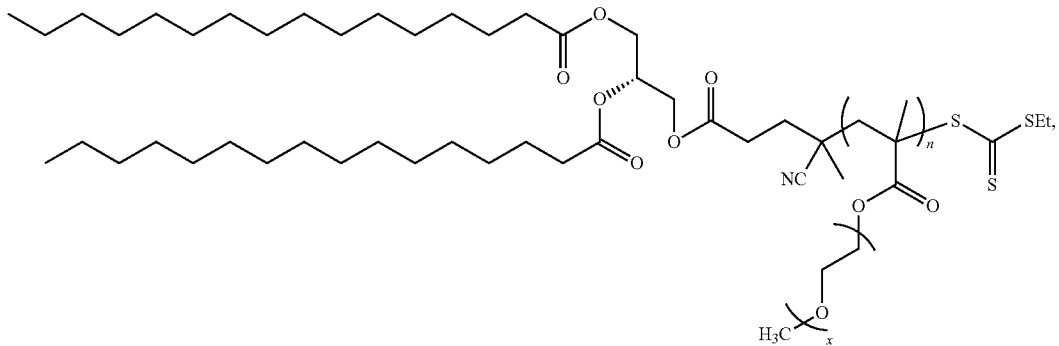

(IIi)

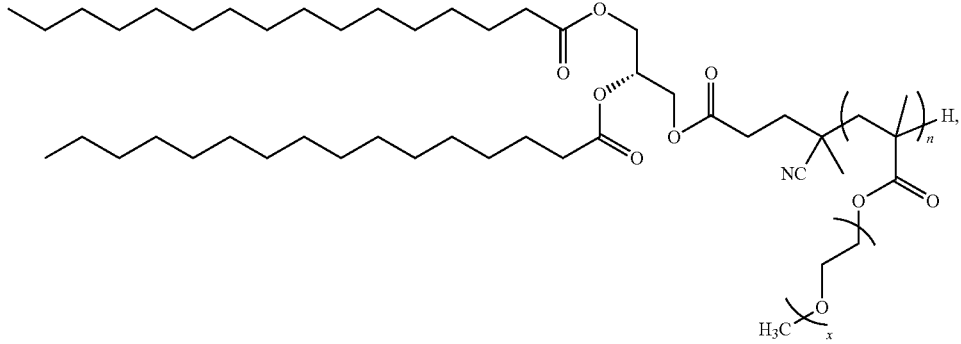

(IIj)

or a pharmaceutically acceptable salt thereof, where x is 4-5 or 7-9, and n is 10-40 (e.g., 10-35, 10-30, or 10-25).

In another aspect, the present invention provides a lipid nanoparticle comprising (a) a mixture of lipid components comprising a branched PEG-lipid as above; and (b) a therapeutic or diagnostic agent.

In some embodiments, a lipid nanoparticle as above includes a cationic lipid. Particularly suitable cationic lipids include N-[1-(2,3-dioleyloxy)propyl]-N,N,N-trimethylammonium chloride (DOTMA); N-[1-(2,3-dioleoyloxy)propyl]-N,N,N-trimethylammonium chloride (DOTAP); 1,2-dioleoyl-sn-glycero-3-ethylphosphocholine (DOEPC); 1,2-dilauroyl-sn-glycero-3-ethylphosphocholine (DLEPC); 1,2-dimyristoyl-sn-glycero-3-ethylphosphocholine (DMEPC); 1,2-dimyristoleoyl-sn-glycero-3-ethylphosphocholine (14:1); N1-[2-((1S)-1-[(3-aminopropyl)amino]-4-[di(3-aminopropyl)amino]butylcarboxamido)ethyl]-3,4-di[oleyloxy]-benzamide (MVL5); Dioctadecylamido-glycylspermine (DOGS); 3b-[N—(N',N'-dimethylaminoethyl)carbamoyl] cholesterol (DC-Chol); Dioctadecyldimethylammonium Bromide (DDAB); SAINT-2, N-methyl-4-(dioleyl)methylpyridinium; 1,2-dimyristyloxypropyl-3-dimethylhydroxyethylammonium bromide (DMRIE); 1,2-dioleoyl-3-dimethyl-hydroxyethyl ammonium bromide (DORIE); 1,2-dioleoyloxypropyl-3-dimethylhydroxyethyl ammonium chloride (DORI); Di-alkylated Amino Acid (DILA$^2$) (e.g., C18:1-norArg-C16); Dioleyldimethylammonium chloride (DODAC); 1-palmitoyl-2-oleoyl-sn-glycero-3-ethylphosphocholine (POEPC); 1,2-dimyristoleoyl-sn-glycero-3-ethylphosphocholine (MOEPC); (R)-5-(dimethylamino)pentane-1,2-diyl dioleate hydrochloride (DODAPen-Cl); (R)-5-guanidinopentane-1,2-diyl dioleate hydrochloride (DOPen-G); and (R)—N,N,N-trimethyl-4,5-bis(oleoyloxy)pentan-1-aminium chloride (DOTAPen). In some variations, the cationic lipid is an ionizable cationic lipid such as, e.g., Dioctadecyldimethylammonium bromide (DDAB); 1,2-dilinoleyloxy-3-dimethylaminopropane (DLinDMA); 2,2-dilinoleyl-4-(2dimethylaminoethyl)-[1,3]-dioxolane (DLin-KC2-DMA); heptatriaconta-6,9,28,31-tetraen-19-yl 4-(dimethylamino)butanoate (DLin-MC3-DMA); 1,2-Dioleoyloxy-3-dimethylaminopropane (DODAP); 1,2-Dioleyloxy-3-dimethylaminopropane (DODMA); and Morpholinocholesterol (Mo-CHOL). In certain embodiments, a lipid nanoparticle includes a combination or two or more cationic lipids (e.g., two or more cationic lipids as above).

In some embodiments, a lipid nanoparticle as above includes an ionizable anionic lipid such as, e.g., cholesteryl hemisuccinate (CHEMS), phosphatidylserine, palmitoylhomoserine, or α-tocopherol hemisuccinate. In certain variations, a lipid nanoparticle includes a combination or two or more ionizable anionic lipids (e.g., two or more ionizable anionic lipids as above).

In some variations, a lipid nanoparticle as above includes a helper lipid. Particularly suitable helper lipids include cholesterol (CHOL); 1,2-distearoyl-sn-glycero-3-phosphocholine (DSPC); 1,2-dipalmitoyl-sn-glycero-3-phosphocholine (DPPC); 1,2-dimyristoyl-sn-glycero-3-phosphocholine (DMPC); 1,2-dioleoyl-sn-glycero-3-phosphoethanolamine (DOPE); 1,2-dilauroyl-sn-glycero-3-phosphoethanolamine (DLPE); 1,2-dimyristoyl-sn-glycero-3-phosphoethanolamine (DMPE); and 1,2-diphytanoyl-sn-glycero-3-phosphoethanolamine (DPHyPE). In certain embodiments, a lipid nanoparticle includes a combination or two or more helper lipids (e.g., two or more helper lipids as above).

In certain embodiments, the lipid nanoparticle includes the therapeutic agent. Suitable therapeutic agents may be selected from polynucleotides (e.g., mRNAs), proteins, peptides, and small molecules.

In some variations of a lipid nanoparticle as above wherein the therapeutic agent is the polynucleotide, the branched PEG-lipid is present in the mixture of lipid components from about 0.1 mole % to about 15 mole % (e.g., from about 0.5 mole % to about 15 mole %), and the mixture of lipid components further includes (i) a cationic lipid that is permanently charged at physiological pH, where the cationic lipid is present in the mixture from about 35 mole % to about 60 mole %; (ii) an ionizable anionic lipid, where the anionic lipid is present in the mixture from about 25 mole % to about 40 mole %; and (iii) a helper lipid, where the helper lipid is present in the mixture from about 5 mole % to about 20 mole %. In some such embodiments, the cationic lipid is DOTAP, the ionizable anionic lipid is CHEMS, the helper lipid is CHOL, and/or the branched PEG-lipid is DSPE-PEGMA, DMPE-PEGMA, DSG-PEGMA, DMG-PEMA, or DPG-PEGMA (e.g., DSPE-PEGMA$_{300}$, DSPE-PEGMA$_{500}$, DMPE-PEGMA$_{300}$, DMPE-PEGMA$_{500}$, DSG-PEGMA$_{300}$, DSG-PEGMA$_{500}$, DMG-PEGMA$_{300}$, DMG-PEGMA$_{500}$, DPG-PEGMA$_{300}$, or DPG-PEGMA$_{500}$). In more specific variations where the cationic lipid is DOTAP, the ionizable anionic lipid is CHEMS, the helper lipid is CHOL, and the branched PEG-lipid is DSPE-PEGMA, DMPE-PEGMA, DSG-PEGMA, DMG-PEGMA, or DPG-PEGMA, the molar ratio of DOTAP:CHEMS:CHOL:[branched PEG-lipid] is about 50:32:16:2 or about 50:32:8:10. In some embodiments of a lipid nanoparticle as above in which the branched PEG-lipid is DSPE-PEGMA, DMPE-PEGMA, DSG-PEGMA, DMG-PEGMA, or DPG-PEGMA, the branched PEG-lipid is a compound of Formula IIa, IIb, IIc, IId, IIe, IIf, IIg, IIh, IIi, or IIj (IIa)

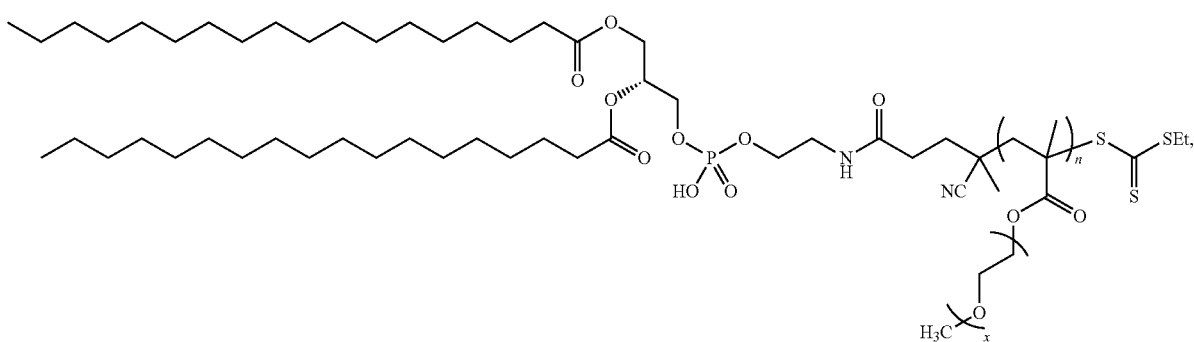

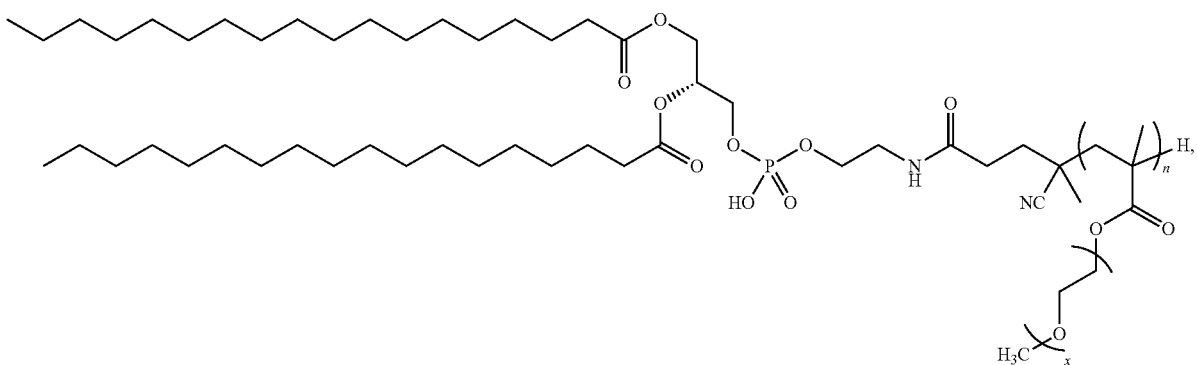
(IIb)
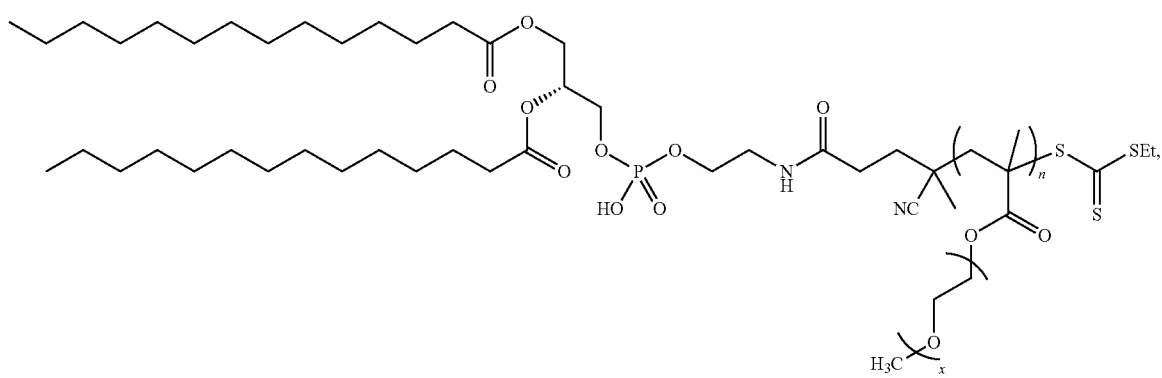
(IIc)
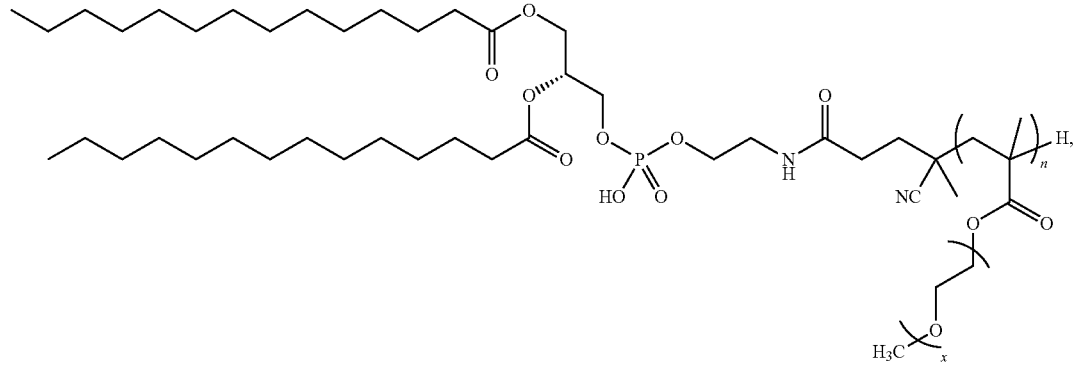
(IId)
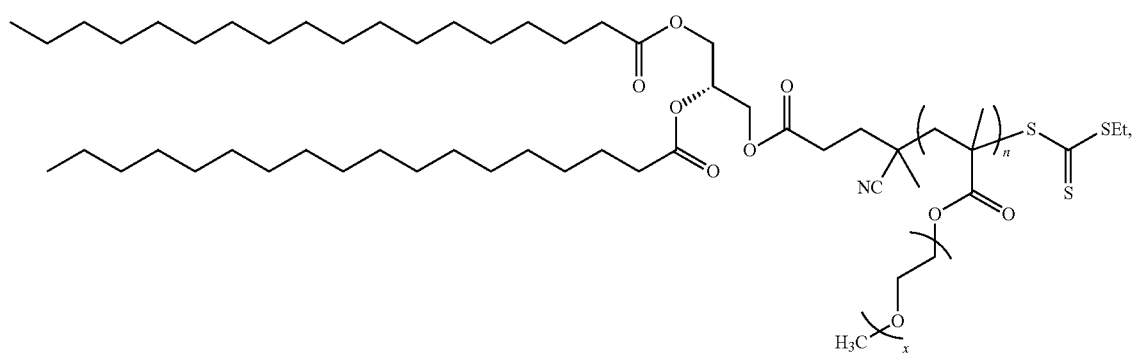
(IIe)

-continued
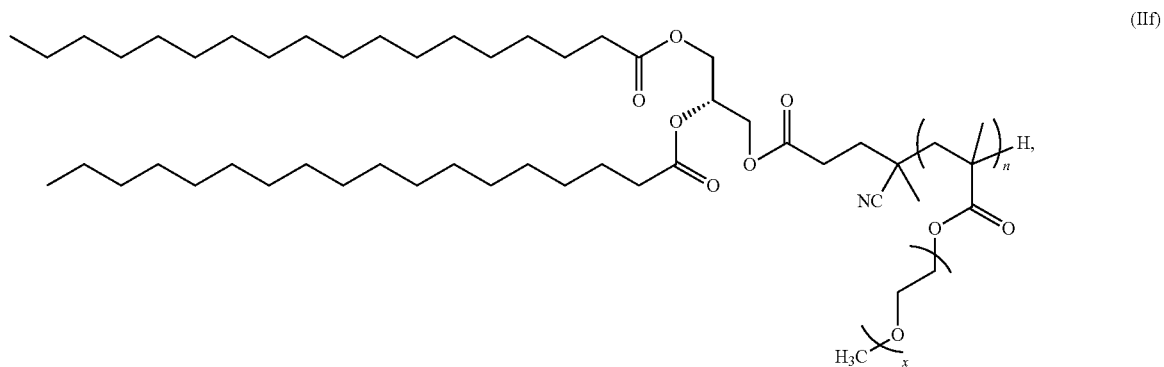
(IIf)
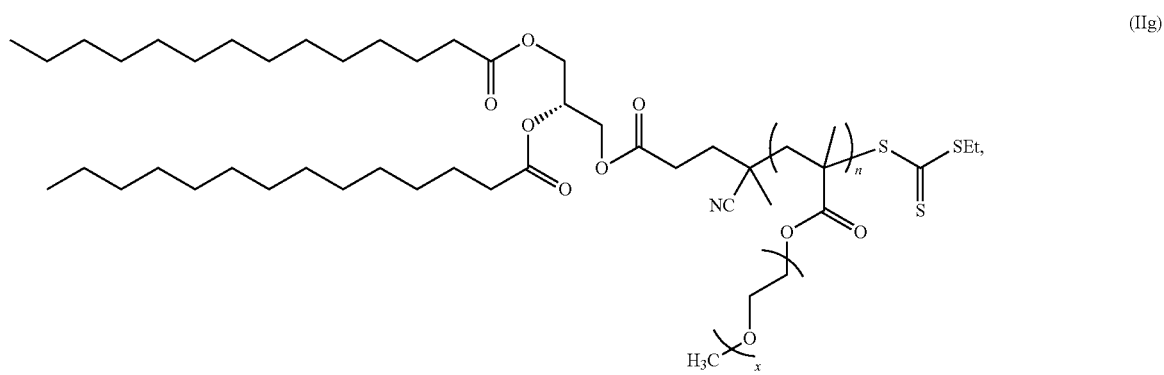
(IIg)
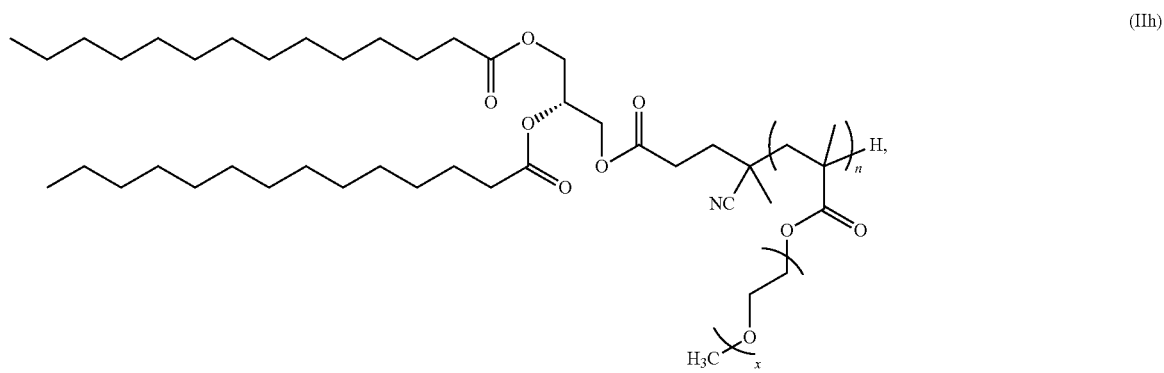
(IIh)
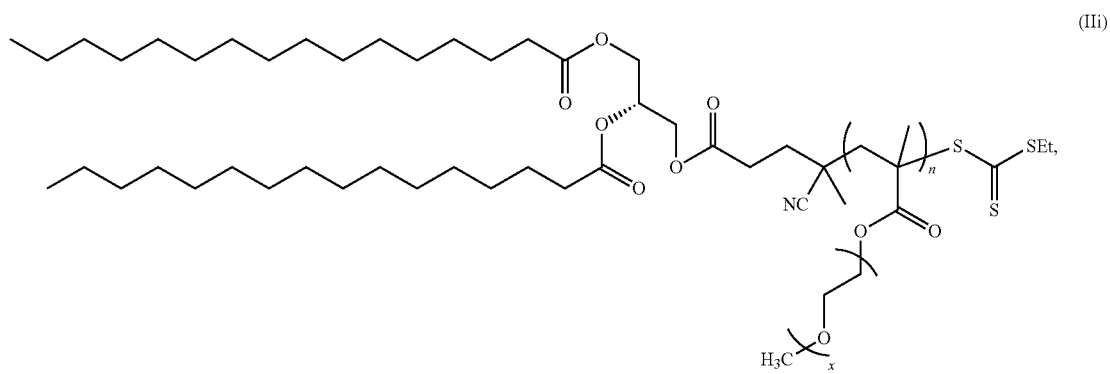
(IIi)

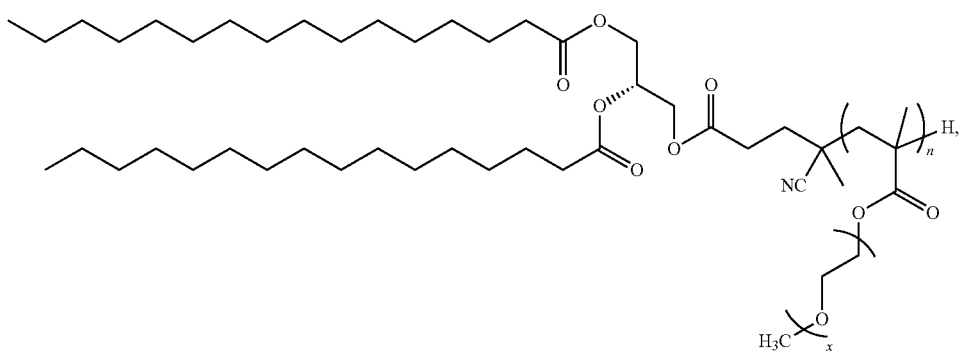

or a pharmaceutically acceptable salt thereof, where x is 4-5 or 7-9, and n is 10-40 (e.g., 10-35, 10-30, or 10-25).

In certain embodiments of a lipid nanoparticle as above comprising a polynucleotide, the polynucleotide is an mRNA. In some such embodiments, the mRNA encodes a functional protein associated with a protein deficiency disease. In particular variations, the mRNA encodes a protein selected from alpha-1-antitrypsin (A1AT), carbamoyl phosphate synthetase I (CPS1), fumarylacetoacetase (FAH) enzyme, alanine:glyoxylate-aminotransferase (AGT), methylmalonyl CoA mutase (MUT), propionyl CoA carboxylase alpha subunit (PCCA), propionyl CoA carboxylase beta subunit (PCCB), a subunit of branched-chain ketoacid dehydrogenase (BCKDH), ornithine transcarbamylase (OTC), copper-transporting ATPase Atp7B, bilirubin uridinediphosphate glucuronyltransferase (BGT) enzyme, hepcidin, glucose-6-phosphatase (G6Pase), glucose 6-phosphate translocase, lysosomal glucocerebrosidase (GB), Niemann-Pick C1 protein (NPC1), Niemann-Pick C2 protein (NPC2), acid sphingomyelinase (ASM), Factor IX, galactose-1-phosphate uridylyltransferase, galactokinase, UDP-galactose 4-epimerase, transthyretin, a complement regulatory protein, phenylalanine hydroxylase (PAH), homogentisate 1,2-dioxygenase, porphobilinogen deaminase, hypoxanthine-guanine phosphoribosyltransferase (HGPRT), argininosuccinate lyase (ASL), argininosuccinate synthetase (ASS1), P-type ATPase protein FIC-1, alpha-galactosidase A, acid ceramidase, acid α-L-fucosidase, acid β-galactosidase, iduronate-2-sulfatase, alpha-L-iduronidase, galactocerebrosidase, acid α-mannosidase, β-mannosidase, arylsulfatase B, arylsulfatase A, N-acetylgalactosamine-6-sulfate sulfatase, acid β-galactosidase, acid α-glucosidase, β-hexosaminidase B, heparan-N-sulfatase, alpha-N-acetylglucosaminidase, acetyl-CoA:α-glucosaminide N-acetyltransferase, N-acetylglucosamine-6-sulfate sulfatase, alpha-N-acetylgalactosaminidase, sialidase, β-glucuronidase, and β-hexosaminidase A.

In certain embodiments, the polynucleotide is an mRNA encoding a secreted protein. Suitable secreted proteins include hormones, cytokines, growth factors, clotting factors, anti-protease proteins, angiogenic proteins, antiangiogenic proteins, chemokines, and antibodies. In particular variations, the secreted protein is selected from erythropoietin (EPO), thrombopoietin (TPO), granulocyte-colony stimulating factor (G-CSF), granulocyte macrophage-colony stimulating factor (GM-CSF), leptin, a platelet-derived growth factor (e.g., platelet-derived growth factor B (PDGF-B)), keratinocyte growth factor (KGF), bone morphogenic protein 2 (BMP-2), bone morphogenic protein 7 (BMP-7), insulin, glucagon-like peptide-1 (GLP-1), human growth hormone (HGF), Factor VII, Factor VIII, Factor IX, a relaxin (e.g., relaxin-2), an interferon (e.g., interferon-α (IFN-α), interferon-3 (IFN-0), interferon-γ (IFN-γ)), interleukin-2 (IL-2), interleukin-4 (IL-4), interleukin-10 (IL-10), interleukin-11 (IL-11), interleukin-12 (IL-12), interleukin-18 (IL-18), interleukin-21 (IL-21), a CC subfamily chemokine, a CXC subfamily chemokine, a C subfamily chemokine, and a CX3C subfamily chemokine. In some embodiments where the secreted protein is an antibody, the antibody is a genetically engineered antibody selected from a chimeric antibody, a humanized antibody, a single-chain antibody (e.g., a single-chain Fv (scFv)), and a bispecific antibody.

In other embodiments where the therapeutic agent is a polynucleotide, the polynucleotide is an oligonucleotide. Suitable oligonucleotide therapeutic agents include siRNAs, antisense oligonucleotides, anti-miRs (also known as antagomiRs), locked nucleic acid (LNA)-based oligonucleotides, dicer substrates, miRNAs, aiRNAs, shRNAs, ribozymes, and nucleic acid aptamers.

In other embodiments, the therapeutic agent is a component of a gene editing system that disrupts or corrects a gene associated with a disease. In some embodiments, the component of the gene editing system is a polynucleotide (e.g., an mRNA) encoding a nuclease. Particularly suitable nucleases include zinc finger nucleases (ZFNs), transcription activator-like effector nucleases (TALENs), CRISPR-associated protein 9 (Cas9), and engineered meganucleases. In particular variations in which the nuclease is Cas9, the lipid nanoparticle further includes a guide RNA that targets the nuclease to a specific site in the target cell genome. In some variations directed to gene editing as above, the lipid nanoparticle further includes a polynucleotide containing a DNA donor sequence for correcting a disease-associated gene by homologous recombination. In other variations, the method further includes administering to the subject an effective amount of a second lipid nanoparticle that includes a polynucleotide containing a DNA donor sequence for correcting a disease-associated gene by homologous recombination.

In some embodiments, the therapeutic agent is an immunogen. Suitable immunogens include peptides, proteins, mRNAs, short RNAs, DNAs, and simple or complex carbohydrates. In certain variations, the immunogen is derived from an infectious agent (e.g., a virus or bacteria) or a cancer cell.

In another aspect, the present invention provides a composition for delivering a therapeutic or diagnostic agent to a subject, the composition generally including (a) a lipid nanoparticle as set forth above and (b) a membrane-destabilizing polymer.

In another aspect, the present invention provides a delivery system for delivering a therapeutic or diagnostic agent to a subject, the system generally including (a) a lipid nanoparticle as set forth above and (b) a membrane-destabilizing polymer.

In yet another aspect, the present invention provides a method for delivering a therapeutic or diagnostic agent to a subject. The method generally includes administering to a subject in need of the therapeutic or diagnostic agent an effective amount of a lipid nanoparticle, where the lipid nanoparticle comprises (a) a mixture of lipid components comprising a branched PEG-lipid as set forth above and (b) the therapeutic or diagnostic agent. In certain embodiments, the lipid nanoparticle is a lipid nanoparticle as defined above. In some variations, the method further includes administering to the subject an effective amount of a membrane-destabilizing polymer.

In some embodiments of a composition, delivery system, or method as above, the membrane-destabilizing polymer is a copolymer, a synthetic peptide, a membrane-destabilizing toxin or derivative thereof, or a viral fusogenic peptide or derivative thereof. In a particular variation, the membrane-destabilizing polymer is a pH-sensitive polymer such as, e.g., a pH-sensitive copolymer. The copolymer may be a block copolymer such as, for example, a diblock copolymer. In some variations, the block copolymer includes a hydrophobic, membrane-destabilizing block and a hydrophilic block. In some such embodiments, the hydrophilic block is polymerized from both hydrophilic monomers and hydrophobic monomers such that there are more hydrophilic monomeric residues than hydrophobic monomeric residues in the hydrophilic block. The hydrophilic block may be cleavably linked to the hydrophobic block, such as through a disulfide bond or a pH-sensitive bond. In some embodiments, the hydrophilic block includes monomeric residues linked to a pendant shielding moiety such as, e.g., a polyethylene glycol (PEG) moiety. The shielding moiety may be cleavably linked to the hydrophilic block, such as through a disulfide bond or a pH-sensitive bond. Particularly suitable pH-sensitive bonds (for linkage of the hydrophilic and hydrophobic blocks or linkage of the shielding moiety to the hydrophilic block) include hydrazone, acetal, ketal, imine, orthoester, carbonate, and maleamic acid linkages.

In some embodiments of a composition, delivery system, or method as above in which the membrane-destabilizing polymer is a pH-sensitive polymer, the pH-sensitive polymer includes monomeric residues having a carboxylic acid functional group, monomeric residues having an amine functional group, and/or monomeric residues having a hydrophobic functional group. In some variations, the pH-sensitive polymer includes monomeric residues derived from polymerization of a ($C_2$-$C_8$) alkylacrylic acid (e.g., propylacrylic acid); monomeric residues derived from polymerization of a ($C_2$-$C_8$) alkyl-ethacrylate, a ($C_2$-$C_8$) alkyl-methacrylate, or a ($C_2$-$C_8$) alkyl-acrylate; and/or monomeric residues derived from polymerization of (N,N-di($C_1$-$C_6$)alkyl-amino($C_1$-$C_6$)alkyl-ethacrylate, (N,N-di($C_1$-$C_6$)alkyl-amino($C_1$-$C_6$)alkyl-methacrylate, or (N,N-di($C_1$-$C_6$)alkyl-amino($C_1$-$C_6$)alkyl-acrylate. In a specific variation, the pH-sensitive polymer includes a random copolymer chain having monomeric residues derived from polymerization of propyl acrylic acid, N,N-dimethylaminoethylmethacrylate, and butyl methacrylate; in some such embodiments, the pH-sensitive polymer is a block copolymer comprising the random copolymer chain as a membrane disrupting polymer block, and further including one or more additional blocks.

In certain embodiments, the pH-sensitive membrane-destabilizing polymer is a diblock copolymer having a hydrophilic random copolymer block and a hydrophobic random copolymer block, where (i) the hydrophilic block is an amphiphilic block comprising both hydrophilic monomeric residues and hydrophobic monomeric residues, where the number of hydrophilic monomeric residues in the hydrophilic block is greater than the number of hydrophobic monomeric residues, (ii) the hydrophobic block is an amphiphilic, membrane-destabilizing block comprising both hydrophobic monomeric residues and hydrophilic monomeric residues and having an overall hydrophobic character at a pH of about 7.4; and (iii) each of the hydrophilic monomeric residues of the hydrophilic and hydrophobic blocks is independently selected from the group consisting of monomeric residues that are ionic at a pH of about 7.4, monomeric residues that are neutral at a pH of about 7.4, and monomeric residues that are zwitterionic at a pH of about 7.4.

In another aspect, the present invention provides a method for treating a disease characterized by a genetic defect that results in a deficiency of a functional protein. The method generally includes administering to a subject having the disease (a) an effective amount of a lipid nanoparticle, where the lipid nanoparticle comprises (i) a mixture of lipid components comprising a branched PEG-lipid as set forth above and (ii) an mRNA that encodes the functional protein or a protein having the same biological activity as the functional protein, and (b) an effective amount of a membrane-destabilizing polymer, where the mRNA is delivered to the cytosol of target cells of a target tissue associated with the disease, and where the mRNA is translated during protein synthesis so as to produce the encoded protein within the target tissue, thereby treating the disease. The lipid nanoparticle and membrane-destabilizing polymer can be administered separately (e.g., the membrane-destabilizing polymer administered after administration of the lipid nanoparticle) or, alternatively, together within a single composition. Typically, the lipid nanoparticle is less than about 200 nm in size. In certain variations, the lipid nanoparticle and the membrane-destabilizing polymer are administered in a repeat dosage regime (e.g., a weekly or bi-weekly repeated administration protocol).

In certain embodiments of a method for treating a protein deficiency disease as above, the branched PEG-lipid is present in the mixture of lipid component from about 0.1 mole % to about 15 mole % (e.g., from about 0.5 mole % to about 15 mole %), and the mixture of lipid components further includes (i) a cationic lipid that is permanently charged at physiological pH, where the cationic lipid is present in the mixture from about 35 mole % to about 55 mole %; (ii) an ionizable anionic lipid, where the anionic lipid is present in the mixture from about 25 mole % to about 40 mole %; and (iii) a helper lipid, where the helper lipid is present in the mixture from about 5 mole % to about 20 mole %. In some such embodiments, the cationic lipid is DOTAP, the ionizable anionic lipid is CHEMS, the helper lipid is CHOL, and/or the branched PEG-lipid is DSPE-PEGMA, DMPE-PEGMA, DSG-PEGMA, DMG-PEGMA, or DPG-PEGMA (e.g., DSPE-PEGMA$_{30}$, DSPE-PEGMA$_{500}$, DMPE-PEGMA$_{300}$, DMPE-PEGMA$_{500}$, DSG-PEGMA$_{300}$, DSG-PEGMA$_{00}$, DMG-PEGMA$_{300}$, DMG-PEGMA$_{500}$, DPG-PEGMA$_{300}$, or DPG-PEGMA$_{500}$). In more specific variations where the cationic lipid is DOTAP, the ionizable anionic lipid is CHEMS, the helper lipid is CHOL, and the branched PEG-lipid is DSPE-PEGMA, DMPE-PEGMA, DSG-PEGMA, DMG-PEGMA, or DPG-PEGMA, the molar ratio of DOTAP:CHEMS:CHOL: [branched PEG-lipid] is about 50:32:16:2 or about 50:32:8:10. In some embodiments of a treatment method as above in which the branched PEG-lipid is DSPE-PEGMA, DMPE-PEGMA, DSG-PEGMA, DMG-PEGMA, or DPG-PEGMA, the branched PEG-lipid is a compound of Formula IIa, IIb, IIc, IId, IIe, IIf, IIg, IIh, IIi, or IIj

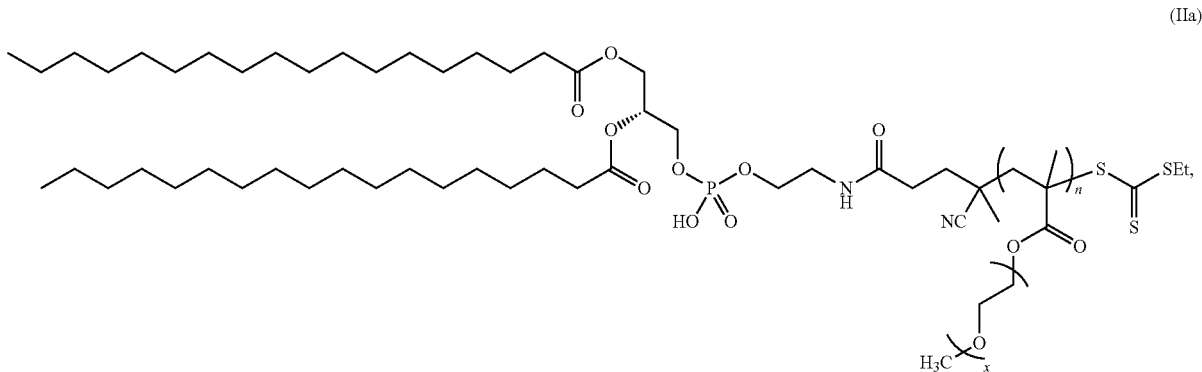

(IIa)

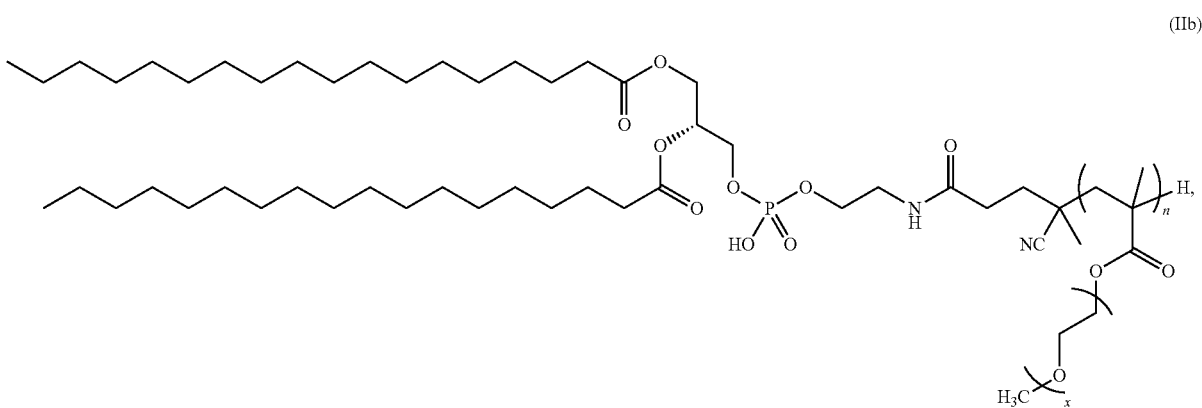

(IIb)

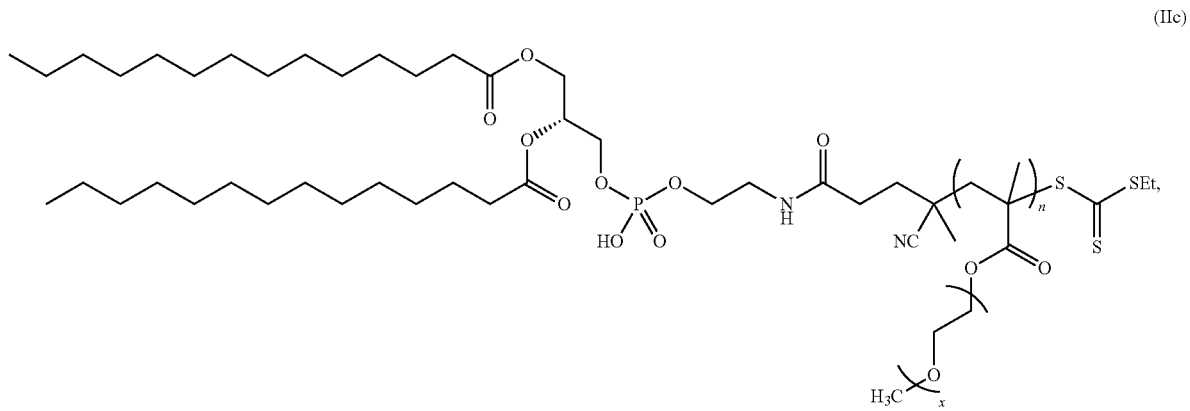

(IIc)

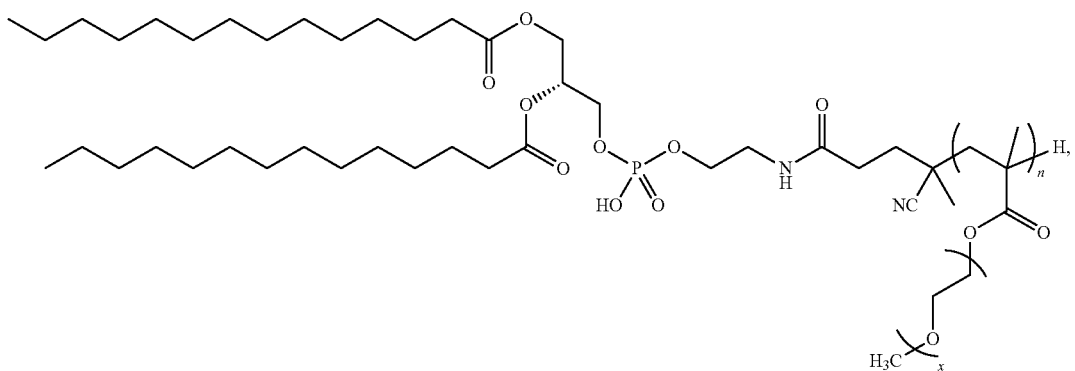
(IId)
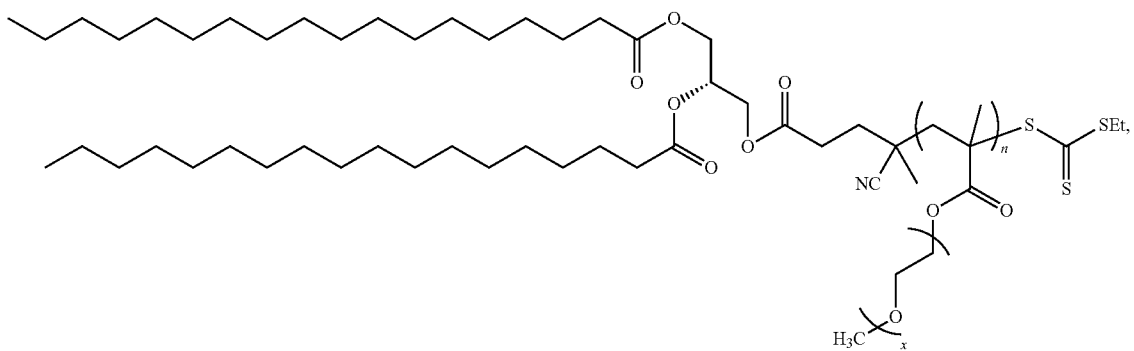
(IIe)
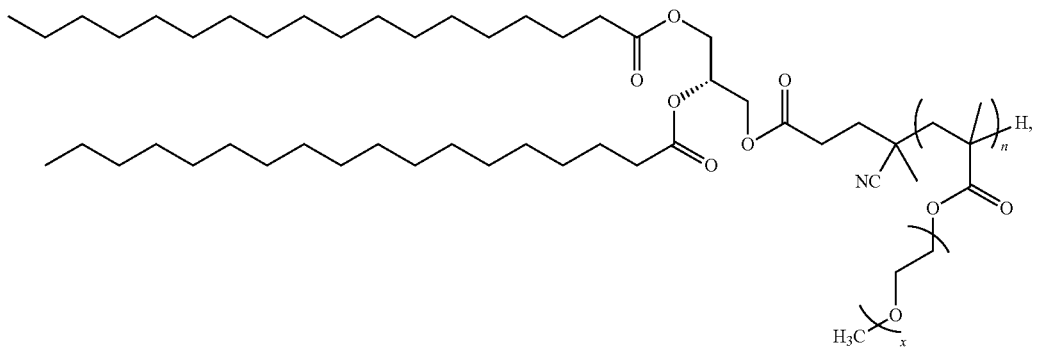
(IIf)
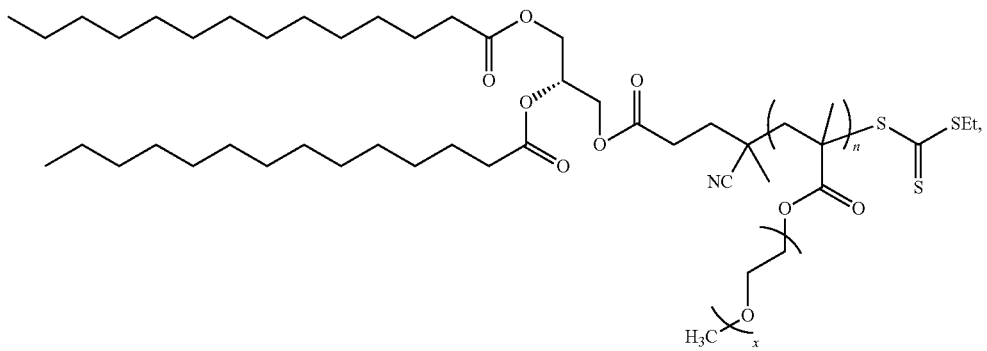
(IIg)

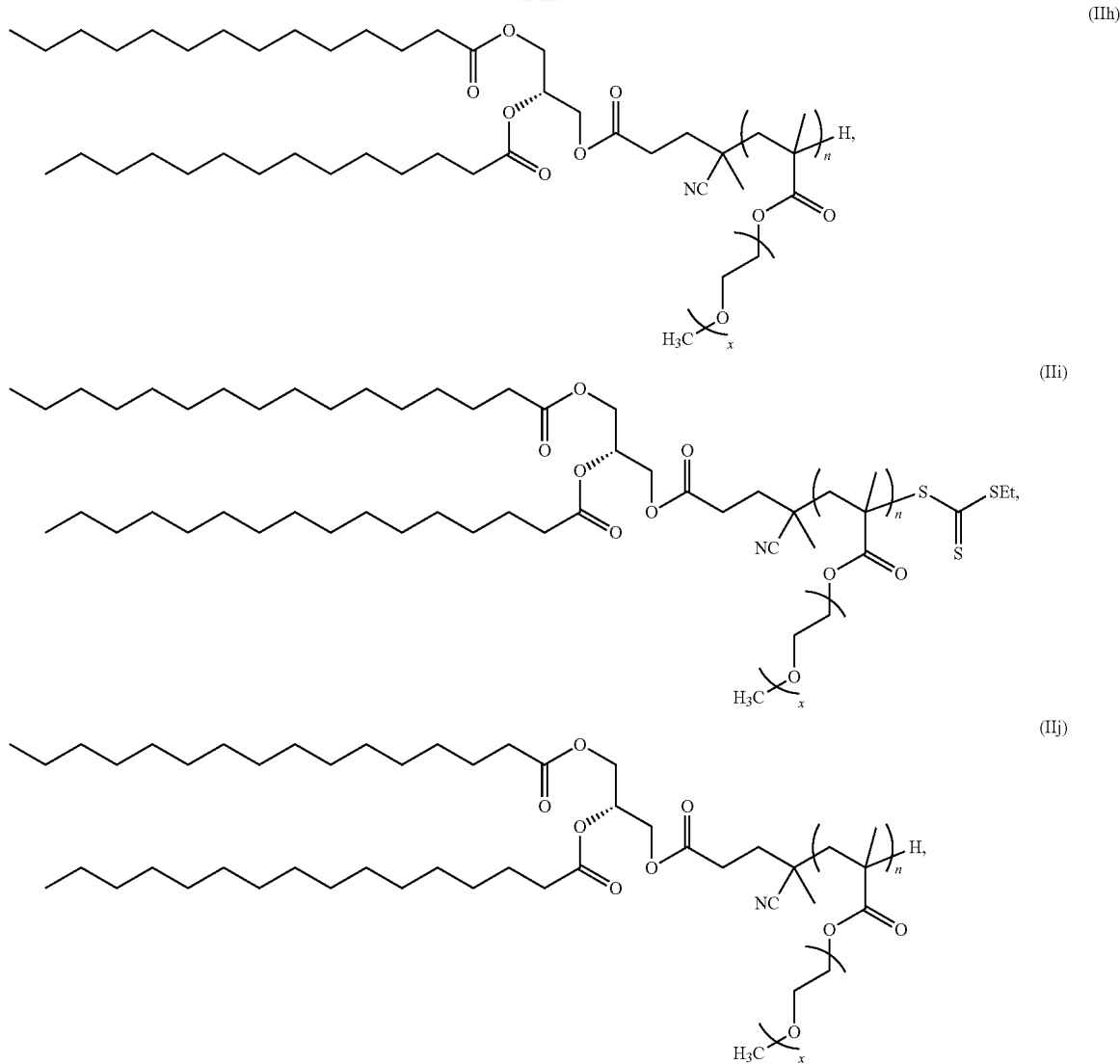

or a pharmaceutically acceptable salt thereof, where x is 4-5 or 7-9, and n is 10-40 (e.g., 10-35, 10-30, or 10-25).

In a particular variation of a method of treating a protein deficiency disease as above, the membrane-destabilizing polymer is a pH-sensitive polymer such as, e.g., a pH-sensitive copolymer. The copolymer may be a block copolymer such as, for example, a diblock copolymer. In some variations, the block copolymer includes a hydrophobic, membrane-destabilizing block and a hydrophilic block. In some such embodiments, the hydrophilic block is polymerized from both hydrophilic monomers and hydrophobic monomers such that there are more hydrophilic monomeric residues than hydrophobic monomeric residues in the hydrophilic block.

In some embodiments of a method of treating a protein deficiency disease as above in which the membrane-destabilizing polymer is a pH-sensitive polymer, the pH-sensitive polymer includes monomeric residues having a carboxylic acid functional group, monomeric residues having an amine functional group, and/or monomeric residues having a hydrophobic functional group. In some variations, the pH-sensitive polymer includes monomeric residues derived from polymerization of a ($C_2$-$C_8$) alkylacrylic acid (e.g., propylacrylic acid); monomeric residues derived from polymerization of a ($C_2$-$C_8$) alkyl-ethacrylate, a ($C_2$-$C_8$) alkyl-methacrylate, or a ($C_2$-$C_8$) alkyl-acrylate; and/or monomeric residues derived from polymerization of (N,N-di($C_1$-$C_6$)alkyl-amino($C_1$-$C_6$)alkyl-ethacrylate, (N,N-di($C_1$-$C_6$)alkyl-amino($C_1$-$C_6$)alkyl-methacrylate, or (N,N-di($C_1$-$C_6$)alkyl-amino($C_1$-$C_6$)alkyl-acrylate. In a specific variation, the pH-sensitive polymer includes a random copolymer chain having monomeric residues derived from polymerization of propyl acrylic acid, N,N-dimethylaminoethylmethacrylate, and butyl methacrylate; in some such embodiments, the pH-sensitive polymer is a block copolymer comprising the random copolymer chain as a membrane disrupting polymer block, and further including one or more additional blocks.

In certain embodiments of a method of treating a protein deficiency disease as above in which the membrane-destabilizing polymer is a pH-sensitive polymer, the polymer is a diblock copolymer having a hydrophilic random copolymer block and a hydrophobic random copolymer block, where (i) the hydrophilic block is an amphiphilic block comprising both hydrophilic monomeric residues and hydrophobic monomeric residues, where the number of hydrophilic monomeric residues in the hydrophilic block is greater than the number of hydrophobic monomeric residues, (ii) the hydrophobic block is an amphiphilic, membrane-destabilizing block comprising both hydrophobic monomeric residues and hydrophilic monomeric residues and having an overall hydrophobic character at a pH of about 7.4; and (iii) each of the hydrophilic monomeric residues of the hydrophilic and hydrophobic blocks is independently selected from the group consisting of monomeric residues that are ionic at a pH of about 7.4, monomeric residues that are neutral at a pH of about 7.4, and monomeric residues that are zwitterionic at a pH of about 7.4.

In certain embodiments of a method of treating a protein deficiency disease as above, the disease is a protein deficiency disease of the liver. In some such embodiments, the mRNA encodes a functional protein selected from alpha-1-antitrypsin (A1AT), carbamoyl phosphate synthetase I (CPS1), fumarylacetoacetase (FAH) enzyme, alanine:glyoxylate-aminotransferase (AGT), methylmalonyl CoA mutase (MUT), propionyl CoA carboxylase alpha subunit (PCCA), propionyl CoA carboxylase beta subunit (PCCB), a subunit of branched-chain ketoacid dehydrogenase (BCKDH), ornithine transcarbamylase (OTC), copper-transporting ATPase Atp7B, bilirubin uridinediphosphate glucuronyltransferase (BGT) enzyme, hepcidin, glucose-6-phosphatase (G6Pase), glucose 6-phosphate translocase, lysosomal glucocerebrosidase (GB), Niemann-Pick C1 protein (NPC1), Niemann-Pick C2 protein (NPC2), acid sphingomyelinase (ASM), Factor IX, galactose-1-phosphate uridylyltransferase, galactokinase, UDP-galactose 4-epimerase, transthyretin, a complement regulatory protein, phenylalanine hydroxylase (PAH), homogentisate 1,2-dioxygenase, porphobilinogen deaminase, hypoxanthine-guanine phosphoribosyltransferase (HGPRT), argininosuccinate lyase (ASL), argininosuccinate synthetase (ASS1), P-type ATPase protein FIC-1, alpha-galactosidase A, acid ceramidase, acid α-L-fucosidase, acid β-galactosidase, iduronate-2-sulfatase, alpha-L-iduronidase, galactocerebrosidase, acid α-mannosidase, β-mannosidase, arylsulfatase B, arylsulfatase A, N-acetylgalactosamine-6-sulfate sulfatase, acid β-galactosidase, acid α-glucosidase, β-hexosaminidase B, heparan-N-sulfatase, alpha-N-acetylglucosaminidase, acetyl-CoA:α-glucosaminide N-acetyltransferase, N-acetylglucosamine-6-sulfate sulfatase, alpha-N-acetylgalactosaminidase, sialidase, β-glucuronidase, and β-hexosaminidase A.

In other embodiments in which the disease is a protein deficiency disease of the liver, the disease is a urea cycle disorder. In some such embodiments, the urea cycle disorder is selected from ornithine transcarbamylase (OTC) deficiency, carbamoyl phosphate synthetase I (CPSI) deficiency, argininosuccinic aciduria (argininosuccinate lyase (ASL) deficiency), and citrullinemia (argininosuccinate synthetase (ASS1) deficiency). In certain variations where the urea cycle disorder is ornithine transcarbamylase (OTC) deficiency, the mRNA encodes a functional OTC protein comprising an amino acid sequence having at least 90% or at least 95% sequence identity with residues 35-354 of SEQ ID NO:1. In certain variations where the urea cycle disorder is argininosuccinic aciduria (argininosuccinate lyase (ASL) deficiency), the mRNA encodes a functional ASL protein comprising an amino acid sequence having at least 90% or at least 95% sequence identity with SEQ ID NO:2. In certain variations where the urea cycle disorder is citrullinemia (argininosuccinate synthetase (ASS1) deficiency), the mRNA encodes a functional ASS1 protein comprising an amino acid sequence having at least 90% or at least 95% sequence identity with SEQ ID NO:3.

In certain embodiments for treating a protein deficiency disease of the liver as above, the membrane-destabilizing polymer comprises a targeting ligand that specifically binds to the asialoglycoprotein receptor (ASGPR). Particularly suitable ASGPR-specific targeting ligands comprise an N-acetylgalactosamine (GalNAc) residue.

In still another aspect, the present invention provides a compound of Formula IIIa, IIIb, IIIc, or IIId

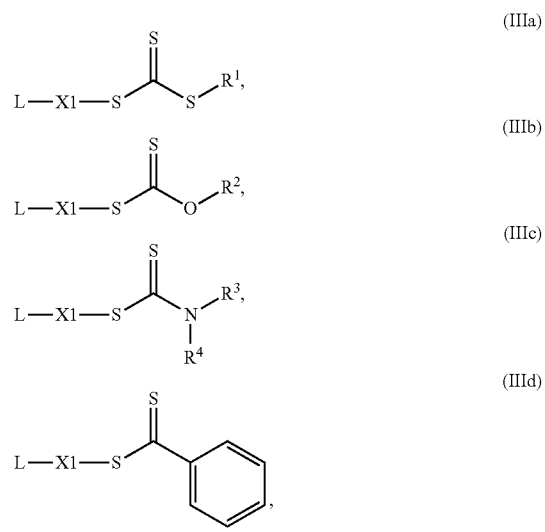

where L is a lipid selected from (i) a lipid comprising two $C_8$-$C_{24}$ hydrocarbon chains (e.g., two $C_{10}$-$C_{18}$ hydrocarbon chains), (ii) a sterol lipid (e.g., cholesterol), and (iii) a sphingolipid (e.g., N-octanoyl-sphingosine); X1 is absent or a linking moiety; $R^1$ is $C_1$-$C_{12}$ alkyl; $R^2$ is $C_1$-$C_{12}$ alkyl; and $R^3$ and $R^4$ are each independently H, alkyl, aryl, or heteroaryl. In some embodiments where L is the lipid comprising two $C_8$-$C_{24}$ hydrocarbon chains, L is a glycerophospholipid such as, for example, 1,2-dimyristoyl-sn-glycero-3-phosphoethanolamine (DMPE) or 1,2-distearoyl-sn-glycero-3-phosphoethanolamine (DSPE). In other embodiments where L is the lipid comprising two $C_8$-$C_{24}$ hydrocarbon chains, L is a glycerolipid such as for example, dimyristolglycerol (DMG), distearoyl glycerol (DSG), or dipalmitoyl glycerol (DPG).

In another aspect, the present invention provides a method of making a branched PEG-lipid. In some embodiments, the method generally includes (a) contacting a compound of Formula IIIa, IIIb, IIIc, or IIId

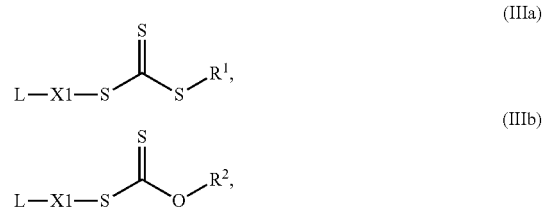

-continued

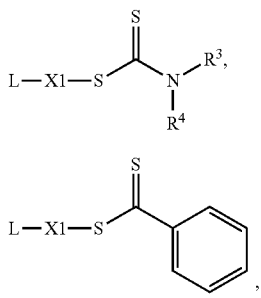
(IIIc)

(IIId)

where
L is a lipid, X1 is absent or a linking moiety,
$R^1$ is $C_1$-$C_{12}$ alkyl, $R^2$ is $C_1$-$C_{12}$ alkyl, and
$R^3$ and $R^4$ are each independently H, alkyl, aryl, or heteroaryl, with a plurality of ethylenic monomers comprising monomers of the formula A1

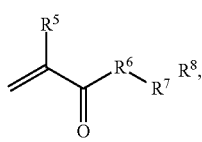
(A1)

where
$R^5$ is H or C1-C6alkyl,
$R^6$ is O, S, $NR^9$, OC1-C6alkyl, OC1-C6alkyl-O, OC1-C6alkyl-OC(O)C1-C6alkyl, OC1-C6alkyl-OC(O)C1-C6alkyl-O, OC1-C6alkyl-OC(O)C1-C6alkyl-NH, OC1-C6alkyl-NH, OC1-C6alkyl-NHC(O)C1-C6alkyl, OC1-C6alkyl-NHC(O)C1-C6alkyl-O, OC1-C6alkyl-NHC(O)C1-C6alkyl-NH, $NR^9$(C1-C6alkyl), $NR^9$(C1-C6alkyl)-O, $NR^9$(C1-C6alkyl)-OC(O)C1-C6alkyl, $NR^9$(C1-C6alkyl)-OC(O)C1-C6alkyl-O, $NR^9$(C1-C6alkyl)-OC(O)C1-C6alkyl-NH, $NR^9$(C1-C6alkyl)-NH, $NR^9$(C1-C6alkyl)-NHC(O)C1-C6alkyl, $NR^9$(C1-C6alkyl)-NHC(O)C1-C6alkyl-O, $NR^9$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6alkyl-O, or C1-C6alkyl-NHC(O)C1-C6alkyl-NH,
$R^7$ is $(CH_2CH_2O)_{2-50}$ (e.g., $(CH_2CH_2O)_{2-40}$, $(CH_2CH_2O)_{2-25}$, or $(CH_2CH_2O)_{2-20}$),
$R^8$ is H or C1-C6alkyl-$R^{10}$,
$R^9$ is H or C1-C6alkyl, and
$R^{10}$ is H, $CO_2H$, $NH_2$, NH(C1-C6alkyl), N(C1-C6alkyl)$_2$, or N(C1-C6alkyl)$_3$, in the presence of a free radical. In some such embodiments, L is selected from (i) a lipid comprising two $C_8$-$C_{24}$ hydrocarbon chains (e.g., two $C_{10}$-$C_{18}$ hydrocarbon chains), (ii) a sterol lipid (e.g., cholesterol), and (iii) a sphingolipid (e.g., N-octanyl-sphingosine). In some embodiments where L is the lipid comprising two $C_8$-$C_{24}$ hydrocarbon chains, L is a glycerophospholipid such as, for example, 1,2-dimyristoyl-sn-glycero-3-phosphoethanolamine (DMPE) or 1,2-distearoyl-sn-glycero-3-phosphoethanolamine (DSPE). In other embodiments where L is the lipid comprising two $C_8$-$C_{24}$ hydrocarbon chains, L is a glycerolipid such as for example, dimyristolglycerol (DMG), distearoyl glycerol (DSG), or dipalmitoyl glycerol (DPG). Suitable A1 monomers include poly(ethylene glycol) methyl ether methacrylates (PEGMAs), poly(ethylene glycol) methyl ether acrylate (PEGAs), poly(ethylene glycol) methyl ether methacrylamides, and poly(ethylene glycol) methyl ether acrylamides.

In some embodiments of a method of making a branched PEG-lipid as above, the plurality of ethylenic monomers further includes a monomer of formula A2

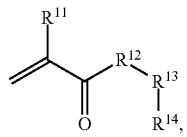
(A2)

where
$R^{11}$ is H or C1-C6alkyl,
$R^{12}$ is O, S, $NR^{15}$, O(C1-C6alkyl), O(C1-C6alkyl)-O, O(C1-C6alkyl)-OC(O)C1-C6alkyl, O(C1-C6alkyl)-OC(O)C1-C6alkyl-O, O(C1-C6 alkyl)-OC(O)C1-C6alkyl-NH, O(C1-C6alkyl)-NH, O(C1-C6alkyl)-NHC(O)C1-C6alkyl, O(C1-C6alkyl)-NHC(O)C1-C6alkyl-O, O(C1-C6alkyl)-NHC(O)C1-C6alkyl-NH, $NR^{15}$(C1-C6alkyl), $NR^{15}$(C1-C6alkyl)-O, $NR^{15}$(C1-C6alkyl)-OC(O)C1-C6alkyl, $NR^{15}$(C1-C6 alkyl)-OC(O)C1-C6alkyl-O, $NR^{15}$(C1-C6alkyl)-OC(O)C1-C6alkyl-NH, $NR^{15}$(C1-C6alkyl)-NH, $NR^{15}$(C1-C6alkyl)-NHC(O)C1-C6alkyl, $NR^{15}$(C1-C6alkyl)-NHC(O)C1-C6alkyl-O, $NR^{15}$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6 alkyl-O, or C1-C6alkyl-NHC(O)C1-C6alkyl-NH,
$R^{13}$ is H, $(CH_2CH_2O)_{1-4}$, or C1-C6alkyl
$R^{14}$ is H or C1-C6alkyl-$R^6$,
$R^{15}$ is H or C1-C6alkyl, and
$R^{16}$ is H, $CO_2H$, $NH_2$, NH(C1-C6alkyl), N(C1-C6alkyl)$_2$, or N(C1-C6alkyl)$_3$.

In certain embodiments of a method of making a branched PEG-lipid as above, the plurality of ethylenic monomers consists of the monomers of formula A1.

In some variations of a method of making a branched PEG-lipid as above, the method further includes (b) removing the thio-carbonyl end group of the product of step (a), and (c) contacting the product of step (b) with a targeting moiety comprising a thiol-reactive group or free radical. In some such variations, the targeting moiety comprises a N-acetyl galactosamine (GalNAc) residue.

In other embodiments of a method of making a branched PEG-lipid, the method generally includes (a) conjugating a lipid to a compound of Formula VIa, VIb, VIc, or VId

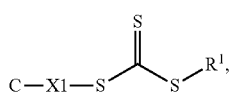
(VIa)

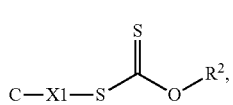
(VIb)

-continued

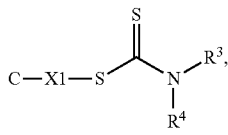
(VIc)

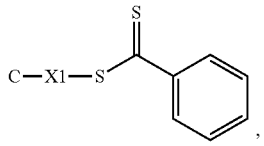
(VId)

where C is a coupling group,
X1 is absent or a linking moiety,
$R^1$ is $C_1$-$C_{12}$ alkyl,
$R^2$ is $C_1$-$C_{12}$ alkyl, and
$R^3$ and $R^4$ are each independently H, alkyl, aryl, or heteroaryl,
where the conjugating of the lipid to the compound of Formula VIa, VIb, VIc, or VId utilizes the coupling group, and (b) contacting the product of step (a) with a plurality of ethylenic monomers comprising monomers of the formula A1

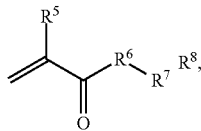
(A1)

where
$R^5$ is H or C1-C6alkyl,
$R^6$ is O, S, $NR^9$, OC1-C6alkyl, OC1-C6alkyl-O, OC1-C6alkyl-OC(O)C1-C6alkyl, OC1-C6alkyl-OC(O)C1-C6alkyl-O, OC1-C6alkyl-OC(O)C1-C6alkyl-NH, OC1-C6alkyl-NH, OC1-C6alkyl-NHC(O)C1-C6alkyl, OC1-C6alkyl-NHC(O)C1-C6alkyl-O, OC1-C6alkyl-NHC(O)C1-C6alkyl-NH, $NR^9$(C1-C6alkyl), $NR^9$(C1-C6alkyl)-O, $NR^9$(C1-C6alkyl)-OC(O)C1-C6alkyl, $NR^9$(C1-C6alkyl)-OC(O)C1-C6alkyl-O, $NR^9$(C1-C6alkyl)-OC(O)C1-C6alkyl-NH, $NR^9$(C1-C6alkyl)-NH, $NR^9$(C1-C6alkyl)-NHC(O)C1-C6alkyl, $NR^9$(C1-C6alkyl)-NHC(O)C1-C6alkyl-O, $NR^9$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6alkyl-O, or C1-C6alkyl-NHC(O)C1-C6alkyl-NH,
$R^7$ is $(CH_2CH_2O)_{2-50}$ (e.g., $(CH_2CH_2O)_{2-40}$, $(CH_2CH_2O)_{2-20}$, or $(CH_2CH_2O)_{2-20}$),
$R^8$ is H or C1-C6alkyl-$R^{10}$,
$R^9$ is H or C1-C6alkyl, and
$R^{10}$ is H, $CO_2H$, $NH_2$, NH(C1-C6alkyl), N(C1-C6alkyl)$_2$, or N(C1-C6alkyl)$_3$,
in the presence of a free radical. In some such embodiments, the lipid is selected from (i) a lipid comprising two $C_8$-$C_{24}$ hydrocarbon chains (e.g., two $C_{10}$-$C_{18}$ hydrocarbon chains), (ii) a sterol lipid (e.g., cholesterol), and (iii) a sphingolipid (e.g., N-octanyl-sphingosine); in particular variations where the lipid comprises two $C_8$-$C_{24}$ hydrocarbon chains, the lipid is a glycerophospholipid (e.g., 1,2-dimyristoyl-sn-glycero-3-phosphoethanolamine (DMPE) or 1,2-distearoyl-sn-glycero-3-phosphoethanolamine (DSPE)) or a glycerolipid (e.g., dimyristolglycerol (DMG), distearoyl glycerol (DSG), or dipalmitoyl glycerol (DPG)). In certain embodiments, the coupling group is an activated ester (e.g., an NHS ester or a pentafluorophenyl ester), an acid halide, a carbodiimide, a maleimide, an acetyl halide (α-haloacyl), an epoxide, an aziridine, an aldehyde, a ketone, an activated disulfide (e.g., a pyridyl disulfide), a sulfhydryl, an amine, an alcohol, a hydrazide, a carbonate, a thiocarbonate, an anhydride, an isocyanate, a photo-reactive group (e.g., an aryl azide, a diazirine, or a nitrene), or a hapten. Suitable A1 monomers include poly(ethylene glycol) methyl ether methacrylates (PEGMAs), poly(ethylene glycol) methyl ether acrylate (PEGAs), poly(ethylene glycol) methyl ether methacrylamides, and poly(ethylene glycol) methyl ether acrylamides. In some embodiments of a method of making a branched PEG-lipid as above, the plurality of ethylenic monomers further includes a monomer of formula A2

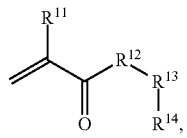
(A2)

where
$R^{11}$ is H or C1-C6alkyl,
$R^{12}$ is O, S, $NR^{15}$, O(C1-C6alkyl), O(C1-C6alkyl)-O, O(C1-C6alkyl)-OC(O)C1-C6alkyl, O(C1-C6alkyl)-OC(O)C1-C6alkyl-O, O(C1-C6 alkyl)-OC(O)C1-C6alkyl-NH, O(C1-C6alkyl)-NH, O(C1-C6alkyl)-NHC(O)C1-C6alkyl, O(C1-C6alkyl)-NHC(O)C1-C6alkyl-O, O(C1-C6alkyl)-NHC(O)C1-C6alkyl-NH, $NR^{15}$(C1-C6alkyl), $NR^{15}$(C1-C6alkyl)-O, $NR^{15}$(C1-C6alkyl)-OC(O)C1-C6alkyl, $NR^{15}$(C1-C6 alkyl)-OC(O)C1-C6alkyl-O, $NR^{15}$(C1-C6alkyl)-OC(O)C1-C6alkyl-NH, $NR^{15}$(C1-C6alkyl)-NH, $NR^{15}$(C1-C6alkyl)-NHC(O)C1-C6alkyl, $NR^{15}$(C1-C6alkyl)-NHC(O)C1-C6alkyl-O, $NR^{15}$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6 alkyl-O, or C1-C6alkyl-NHC(O)C1-C6alkyl-NH,
$R^{13}$ is H, $(CH_2CH_2O)_{1-4}$, or C1-C6alkyl
$R^{14}$ is H or C1-C6alkyl-$R^6$,
$R^{15}$ is H or C1-C6alkyl, and
$R^{16}$ is H, $CO_2H$, $NH_2$, NH(C1-C6alkyl), N(C1-C6alkyl)$_2$, or N(C1-C6alkyl)$_3$.
In certain embodiments of a method of making a branched PEG-lipid as above, the plurality of ethylenic monomers consists of the monomers of formula A1. In some variations, the method further includes (c) removing the thio-carbonyl end group of the product of step (b), and (d) contacting the product of step (c) with a targeting moiety (e.g., a N-acetyl galactosamine (GalNAc) residue) comprising a thiol-reactive group or free radical.

In yet other embodiments of making a branched PEG-lipid, the method generally includes conjugating a lipid and a polymer utilizing a coupling group, where the polymer comprises (i) an alkylenic or heteroalkylenic backbone of chain atoms and (ii) a plurality of pendant polyethylene glycol (PEG) moieties distributed along said polymer backbone. In some such embodiments, the ratio of chain atoms to pendant PEG moieties is less than 4:1, and/or the polymer comprises at least five pendant PEG moieties. In some embodiments, the lipid is selected from (i) a lipid comprising two $C_8$-$C_{24}$ hydrocarbon chains (e.g., two $C_{10}$-$C_{18}$ hydrocarbon chains), (ii) a sterol lipid (e.g., cholesterol), and (iii) a sphingolipid (e.g., N-octanyl-sphingosine); in particular variations where the lipid comprises two $C_8$-$C_{24}$ hydrocarbon chains, the lipid is a glycerophospholipid (e.g., 1,2-dimyristoyl-sn-glycero-3-phosphoethanolamine (DMPE) or 1,2-distearoyl-sn-glycero-3-phosphoethanolamine (DSPE)) or a glycerolipid (e.g., dimyristolglycerol (DMG), distearoyl glycerol (DSG), or dipalmitoyl glycerol (DPG)). In certain embodiments, the coupling group is an activated ester (e.g., an NHS ester or a pentafluorophenyl ester), an acid halide, a carbodiimide, a maleimide, an acetyl halide (α-haloacyl), an epoxide, an aziridine, an aldehyde, a ketone, an activated disulfide (e.g., a pyridyl disulfide), a sulfhydryl, an amine, an alcohol, a hydrazide, a carbonate, a thiocarbonate, an anhydride, an isocyanate, a photo-reactive group (e.g., an aryl azide, a diazirine, or a nitrene), or a hapten.

In some embodiments of a method of making a branched PEG-lipid as above where the method includes conjugating a lipid and a polymer utilizing a coupling group, the method further includes synthesizing the polymer before the conjugation step. In some such variations, the polymer synthesis step comprises contacting a compound of Formula VIa, VIb, VIc, or VId

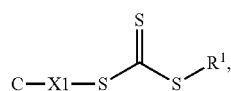  (VIa)

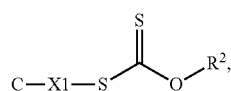  (VIb)

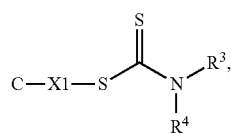  (VIc)

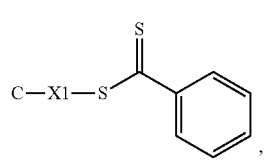  (VId)

where

C is the coupling group,

X1 is absent or a linking moiety, $R^1$ is $C_1$-$C_{12}$ alkyl, $R^2$ is $C_1$-$C_{12}$ alkyl, and $R^3$ and $R^4$ are each independently H, alkyl, aryl, or heteroaryl, with a plurality of ethylenic monomers comprising monomers of the formula A1

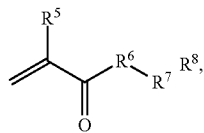  (A1)

where $R^5$ is H or C1-C6alkyl, $R^6$ is O, S, $NR^9$, OC1-C6alkyl, OC1-C6alkyl-O, OC1-C6alkyl-OC(O)C1-C6alkyl, OC1-C6alkyl-OC(O)C1-C6alkyl-O, OC1-C6alkyl-OC(O)C1-C6alkyl-NH, OC1-C6alkyl-NH, OC1-C6alkyl-NHC(O)C1-C6alkyl, OC1-C6alkyl-NHC(O)C1-C6alkyl-O, OC1-C6alkyl-NHC(O)C1-C6alkyl-NH, $NR^9$(C1-C6alkyl), $NR^9$(C1-C6alkyl)-O, $NR^9$(C1-C6alkyl)-OC(O)C1-C6alkyl, $NR^9$(C1-C6alkyl)-OC(O)C1-C6alkyl-O, $NR^9$(C1-C6alkyl)-OC(O)C1-C6alkyl-NH, $NR^9$(C1-C6alkyl)-NH, $NR^9$(C1-C6alkyl)-NHC(O)C1-C6alkyl, $NR^9$(C1-C6alkyl)-NHC(O)C1-C6alkyl-O, $NR^9$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6alkyl-O, or C1-C6alkyl-NHC(O)C1-C6alkyl-NH, $R^7$ is $(CH_2CH_2O)_{2-50}$ (e.g., $(CH_2CH_2O)_{2-40}$, $(CH_2CH_2O)_{2-25}$, or $(CH_2CH_2O)_{2-20}$), $R^8$ is H or C1-C6alkyl-$R^{10}$, $R^9$ is H or C1-C6alkyl, and $R^{10}$ is H, $CO_2H$, $NH_2$, NH(C1-C6alkyl), N(C1-C6alkyl)$_2$, or N(C1-C6alkyl)$_3$, in the presence of a free radical. Suitable A1 monomers include poly(ethylene glycol) methyl ether methacrylates (PEGMAs), poly(ethylene glycol) methyl ether acrylate (PEGAs), poly(ethylene glycol) methyl ether methacrylamides, and poly(ethylene glycol) methyl ether acrylamides. In some embodiments, the plurality of ethylenic monomers further includes a monomer of formula A2

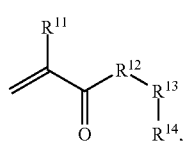  (A2)

where $R^{11}$ is H or C1-C6alkyl, $R^{12}$ is O, S, $NR^{15}$, O(C1-C6alkyl), O(C1-C6alkyl)-O, O(C1-C6alkyl)-OC(O)C1-C6alkyl, O(C1-C6alkyl)-OC(O)C1-C6alkyl-O, O(C1-C6 alkyl)-OC(O)C1-C6alkyl-NH, O(C1-C6alkyl)-NH, O(C1-C6alkyl)-NHC(O)C1-C6alkyl, O(C1-C6alkyl)-NHC(O)C1-C6alkyl-0, O(C1-C6alkyl)-NHC(O)C1-C6alkyl-NH, $NR^{15}$(C1-C6alkyl), $NR^{15}$(C1-C6alkyl)-O, $NR^{15}$(C1-C6alkyl)-OC(O)C1-C6alkyl, $NR^{15}$(C1-C6 alkyl)-OC(O)C1-C6alkyl-O, $NR^{15}$(C1-C6alkyl)-OC(O)C1-C6alkyl-NH, $NR^{15}$(C1-C6alkyl)-NH, $NR^{15}$(C1-C6alkyl)-NHC(O)C1-C6alkyl, $NR^{15}$(C1-C6alkyl)-NHC(O)C1-C6alkyl-O, $NR^{15}$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6 alkyl-O, or C1-C6alkyl-NHC(O)C1-C6alkyl-NH, $R^{13}$ is H, $(CH_2CH_2O)_{1-4}$, or C1-C6alkyl $R^{14}$ is H or C1-C6alkyl-$R^6$, $R^{15}$ is H or C1-C6alkyl, and $R^{16}$ is H, $CO_2H$, $NH_2$, NH(C1-C6alkyl), N(C1-C6alkyl)$_2$, or N(C1-C6alkyl)$_3$.

In certain embodiments of a method of making a branched PEG-lipid as above, the plurality of ethylenic monomers consists of the monomers of formula A1. In some variations, the method further includes (i) removing the thio-carbonyl end group of the polymer synthesis step and (ii) contacting the product of step (ii) with a targeting moiety (e.g., a N-acetyl galactosamine (GalNAc) residue) comprising a thiol-reactive group or free radical.

In another aspect, the present invention provides a branched PEG-protein of Formula IV

$$Y-X1-P-X2-T \qquad (IV)$$

where Y is a therapeutic protein; X1 is a first linking moiety; P is a polymer comprising (i) an alkylenic or heteroalkylenic backbone of chain atoms and (ii) a plurality of pendant polyethylene glycol (PEG) moieties distributed along the polymer backbone; X2 is absent or a second linking moiety; and T is absent or a targeting moiety. In some embodiments, the ratio of chain atoms to pendant PEG moieties is less than 4:1. Particularly suitable polymers of a branched PEG-protein as above comprise at least five pendant PEG moieties. The therapeutic protein may be, for example, a cytokine (e.g., an interferon or an interleukin), a soluble receptor, an anticoagulant, a blood factor, a bone morphogenetic protein, an enzyme, a growth factor, a hormone, a thrombolytic, or an antibody. In some embodiments, the therapeutic protein is a peptide.

In certain embodiments of a branched PEG-protein as above, the polymer chain atoms are carbon atoms or a combination of carbon and oxygen atoms.

In some embodiments of a branched PEG-protein as above, each of the pendant PEG moieties comprises from 2 to 50 (e.g., from 2 to 40, from 2 to 25, or from 2 to 20) ethylene oxide units. In more specific variations, each of the pendant PEG moieties comprises from 4 to 5 ethylene oxide units. In other variations, each of the pendant PEG moieties comprises from 7 to 9 ethylene oxide units. In certain embodiments, the polymer comprising the pendant PEG moieties is a polymer comprising monomeric residues derived from polymerization of a monomer of formula A1

(A1)

where $R^5$ is H or C1-C6alkyl, $R^6$ is O, S, $NR^9$, OC1-C6alkyl, OC1-C6alkyl-O, OC1-C6alkyl-OC(O)C1-C6alkyl, OC1-C6alkyl-OC(O)C1-C6alkyl-O, OC1-C6alkyl-OC(O)C1-C6alkyl-NH, OC1-C6alkyl-NH, OC1-C6alkyl-NHC(O)C1-C6alkyl, OC1-C6alkyl-NHC(O)C1-C6alkyl-O, OC1-C6alkyl-NHC(O)C1-C6alkyl-NH, $NR^9$(C1-C6alkyl), $NR^9$(C1-C6alkyl)-O, $NR^9$(C1-C6alkyl)-OC(O)C1-C6alkyl, $NR^9$(C1-C6alkyl)-OC(O)C1-C6alkyl-O, $NR^9$(C1-C6alkyl)-OC(O)C1-C6alkyl-NH, $NR^9$(C1-C6alkyl)-NH, $NR^9$(C1-C6alkyl)-NHC(O)C1-C6alkyl, $NR^9$(C1-C6alkyl)-NHC(O)C1-C6alkyl-O, $NR^9$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6alkyl-O, or C1-C6alkyl-NHC(O)C1-C6alkyl-NH, $R^7$ is $(CH_2CH_2O)_{2-50}$ (e.g., $(CH_2CH_2O)_{2-40}$, $(CH_2CH_2O)_{2-25}$, or $(CH_2CH_2O)_{2-20}$), $R^8$ is H or C1-C6alkyl-$R^{10}$, $R^9$ is H or C1-C6alkyl, and $R^{10}$ is H, $CO_2H$, $NH_2$, NH(C1-C6alkyl), N(C1-C6alkyl)$_2$, or N(C1-C6alkyl)$_3$.

Particularly suitable polymers comprising pendant PEG moieties are polymers comprising monomeric residues derived from polymerization of a monomer selected from a poly(ethylene glycol) methyl ether methacrylate (PEGMA), a poly(ethylene glycol) methyl ether acrylate (PEGA), a poly(ethylene glycol) methyl ether methacrylamide, and a poly(ethylene glycol) methyl ether acrylamide, where the monomer has from 2 to 50 (e.g., from 2 to 40, from 2 to 25, or from 2 to 20) ethylene oxide units; in some such variations in which the polymer comprises monomeric residues derived from polymerization of the PEGMA, the PEGMA has from 4 to 5 ethylene oxide units (PEGMA$_{300}$) or from 7 to 9 ethylene oxide units (PEGMA$_{500}$).

In some embodiments of a branched PEG-protein as above, the polymer is a homopolymer.

In another aspect, the present invention provides a composition comprising a branched PEG-protein as above and a pharmaceutically acceptable excipient.

In another aspect, the present invention provides a compound of Formula Va, Vb, Vc, or Vd

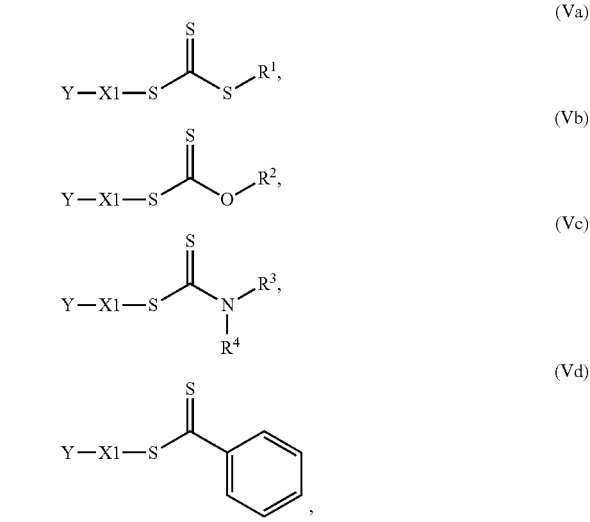

where Y is a therapeutic protein, X1 is absent or a linking moiety, $R^1$ is $C_1$-$C_{12}$ alkyl, $R^2$ is $C_1$-$C_{12}$ alkyl, and $R^3$ and $R^4$ are each independently H, alkyl, aryl, or heteroaryl. The therapeutic protein may be, for example, a cytokine (e.g., an interferon or an interleukin), a soluble receptor, an anticoagulant, a blood factor, a bone morphogenetic protein, an enzyme, a growth factor, a hormone, a thrombolytic, or an antibody. In some embodiments, the therapeutic protein is a peptide.

In yet another aspect, the present invention provides a method a making a branched PEG-protein as above. In some embodiments, the method generally includes conjugating the therapeutic protein and the polymer utilizing a coupling group. In some such embodiments, the coupling group is an amine-reactive group, a thiol-reactive group, a maleimide group, a thiol group, an aldehyde group, an NHS-ester group, an NHS-maleimide group, a haloacetyl group, an iodoacetyl group, a bromoacetyl group, a succinimidyl 4-(N-maleimidomethyl)cyclohexane-1-carboxylate (SMCC) group, a sulfosuccinimidyl 4-(N-maleimidomethyl)cyclohexane-1-carboxylate (Sulfo-SMCC) group, or a carbodiimide group.

In other embodiments of a method of making a branched PEG-protein, the method includes (a) contacting a compound of Formula Va, Vb, Vc, or Vd

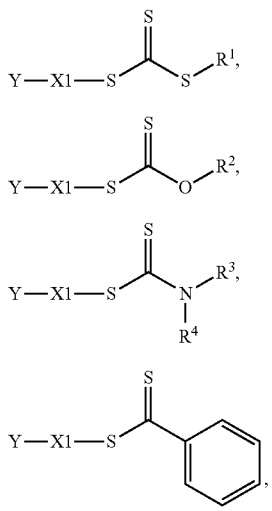

where
Y is a therapeutic protein,
X1 is absent or a linking moiety,
$R^1$ is $C_1$-$C_{12}$ alkyl,
$R^2$ is $C_1$-$C_{12}$ alkyl, and
$R^3$ and $R^4$ are each independently H, alkyl, aryl, or heteroaryl,
with a plurality of ethylenic monomers comprising monomers of the formula A1

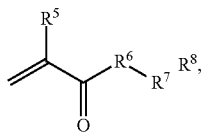

wherein
$R^5$ is H or C1-C6alkyl,
$R^6$ is O, S, $NR^9$, OC1-C6alkyl, OC1-C6alkyl-O, OC1-C6alkyl-OC(O)C1-C6alkyl, OC1-C6alkyl-OC(O)C1-C6alkyl-0, OC1-C6alkyl-OC(O)C1-C6alkyl-NH, OC1-C6alkyl-NH, OC1-C6alkyl-NHC(O)C1-C6alkyl, OC1-C6alkyl-NHC(O)C1-C6alkyl-O, OC1-C6alkyl-NHC(O)C1-C6alkyl-NH, $NR^9$(C1l-C6alkyl), $NR^9$(C1-C6alkyl)-O, $NR^9$(C1-C6alkyl)-OC(O)C1-C6alkyl, $NR^9$(C1-C6alkyl)-OC(O)C1-C6alkyl-O, $NR^9$(C1-C6alkyl)-OC(O)C1-C6alkyl-NH, $NR^9$(C1-C6alkyl)-NH, $NR^9$(C1-C6alkyl)-NHC(O)C1-C6alkyl, $NR^9$(C1-C6alkyl)-NHC(O)C1-C6alkyl-O, $NR^9$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6alkyl-O, or C1-C6alkyl-NHC(O)C1-C6alkyl-NH,
$R^7$ is $(CH_2CH_2O)_{2-25}$,
$R^8$ is H or C1-C6alkyl-$R^{10}$,
$R^9$ is H or C1-C6alkyl, and
$R^{10}$ is H, $CO_2H$, $NH_2$, NH(C1-C6alkyl), N(C1-C6alkyl)$_2$, or N(C1-C6alkyl)$_3$, in the presence of a free radical. Suitable A1 monomers include poly(ethylene glycol) methyl ether methacrylates (PEGMAs), poly(ethylene glycol) methyl ether acrylate (PEGAs), poly(ethylene glycol) methyl ether methacrylamides, and poly(ethylene glycol) methyl ether acrylamides. In some embodiments of a method of making a branched PEG-protein as above, the plurality of ethylenic monomers further includes a monomer of formula A2

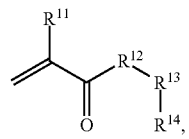

where
$R^{11}$ is H or C1-C6alkyl,
$R^{12}$ is O, S, $NR^{15}$, O(C1-C6alkyl), O(C1-C6alkyl)-O, O(C1-C6alkyl)-OC(O)C1-C6alkyl, O(C1-C6alkyl)-OC(O)C1-C6alkyl-O, O(C1-C6 alkyl)-OC(O)C1-C6alkyl-NH, O(C1-C6alkyl)-NH, O(C1-C6alkyl)-NHC(O)C1-C6alkyl, O(C1-C6alkyl)-NHC(O)C1-C6alkyl-O, O(C1-C6alkyl)-NHC(O)C1-C6alkyl-NH, $NR^{15}$(C1-C6alkyl), $NR^{15}$(C1-C6alkyl)-O, $NR^{15}$(C1-C6alkyl)-OC(O)C1-C6alkyl, $NR^{15}$(C1-C6 alkyl)-OC(O)C1-C6alkyl-O, $NR^{15}$(C1-C6alkyl)-OC(O)C1-C6alkyl-NH, $NR^{15}$(C1-C6alkyl)-NH, $NR^{15}$(C1-C6alkyl)-NHC(O)C1-C6alkyl, $NR^{15}$(C1-C6alkyl)-NHC(O)C1-C6alkyl-O, $NR^{15}$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6 alkyl-O, or C1-C6alkyl-NHC(O)C1-C6alkyl-NH,
$R^{13}$ is H, $(CH_2CH_2O)_{1-4}$, or C1-C6alkyl
$R^{14}$ is H or C1-C6alkyl-$R^6$,
$R^{15}$ is H or C1-C6alkyl, and
$R^{16}$ is H, $CO_2H$, $NH_2$, NH(C1-C6alkyl), N(C1-C6alkyl)$_2$, or N(C1-C6alkyl)$_3$.

In certain embodiments of a method of making a branched PEG-protein as above, the plurality of ethylenic monomers consists of the monomers of formula A1. In some variations, the method further includes (b) removing the thio-carbonyl end group of the product of step (a), and (c) contacting the product of step (b) with a targeting moiety comprising a thiol-reactive group or free radical.

In yet other embodiments of a method of making a branched PEG-protein, the method includes (a) conjugating a therapeutic protein to a compound of Formula VIa, VIb, VIc, or VId

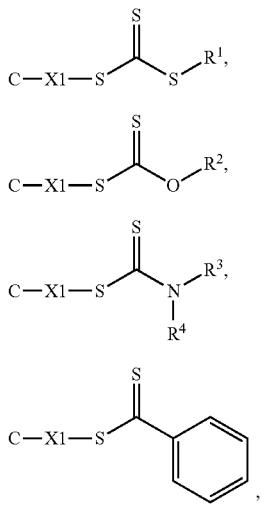

where
C is a coupling group,
X1 is absent or a linking moiety,
$R^1$ is $C_1$-$C_{12}$ alkyl,
$R^2$ is $C_1$-$C_{12}$ alkyl, and
$R^3$ and $R^4$ are each independently H, alkyl, aryl, or heteroaryl, where the conjugating of the therapeutic protein to the compound of Formula VIa, VIb, VIc, or VId utilizes the coupling group C, and (b) contacting the product of step (a) with a plurality of ethylenic monomers comprising monomers of the formula A1

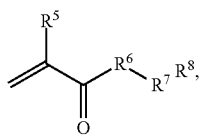

where
$R^5$ is H or C1-C6alkyl,
$R^6$ is O, S, $NR^9$, OC1-C6alkyl, OC1-C6alkyl-O, OC1-C6alkyl-OC(O)C1-C6alkyl, OC1-C6alkyl-OC(O)C1-C6alkyl-O, OC1-C6alkyl-OC(O)C1-C6alkyl-NH, OC1-C6alkyl-NH, OC1-C6alkyl-NHC(O)C1-C6alkyl, OC1-C6alkyl-NHC(O)C1-C6alkyl-O, OC1-C6alkyl-NHC(O)C1-C6alkyl-NH, $NR^9$(C1-C6alkyl), $NR^9$(C1-C6alkyl)-O, $NR^9$(C1-C6alkyl)-OC(O)C1-C6alkyl, $NR^9$(C1-C6alkyl)-OC(O)C1-C6alkyl-O, $NR^9$(C1-C6alkyl)-OC(O)C1-C6alkyl-NH, $NR^9$(C1-C6alkyl)-NH, $NR^9$(C1-C6alkyl)-NHC(O)C1-C6alkyl, $NR^9$(C1-C6alkyl)-NHC(O)C1-C6alkyl-O, $NR^9$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6alkyl-O, or C1-C6alkyl-NHC(O)C1-C6alkyl-NH, $R^7$ is $(CH_2CH_2O)_{2-25}$,
$R^8$ is H or C1-C6alkyl-$R^{10}$,
$R^9$ is H or C1-C6alkyl, and
$R^{10}$ is H, $CO_2H$, $NH_2$, NH(C1-C6alkyl), N(C1-C6alkyl)$_2$, or N(C1-C6alkyl)$_3$, in the presence of a free radical. In some such embodiments, the coupling group is an amine-reactive group, a thiol-reactive group, a maleimide group, a thiol group, an aldehyde group, an NHS-ester group, an NHS-maleimide group, a haloacetyl group, an iodoacetyl group, a bromoacetyl group, a succinimidyl 4-(N-maleimidomethyl)cyclohexane-1-carboxylate (SMCC) group, a sulfosuccinimidyl 4-(N-maleimidomethyl)cyclohexane-1-carboxylate (Sulfo-SMCC) group, or a carbodiimide group. Suitable A1 monomers include poly(ethylene glycol) methyl ether methacrylates (PEGMAs), poly(ethylene glycol) methyl ether acrylate (PEGAs), poly(ethylene glycol) methyl ether methacrylamides, and poly(ethylene glycol) methyl ether acrylamides. In some embodiments of a method of making a branched PEG-protein as above, the plurality of ethylenic monomers further includes a monomer of formula A2

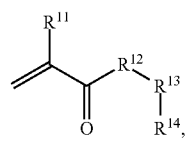

where
$R^{11}$ is H or C1-C6alkyl,
$R^{12}$ is O, S, $NR^{15}$, O(C1-C6alkyl), O(C1-C6alkyl)-O, O(C1-C6alkyl)-OC(O)C1-C6alkyl, O(C1-C6alkyl)-OC(O)C1-C6alkyl-O, O(C1-C6 alkyl)-OC(O)C1-C6alkyl-NH, O(C1-C6alkyl)-NH, O(C1-C6alkyl)-NHC(O)C1-C6alkyl, O(C1-C6alkyl)-NHC(O)C1-C6alkyl-O, O(C1-C6alkyl)-NHC(O)C1-C6alkyl-NH, $NR^{15}$(C1-C6alkyl), $NR^{15}$(C1-C6alkyl)-O, $NR^{15}$(C1-C6alkyl)-OC(O)C1-C6alkyl, $NR^{15}$(C1-C6 alkyl)-OC(O)C1-C6alkyl-O, $NR^{15}$(C1-C6alkyl)-OC(O)C1-C6alkyl-NH, $NR^{15}$(C1-C6alkyl)-NH, $NR^{15}$(C1-C6alkyl)-NHC(O)C1-C6alkyl, $NR^{15}$(C1-C6alkyl)-NHC(O)C1-C6alkyl-O, $NR^{15}$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6 alkyl-O, or C1-C6alkyl-NHC(O)C1-C6alkyl-NH,
$R^{13}$ is H, $(CH_2CH_2O)$—$_4$, or C1-C6alkyl
$R^{14}$ is H or C1-C6alkyl-$R^6$,
$R^{15}$ is H or C1-C6alkyl, and
$R^{16}$ is H, $CO_2H$, $NH_2$, NH(C1-C6alkyl), N(C1-C6alkyl)$_2$, or N(C1-C6alkyl)$_3$.

In certain embodiments of a method of making a branched PEG-protein as above, the plurality of ethylenic monomers consists of the monomers of formula A1. In some variations, the method further includes (c) removing the thio-carbonyl end group of the product of step (b), and (d) contacting the product of step (c) with a targeting moiety comprising a thiol-reactive group or free radical.

These and other aspects of the invention will become evident upon reference to the following detailed description of the invention.

Definitions

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise.

The term "polyethylene glycol moiety" or "PEG moiety" refers to a moiety comprising a polyethylene glycol (PEG) oligomer (e.g., having 20 or less repeat units) or polymer (e.g., having more than 20 repeat units), irrespective of a particular end group. "Polyethylene glycol" and "PEG" are used herein interchangeably with "polyethylene oxide," and are understood to mean an oligomer or polymer of —CH2-CH2-O— repeat units (which repeat units are also referred to herein as "ethylene glycol units" or "ethylene oxide units").

As is well-known in the art, nomenclature of PEG molecular weight can use the overall molecular weight (including the PEG end groups) or the number of repeat units. For example $PEG_{12}$ is also known as $PEG_{0.6kDa}$ or $PEG_{0.6k}$. $PEG_{36}$ is also known as $PEG_{1.6kDa}$ or $PEG_{1.6k}$. $PEG_{48}$ is also known as $PEG_{2.2kD}$, or $PEG_{2.2k}$. A particular form of $PEG_{48}$ is also known as $PEG_{24}$-amido-$PEG_{24}$, but has also been generally described as $PEG_{2.2k}$, or $PEG_{2.2k}$.

$PEGMA_{4-5}$ (Poly(ethylene glycol) methyl ether methacrylate, average Mn=300) is also known as $PEGMA_{0.3kDa}$ or $PEGMA_{0.3k}$ or $PEGMA_{300}$, which is the average molecular weight of a mixture of $PEGMA_4$ and $PEGMA_5$. Similarly, $PEGMA_{7-9}$(Poly(ethylene glycol) methyl ether methacrylate, average Mn=500) is also known as $PEGMA_{0.5kDA}$ or $PEGMA_{0.5k}$ or $PEGMA_{500}$, which is the average molecular weight of a mixture of $PEG_7$ and $PEG_9$. Similarly, $PEGMA_{17-19}$ (Poly(ethylene glycol) methyl ether methacrylate, average Mn=1000) is also known as $PEGMA_{1kDA}$ or $PEGMA_{1k}$ or $PEGMA_{1000}$, which is the average molecular weight of a mixture of $PEGMA_{17}$ and $PEGMA_{19}$.

The term "alkylenic backbone," in the context of a polymer comprising pendant PEG moieties as described herein, means a polymer backbone in which the chain atoms are carbon atoms.

The term "heteroalkylenic backbone," in the context of a polymer comprising pendant PEG moieties as described herein, means a polymer backbone in which the chain atoms are a combination of carbon atoms and at least one heteroatoms.

The term "branched PEG polymer" as used herein means a polymer comprising (i) an alkylenic or heteroalkylenic backbone of chain atoms and (ii) a plurality of pendant PEG moieties distributed along the polymer backbone. Examples of branched PEG polymers include polymers comprising monomeric residues derived from polymerization of a monomer selected from a poly(ethylene glycol) methyl ether methacrylate (PEGMA), a poly(ethylene glycol) methyl ether acrylate (PEGA), a poly(ethylene glycol) methyl ether methacrylamide, and a poly(ethylene glycol) methyl ether acrylamide, where the monomer has from 2 to 50 (e.g., from 2 to 40, from 2 to 25, or from 2 to 20) ethylene oxide units.

As used herein, the term "lipid nanoparticle" or "LNP" refers to a particle of less than about 1,000 nm, typically less than about 200 nm, that is formulated with at least one lipid molecular species. Lipid nanoparticles include (but are not limited to) liposomes, irrespective of their lamellarity, shape, or structure. As used herein, a "liposome" is a structure having lipid-containing membranes enclosing an aqueous interior. Liposomes may have one or more lipid membranes. Single-layered liposomes are referred to as "unilamellar," and multi-layered liposomes are referred to as "multilamellar." Lipid nanoparticles may further include one or more additional lipids and/or other components, which may be included in the liposome compositions for a variety of purposes, such as to stabilize a lipid membrane, to prevent lipid oxidation, or to attach ligands on the liposome surface. Any number of lipids may be present, including amphipathic, neutral, cationic, and anionic lipids. Lipid nanoparticles can be complexed with therapeutic or diagnostic agents, including polynucleotides, proteins, peptides, or small molecules, and are useful as in vivo delivery vehicles.

The term "cationic lipid" refers to any of a number of lipid species which carry a net positive charge at physiological pH. Such lipids include, but are not limited to, DODAC, DOTMA, DOTAP, DC-Chol, DMRIE, DOEPC, DLEPC, DMEPC, 14:1, MVL5, DOGS, DORIE, DORI, and $DILA^2$.

The term "neutral lipid" refers to any of a number of lipid species that exist either in an uncharged or neutral zwitterionic form at physiological pH. Such lipids include, for example cholesterol, DOPE, DLPE, DLPC, phosphatidylcholines, phosphatidylethanolamines, phosphatidylserines, ceramide, sphingomyelin, cephalin, and cerebrosides.

The term "non-cationic lipid" refers to any neutral lipid as described above as well as anionic lipids (i.e., lipid species that carry a net negative charge at physiological pH). Examples of anionic lipids include, but are not limited to, cardiolipin, phosphatidylserine and phosphatidic acid.

An "ionizable anionic lipid" means an anionic lipid that undergoes protonation as the pH is reduced toward the $pK_a$ of the lipid. At the $pK_a$ of the ionizable anionic lipid, half of the lipid is in the anionic form and half of the lipid is in the protonated form. In the context of lipid nanoparticles, at pH values above the $pK_a$ of the ionizable anionic lipid, more of the lipid is negatively charged, and the negatively charged form of the lipid can stabilize other lipids in a bilayer organization, allowing the formation of bilayer vesicles. These vesicles then fuse as the pH is reduced toward the $pK_a$ of the ionizable anionic lipid, such as in the endosomal environment, and more of the ionizable anionic lipid becomes protonated. Examples of ionizable anionic lipids include cholesteryl hemisuccinate (CHEMS), phosphatidylserine, palmitoylhomoserine, and α-tocopherol hemisuccinate.

An "ionizable cationic lipid" means a cationic lipid that undergoes protonation as the pH is reduced toward the $pK_a$ of the lipid. At the $pK_a$ of the ionizable cationic lipid, half of the lipid in the protonated form and half of the lipid is in the neutral form. In the context of lipid nanoparticles, at pH values below the $pK_a$ of the ionizable cationic lipid, the positively charged form of the lipid can interact with negatively charged oligonucleotides, allowing for encapsulation of the oligonucleotides inside of vesicles and nanoparticles. At pH values above the $pK_a$, more of the cationic lipid is neutral and this lack of charge can affect the surface potential of lipid nanoparticles as well as affect release of oligonucleotides from these lipids. Additionally, appropriately designed cationic lipids with unsaturated tails can mediate fusion events with other membranes by undergoing lamellar to inverse hexagonal phase transitions. Such fusion events can result in endosomolysis which can enable delivery of material into the cytosol. Examples of ionizable anionic lipids include DDAB, DlinDMA, DLin-KC2-DMA, MC3 lipid (DLin-MC3-DMA), DODAP, DODMA, and Mo-CHOL.

A "lipid comprising two $C_8$-$C_{24}$ hydrocarbon chains" means a lipid comprising at least two hydrocarbon chains (also referred to as "hydrocarbon tails"), where each chain independently contains from 8 to 24 carbon atoms. In some variations, each of the two $C_8$-$C_{24}$ hydrocarbon chains contain the same number of carbon atoms; in other variations, the two $C_8$-$C_{24}$ hydrocarbon chains contain a different number of carbon atoms. In certain embodiments, the lipid's non-polar region consists of the two $C_8$-$C_{24}$ hydrocarbon chains; for example, a lipid comprising two $C_8$-$C_{24}$ hydrocarbon chains may be a di-substituted glycerol such as, e.g., distearoyl glycerol (DSG). Alternatively, the lipid's non-polar region may include one or more hydrocarbon chains in addition to the two $C_8$-$C_{24}$ chains; in such variations, each of the one or more additional hydrocarbon chains typically contains from four to 24 carbon atoms. Lipids having more than two hydrocarbon chains include, for example, certain synthetically derived lipids termed "lipidoids" (see. e.g., Love et al., *Proc. Natl. Acad. Sci. USA* 107:1864-1869, 2010; Fenton et al., *Adv. Mater.* 2016, DOI 10.1002/adma.201505822).

A "sterol lipid" means a lipid comprising the "ABCD" steroid ring structure. The core ABCD steroid ring system is well-known in the art and is composed of four fused rings (three cyclohexane rings known as the A, B, and C rings, and one cyclopentane ring known as the D ring) in a specific configuration. Examples of sterol lipids include cholesterol, cholesteryl hemisuccinate, sitoindoside I, sitoindoside II, glucosyl stigmasterol, 16:0 stigmasteryl glucose, 18:1 stigmasteryl glucose, glucosyl sitosterolB, cholesterol sulfate, DHEA, DHEA sulfate, FF-MAS, campesterol, campestanol, zymostenol, sitostanol, sitosterol, stigmasterol, diosgenin, 7-dehydrodesmosterol, lanosterol, lanosterol-95, dihydrolanosterol, 14-demethyl-lanosterol, zymosterol, desmosterol, lathosterol, and pregnenolone. A sterol lipid may further comprise one or more hydrocarbon chains such as, e.g., one or more $C_8$-$C_{24}$ (e.g., $C_{10}$-$C_{18}$) hydrocarbon chains.

"DSPE-PEGMA," "DMPE-PEGMA," "DSG-PEGMA," "DMG-PEGMA," or "DPG-PEGMA" means a compound comprising, respectively, 1,2-distearoyl-sn-glycero-3-phosphoethanolamine (DSPE), 1,2-dimyristoyl-sn-glycero-3-phosphoethanolamine (DMPE), dimyristolglycerol (DMG), distearoyl glycerol (DSG), or dipalmitoyl glycerol (DPG), in each case covalently linked, either directly or via an intervening linker, to a homopolymer of monomeric residues derived from polymerization of poly(ethylene glycol) methyl ether methacrylate (PEGMA). Typically, each PEGMA monomer of a DSPE-PEGMA, DMPE-PEGMA, DSG-PEGMA, DMG-PEGMA, or DPG-PEGMA has from 2 to 50 (e.g., from 2 to 40, from 2 to 25, or from 2 to 20) ethylene oxide units. In particular variations, the PEGMA has from 4 to 5 ethylene oxide units ($PEGMA_{300}$) or from 7 to 9 ethylene oxide units ($PEGMA_{500}$).

As used herein, "amphipathic" or "amphiphilic" compounds have both hydrophilic (water-soluble) and hydrophobic (water-insoluble) parts.

As used herein, the term "therapeutic agent" refers to any molecular species (e.g., polynucleotide, protein, peptide, or small molecule) that may have a therapeutic effect upon delivery into a cell. In the case of a polynucleotide, this effect can be mediated by the nucleic acid itself (e.g., anti-sense polynucleotide), following transcription (e.g., anti-sense RNA, ribozymes, interfering dsRNA, mRNA), or following expression into a protein. A "therapeutic" effect of an expressed protein in attenuating or preventing the disease state can be accomplished by the protein either staying within the cell, remaining attached to the cell in the membrane, or being secreted and dissociated from the cell where it can enter the general circulation and blood. Secreted proteins that can be therapeutic include hormones, cytokines, growth factors, clotting factors, anti-protease proteins (e.g., alpha1-antitrypsin), angiogenic proteins (e.g., vascular endothelial growth factor, fibroblast growth factors), anti-angiogenic proteins (e.g., endostatin, angiostatin), and other proteins that are present in the blood. Proteins on the membrane can have a therapeutic effect by providing a receptor for the cell to take up a protein or lipoprotein. Therapeutic proteins that stay within the cell (intracellular proteins) can be enzymes that clear a circulating toxic metabolite as in phenylketonuria. They can also cause a cancer cell to be less proliferative or cancerous (e.g., less metastatic), or interfere with the replication of a virus. Intracellular proteins can be part of the cytoskeleton (e.g., actin, dystrophin, myosins, sarcoglycans, and dystroglycans) and thus have a therapeutic effect in cardiomyopathies and musculoskeletal diseases (e.g., Duchenne muscular dystrophy, limb-girdle disease). Protein agents may also be delivered directly into a cell (i.e., in protein form, rather than as an encoding polynucleotide to be expressed). Other therapeutic proteins of particular interest to treating heart disease include polypeptides affecting cardiac contractility (e.g., calcium and sodium channels), inhibitors of restenosis (e.g., nitric oxide synthetase), angiogenic factors, and anti-angiogenic factors. Protein agents may also include antibodies (e.g., small single-chain antibodies or bispecific antibodies) directed at intracellular targets. Other exemplary "therapeutic agents" include small molecules, such as, for example, small molecule inhibitors or agonists of intracellular target molecules (e.g., kinase inhibitors, inhibitors of DNA synthesis pathways) or small molecules having a cytotoxic or cytostatic effect on a cell (such as chemotherapeutic agents for cancer treatment); anti-infective agents (e.g., anti-viral agents or anti-bacterial agents); or vaccines (which may include proteins, peptides, DNA, or RNA). In some embodiments, a "therapeutic agent" is a component of a gene editing system that disrupts or corrects genes that cause disease (e.g., a polynucleotide encoding a nuclease; a guide RNA that may be formulated with a polynucleotide encoding a nuclease; or a donor DNA sequence for correcting a gene by homologous recombination).

As used herein, the term "diagnostic agent" refers to a component that can be detected in a subject or test sample from a subject. Exemplary diagnostic agents include radioactive agents, fluorescent agents, contrast agents (e.g., an MRI or X-ray contrast agent), and other imaging reagents. Diagnostic reagents also include, for example, immunodiagnostic reagents (e.g., antibodies directed to intracellular targets) as well as other specific binding agents. A diagnostic agent may consist of, for example, a diagnostically detectable label that is complexed with a lipid nanoparticle, or may comprise a diagnostically detectable label conjugated to another molecule (e.g., a specific binding molecule, such as, e.g., a peptide, protein, or polynucleotide). Many different labels exist in the art and methods of labeling are well-known by the skilled artisan. General classes of labels that can be used in the present invention include, but are not limited to, radioactive isotopes, paramagnetic isotopes, compounds that can be imaged by positron emission tomography (PET), fluorescent or colored compounds, compounds which can be imaged by magnetic resonance, chemiluminescent compounds, bioluminescent compounds, and the like. Particularly suitable detectable labels include, but are not limited to, radioactive, fluorescent, fluorogenic, or chromogenic labels. Useful radiolabels (radionuclides), which are detected simply by γ counter, scintillation counter or autoradiography include, but are not limited to, $^3$H, $^{125}$I, $^{131}$I, $^{35}$S, and $^{14}$C.

As used herein, the term "membrane-destabilizing polymer" refers to a polymer that is capable of inducing one or more of the following effects upon a biological membrane: an alteration or disruption that allows small molecule permeability, pore formation in the membrane, a fusion and/or fission of membranes, an alteration or disruption that allows large molecule permeability, a dissolving of the membrane, or causing membrane perturbation that opens tight junctions and enables paracellular transport. This alteration can be functionally defined by the compound's activity in at least one the following assays: red blood cell lysis (hemolysis), liposome leakage, liposome fusion, cell fusion, cell lysis, and release of endosomal contents. Typically, a membrane-destabilizing polymer allows for the transport of molecules with a molecular weight greater than 50 atomic mass units to cross a membrane. This transport may be accomplished by either the loss of membrane structure or the formation of holes or pores in the membrane. In particular variations, a membrane-destabilizing polymer is a copolymer (e.g., an amphipathic copolymer), a synthetic amphipathic peptide, a membrane active toxin (e.g., pardaxin, melittin, cecropin, magainin, PGLa, indolicidin, dermaseptin, or a derivative thereof), or a viral fusogenic peptide (e.g., the influenza virus hemagglutinin subunit HA-2 peptide).

As used herein, a "block copolymer" refers to a structure comprising one or more sub-combination of constitutional or monomeric units. In some embodiments, the block copolymer is a diblock copolymer, a tri-block copolymer or a higher-ordered block copolymer. For example, a diblock copolymer can comprise two blocks; a schematic generalization of such a polymer is represented by the following: $[A_a\text{-}B_b\text{-}C_c\text{-} \ldots ]_m\text{-}[X_x\text{-}Y_y\text{-}Z_z\text{-} \ldots ]_n$ or $[A_a\text{-}B_b\text{-}C_c\text{-} \ldots ]_m\text{-}b\text{-}[X_x\text{-}Y_y\text{-}Z_z\text{-} \ldots ]_n$, wherein each letter stands for a constitutional or monomeric unit, and wherein each subscript to a constitutional unit represents the mole fraction of that unit in the particular block, the three dots indicate that there may be more (there may also be fewer) constitutional units in each block, and m and n indicate the molecular weight (or weight fraction) of each block in the diblock copolymer. As suggested by such schematic representation, in some instances, the number and the nature of each constitutional unit is separately controlled for each block. The schematic is not meant to, and should not be construed to, infer any relationship whatsoever between the number of constitutional units or between the number of different types of constitutional units in each of the blocks. Nor is the schematic meant to describe any particular number or arrangement of the constitutional units within a particular block. In each block the constitutional units may be disposed in a purely random, an alternating random, a regular alternating, a regular block or a random block configuration unless expressly stated to be otherwise. A purely random configuration, for example, may have the form: x-x-y-z-x-y-z-y-z-z-z . . . An exemplary alternating random configuration may have the form: x-y-x-z-y-x-y-z-y-x-z . . . , and an exemplary regular alternating configuration may have the form: x-y-z-x-y-z-x-y-z . . . An exemplary regular block configuration may have the following general configuration: . . . x-x-x-y-y-y-z-z-z-x-x-x . . . , while an exemplary random block configuration may have the general configuration: . . . x-x-x-z-z-x-x-y-y-y-y-z-z-z-x-x-z-z-z- . . . . In a gradient polymer, the content of one or more monomeric units increases or decreases in a gradient manner from the α end of the polymer to the ω end. In none of the preceding generic examples is the particular juxtaposition of individual constitutional units or blocks or the number of constitutional units in a block or the number of blocks meant nor should they be construed as in any manner bearing on or limiting the actual structure of block copolymers forming the polymeric carrier of this invention.

As used herein, the brackets enclosing the constitutional units are not meant and are not to be construed to mean that the constitutional units themselves form blocks. That is, the constitutional units within the square brackets may combine in any manner with the other constitutional units within the block, i.e., purely random, alternating random, regular alternating, regular block or random block configurations. The block copolymers described herein are, optionally, alternate, gradient or random block copolymers.

As used herein, the term "molecular weight" for a polymer or polymer block is the number average molecular weight. It is understood in the art that a population of polymer molecules will have a distribution of different molecular weights. This distribution of molecular weights can be described by the term dispersity index or polydispersity index (PI or PDI), which is the weight average molecular weight/number average molecular weight.

As used herein, the term "polynucleotide" refers to a polymer comprising two or more nucleotide monomeric units ("nucleotides"). Typical polynucleotides in accordance with certain embodiments of the present invention include those comprising 7-20,000 nucleotide monomeric units, 7-15,000 nucleotide monomeric units, 7-10,000 nucleotide monomeric units, 7-5,000 nucleotide monomeric units and 7-1000 nucleotide monomeric units. Polynucleotides of less than 200 nucleotides are generally referred to as "oligonucleotides." Polynucleotides include deoxyribonucleic acid (DNA) and ribonucleic acid (RNA), or their derivatives, and combinations of DNA, RNA. DNA may be in form of cDNA, in vitro polymerized DNA, plasmid DNA, parts of a plasmid DNA, genetic material derived from a virus, linear DNA, vectors (Pl, PAC, BAC, YAC, and artificial chromosomes), expression vectors, expression cassettes, chimeric sequences, recombinant DNA, chromosomal DNA, anti-sense DNA, or derivatives of these groups. RNA may be in the form of messenger RNA (mRNA), in vitro polymerized RNA, recombinant RNA, transfer RNA (tRNA), small nuclear RNA (snRNA), ribosomal RNA (rRNA), chimeric sequences, dicer substrate and the precursors thereof, locked nucleic acids, anti-sense RNA, interfering RNA (RNAi), asymmetric interfering RNA (aiRNA), small interfering RNA (siRNA), microRNA (miRNA), ribozymes, external guide sequences, small non-messenger RNAs (snmRNA), untranslatedRNA (utRNA), snoRNAs (24-mers, modified snmRNA that act by an anti-sense mechanism), tiny non-coding RNAs (tncRNAs), small hairpin RNA (shRNA), or their derivatives. In addition, DNA and RNA may be single, double, triple, or quadruple stranded. Double stranded RNA (dsRNA) and siRNA are of interest particularly in connection with the phenomenon of RNA interference. Examples of oligonucleotides as used herein include, but are not limited to, siRNA, an antisense oligonucleotide, a dicer substrate, a miRNA, an aiRNA or an shRNA. Further examples of oligonucleotides as used herein include, but are not limited to dsRNA having a length of from 17 to 29 nucleotides, or from 19 to 25 nucleotides, and being at least 90 percent, or 95 percent or 100 percent (of the nucleotides of a dsRNA) complementary to a coding or a non-coding section of the nucleic acid sequence of a therapeutically relevant protein or antigen. Ninety percent complementary means that a 20 nucleotide length of a dsRNA contains not more than 2 nucleotides without a corresponding complementarity with the corresponding section of the mRNA. Yet further examples of polynucleotides as used herein include, but are not limited to single stranded mRNA which can be modified or unmodified. Modified mRNA includes at least one modification and a translatable region. Modification(s) may be located on the backbone, a nucleoside of the nucleic acid molecule, and/or a 5' cap structure. For example, a modification may be located on a nucleoside (e.g., substitution of uridine residues with pseudouridine), or modifications may be located on both a nucleoside and a backbone linkage. Typically, mRNAs in accordance with certain compositions and methods of the present invention include those comprising 300-20,000 nucleotide monomeric units, 300-15,000 nucleotide monomeric units, 300-10,000 nucleotide monomeric units, 300-5,000 nucleotide monomeric units, 300-2000 nucleotide monomeric units, 300-1,500 nucleotide monomeric units, and 300-1000 nucleotide monomeric units. In some variations, an mRNA in accordance with compositions and methods of the present disclosure is at least 500, at least 1,000, at least 1,200, or at least 1,500 nucleotide monomeric units.

Polynucleotides may include nucleotides that have been modified relative to naturally occurring nucleotides. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as azasugars and carbocyclic sugar analogs. Examples of modifications in a base moiety include alkylated purines and pyrimidines, acylated purines or pyrimidines, or other well-known heterocyclic substitutes. Nucleotide monomeric units can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "polynucleotide" also includes so-called "peptide nucleic acids," which comprise naturally-occurring or modified nucleic acid bases attached to a polyamide backbone.

A "polypeptide" is a polymer of amino acid residues joined by peptide bonds, whether produced naturally or synthetically. Polypeptides of less than about 50 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

With regard to proteins as described herein, reference to amino acid residues corresponding to those specified by SEQ ID NO includes post-translational modifications of such residues.

As used herein, the term "antibody" refers to any immunoglobulin protein that specifically binds to an antigen, as well as antigen-binding fragments thereof and engineered variants thereof. Hence, the term "antibody" includes, for example, polyclonal antibodies, monoclonal antibodies, and antigen-binding antibody fragments that contain the paratope of an intact antibody, such as Fab, Fab', F(ab')$_2$ and F(v) fragments. Genetically engineered intact antibodies and fragments, such as chimeric antibodies, humanized antibodies, single-chain Fv fragments, single-chain antibodies, diabodies, minibodies, linear antibodies, multivalent or multi-specific hybrid antibodies, and the like are also included. Thus, the term "antibody" is used expansively to include any protein that comprises an antigen binding site of an antibody and is capable of binding to its antigen. In some embodiments, an antibody has affinity to a cell surface molecule.

The term "genetically engineered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with cells and other effector functions. Typically, changes in the variable region will be made in order to improve the antigen binding characteristics, improve variable region stability, or reduce the risk of immunogenicity.

An "antigen-binding site of an antibody" is that portion of an antibody that is sufficient to bind to its antigen. The minimum such region is typically a variable domain or a genetically engineered variant thereof. Single-domain binding sites can be generated from camelid antibodies (see Muyldermans and Lauwereys, *J. Mol. Recog.* 12:131-140, 1999; Nguyen et al., *EMBO J.* 19:921-930, 2000) or from $V_H$ domains of other species to produce single-domain antibodies ("dAbs"; see Ward et al., *Nature* 341:544-546, 1989; U.S. Pat. No. 6,248,516 to Winter et al.). In certain variations, an antigen-binding site is a polypeptide region having only 2 complementarity determining regions (CDRs) of a naturally or non-naturally (e.g., mutagenized) occurring heavy chain variable domain or light chain variable domain, or combination thereof (see. e.g., Pessi et al., *Nature* 362: 367-369, 1993; Qiu et al., *Nature Biotechnol.* 25:921-929, 2007). More commonly, an antigen-binding site of an antibody comprises both a heavy chain variable domain and a light chain variable domain that bind to a common epitope. Examples of molecules comprising an antigen-binding site of an antibody are known in the art and include, for example, Fv fragments, single-chain Fv fragments (scFv), Fab fragments, diabodies, minibodies, Fab-scFv fusions, bispecific (scFv)$_4$-IgG, and bispecific (scFv)$_2$-Fab. (See. e.g., Hu et al., *Cancer Res.* 56:3055-3061, 1996; Atwell et al., *Molecular Immunology* 33:1301-1312, 1996; Carter and Merchant, *Curr. Opin. Biotechnol.* 8:449-454, 1997; Zuo et al., *Protein Engineering* 13:361-367, 2000; and Lu et al., *J. Immunol. Methods* 267:213-226, 2002.)

As used herein, the terms "single-chain Fv" and "single-chain antibody" refer to antibody fragments that comprise, within a single polypeptide chain, the variable regions from both heavy and light chains, but lack constant regions. In general, a single-chain antibody further comprises a polypeptide linker between the $V_H$ and $V_L$ domains, which enables it to form the desired structure that allows for antigen binding. Single-chain antibodies are discussed in detail by, for example, Pluckthun in *The Pharmacology of Monoclonal Antibodies*, vol. 113 (Rosenburg and Moore eds., Springer-Verlag, New York, 1994), pp. 269-315. (See also WIPO Publication WO 88/01649; U.S. Pat. Nos. 4,946, 778 and 5,260,203; Bird et al., *Science* 242:423-426, 1988.) Single-chain antibodies can also be bi-specific and/or humanized.

A "bispecific antibody" is a hybrid antibody having two different heavy/light chain pairs and two different binding sites. Bispecific antibodies are well-established in the art as a standard technique to create a single protein that binds to two different determinants. See. e.g., Kufer et al., *Trends Biotechnol.* 22:238-244, 2004. Bispecific antibodies may be made in many different formats, including but not limited to quadroma, F(ab')2, tetravalent, heterodimeric scFv, bispecific scFv, tandem scFv, diabody and minibody formats, or scFvs appended to or recombinantly fused with whole antibodies. See e.g., Kufer et al., 2004; Holliger and Hudson *Nature Biotechnology* 23:1126-1136, 2005; Morrison and Coloma, WO 95/09917.

As used herein, an "immunogen" is an entity (e.g., a peptide, protein, a nucleic acid, or a carbohydrate) that induces an immune response, which may include an innate or an adaptive immune response (e.g., that protects a subject from an infection or cancer). An adaptive immune response can be a humoral and/or cell-mediated immune response. In certain embodiments, an immunogen in the context of the present disclosure is used as a vaccine.

As used herein the term "sugar" refers to saccharides such as monosaccharides, disaccharides, oligosaccharides, and polysaccharides for example. Typically, sugars as used herein target or deliver copolymers to target cells or tissues, or specific cells types and enhance the association of molecules with the target cells. For example, liver hepatocytes contain asialoglycoprotein (ASGP) receptors. Therefore, galactose-containing targeting groups may be used to target hepatocytes. Examples of galactose containing targeting groups include, but are not limited to, galactose or galactose derivatives such as its protected analogs, N-acetylgalactosamine (NAG, also referred to as GalNAc) or N-acetylgalactosamine derivatives such as its protected analogs, oligosaccharides, and saccharide clusters such as Tyr-Glu-Glu-(aminohexyl GalNAc)3, lysine-based galactose clusters, and cholane-based galactose clusters. Other examples of sugars include, but are not limited to, mannose and mannose derivatives such as its protected analogs. In some variations, a sugar is a multivalent structure comprising two or more sugar moieties (e.g., three or four moieties). In some such multivalent sugar embodiments, each moiety is connected to a common branching point via a linker. An exemplary multivalent sugar is a tri-N-acetylgalactosamine (tri-NAG) structure having three NAG moieties. Tri-NAG structures are generally known in the art and are described, for example, in Lee et al., *Carbohydrates and Chemistry and Biology* (B. Ernst, G. W. Hart, & P. Sinay, Eds., Wiley-WCH: Weinheim, 2000), Vol. 4, p 459 (and references cited therein); Biessen et al. *J. Med. Chem.* 38:1538, 1995; Sliedregt et al., *J. Med. Chem.* 42:609, 1999; Rensen et al., *J. Med. Chem.* 47:5798, 2004; Khorev et al., *Bioorg. Med. Chem.* 16:5216, 2008. Another exemplary multivalent sugar is a bis-mannose-6-phosphate (bis-M6P) structure having two mannose-6-phosphate moieties (see. e.g., U.S. Pat. No. 8,399,657 to Zhu et al.).

As used herein the term "vitamin" refers any of various fat-soluble or water-soluble organic substances that are essential in minute amounts for normal growth and activity of living organisms. Exemplary vitamins include Vitamin A (Retinol), Vitamin B1 (Thiamine), Vitamin C (Ascorbic acid), Vitamin D (Calciferol), Vitamin B2 (Riboflavin), Vitamin E (Tocopherol), Vitamin B12 (Cobalamins), Vitamin K1 (Phylloquinone), Vitamin B5 (Pantothenic acid), Vitamin B7 (Biotin), Vitamin B6 (Pyridoxine), Vitamin B3 (Niacin), Vitamin B9 (Folic acid) and their derivatives. Typically, vitamins as used herein target or deliver lipid nanoparticles and/or membrane-destabilizing polymers to target cells or tissues, or specific cells types and enhance the association of molecules with the target cells. An example of a vitamin as used herein includes Vitamin $B_9$, including folic acid, folate and their derivatives.

As used herein, a "targeting moiety" refers to a moiety that is capable of specifically binding to a molecule on the surface of a target cell, such as a cell within a target tissue of a subject. A molecule (e.g., cell surface molecule) that specifically binds to a targeting moiety is also referred to herein as a "binding partner."

As used herein, "alkyl" refers to a straight or branched chain fully saturated (no double or triple bonds) hydrocarbon (carbon and hydrogen only) group, optionally having a cycloalkyl group as part of the hydrocarbon chain (either at a terminal position or non-terminal position in the chain). An alkyl group herein contains from one to ten carbon atoms in the principal chain and up to 20 carbon atoms, and may be linear or branched. Examples of alkyl groups include, but are not limited to, methyl, ethyl, propyl, isopropyl, butyl, isobutyl, sec-butyl, tertiary butyl, pentyl and hexyl. As used herein, "alkyl" includes "alkylene" groups, which refer to straight or branched fully saturated hydrocarbon groups having two rather than one open valences for bonding to other groups. Examples of alkylene groups include, but are not limited to methylene (—$CH_2$—), ethylene (—$CH_2CH_2$—), propylene (—$CH_2CH_2CH_2$—), n-butylene (—$CH_2CH_2CH_2CH_2$—), sec-butylene (—$CH_2CH_2CH(CH_3)$—), and the like. An alkyl group of this disclosure may optionally be substituted with one or more fluorine groups.

As used herein, "mC to nC," "Cm to Cn," or "$C_m$ to $C_n$," wherein m and n are integers, refers to the number of possible carbon atoms in the indicated group. That is, the group can contain from "m" to "n", inclusive, carbon atoms. An alkyl group of this disclosure may comprise from 1 to 24 carbon atoms, that is, m is 1 and n is 24. Of course, a particular alkyl group may be more limited. For instance without limitation, an alkyl group of this disclosure may consist of 1 to 18 carbon atoms, in which case it would be designated as a (1C-18C)alkyl group, or 3 to 8 carbon atoms, in which case it would be designated as a (3C-8C)alkyl group. The numbers are inclusive and incorporate all straight or branched chain structures having the indicated number of carbon atoms. For example without limitation, a "$^1$C to 4C alkyl" or "(1C-4C)alkyl" group refers to all alkyl groups having from 1 to 4 carbons, that is, $CH_3$—, $CH_3CH_2$—, $CH_3CH_2CH_2$—, $CH_3CH(CH_3)$—, $CH_3CH_2CH_2CH_2$—, $CH_3CH_2CH(CH_3)$—, $(CH_3)_2CHCH_2$— and $(CH_3)_3CH$—.

As used herein, the term "aryl" or "aryl group" refers to optionally substituted monocyclic, bicyclic, and tricyclic ring systems having a total of five to fourteen ring members, wherein at least one ring in the system is aromatic and wherein each ring in the system contains three to seven ring members. The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

As used herein, the term "heteroalkyl" means an alkyl group wherein at least one of the backbone carbon atoms is replaced with a heteroatom.

As used herein, the term "heteroaryl" means an aryl group wherein at least one of the ring members is a heteroatom, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbonyl, substituted hydrocarbonyl, keto (i.e., =O), hydroxy, protected hydroxy, acyl, acyloxy, alkoxy, alkenoxy, alkynoxy, aryloxy, halogen, amido, amino, nitro, cyano, thiol, ketals, acetals, esters and ethers.

As use herein, "cycloalkyl" refers to an alkyl group in which the end carbon atoms of the alkyl chain are covalently bonded to one another. The numbers "m" and "n" refer to the number of carbon atoms in the ring formed. Thus for instance, a (3C-8C) cycloalkyl group refers to a three, four, five, six, seven or eight member ring, that is, cyclopropane, cyclobutane, cyclopentane, cyclohexane, cycloheptane and cyclooctane. A cycloalkyl group of this invention may optionally be substituted with one or more fluorine groups and/or one or more alkyl groups.

As used herein, the term "heterocycloalkyl" means a cycloalkyl group wherein at least one of the backbone carbon atoms is replaced with a heteroatom.

As used herein, the term "alkynyl" refers to an unsaturated, straight chain hydrocarbon group having from two to ten carbon atoms therein and in which at least two carbon atoms are bonded together by a triple bond.

As used herein, the term "alkenyl" refers to an unsaturated, straight chain hydrocarbon group having from two to ten carbon atoms therein and in which at least two carbon atoms are bonded together by a double bond.

When a functional group, such as an amine, is termed "protected," this means that the group is in modified form to preclude undesired side reactions at the protected site. Suitable protecting groups for the copolymers of the present disclosure will be recognized from the present application taking into account the level of skill in the art, and with reference to standard textbooks, such as Greene, T. W. et al., Protective Groups in Organic Synthesis Wiley, New York (1991). Carboxy groups can be protected as esters thereof, for example methyl, ethyl, tert-butyl, benzyl, and 4-nitrobenzyl esters. Hydroxy groups can be protected as ethers or esters thereof, for example methoxymethyl ethers, tetrahydropyranyl ethers, benzyl ethers, acetates or benzoates. Mercapto groups can be protected as thioethers or thioesters, for example pyridyl thioethers, maleimide thioethers, tert-butyl thioethers, thioacetates or thiobenzoates. Amino groups can be protected as carbamates, such as tert-butoxycarbonyl derivatives, or as amides, such as acetamides and benzamides.

As used herein, a "labile bond" is a covalent bond that is capable of being selectively broken. That is, the labile bond may be broken in the presence of other covalent bonds without the breakage of the other covalent bonds. For example, a disulfide bond is capable of being broken in the presence of thiols without cleavage of other bonds, such as carbon-carbon, carbon-oxygen, carbon-sulfur, carbon-nitrogen bonds, which may also be present in the molecule. Labile also means "cleavable."

As used herein, a "labile linkage" is a chemical compound that contains a labile bond and provides a link or spacer between two other groups. The groups that are linked may be chosen from compounds such as biologically active compounds, membrane active compounds, compounds that inhibit membrane activity, functional reactive groups, monomers, and cell targeting signals. The spacer group may contain chemical moieties chosen from a group that includes alkanes, alkenes, esters, ethers, glycerol, amide, saccharides, polysaccharides, and heteroatoms such as oxygen, sulfur, or nitrogen. The spacer may be electronically neutral, may bear a positive or negative charge, or may bear both positive and negative charges with an overall charge of neutral, positive or negative.

As used herein, "pH-labile" or "pH-sensitive" refers to the selective breakage of a covalent bond under acidic conditions (pH<7), or that the covalent bond is broken more rapidly under acidic conditions (pH<7) than under neutral conditions. That is, the pH-labile bond may be broken under acidic conditions in the presence of other covalent bonds that are not broken.

The term "effective amount" or "therapeutically effective amount," in the context of treatment of a disease by administering to a subject either (i) a therapeutic agent-containing lipid nanoparticle as described herein or (ii) a therapeutic PEG-protein as described herein, refers to an amount of the lipid nanoparticle or PEG-protein that is sufficient to inhibit the occurrence or ameliorate one or more symptoms of the disease in the subject. An effective amount of an agent-containing lipid nanoparticle or PEG-protein is administered according to the present methods in an "effective regime." The term "effective regime" refers to a combination of agent-containing lipid nanoparticle or PEG-protein being administered and dosage frequency adequate to accomplish treatment or prevention of the disease. Delivery of an agent-containing lipid nanoparticle or PEG-protein in an "effective regime" may be in the context of delivery of the lipid nanoparticle or PEG-protein in combination with another delivery agent (e.g., a membrane-destabilizing polymer) and/or in the context of a combination therapy. For example, in the context of treatment of a disease by administering to a subject a lipid nanoparticle and membrane-destabilizing polymer as described herein, (i) the term "effective amount" or "therapeutically effective amount" refers to an amount the agent-containing lipid nanoparticle and an amount of the membrane-destabilizing polymer that together is sufficient to inhibit the occurrence or ameliorate one or more symptoms of the disease in the subject, and (ii) the term "effective regime" refers to a combination of agent-containing lipid nanoparticle being administered, membrane-destabilizing polymer being administered, and dosage frequency adequate to accomplish treatment or prevention of the disease.

"Combination therapy," in the context of a treatment as described herein, means that a subject is administered at least one therapeutically effective dose of (a) either a therapeutic agent-containing lipid nanoparticle or a therapeutic PEG-protein as described herein and (b) at least one additional therapeutic agent. Such additional therapeutic agent may or may not be contained within a lipid nanoparticle as described herein, and may or may not be a PEG-protein as described herein.

The term "patient" or "subject," in the context of therapeutic or diagnostic agent delivery in vivo as described herein, includes human and other mammalian subjects.

Percent sequence identity is determined by conventional methods. See. e.g., Altschul et al., *Bull. Math. Bio.* 48:603, 1986, and Henikoff and Henikoff, *Proc. Natl. Acad. Sci. USA* 89:10915, 1992. For example, two amino acid sequences can be aligned to optimize the alignment scores using a gap opening penalty of 10, a gap extension penalty of 1, and the "BLOSUM62" scoring matrix of Henikoff and Henikoff, supra. The percent identity is then calculated as: ([Total number of identical matches]/[length of the longer sequence plus the number of gaps introduced into the longer sequence in order to align the two sequences]X(100). Those skilled in the art appreciate that there are many established algorithms available to align two amino acid sequences. The "FASTA" similarity search algorithm of Pearson and Lipman (*Proc. Nat'l Acad. Sci. USA* 85:2444, 1988, and by Pearson, *Meth. Enzymol.* 183:63, 1990) is a suitable protein alignment method for examining the level of identity shared by an amino acid sequence disclosed herein and a second amino acid sequence.

When such a value is expressed as "about" X or "approximately" X, the stated value of X will be understood to be accurate to +10%.

BRIEF DESCRIPTION OF THE DRAWINGS

FIG. 1D depicts PEGylated lipids comprising multiple linear PEG chains branched off of a polymer backbone (straight line, 6) and covering the lipid nanoparticle in a mushroom-type configuration.

DESCRIPTION OF THE INVENTION

The present invention is generally directed to branched PEG molecules, compositions comprising such branched PEG molecules, and related methods for in vivo delivery of therapeutic or diagnostic agents. In some aspects, the present invention is particularly directed to highly branched PEG-lipids, lipid nanoparticle (LNP) formulations comprising a highly branched PEG-lipid, and the use of such LNP formulations for in vivo delivery of therapeutic and diagnostic agents, including polynucleotide, protein, and small molecule agents. In other aspects, the present invention is particularly directed to therapeutic proteins modified to include a highly branched PEGylated system and the use of such highly branched PEG-proteins for in vivo delivery of the therapeutic protein. In yet other aspects, the present invention is directed to compositions and methods for making the highly branched PEG-lipids and PEG-proteins.

Figure 1A:
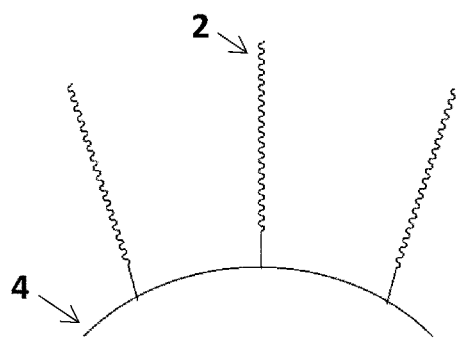
FIGS. 1A-1D each schematically depict PEGylated lipids with linear PEG chains (wavy lines, 2) on the surface of a lipid nanoparticle (curved line, 4). The PEGylated lipids shown in FIGS. 1A-1C have either one (FIG. 1A), two (FIG. 1B), or three (FIG. 1C) linear PEG chains covering the lipid nanoparticle surface in a brush-type configuration. In contrast.
Figure 1B:
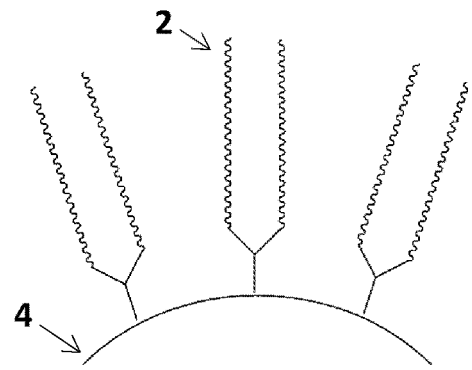
Figure 1C:
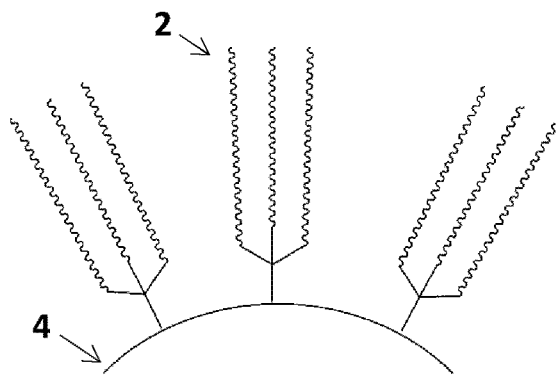
Figure 1D:
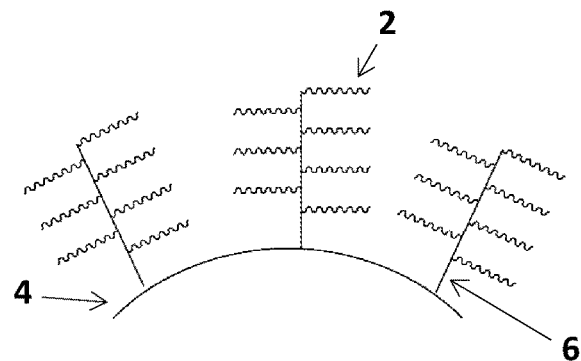

In certain embodiments, the branched PEG molecules as disclosed herein have particularly advantageous applications for delivery of molecular agents upon repeat dosing. For example, and while not intending to be bound by theory, it is believed that instead of presenting PEG in a brush-type configuration at the surface of a nanoparticle (see, e.g., FIGS. 1A-1C), a highly branched PEG system as described herein presents with a mushroom-type configuration on the surface of a nanoparticle (see, e.g., FIG. 1D). It is further believed that such a highly branched PEG system, with this type of orientation, still provides for beneficial steric shielding from serum opsonins while also interfering with or preventing immune system recognition of the PEG moieties, and that avoiding an anti-PEG immune response (e.g., preventing induction of anti-PEG antibodies) improves delivery of a molecular agent upon repeat dosing.

In one aspect, the present invention provides a branched PEG-lipid of Formula I

L-X1-P-X2-T (I)

where P is a polymer comprising (i) an alkylenic or heteroalkylenic backbone of chain atoms and (ii) a plurality of pendant polyethylene glycol (PEG) moieties distributed along the polymer backbone; L is a lipid attached to a first end of the polymer; X1 is absent or a first linking moiety; T is absent or a targeting moiety attached to a second end of the polymer; and X2 is absent or a second linking moiety.

In another aspect, the present invention provides a branched PEG-protein of Formula IV

Y-X1-P-X2-T (IV)

where Y is a therapeutic protein; X1 is a first linking moiety; P is a polymer comprising (i) an alkylenic or heteroalkylenic backbone of chain atoms and (ii) a plurality of pendant polyethylene glycol (PEG) moieties distributed along the polymer backbone; X2 is absent or a second linking moiety; and T is absent or a targeting moiety.

In certain variations of branched PEG-lipid of Formula I or a branched PEG-protein of Formula IV, the lipid or protein respectively, is attached to the α end of the polymer.

In some embodiments of a PEG-lipid of Formula I or a PEG-protein of Formula IV, the ratio of chain atoms to pendant PEG moieties of the polymer is less than about 4:1 (e.g., from about 2:1 to about 4:1). In more particular variations, the ratio of chain atoms to pendant PEG moieties of the polymer is less than about 3.5:1, less than about 3:1, or less than about 2.5:1 (e.g., from about 2:1 to about 3.5:1, from about 2:1 to about 3:1, or from about 2:1 to about 2.5:1). In a specific variation, the ratio of chain atoms to pendant PEG moieties of the polymer is about 2:1.

Typically, a branched PEG-lipid of Formula I or a branched PEG-protein of Formula IV includes at least about five pendant PEG moieties. In some variations, the branched PEG-lipid or branched PEG-protein includes at least about 10, at least about 15, or at least about 20 pendant PEG moieties. In certain embodiments, the branched PEG-lipid or branched PEG-protein includes from about five to about 40, from about five to about 35, from about five to about 30, from about five to about 25, from about 10 to about 40, from about 10 to about 35, from about 10 to about 30, from about 10 to about 25, from about 15 to about 40, from about 15 to about 35, from about 15 to about 30, or from about 15 to about 25 pendant PEG moieties.

The polymer chain atoms of branched PEG-lipid of Formula I or a branched PEG-protein of Formula IV are typically carbon atoms or a combination of (i) carbon atoms and (ii) oxygen, sulfur, and/or nitrogen atoms. For example, repeat units of the polymer backbone may be independently selected from the group consisting of alkylene, ester, thioester, and amide repeat units, and combinations thereof, any of which may be substituted (e.g., with a pendant PEG moiety from among the plurality of pendant PEG moieties distributed along the polymer backbone). In some variations, one or more polymer chain atoms are substituted with a pendant group that does not contain a PEG moiety. In some embodiments, the polymer chain atoms are carbon atoms. In other embodiments, the polymer chain atoms are a combination of carbon and oxygens atoms. Independent of the selection of the chain atoms, a pendant group may be selected from hydrocarbyl, substituted hydrocarbyl, substituted carbonyl, ester, amide, and carboxylic acid.

Typically, each of the pendant PEG moieties of a branched PEG-lipid of Formula I or a branched PEG-protein of Formula IV comprises from 2 to 50 ethylene oxide units. For example, each of the pendant PEG moieties may comprise from 2 to 40, from 2 to 35, from 2 to 30, from 2 to 25, from 2 to 21, or from 2 to 20 ethylene oxide units. In some embodiments, each of the pendant PEG moieties comprises from 4 to 40, from 4 to 35, from 4 to 30, from 4 to 25, from 4 to 21, or from 4 to 20 ethylene oxide units. In other embodiments, each of the pendant PEG moieties comprises from 7 to 40, from 7 to 35, from 7 to 30, from 7 to 25, from 7 to 21, or from 7 to 20 ethylene oxide units. In yet other embodiments, each of the pendant PEG moieties comprises from 4 to 9 ethylene oxide units. In more specific variations, each of the pendant PEG moieties comprises from 4 to 5 ethylene oxide units or from 7 to 9 ethylene oxide units.

Conveniently, the polymer of a branched PEG-lipid of Formula I or a branched PEG-protein of Formula IV may be prepared from readily polymerizable monomers. For example, in one embodiment, the repeat units are residues of ethylenically unsaturated monomer(s). In some embodiments, the polymer comprises repeat units independently derived from optionally substituted acrylate monomers, optionally substituted acrylamide monomers, and combinations thereof.

In certain embodiments, the polymer is a polymer comprising monomeric residues derived from polymerization of a monomer of formula A1

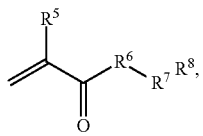

(A1)

where
$R^5$ is H or C1-C6alkyl,
$R^6$ is O, S, $NR^9$, OC1-C6alkyl, OC1-C6alkyl-O, OC1-C6alkyl-OC(O)C1-C6alkyl, OC1-C6alkyl-OC(O)C1-C6alkyl-O, OC1-C6alkyl-OC(O)C1-C6alkyl-NH, OC1-C6alkyl-NH, OC1-C6alkyl-NHC(O)C1-C6alkyl, OC1-C6alkyl-NHC(O)C1-C6alkyl-O, OC1-C6alkyl-NHC(O)C1-C6alkyl-NH, $NR^9$(C1-C6alkyl), $NR^9$(C1-C6alkyl)-O, $NR^9$(C1-C6alkyl)-OC(O)C1-C6alkyl, $NR^9$(C1-C6alkyl)-OC(O)C1-C6alkyl-O, $NR^9$(C1-C6alkyl)-OC(O)C1-C6alkyl-NH, $NR^9$(C1-C6alkyl)-NH, $NR^9$(C1-C6alkyl)-NHC(O)C1-C6alkyl, $NR^9$(C1-C6alkyl)-NHC(O)C1-C6alkyl-O, $NR^9$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6alkyl-O, or C1-C6alkyl-NHC(O)C1-C6alkyl-NH,
$R^7$ is $(CH_2CH_2O)_{2-50}$ (e.g., $(CH_2CH_2O)_{2-40}$, $(CH_2CH_2O)_{2-25}$, or $(CH_2CH_2O)_{220}$),
$R^8$ is H or C1-C6alkyl-$R^{10}$,
$R^9$ is H or C1-C6alkyl, and
$R^{10}$ is H, $CO_2H$, $NH_2$, $NH(C1-C6alkyl)$, $N(C1-C6alkyl)_2$, or $N(C1-C6alkyl)_3$.

In some embodiments, a polymer comprising pendant PEG moieties is a polymer comprising monomeric residues derived from polymerization of a monomer selected from the following:
(a) a poly(ethylene glycol) methyl ether methacrylate (PEGMA) having from 2 to 50 (e.g., from 2 to 40, from 2 to 25, or from 2 to 20) ethylene oxide units (i.e., a monomer of formula A1 as above where $R^5$ is $CH_3$, $R^6$ is O, and $R^8$ is $CH_3$);
(b) a poly(ethylene glycol) methyl ether acrylate (PEGA) having from 2 to 50 (e.g., from 2 to 40, from 2 to 25, or from 2 to 20) ethylene oxide units (i.e., a monomer of formula A1 as above where $R^5$ is H, $R^6$ is 0, and $R^8$ is $CH_3$);
(c) a poly(ethylene glycol) methyl ether methacrylamide having from 2 to 50 (e.g., from 2 to 40, from 2 to 25, or from 2 to 20) ethylene oxide units (i.e., a monomer of formula A1 as above where $R^5$ is $CH_3$, $R^6$ is $NR^9$, $R^8$ is $CH_3$, and $R^9$ is H); and
(d) a poly(ethylene glycol) methyl ether acrylamide having from 2 to 50 (e.g., from 2 to 40, from 2 to 25, or from 2 to 20) ethylene oxide units (i.e., a monomer of formula A1 as above where $R^5$ is H, $R^6$ is $NR^9$, $R^8$ is $CH_3$, and $R^9$ is H).

In some variations of a monomer selected from (a)-(d) above, the monomer has from 3 to 40, from 3 to 35, from 3 to 30, from 3 to 25, from 3 to 21, from 3 to 20, from 3 to 15, or from 3 to 10 ethylene oxide units (i.e., in the monomer of formula A1, $R^7$ is $(CH_2CH_2O)_{3-40}$, $(CH_2CH_2O)_{3-35}$, $(CH_2CH_2O)_{3-30}$, $(CH_2CH_2O)_{3-25}$, $(CH_2CH_2O)_{3-21}$, $(CH_2CH_2O)_{3-20}$, $(CH_2CH_2O)_{3-15}$, or $(CH_2CH_2O)_{3-10}$). In more specific variations of a monomer selected from (a)-(d) above, the monomer has from 4 to 5 or from 7 to 9 ethylene oxide units (i.e., in the monomer of formula A1, $R^7$ is $(CH_2CH_2O)_{4-5}$ or $(CH_2CH_2O)_{7-9}$).

In certain embodiments of a branched PEG-lipid of Formula I or a branched PEG-protein of Formula IV, the polymer is a homopolymer. For example, in particular variations, the polymer is a homopolymer of monomeric residues derived from polymerization of a monomer of formula A1 as described above. In other embodiments, the polymer is a copolymer such as, for example, a random copolymer. In some embodiments in which the polymer is a copolymer, the polymer is derived from polymerization of a first ethylenic monomer comprising a PEG moiety (e.g., a PEG moiety having from 2 to 50, from 2 to 40, from 2 to 25, or from 2 to 20 ethylene oxide units) and a second monomer of formula A2

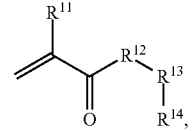

(A2)

where
$R^{11}$ is H or C1-C6alkyl,
$R^{12}$ is O, S, $NR^{15}$, O(C1-C6alkyl), O(C1-C6alkyl)-O, O(C1-C6alkyl)-OC(O)C1-C6alkyl, O(C1-C6alkyl)-OC(O)C1-C6alkyl-O, O(C1-C6 alkyl)-OC(O)C1-C6alkyl-NH, O(C1-C6alkyl)-NH, O(C1-C6alkyl)-NHC(O)C1-C6alkyl, O(C1-C6alkyl)-NHC(O)C1-C6alkyl-O, O(C1-C6alkyl)-NHC(O)C1-C6alkyl-NH, $NR^{15}$(C1-C6alkyl), $NR^{15}$(C1-C6alkyl)-O, $NR^{15}$(C1-C6alkyl)-OC(O)C1-C6alkyl, $NR^{15}$(C1-C6 alkyl)-OC(O)C1-C6alkyl-O, $NR^{15}$(C1-C6alkyl)-OC(O)C1-C6alkyl-NH, $NR^{15}$(C1-C6alkyl)-NH, $NR^{15}$(C1-C6alkyl)-NHC(O)C1-C6alkyl, $NR^{15}$(C1-C6alkyl)-NHC(O)C1-C6alkyl-O, $NR^{15}$(C1-C6alkyl)-NHC(O) C1-C6alkyl-NH, C1-C6alkyl, C1-C6alkyl-O, C1-C6alkyl-OC(O)C1-C6alkyl, C1-C6alkyl-OC(O) C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6 alkyl-O, or C1-C6alkyl-NHC(O)C1-C6alkyl-NH, $R^{13}$ is H, $(CH_2CH_2O)_{1-4}$, or C1-C6alkyl $R^{14}$ is H or C1-C6alkyl-$R^6$, $R^{15}$ is H or C1-C6alkyl, and $R^{16}$ is H, $CO_2H$, $NH_2$, NH(C1-C6alkyl), N(C1-C6alkyl)$_2$, or N(C1-C6alkyl)$_3$.

In some such embodiments of a PEG-lipid or PEG-protein in which the polymer is a copolymer derived from polymerization of first PEG-containing monomer and a second monomer of formula A2, the first monomer is a monomer of formula A1 as described above.

If present, a targeting moiety (T) of a PEG-lipid of Formula I or a PEG-protein of Formula IV specifically recognizes a molecule on the surface of the target cell, such as, e.g., a cell surface receptor. Particularly suitable targeting moieties include antibodies, antibody-like molecules, polypeptides, proteins (e.g., insulin-like growth factor II (IGF-II)), peptides (e.g., an integrin-binding peptide such as an RGD-containing peptide), and small molecules such as, for example, sugars (e.g., lactose, galactose, N-acetyl galactosamine (GalNAc), mannose, mannose-6-phosphate (M6P)) or vitamins (e.g., folate). In some variations, a targeting moiety is a protein derived from a natural ligand of a cell-surface molecule (e.g., derived from a cytokine or from the extracellular domain of a cell-surface receptor that binds to a cell surface counter-receptor). Examples of cell surface molecules that may be targeted by a targeting moiety of a copolymer provided herein include, but are not limited to, the transferrin receptor type 1 and 2, the EGF receptor, HER2/Neu, VEGF receptors, integrins, NGF, CD2, CD3, CD4, CD8, CD19, CD20, CD22, CD33, CD43, CD38, CD56, CD69, the asialoglycoprotein receptor, mannose receptor, the cation-independent mannose-6-phosphate/IGF-II receptor, prostate-specific membrane antigen (PSMA), a folate receptor, and a sigma receptor.

In particular variations, a targeting moiety includes an N-acetylgalactosamine (GalNAc) sugar residue, which specifically binds to the asialoglycoprotein receptor (ASGPR) on hepatocytes. In some such embodiments, the targeting moiety has the formula

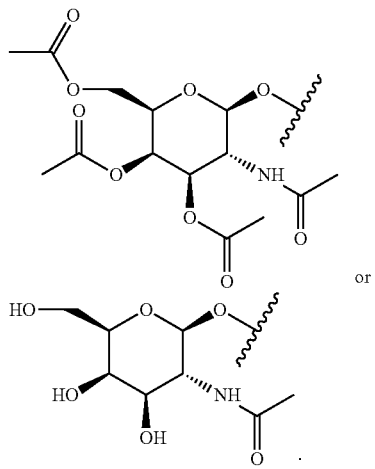

or

In other embodiments comprising a GalNAc sugar residue, the targeting moiety comprises multiple GalNAc sugar residues (e.g., three GalNAc residues, also referred to herein as a "tri-GalNAc" structure), which may increase avidity for the asialoglycoprotein receptor relative to a monovalent GalNAc moiety. In some such embodiments, a tri-GalNAc structure has the formula

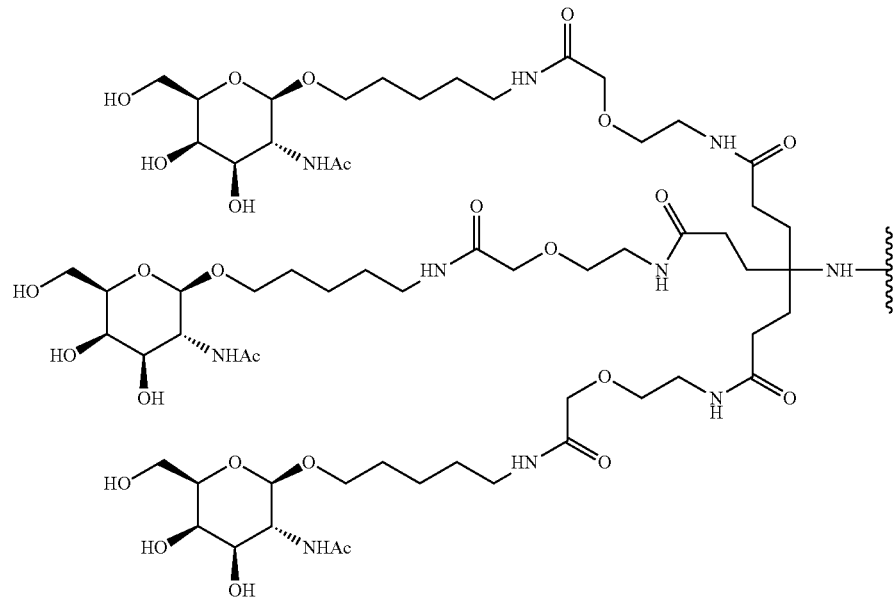 [SMILES: *NC(CCC(=O)NCCOCC(=O)NCCCCCO[C@@H]1O[C@H](CO)[C@H](O)[C@H](O)[C@H]1NC(C)=O)(CCC(=O)NCCOCC(=O)NCCCCCO[C@@H]1O[C@H](CO)[C@H](O)[C@H](O)[C@H]1NC(C)=O)CCC(=O)NCCOCC(=O)NCCCCCO[C@@H]1O[C@H](CO)[C@H](O)[C@H](O)[C@H]1NC(C)=O]

where ∿∿ designates a point of attachment.

Linking moieties suitable for attachment of a lipid or therapeutic protein to a polymer, or for attachment of a targeting moiety to a polymer, are generally known in the art and may be readily used in the context of a branched PEG-lipid of Formula I or a branched PEG-protein of Formula IV. In some embodiments of a branched PEG-lipid of Formula I, a linking moiety X1, if present, is selected from hydrocarbyl, substituted hydrocarblyl, ester, amide, ether, PEG (2-15), amine, PEI (2-15), carbonyl, substituted carbonyl, or an amino acid, disulfide, imine, and hydrozone.

In some embodiments of a branched PEG-protein of Formula IV, a linking moiety X1 is selected from hydrocarbyl, substituted hydrocarblyl, ester, amide, ether, PEG (2-15), amine, PEI (2-15), carbonyl, substituted carbonyl, or an amino acid, disulfide, imine, and hydrozone. In some embodiments of a branched PEG-lipid of Formula I or of a branched PEG-protein of Formula IV, a linking moiety X2 is selected from hydrocarbyl, substituted hydrocarblyl, ester, amide, ether, PEG (2-15), amine, PEI (2-15), carbonyl, substituted carbonyl, or an amino acid, disulfide, imine, and hydrozone.

In certain embodiments of a branched PEG-protein of Formula IV, the therapeutic protein is selected from a cytokine (e.g., an interferon or an interleukin), a soluble receptor, an anticoagulant, a blood factor, a bone morphogenetic protein, an enzyme, a growth factor, a hormone, a thrombolytic, and an antibody. In some embodiments, the therapeutic protein is a peptide. In some embodiments comprising an interferon as the therapeutic protein, the interferon is selected from interferon-α (e.g., interferon-α2a, interferon-α2b, interferon-αn3), interferon-β (e.g., interferon-β1α, interferon-β1b), and interferon-γ (e.g., interferon-γ1b). In certain variations, the therapeutic protein is a protein with enzymatic or regulatory activity; in some such embodiments, the therapeutic protein is selected from insulin, growth hormone (GH), insulin-like growth factor (IGF-1), factor VIII, factor IX, antithrombin III, protein C, β-glucocerebrosidase, alglucosidase-α, iduronidase, idursulphase, galsulfase, α-galactosidase A, α-1-proteinase inhibitor, lactase, a pancreatic enzyme, adenosine deaminase, albumin, erythropoietin, darbepoetin-α, granulocyte colony stimulating factor (G-CSF), granulocyte-macrophage colony stimulating factor (GM-CSF), interleukin 11 (IL-11), interferon-α2a, interferon-α2b, interferon-αn3, interferon-β1a, interferon-β1b, interferon-γ1b, interleukin 2 (IL-2), tissue plasminogen activator (tPA), reteplase (deletion mutein of tPA), tenecteplase, urokinase, factor VIIa, drotrecogin-α (activated protein C), teriparatide, exenatide, octreotide, bone morphogenic protein 2, bone morphogenic protein 7, gonadotropin releasing hormone (GnRH), keratinocyte growth factor (KGF), platelet-derived growth factor (PDGF), trypsin, B-type natriuretic peptide, botulinum toxin type A, botulinum toxin type B, collagenase, deoxyribonuclease I, hyaluronidase, papain, aspariginase, rasburicase, lepirudin, bivalirudin, streptokinase, and anisolylated plasminogen streptokinase activator complex (APSAC). In other variations, the therapeutic protein is a protein with targeting activity (e.g., to interfere with molecules or organisms by specifically binding to them and blocking their function, targeting them or destruction, or stimulating a signaling pathway); in some such embodiments, the therapeutic protein is selected from an anti-VEGF-A antibody (e.g., bevacizumab, ranibizumab), an anti-EGF-R antibody (e.g., cetuximab, panitumumab), an antiCD52 antibody (e.g., alemtuzumab), an anti-CD20 antibody (e.g., rituximab), an anti-HER2/Neu antibody (e.g., trastuzumab), a soluble CTLA4 Fc fusion protein (e.g., abatacept), interleukin 1 (IL-1), an anti-TNFα antibody (e.g., adalimumab, infliximab), a soluble TNF receptor (TNF-R) Fc fusion protein (e.g., etanercept), a soluble LFA-3 Fc fusion protein (e.g., alefacept), an anti-CD11a antibody (e.g., efalizumab), and anti-α4 integrin subunit antibody (e.g., natalizumab), an anti-C5 complement protein antibody (e.g., eculizumab), an anti-IL-2 receptor (IL2-R) antibody (e.g., basiliximab, daclizumab), an anti-CD3 antibody (e.g., muromonab-CD3), an anti-FcεR11 antibody (e.g., omalizumab), an antibody that binds the A antigenic site of the F protein of respiratory syncytial virus (e.g., palivizumab), a peptide that binds to the HIV envelope protein gp120/gp41 (e.g., enfuvirtide), and an anti-glycoprotein IIb/IIIa (GPIIb/III) antibody (e.g., abciximab).

In certain embodiments of a branched PEG-lipid of Formula I, L is a lipid comprising two $C_8$-$C_{24}$ hydrocarbon chains. In some such embodiments, the two $C_8$-$C_{24}$ hydrocarbon chains are selected from two $C_8$-$C_{22}$ hydrocarbon chains, two $C_8$-$C_{20}$ hydrocarbon chains, two $C_8$-$C_{19}$ hydrocarbon chains, two $C_8$-$C_{18}$ hydrocarbon chains, two $C_8$-$C_{17}$ hydrocarbon chains, two $C_{10}$-$C_{24}$ hydrocarbon chains, two $C_{10}$-$C_{22}$ hydrocarbon chains, two $C_{10}$-$C_{20}$ hydrocarbon chains, two $C_{10}$-$C_{19}$ hydrocarbon chains, two $C_{10}$-$C_{18}$ hydrocarbon chains, two $C_{10}$-$C_{17}$ hydrocarbon chains, two $C_{12}$-$C_{24}$ hydrocarbon chains, two $C_{12}$-$C_{22}$ hydrocarbon chains, two $C_{12}$-$C_{20}$ hydrocarbon chains, two $C_{12}$-$C_{19}$ hydrocarbon chains, two $C_{12}$-$C_{18}$ hydrocarbon chains, two $C_{12}$-$C_{17}$ hydrocarbon chains, two $C_{13}$-$C_{24}$ hydrocarbon chains, two $C_{13}$-$C_{22}$ hydrocarbon chains, two $C_{13}$-$C_{20}$ hydrocarbon chains, two $C_{13}$-$C_{19}$ hydrocarbon chains, two $C_{13}$-$C_{18}$ hydrocarbon chains, or two $C_{13}$-$C_{17}$ hydrocarbon chains. In certain variations, the lipid comprising two $C_8$-$C_{24}$ hydrocarbon chains is a glycerophospholid or a glycerolipids. Particularly suitable glycerophospholipids include 1,2-dilauroyl-sn-glycero-3-phosphoethanolamine, 1,2-ditridecyloyl-sn-glycero-3-phosphoethanolamine, 1,2-dimyristoyl-sn-glycero-3-phosphoethanolamine (DMPE), 1,2-dipentadecyloyl-sn-glycero-3-phosphoethanolamine, 1,2-dipalmitoyl-sn-glycero-3-phosphoethanolamine (DPPE), 1,2-dimargaroyl-sn-glycero-3-phosphoethanolamine, 1,2-distearoyl-sn-glycero-3-phosphoethanolamine (DSPE), 1,2-dinanodecyloyl-sn-glycero-3-phosphoethanolamine, 1,2-diarachidoyl-sn-glycero-3-phosphoethanolamine, 1,2-dimyristoleoyl-sn-glycero-3-phosphoethanolamine, 1,2-dipalmitoleoyl-sn-glycero-3-phosphoethanolamine, 1,2-disapieneoyl-sn-glycero-3-phosphoethanolamine, 1,2-dioleoyl-sn-glycero-3-phosphoethanolamine, 1,2-dielaideoyl-sn-glycero-3-phosphoethanolamine, 1,2-divacceneoyl-sn-glycero-3-phosphoethanolamine, 1,2-dilinoleoyl-sn-glycero-3-phosphoethanolamine, 1,2-dilinoelaideoyl-sn-glycero-3-phosphoethanolamine, 1,2-di-α-linoleneoyl-sn-glycero-3-phosphoethanolamine, and 1,2-diarachioneoyl-sn-glycero-3-phosphoethanolamine. Particularly suitable glycerolipids include dimyristolglycerol (DMG), distearoyl glycerol (DSG), dipalmitoyl glycerol (DPG), dilauroyl glycerol, ditridecyloyl glycerol, dipentadecyloyl glycerol, dimargaroyl glycerol, dinanodecyloyl glycerol, diarachidoyl glycerol, dimyristoleoyl glycerol, dipalmitoleoyl glycerol, disapieneoyl glycerol, dioleoyl glycerol, dielaideoyl glycerol, divacceneoyl glycerol, dilinoleoyl glycerol, dilinoelaideoyl glycerol, di-α-linoleneoyl glycerol, and diarachioneoylglycerol.

In other embodiments of a branched PEG-lipid of Formula I, L is a sterol lipid. In some such variations, the lipid is selected from cholesterol, cholesteryl hemisuccinate, sitoindoside I, sitoindoside II, glucosyl stigmasterol, 16:0 stigmasteryl glucose, 18:1 stigmasteryl glucose, glucosyl sitosterolB, cholesterol sulfate, DHEA, DHEA sulfate, FF-MAS, campesterol, campestanol, zymostenol, sitostanol, sitosterol, stigmasterol, diosgenin, 7-dehydrodesmosterol, lanosterol, lanosterol-95, dihydrolanosterol, 14-demethyl-lanosterol, zymosterol, desmosterol, lathosterol, and pregnenolone.

In other embodiments of a branched PEG-lipid of Formula I, L is a sphingolipid. In some such variations, the sphingolipid is selected from N-octanoyl-sphingosine, sphinganine-1-phosphate (d17:0), sphingosine-1-phosphate (d17:1), sphinganine-1-phosphate (d18:0), sphingosine-1-phosphate (d18:1), sphinganine-1-phosphate (d20:0), sphingosine-1-phosphate (d20:1), 1-deoxysphinganine, 1-desoxymethylsphinganine, sphinganine (d17:0), sphinganine (d18:0), safingol, sphinganine (d20:0), sphingosine (d14:1), sphingosine (d17:1), sphingosine (d18:1), sphingosine (d20:1), 1-deoxysphingosine, 4E,8Z-sphingadiene, 4E,11Z-sphingadiene, and 4E,14Z-sphingadiene.

In some embodiments, a branched PEG-lipid of Formula I is DSPE-PEGMA. In more particular variations, the DSPE-PEGMA is a compound of Formula IIa or IIb

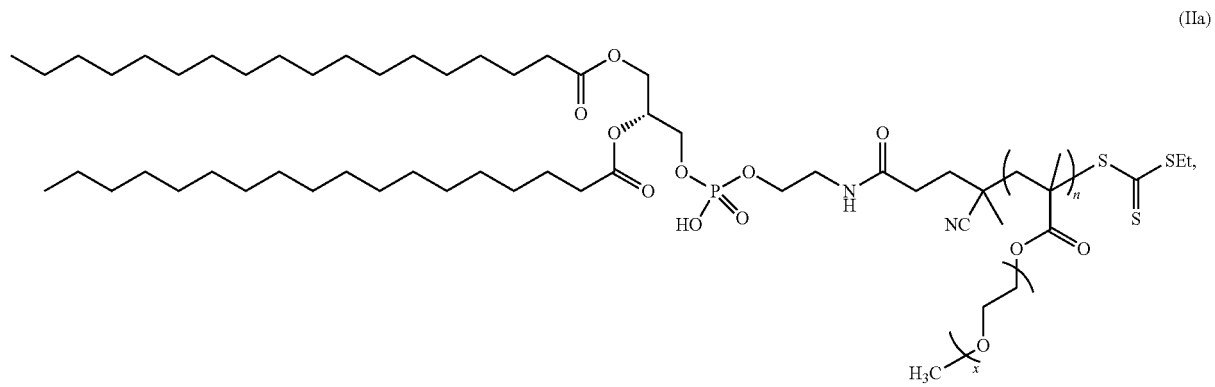

(IIa)

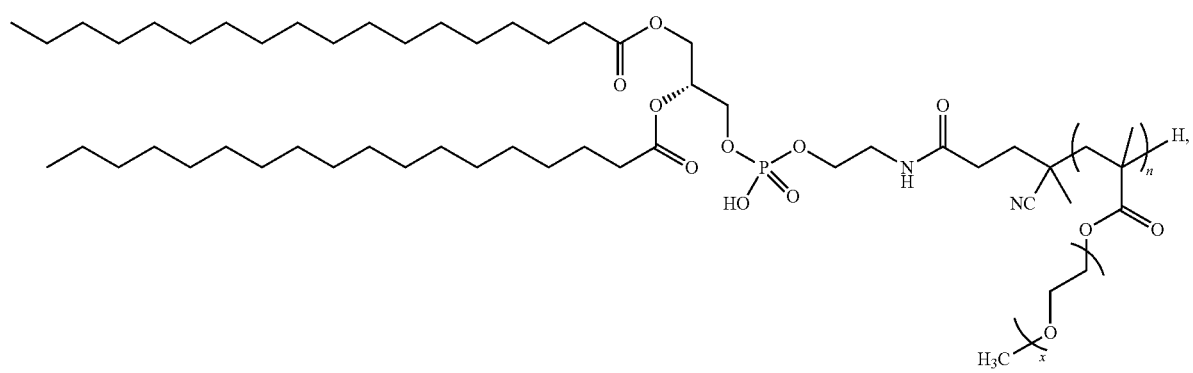

(IIb)

or a pharmaceutically acceptable salt thereof, where x is 2-50 and n is 5-40. In some such variations, x is 2-40, 2-35, 2-30, 2-25, 2-21, 2-20, 4-40, 4-35, 4-30, 4-25, 4-21, 4-20, 4-9, 7-40, 7-35, 7-30, 7-25, 7-21, or 7-20; and/or n is 5-35, 5-30, 5-25, 10-40, 10-35, 10-30, 10-25, 15-40, 15-35, 15-30, 15-25, 20-40, 20-35, or 20-30. In some embodiments, the DSPE-PEGMA is selected from (i) a DSPE-PEGMA$_{300}$ (e.g. a DSPE-PEGMA of Formula IIa or IIb where n is 4-5) and (ii) a DSPE-PEGMA$_{500}$ (e.g., a DSPE-PEGMA of Formula IIa or IIb where n is 7-9).

In some embodiments, a branched PEG-lipid of Formula I is DMPE-PEGMA. In more particular variations, the DMPE-PEGMA is a compound of Formula IIc or IId

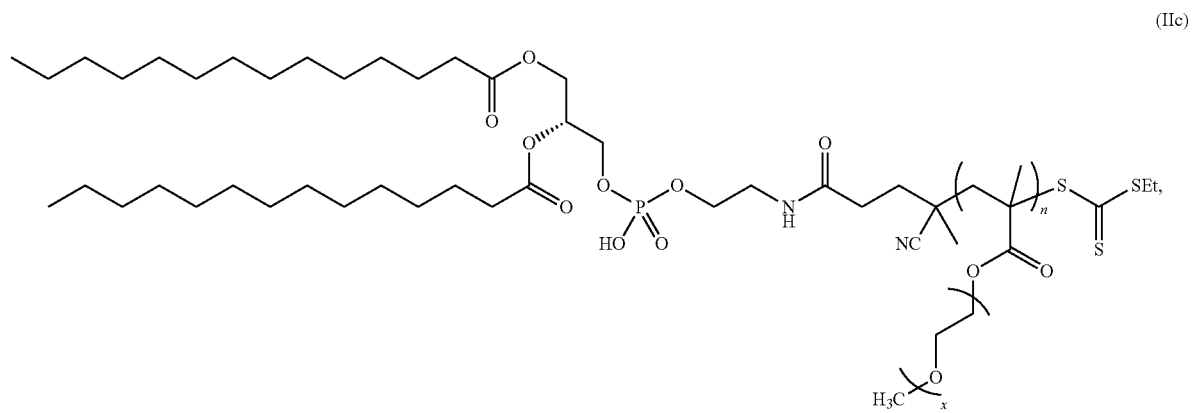

(IIc)

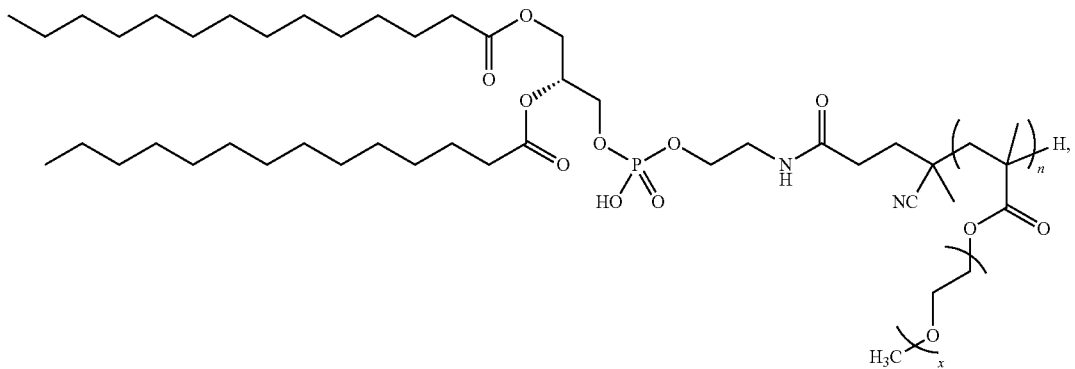

(IId)

or a pharmaceutically acceptable salt thereof, where x is 2-50 and n is 5-40. In some such variations, x is 2-40, 2-35, 2-30, 2-25, 2-21, 2-20, 4-40, 4-35, 4-30, 4-25, 4-21, 4-20, 4-9, 7-40, 7-35, 7-30, 7-25, 7-21, or 7-20; and/or n is 5-35, 5-30, 5-25, 10-40, 10-35, 10-30, 10-25, 15-40, 15-35, 15-30, 15-25, 20-40, 20-35, or 20-30. In some embodiments, the DMPE-PEGMA is selected from (i) a DMPE-PEGMA$_{300}$ (e.g. a DMPE-PEGMA of Formula IIc or IId where n is 4-5) and (ii) a DMPE-PEGMA$_{500}$ (e.g., a DMPE-PEGMA of Formula IIc or IId where n is 7-9).

In some embodiments, a branched PEG-lipid of Formula I is DSG-PEGMA. In more particular variations, the DSG-PEGMA is a compound of Formula IIe or IIf

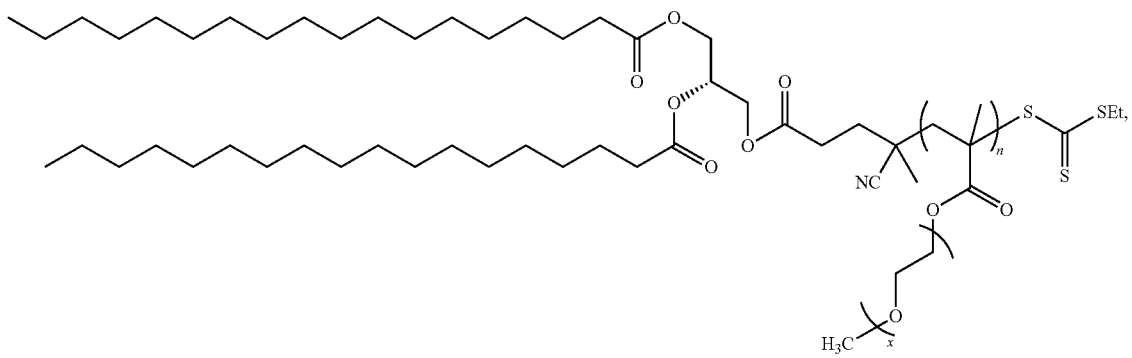

(IIe)

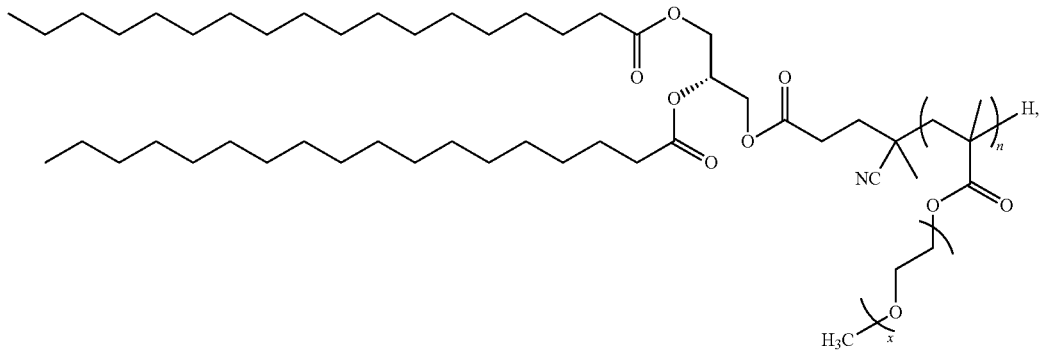

(IIf)

or a pharmaceutically acceptable salt thereof, where x is 2-50 and n is 5-40. In some such variations, x is 2-40, 2-35, 2-30, 2-25, 2-21, 2-20, 4-40, 4-35, 4-30, 4-25, 4-21, 4-20, 4-9, 7-40, 7-35, 7-30, 7-25, 7-21, or 7-20; and/or n is 5-35, 5-30, 5-25, 10-40, 10-35, 10-30, 10-25, 15-40, 15-35, 15-30, 15-25, 20-40, 20-35, or 20-30. In some embodiments, the DSG-PEGMA is selected from (i) a DSG-PEGMA$_{300}$ (e.g. a DSG-PEGMA of formula IIe or IIf where n is 4-5) and (ii) a DSG-PEGMA$_{500}$ (e.g., a DSG-PEGMA of formula IIe or IIf where n is 7-9).

In some embodiments, a branched PEG-lipid of Formula I is DMG-PEGMA. In more particular variations, the DMG-PEGMA is a compound of Formula IIg or IIh

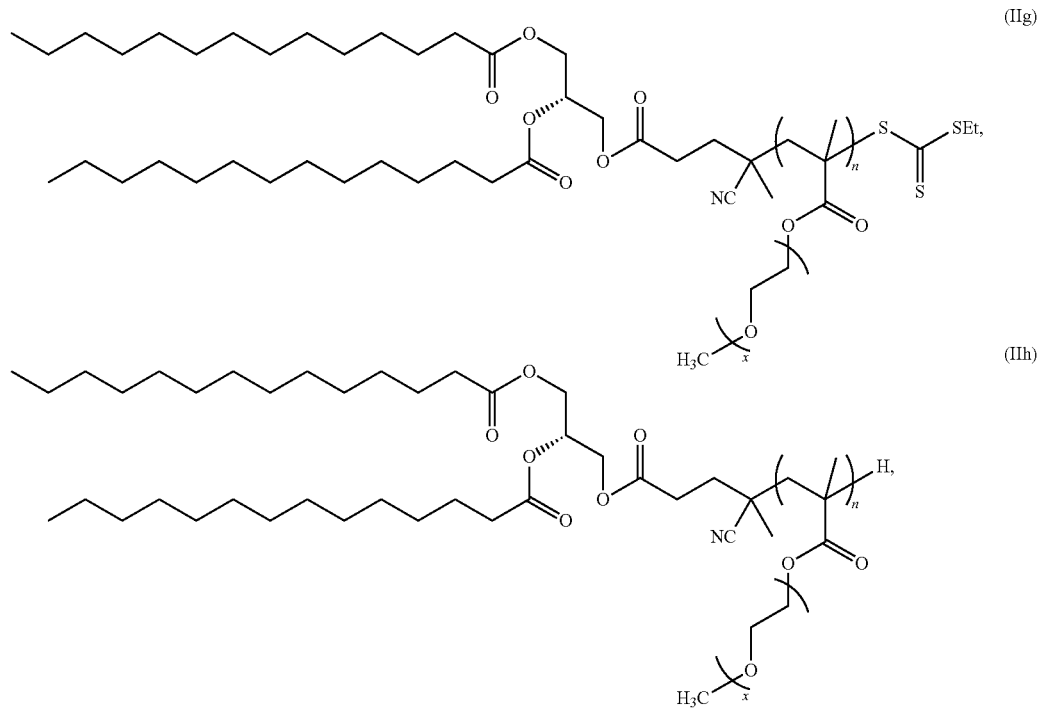

or a pharmaceutically acceptable salt thereof, where x is 2-50 and n is 5-40. In some such variations, x is 2-40, 2-35, 2-30, 2-25, 2-21, 2-20, 4-40, 4-35, 4-30, 4-25, 4-21, 4-20, 4-9, 7-40, 7-35, 7-30, 7-25, 7-21, or 7-20; and/or n is 5-35, 5-30, 5-25, 10-40, 10-35, 10-30, 10-25, 15-40, 15-35, 15-30, 15-25, 20-40, 20-35, or 20-30. In some embodiments, the DMG-PEGMA is selected from (i) a DMG-PEGMA$_{300}$ (e.g. a DMG-PEGMA of Formula IIe or IIf where n is 4-5) and (ii) a DMG-PEGMA$_{500}$ (e.g., a DMG-PEGMA of Formula IIe or IIf where n is 7-9).

In some embodiments, a branched PEG-lipid of Formula I is DPG-PEGMA. In more particular variations, the DPG-PEGMA is a compound of Formula IIi or IIj

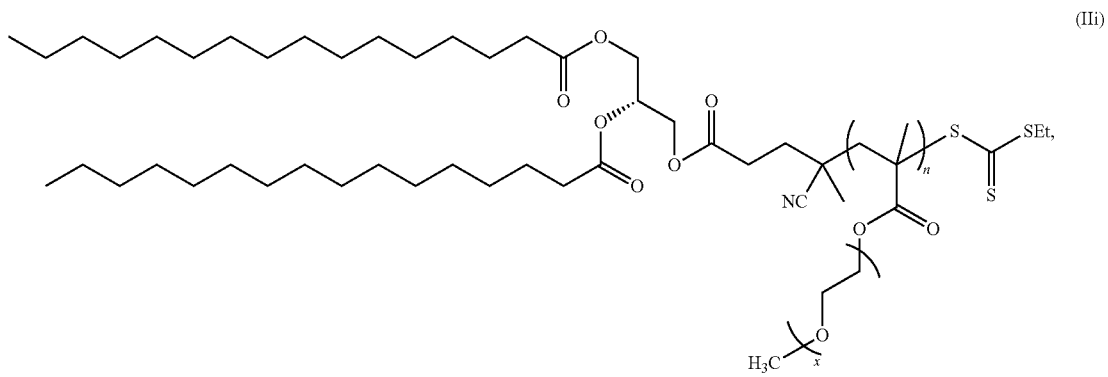

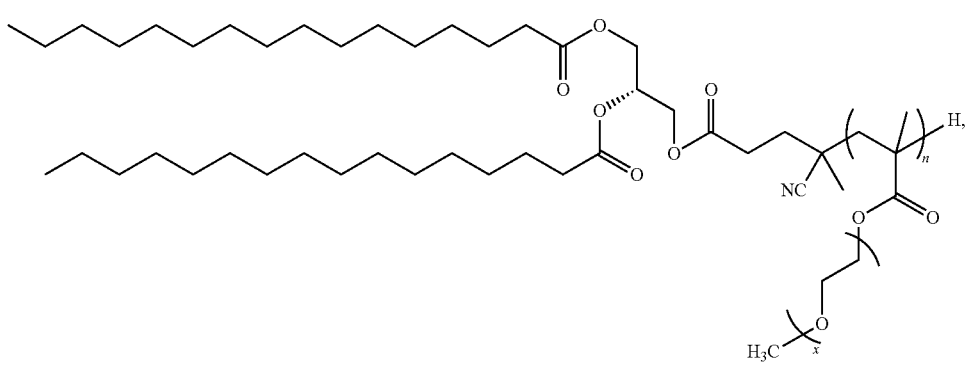

(IIj)

or a pharmaceutically acceptable salt thereof, where x is 2-50 and n is 5-40. In some such variations, x is 2-40, 2-35, 2-30, 2-25, 2-21, 2-20, 4-40, 4-35, 4-30, 4-25, 4-21, 4-20, 4-9, 7-40, 7-35, 7-30, 7-25, 7-21, or 7-20; and/or n is 5-35, 5-30, 5-25, 10-40, 10-35, 10-30, 10-25, 15-40, 15-35, 15-30, 15-25, 20-40, 20-35, or 20-30. In some embodiments, the DPG-PEGMA is selected from (i) a DPG-PEGMA$_{300}$ (e.g. a DPG-PEGMA of Formula IIi or IIj where n is 4-5) and (ii) a DPG-PEGMA$_{500}$ (e.g., a DPG-PEGMA of Formula IIi or IIj where n is 7-9).

In another aspect, the present invention provides a lipid nanoparticle comprising (a) a mixture of lipid components comprising a branched PEG-lipid as above; and (b) a therapeutic or diagnostic agent. Lipid nanoparticles as described herein are particularly useful for in vivo delivery of the therapeutic or diagnostic agent, including, for example, in vivo delivery utilizing a repeat dosing regime.

A wide variety of therapeutic and diagnostic agents are generally known and may be used in accordance with the present disclosure. The therapeutic or diagnostic agent can be, for example, a polynucleotide, a protein, a peptide, or a small molecule. Suitable classes of therapeutic agents include, for example, anti-cancer agents, anti-infective agents (e.g., anti-viral or anti-bacterial agents), immunomodulatory agents (e.g., immunosuppressive or immunostimulatory agents), anti-inflammatory agents, or agents that modulate a cellular metabolic activity. Suitable diagnostic agents include, e.g., a variety of detectable agents, which may be used alone or as a conjugate (label) to another molecule (e.g., a polynucleotide, a protein, a peptide, or a small molecule) having a desired property useful in a diagnostic method (e.g., a binding specificity for a desired intracellular target). General classes of labels that can be used in the present invention include, but are not limited to, radioactive isotopes, paramagnetic isotopes, compounds that can be imaged by positron emission tomography (PET), fluorescent or colored compounds, compounds which can be imaged by magnetic resonance, chemiluminescent compounds, bioluminescent compounds, and other imaging reagents.

Methods for formulating lipid nanoparticles for drug delivery are generally known in the art and may be adapted for use in the context of the present invention. For example, lipid nanoparticle formulations for delivery of small RNAs are discussed in, e.g., Hong and Nam, *Theranostics* 4:1211-1232, 2014; Asai and Oku, *Biol. Pharm. Bull.* 37:201-205, 2014; and Tam et al., *Pharmaceutics* 5:498-507, 2013. Lipid particle formulations and lipid design for drug delivery are also discussed in, e.g., Samad et al., *Current Drug Delivery* 4:297-305, 2007; Martin et al., *Current Pharmaceutical Design* 11:375-394, 2005; Hafez et al., *Biophysical Journal* 79:1438-1446, 2000; Jayaraman et al., *Angew. Chem. Int. Ed.* 51:8529-8533, 2012; Li and Schick, *Biophysical Journal* 80:1703-1711, 2001; Adami et al., *Molecular Therapy* 19:1141-1151, 2011); Dabkowska et al., *J. R. Soc. Interface* 9:548-561, 2012; Gubernator, *Expert Opinion on Drug Delivery* 8:565-80, 2011; Whitehead et al., *Nat. Commun.* 5:4277, 2014; and Dong et al., *Proc. Natl. Acad. Sci. USA* 111:3955-60, 2014.

In some embodiments, in addition to a branched PEG-lipid as described herein, an LNP mixture of lipid components includes one or more cationic lipids. For LNP formulations comprising a polynucleotide agent, cationic lipids are particularly useful, inter alia, in complexing with the polynucleotide via electrostatic interactions. Lipid nanoparticles comprising polynucleotides are typically formulated with a N:P ratio ranging from about 1 to about 30. In more specific variations, the N:P ratio is from about 1 to about 14, from 1 to about 7, or from about 3 to about 7 (e.g., an N:P ratio of about 3, about 3.5, or about 7).

In certain embodiments, a cationic lipid for forming the lipid nanoparticle comprises a quaternary amine and is consequently permanently positively charged. Particularly suitable, permanently charged cationic lipids that may be used in polynucleotide LNP formulations include, for example, N-[1-(2,3-dioleyloxy)propyl]-N,N,N-trimethylammonium chloride (DOTMA), N-[1-(2,3-dioleoyloxy)propyl]-N,N,N-trimethylammonium chloride (DOTAP), 1,2-dioleoyl-sn-glycero-3-ethylphosphocholine (DOEPC), 1,2-dilauroyl-sn-glycero-3-ethylphosphocholine (DLEPC), 1,2-dimyristoyl-sn-glycero-3-ethylphosphocholine (DMEPC), 1,2-dimyristoleoyl-sn-glycero-3-ethylphosphocholine (14:1), N1-[2-((1S)-1-[(3-aminopropyl)amino]-4-[di(3-aminopropyl)amino]butylcarboxamido)ethyl]-3,4-di[oleyloxy]-benzamide (MVL5), Dioctadecylamido-glycylspermine (DOGS), 3b-[N—(N',N'-dimethylaminoethyl)carbamoyl] cholesterol (DC-Chol), Dioctadecyldimethylammonium Bromide (DDAB), Saint lipids such as SAINT-2, N-methyl-4-(dioleyl)methylpyridinium, 1,2-dimyristyloxypropyl-3-dimethylhydroxyethylammonium bromide (DMRIE), 1,2-dioleoyl-3-dimethyl-hydroxyethyl ammonium bromide (DORIE), 1,2-dioleoyloxypropyl-3-dimethylhydroxyethyl ammonium chloride (DORI), Di-alkylated Amino Acid (DILA$^2$) (e.g., C18:1-norArg-C16), Dioleyldimethylammonium chloride (DODAC), 1-palmitoyl-2-oleoyl-sn-glycero-3-ethylphosphocholine (POEPC), 1,2-dimyristoleoyl-sn-glycero-3-ethylphosphocholine (MOEPC), and (R)—N,N,N-trimethyl-4,5-bis(oleoyloxy)pentan-1-aminium chloride (DOTAPen). Also suitable are cationic lipids with headgroups that are charged at physiological pH, such as primary amines (e.g., DODAG N',N'-dioctadecyl-N-4,8-diaza-10-aminodecanoylglycine amide) and guanidinium head groups (e.g., bis-guanidinium-spermidine-cholesterol (BGSC), bis-guanidiniumtren-cholesterol (BGTC), PONA, and (R)-5-guanidinopentane-1,2-diyl dioleate hydrochloride (DOPen-G)). Yet another suitable cationic lipid is (R)-5-(dimethylamino)pentane-1,2-diyl dioleate hydrochloride (DODAPen-Cl). In certain embodiments, the cationic lipid is a particular enantiomer or the racemic form, and includes the various salt forms of a cationic lipid as above (e.g., chloride or sulfate). For example, in some embodiments, the cationic lipid is N-[1-(2,3-dioleoyloxy)propyl]-N,N,N-trimethylammonium chloride (DOTAP-Cl) or N-[1-(2,3-dioleoyloxy)propyl]-N,N,N-trimethylammonium sulfate (DOTAP-Sulfate).

In certain variations, a cationic lipid for forming the lipid nanoparticle utilizes side chains of amino acids as the head groups, where the α-amino and α-carboxyl groups serve as attachment sites for the hydrophobic tails (also referred to as a "DiLA$^2$" architecture; see Adami et al., *Molecular Therapy* 19:1141-1151, 2011). A particular variant of a cationic lipid having a DiLA$^2$ structure is C18:1-norArg-C16. See Adami et al., supra.

In some embodiments, in addition to a branched PEG-lipid as described herein, an LNP mixture of lipid components includes one or more non-cationic lipids. Non-cationic lipid components may include lipids serving various purposes such as, for example, aiding manufacturing and storage stability as well as modulation of the biodistribution. Additional lipids suitable to be incorporated into the lipid nanoparticles may include one or more of an anionic lipid and a neutral helper lipid. In certain embodiments, lipid nanoparticles are provided that comprise a cationic lipid as above and one or more additional lipids selected from an anionic lipid and a helper lipid.

Anionic lipids for use in cationic lipid-containing LNP formulations are typically ionizable anionic lipids. While negatively charged at pH values above the $pK_a$ of the anionic lipid, an ionizable anionic lipid will generally stabilize other lipids in the LNP and allow the formation of bilayer vesicles, but will facilitate fusion of these vesicles as the pH is reduced toward the $pK_a$, such as in the acidic endosomal environment of a cell. Suitable ionizable anionic lipids include cholesteryl hemisuccinate (CHEMS), phosphatidylserine, palmitoylhomoserine, and α-tocopherol hemisuccinate.

Helper lipids are neutral lipids that help make a stable liposome dispersion and may also enhance the effectiveness of cationic lipid-based delivery formulations. Cholesterol (CHOL) is one particularly suitable helper lipid for used in lipid nanoparticle formulations. Suitable helper lipids also include neutral zwitterionic lipids such as, for example, 1,2-distearoyl-sn-glycero-3-phosphocholine (DSPC), 1,2-dipalmitoyl-sn-glycero-3-phosphocholine (DPPC), 1,2-dimyristoyl-sn-glycero-3-phosphocholine (DMPC), or any related phosphatidylcholine such as natural sphingomyelin (SM) and synthetic derivatives thereof such as 1-oleoyl-2-cholesteryl-hemisuccinoyl-sn-glycero-3-phosphocholine (OChemsPC). Other suitable helper lipids include 1,2-dioleoyl-sn-glycero-3-phosphoethanolamine (DOPE), 1,2-dilauroyl-sn-glycero-3-phosphoethanolamine (DLPE), 1,2-dimyristoyl-sn-glycero-3-phosphoethanolamine (DMPE), and 1,2-diphytanoyl-sn-glycero-3-phosphoethanolamine (DPHyPE).

In certain embodiments, in addition to a branched PEG-lipid as described herein, an LNP mixture of lipid components comprises an ionizable cationic lipid, typically in lieu of any permanently charged cationic lipid. The ionizable cationic lipid will have at least one protonatable or deprotonatable group, typically such that the lipid is positively charged at a pH at or below physiological pH (e.g., pH 7.4), and neutral at a second pH, preferably at or above physiological pH. It will be understood that the addition or removal of protons as a function of pH is an equilibrium process, and that the reference to a charged or a neutral lipid refers to the nature of the predominant species and does not require that all of the lipid be present in the charged or neutral form. In certain embodiments, ionizable cationic lipids have a $pK_a$ of the protonatable group in the range of about 4 to about 11. Most preferred is a $pK_a$ of about 4 to about 7, because these lipids will be cationic at a lower pH formulation stage, while particles will be largely (though not completely) surface neutralized at physiological pH around pH 7.4. For LNP embodiments comprising a polynucleotide agent, one of the benefits of this $pK_a$ is that at least some nucleic acid associated with the outside surface of the particle will lose its electrostatic interaction at physiological pH and be removed by simple dialysis; thus greatly reducing the particle's susceptibility to clearance. Suitable ionizable cationic lipids for use in accordance with the present invention include, for example, Dioctadecyldimethylammonium bromide (DDAB), 1,2-dilinoleyloxy-3-dimethylaminopropane (DLinDMA), 2,2-dilinoleyl-4-(2dimethylaminoethyl)-[1,3]-dioxolane (DLin-KC2-DMA), heptatriaconta-6,9,28, 31-tetraen-19-yl 4-(dimethylamino)butanoate (DLin-MC3-DMA), 1,2-Dioleoyloxy-3-dimethylaminopropane (DODAP), 1,2-Dioleyloxy-3-dimethylaminopropane (DODMA), Morpholinocholesterol (Mo-CHOL), lipidoids such as C12-200 (see Love et al., *Proc. Natl. Acad. Sci. USA* 107:1864-9, 2010), lipopeptide type compounds such as cKK-E12 (Dong et al., *Proc. Natl. Acad. Sci. USA* 111:3955-60, 2014), and lipids such as AIC-0217 and AIC-0218 (Acuitas Therapeutics, Vancouver, BC). Other suitable ionizable cationic lipids may, for example, be derived from cationic lipid structures previously described herein.

In some embodiments of a lipid nanoparticle composition in accordance with the present invention, one or more branched PEG-lipids as described herein are present in the lipid component mixture from about 0.1% to about 20% (mol %) of the total amount of lipid and delivery-enhancing components, including any polymeric (e.g., PEG) component, but not including the therapeutic or diagnostic agent (e.g., polynucleotide) component. In some embodiments, a lipid nanoparticle composition contains one or more branched PEG-lipids as described herein from about 0.1% to about 15%, from about 0.1% to about 10%, from about 0.2% to about 20%, from about 0.2% to about 15%, from about 0.2% to about 10%, from about 0.5% to about 20%, from about 0.5% to about 15%, from about 0.5% to about 10%, from about 1% to about 20%, from about 1% to about 15%, from about 1% to about 10%, from about 2% to about 20%, from about 2% to about 15%, or from about 2% to about 10% of the composition.

In some embodiments of a lipid nanoparticle composition in accordance with the present invention, in addition to a branched PEG-lipid as described herein, one or more cationic lipids are present in the lipid component mixture from about 0.5% to about 70% (mol %) of the total amount of lipid and delivery-enhancing components, including any polymeric (e.g., PEG) component, but not including the therapeutic or diagnostic agent (e.g., polynucleotide) component. In more particular variations, a lipid nanoparticle composition contains one or more cationic lipids from about 5% to about 70%, from about 5% to about 60%, from about 5% to about 55%, from about 5% to about 45%, from about 5% to about 35%, from about 10% to about 70%, from about 10% to about 60%, from about 10% to about 55%, from about 10% to about 45%, from about 10% to about 35%, from about 15% to about 70%, from about 15% to about 60%, from about 15% to about 55%, from about 15% to about 45%, from about 15% to about 35%, from about 20% to about 70%, from about 20% to about 60%, from about 20% to about 55%, from about 20% to about 45%, from about 20% to about 35%, from about 30% to about 70%, from about 30% to about 60%, from about 30% to about 55%, from about 30% to about 45%, from about 35% to about 70%, from about 35% to about 60%, or from about 35% to about 55% of the composition.

In certain embodiments of a lipid nanoparticle composition in accordance with the present invention, in addition to a branched PEG-lipid as described herein, one or more non-cationic lipids are present in the lipid component mixture from about 2% to about 95% (mol %) of the total amount of lipid and delivery-enhancing components, including any polymeric (e.g., PEG) component, but not including the therapeutic or diagnostic agent (e.g., polynucleotide) component. In some embodiments, a lipid nanoparticle composition contains one or more non-cationic lipids from about 5% to about 75%, from about 5% to about 65%, from about 5% to about 55%, from about 5% to about 50%, from about 10% to about 75%, from about 10% to about 65%, from about 10% to about 55%, from about 10% to about 50%, from about 20% to about 75%, from about 20% to about 65%, from about 20% to about 55%, from about 20% to about 50%, from about 35% to about 75%, from about 35% to about 65%, from about 35% to about 55%, from about 45% to about 70%, from about 45% to about 65%, or from about 45% to about 55% of the composition.

In some variations, a lipid nanoparticle comprising a branched PEG-lipid as described herein comprises a small molecule agent. Methods for formulating lipid nanoparticles containing small molecule agents are generally known (see, e.g., Gubernator, *Expert Opinion on Drug Delivery* 8:565-80, 2011), and may be readily adapted for formulation of branched-PEG-lipid-containing lipid nanoparticles in accordance with the present disclosure. For example, small molecules can be encapsulated in liposome using a passive or an active loading method. Basically, for a passive loading method, the lipids are solubilized in organic solvent, then the solvent is evaporated to form a thin lipid film which is hydrated with an aqueous solution containing a hydrophilic or hydrophobic drug to be encapsulated. The liposome mixture is then typically homogenized by vortex and extruded through polycarbonate membrane in order to reduce the particle size (e.g., to ~100 nm). Non-encapsulated drug can be removed using dialysis or column filtration.

Ionizable small molecules can be actively trapped into liposomes (remote loading method). Typically, in this particular case, the drug is protonated or precipitated inside the preformed liposomes thus remaining entrapped in the liposome core. Typically, a pH gradient (acetate, citrate or ammonium sulfate) where there is a 1 to 3 pH unit difference between the liposome inner and outer compartment is used to encapsulate the ionizable small molecules. A metal gradient ($Cu^{2+}$, $Mn^{2+}$ or $Mg^{2+}$ gradient) can also be used to actively load a drug into liposomes. Ionophores such as A23187 can also be used generate a pH gradient in the liposome using $K^+$, $Mn^{2+}$ or $Mg^{2+}$. An EDTA gradient method can also be used to actively trap small molecules inside a liposome. In the remote loading method, the liposomes typically are formed by a simple lipid-film hydration technique (e.g., as described above for the passive entrapment method with the exception that the hydration buffer contain the solute required to generate the gradient across the lipid bilayer). The non-encapsulated solute is typically removed by dialysis or column filtration. Following the liposome formation and establishment of a gradient across the liposomal bilayers, an unprotonated drug is added in the loading buffer outside the liposome and can cross the lipid bilayer and becomes protonated inside the liposome, and then become stabilized by the anions present in the internal aqueous compartment of the liposome. The suspension may need to be incubated above the phase transition temperature of the liposomal lipids to accelerate the drug loading. The non-encapsulated free drug can be removed, by dialysis or by ion exchange chromatography.

In some variations, a lipid nanoparticle comprising a branched PEG-lipid as described herein comprises a protein or peptide agent. Methods for formulating lipid nanoparticles containing protein or peptide agents are also generally known and may be readily adapted for formulation of branched-PEG-lipid-containing lipid nanoparticles in accordance with the present disclosure. For example, in some embodiments, proteinaceous agents are incorporated into liposomes by a lipid film hydration method (see e.g., Kim et al., *Biomaterials* 30:5751-5756, 2009).

In some embodiments of a lipid nanoparticle in accordance with the present invention, the mixture of lipid components includes a branched PEG-lipid as described herein, a cationic lipid, an anionic lipid, and a helper lipid. Such a mixture of LNP lipid components can be represented by the formula [cationic lipid]$_w$:[anionic lipid]$_x$:[helper lipid]$_y$:[branched PEG-lipid]$_z$, where the subscripts w, x, y, and z represent the mole % of each lipid component within the mixture (not including the therapeutic or diagnostic agent component (e.g., polynucleotide) of the LNP). This formula can be alternatively expressed as [cationic lipid]:[anionic lipid]:[helper lipid]:[branched PEG-lipid] (w:x:y:z), where w, x, y, and z represent the mole % of the cationic lipid, anionic lipid, helper lipid, and branched PEG-lipid, respectively. In various embodiments, each of the cationic lipid, anionic lipid, helper lipid, and branched PEG-lipid are selected from the exemplary lipids disclosed herein. In some embodiments, w is from about 10 to about 70, from about 30 to about 60, from about 35 to about 60, or from about 35 to about 55; x is from 0 to about 60, from 0 to about 50, from about 10 to about 50, from about 20 to about 45, or from about 25 to about 40; y is from about 5 to about 40, from about 5 to about 30, or from about 5 to about 20; and z is from about 0.5 to about 20, from about 0.5 to about 15, from about 0.5 to about 10, from about 1 to about 20, from about 1 to about 15, from about 1 to about 10, from about 2 to about 20, from about 2 to about 15, or from about 2 to about 10. For example, a lipid mixture having the cationic lipid DOTAP present at about 50 mole %, the anionic lipid CHEMS present at about 32 mole %, the helper lipid CHOL present at about 16 mole %, and the branched PEG-lipid DSPE-PEGMA$_{500}$ present at about 2 mole % can be expressed as DOTAP$_{50}$:CHEMS$_{32}$:CHOL$_{16}$:DSPE-PEGMA500$_2$ or as DOTAP:CHEMS:CHOL:DSPE-PEGMA$_{500}$ (50:32:16:2).

In particular embodiments, a lipid nanoparticle for use in accordance with the present invention includes a mixture of lipid components comprising (i) a cationic lipid from about 30 mole % to about 60 mole %; (ii) an anionic lipid from 0 mole % to about 50 mole %; (iii) a helper lipid from about 1 mole % to about 50 mole %; and (iv) a branched PEG-lipid from about 0.5 mole % to about 20 mole %. Typically, the cationic lipid is a cationic lipid that is permanently charged at physiological pH (e.g., DOTAP). If present, the anionic lipid is typically an ionizable anionic lipid such as, for example, CHEMS. A particularly suitable helper lipid for use such embodiments is cholesterol (CHOL), and particularly suitable branched PEG-lipids include DSPE-PEGMA (e.g., DSPE-PEGMA$_{300}$ or DSPE-PEGMA$_{500}$), DMPE-PEGMA (e.g., DMPE-PEGMA$_{300}$ or DMPE-PEGMA$_{500}$), DSG-PEGMA (e.g., DSG-PEGMA$_{300}$ or DSG-PEGMA$_{500}$), DMG-PEGMA (e.g., DMG-PEGMA$_{300}$ or DMG-PEGMA$_{500}$), and DPG-PEGMA (e.g., DPG-PEGMA$_{300}$ or DPG-PEGMA$_{500}$). An excess of cationic lipid to anionic lipid, if present, is preferred. In some variations, (i) the cationic lipid (e.g., DOTAP) is present in the lipid mixture from about 35% mole % to about 60 mole %, from about 35 mole % to about 55 mole %, from about 40 mole % to about 55 mole %, from about 45 mole % to about 55 mole %, or from about 40 mole % to about 50 mole %; (ii) the anionic lipid (e.g., CHEMS) is present in the lipid mixture from 0 mole % to about 45 mole %, from about 10 mole % to about 45 mole %, from about 20 mole % to about 45 mole %, from about 30 mole % to about 45 mole %, from about 25 mole % to about 40 mole %, or from about 30 mole % to about 40 mole %; (iii) the helper lipid (e.g., CHOL) is present in the lipid mixture from about 5 mole % to about 50 mole %, from about 5 mole % to about 40 mole %, from about 5 mole % to about 30 mole %, from about 5 mole % to about 20 mole %, or from about 5 mole % to about 10 mole %; and (iv), the branched PEG-lipid (e.g., DSPE-PEGMA, DMPE-PEGMA, DSG-PEGMA, DMG-PEGMA, or DPG-PEGMA) is present in the lipid mixture from about 0.2 mole % to about 20 mole %, from about 0.2 mole % to about 15 mole %, from about 0.2 mole % to about 10 mole %, from about 0.2 mole % to about 5 mole %, from about 0.5 mole % to about 20 mole %, from about 0.5 mole % to about 15 mole %, from about 0.5 mole % to about 10 mole %, from about 0.5 mole % to about 5 mole %, from about 1 mole % to about 20 mole %, from about 1 mole % to about 15 mole %, from about 1 mole % to about 10 mole %, from about 1 mole % to about 5 mole %, from about 2 mole % to about 20 mole %, from about 2 mole % to about 15 mole %, from about 2 mole % to about 10 mole %, or from about 2 mole % to about 5 mole %. In some embodiments of an LNP composition as above wherein an anionic lipid is present, the cationic lipid (e.g., DOTAP) is present in the lipid mixture from about 35 mole % to about 60 mole %; the anionic lipid (e.g., CHEMS) is present in the lipid mixture from about 25 mole % to about 40 mole %; the helper lipid (e.g., CHOL) is present in the lipid mixture from about 5 mole % to about 20 mole %; and the branched PEG-lipid (e.g., DSPE-PEGMA, DMPE-PEGMA, DSG-PEGMA, DMP-PEGMA, or DPG-PEGMA) is present in the lipid mixture from about 0.5 mole % to about 15 mole %, from about 0.5% to about 10 mole %, from about 1 mole % to about 15 mole %, from about 1 mole % to about 10 mole %, from about 2 mole % to about 15 mole %, or from about 2 mole % to about 10 mole %; in some such embodiments, the molar ratio of [cationic lipid]:[anionic lipid]:[helper lipid]:[branched PEG-lipid] is about 50:32:16:2 or about 50:32:8:10. In more specific variations, the LNP composition includes a mixture of lipid components (with the molar ratio of components specified in parentheses) selected from (a) DOTAP:CHEMS:CHOL:DSPE-PEGMA (50:32:16:2); (b) DOTAP:CHEMS:CHOL:DSPE-PEGMA (50:32:8:10); (c) DOTAP:CHEMS:CHOL:DMPE-PEGMA (50:32:16:2); (d) DOTAP:CHEMS:CHOL:DMPE-PEGMA (50:32:8:10); (e) DOTAP:CHEMS:CHOL:DSG-PEGMA (50:32:16:2); (f) DOTAP:CHEMS:CHOL:DSG-PEGMA (50:32:8:10); (g) DOTAP:CHEMS:CHOL:DMG-PEGMA (50:32:16:2); (h) DOTAP:CHEMS:CHOL:DMG-PEGMA (50:32:8:10); (i) DOTAP:CHEMS:CHOL:DPG-PEGMA (50:32:16:2); and (j) DOTAP:CHEMS:CHOL:DPG-PEGMA (50:32:8:10). In some embodiments of lipid nanoparticle as above, the branched PEG-lipid is (i) a DSPE-PEGMA of Formula IIa or IIb as described herein, (ii) a DMPE-PEGMA of Formula IIc or IId as described herein, (iii) a DSG-PEGMA of Formula IIe or IIf as described herein, (iv) a DMG-PEGMA of Formula IIg or IIh as described herein, or (v) a DPG-PEGMA of Formula IIi or IIj as described herein. Mixtures of lipid components as described above are particularly suitable for lipid nanoparticle compositions comprising a polynucleotide such as, for example, an mRNA.

In some embodiments, a lipid nanoparticle is less than about 200 nm in size. For example, the lipid nanoparticle may be from about 30 nm to about 150 nm in size. In certain variations, the size of the lipid nanoparticle (e.g., between about 30 nm and about 150 nm) facilitates delivery to the liver by an enhanced permeation and retention effect. The lipid nanoparticle may further include a targeting moiety (e.g., targeting moiety T contained in a branched PEG-lipid of Formula I) to target the particle to a desired tissue. The lipid nanoparticle may have a positive or negative zeta potential; in some variations, the zeta potential of the lipid nanoparticle is substantially neutral.

Particular embodiments of the present invention are directed at in vivo delivery of therapeutic agents utilizing a lipid nanoparticle as described herein. In some embodiments, the therapeutic agent is a polynucleotide. Suitable polynucleotide therapeutic agents include DNA agents, which may be in the form of cDNA, in vitro polymerized DNA, plasmid DNA, genetic material derived from a virus, linear DNA, vectors, expression vectors, expression cassettes, chimeric sequences, recombinant DNA, anti-sense DNA, or derivatives of these groups. Other suitable polynucleotide therapeutic agents include RNA, which may be in the form of messenger RNA (mRNA), in vitro polymerized RNA, recombinant RNA, transfer RNA (tRNA), small nuclear RNA (snRNA), ribosomal RNA (rRNA), chimeric sequences, dicer substrate and the precursors thereof, locked nucleic acids, anti-sense RNA, interfering RNA (RNAi), asymmetric interfering RNA (aiRNA), small interfering RNA (siRNA), microRNA (miRNA), ribozymes, external guide sequences, small non-messenger RNAs (snmRNA), untranslatedRNA (utRNA), snoRNAs (24-mers, modified snmRNA that act by an anti-sense mechanism), tiny non-coding RNAs (tncRNAs), small hairpin RNA (shRNA), or their derivatives. Double stranded RNA (dsRNA) and siRNA are of interest particularly in connection with the phenomenon of RNA interference. Examples of therapeutic oligonucleotides as used herein include, but are not limited to, siRNA, an antisense oligonucleotide, a dicer substrate, a miRNA, an aiRNA or an shRNA. An example of a large therapeutic polynucleotide as used herein includes, but is not limited to, messenger RNAs (mRNAs) encoding functional proteins for gene replacement therapy. Polynucleotide therapeutic agents may also be nucleic acid aptamers, which are nucleic acid oligomers that specifically bind other macromolecules; such aptamers that bind specifically to other macromolecules can be readily isolated from libraries of such oligomers by known technologies such as SELEX. See. e.g., Stoltenburg et al., *Biomol. Eng.*, 24:381, 2007.

In other embodiments, the therapeutic agent is a protein or a peptide. For example, in certain variations, the agent is an antibody that binds to and either antagonizes or agonizes a molecular target such as, e.g., an intracellular target. Antibodies for use in the present invention may be raised through any known method, such as through injection of immunogen into mice and subsequent fusions of lymphocytes to create hybridomas. Such hybridomas may then be used either (a) to produce antibody directly, or (b) to clone cDNAs encoding antibody fragments for subsequent genetic manipulation. To illustrate one method employing the latter strategy, mRNA is isolated from the hybridoma cells, reverse-transcribed into cDNA using antisense oligo-dT or immunoglobulin gene-specific primers, and cloned into a plasmid vector. Clones are sequenced and characterized. They may then be engineered according to standard protocols to combine the heavy and light chains of the antibody into a bacterial or mammalian expression vector to generate, e.g., a single-chain scFv. A similar approach may be used to generate recombinant bispecific antibodies by combining the heavy and light chains of each of two different antibodies, separated by a short peptide linker, into a bacterial or mammalian expression vector. Recombinant antibodies are then expressed and purified according to well-established protocols in bacteria or mammalian cells. See. e.g., Kufer et al., 2004, supra; *Antibody Engineering: A Practical Approach*, McCafferty, Hoogenboom and Chiswell Eds, IRL Press 1996. Antibodies or other proteinaceous therapeutic molecules such as peptides, may also be created through display technologies that allow selection of interacting affinity reagents through the screening of very large libraries of, for example, immunoglobulin domains or peptides expressed by bacteriophage (*Antibody Engineering: A Practical Approach*, McCafferty, Hoogenboom and Chiswell Eds, IRL Press 1996). Antibodies may also be humanized through grafting of human immunoglobulin domains, or made from transgenic mice or bacteriophage libraries that have human immunoglobulin genes/cDNAs. In some embodiments of the invention, a specific binding protein therapeutic may include structures other than antibodies that are able to bind to targets specifically, including but not limited to avimers (see Silverman et al., *Nature Biotechnology* 23:1556-1561, 2005), ankyrin repeats (see Zahnd et al., *J. Mol. Biol.* 369:1015-1028, 2007) and adnectins (see U.S. Pat. No. 7,115,396), and other such proteins with domains that can be evolved to generate specific affinity for antigens, collectively referred to as "antibody-like molecules". Modifications of protein therapeutics through the incorporation of unnatural amino acids during synthesis may be used to improve their properties (see Datta et al., *J. Am. Chem. Soc.* 124:5652-5653, 2002; and Liu et al., *Nat. Methods* 4:239-244, 2007). Such modifications may have several benefits, including the addition of chemical groups that facilitate subsequent conjugation reactions.

In some embodiments, the therapeutic agent is a peptide. In certain variations, the peptide is a bispecific peptide. Peptides can readily be made and screened to create affinity reagents that recognize and bind to macromolecules such as, e.g., proteins. See. e.g., Johnsson and Ge, *Current Topics in Microbiology and Immunology,* 243:87-105, 1999.

In other embodiments, a protein therapeutic is a peptide aptamer. A peptide aptamer comprises a peptide molecule that specifically binds to a target protein and interferes with the functional ability of that target protein. See, e.g., Kolonin et al., *Proc. Natl. Acad. Sci. USA* 95:14266, 1998. Peptide aptamers consist of a variable peptide loop attached at both ends of a protein scaffold. Such peptide aptamers can often have a binding affinity comparable to that of an antibody (nanomolar range). Due to the highly selective nature of peptide aptamers, they can be used not only to target a specific protein, but also to target specific functions of a given protein (e.g., a signaling function). Further, peptide aptamers can be expressed in a controlled fashion by use of promoters that regulate expression in a temporal, spatial or inducible manner. Peptide aptamers act dominantly, therefore, they can be used to analyze proteins for which loss-of-function mutants are not available. Peptide aptamers are usually prepared by selecting the aptamer for its binding affinity with the specific target from a random pool or library of peptides. Peptide aptamers can be isolated from random peptide libraries by yeast two-hybrid screens. See. e.g., Xu et al., *Proc. Natl. Acad Sci. USA* 94:12473, 1997. They can also be isolated from phage libraries (see, e.g., Hoogenboom et al., Immunotechnology 4:1, 1998) or from chemically generated peptides/libraries.

In yet other embodiments, the therapeutic agent is a small molecule therapeutic. Small molecule therapeutics are generally well-known in the art and may be used in accordance with the present invention. Such molecules include anti-infective (e.g., anti-viral) small molecules, immunomodulatory small molecules, and anti-cancer small molecules, to name a few broad categories. In some variations, the small molecule therapeutic is a hydrophobic small molecule. Small molecule anti-cancer therapeutics include, e.g., a variety of chemotherapeutic drugs such as, for example, tyrosine kinase inhibitors (TKIs), small molecules that influence either DNA or RNA, or small molecules that inhibit cell mitosis by preventing polymerization or depolymerization of microtubules. Particular examples of small molecule chemotherapeutic agents include anti-metabolites (such as Azathioprine, Cytarabine, Fludarabine phosphate, Fludarabine, Gemcitabine, cytarabine, Cladribine, capecitabine 6-mercaptopurine, 6-thioguanine, methotrexate, 5-fluorouracil and hyroxyurea); alkylating agents (such as Melphalan, Busulfan, Cis-platin, Carboplatin, Cyclophosphamide, Ifosphamide, Dacarabazine, Procarbazine, Chlorambucil, Thiotepa, Lomustine, Temozolamide); anti-mitotic agents (such as Vinorelbine, Vincristine, Vinblastine, Docetaxel, Paclitaxel); topoisomerase inhibitors (such as Doxorubincin, Amsacrine, Irinotecan, Daunorubicin, Epirubicin, Mitomycin, Mitoxantrone, Idarubicin, Teniposide, Etoposide, Topotecan); antibiotics (such as Actinomycin and Bleomycin); Asparaginase; anthracyclines; and taxanes. In certain variations, the small molecule chemotherapeutic is selected from an anti-tubulin agent, a DNA minor groove binding agent, a DNA replication inhibitor, and a tyrosine kinase inhibitor. In other specific variations, the small molecule chemotherapeutic is an anthracycline, an auristatin, a camptothecin, a duocarmycin, an etoposide, a maytansinoid, a *vinca* alkaloid, or a platinum (II) compound.

In still other embodiments, the therapeutic agent is a component of a gene editing system that disrupts or corrects genes that cause disease. These include, for example, zinc finger nucleases (ZFNs) (see, e.g., Smith et al., *Nucleic Acids Res.* 28:3361-3369, 2000), transcription activator-like effector nucleases (TALENs) (see, e.g., Li et al., *Nucleic Acids Res.* 39:359-372, 2011), the CRISPR/Cas system (see, e.g., Richter et al., *Int. J. Mol. Sci.* 14:14518-14531, 2013), and engineered meganucleases (see, e.g., Silva et al., *Curr. Gene Ther.* 11:11-27, 2011). In such embodiments, the nuclease(s) are encoded by one or more nucleic acids such as mRNA or DNA that are formulated in the lipid nanoparticle. In some variations, multiple mRNAs are formulated in the LNP carrier to deliver two nucleases to the same cell for gene editing to occur (e.g., for a ZFNs or TALENs gene editing system, which typically requires two nucleases to recognize the specific target site within the genome to cause a modification at that site). In the context of the present disclosure, the membrane destabilizing polymer facilitates delivery of the nucleic acid(s) to the cytoplasm, where translation or subsequent nuclear delivery occur. In some variations, one or more additional components of a gene editing system are delivered to a target cell together with the one or more nucleic acids encoding the nuclease(s). For example, in the CRISPR/Cas system, in addition to a nucleic acid encoding the Cas9 protein, a short guide RNA to target the enzyme to a specific site in the genome is typically formulated within the LNP carrier. In certain embodiments, to correct a gene by homologous recombination, a donor DNA sequence may also be delivered and formulated either in the same or a different LNP than with the nucleic acid(s) that encode the nuclease(s). In certain embodiments where the gene editing system corrects a gene associated with a disease, the disease is characterized by deficiency of a functional protein as disclosed herein (see, e.g., discussion of protein deficiency diseases, infra.)

In some embodiments, the therapeutic agent is an immunogen. Using methods as disclosed herein, an immunogen can be effectively delivered to a variety of immune cells to elicit an immune response. Suitable immunogens include peptides, proteins, mRNAs, short RNAs, DNAs, simple or complex carbohydrates as well as substances derived from viruses, bacteria, cancer cells, and the like. In some variations, a hapten or adjuvant component is attached (conjugated) or self-associated with the lipid nanoparticle. For example, in some variations, a immunogenic peptide that is a promiscuous T-cell epitope is attached to the LNP to enable a more robust immune response. This hapten can be derived from, e.g., the protein sequence encoded by an mRNA component of the LNP or can be from another protein or a combination of more than one T-cell epitope. As another example, the immunogen may be a component of a bacterial cell wall that is attached to the LNP to enhance the immune response by acting as an adjuvant. In yet other variations, an immmunostimulating oligonucleotide or long nucleic acid is attached or self-associated with the LNP to activate the innate immune response. A lipid nanoparticle may be used to elicit an innate immune response, a T-cell response, a B-cell response, or a combination thereof through the attachment or self-association of immunogenic substances. In certain embodiments for delivering an immunogen to a cell as disclosed herein, the LNP has a targeting moiety (e.g., targeting moiety T contained in a branched PEG-lipid of Formula I) to direct the LNP to an immune cell of interest.

In particular LNP embodiments comprising a polynucleotide as the therapeutic agent, the polynucleotide is an mRNA molecule encoding a functional protein, such as a functional protein associated with a protein deficiency disease. Such embodiments are particularly useful in methods for increasing the amount of the functional protein within a target cell, where the method includes administering an effective amount of a lipid nanoparticle comprising the mRNA to a subject. For example, in some embodiments, the mRNA encodes a functional protein associated with a protein deficiency disease; in some such variations, the mRNA encodes a protein selected from alpha-1-antitrypsin (A1AT), carbamoyl phosphate synthetase I (CPS1), fumarylacetoacetase (FAH) enzyme, alanine:glyoxylate-aminotransferase (AGT), methylmalonyl CoA mutase (MUT), propionyl CoA carboxylase alpha subunit (PCCA), propionyl CoA carboxylase beta subunit (PCCB), a subunit of branched-chain ketoacid dehydrogenase (BCKDH), ornithine transcarbamylase (OTC), copper-transporting ATPase Atp7B, bilirubin uridinediphosphate glucuronyltransferase (BGT) enzyme, hepcidin, glucose-6-phosphatase (G6Pase), glucose 6-phosphate translocase, lysosomal glucocerebrosidase (GB), Niemann-Pick C1 protein (NPC1), Niemann-Pick C2 protein (NPC2), acid sphingomyelinase (ASM), Factor VII, Factor VIII, Factor IX, galactose-1-phosphate uridylyltransferase, galactokinase, UDP-galactose 4-epimerase, transthyretin, a complement regulatory protein, phenylalanine hydroxylase (PAH), homogentisate 1,2-dioxygenase, porphobilinogen deaminase, hypoxanthine-guanine phosphoribosyltransferase (HGPRT), argininosuccinate lyase (ASL), argininosuccinate synthetase (ASS1), P-type ATPase protein FIC-1, alpha-galactosidase A, acid ceramidase, acid α-L-fucosidase, acid β-galactosidase, iduronate-2-sulfatase, alpha-L-iduronidase, galactocerebrosidase, acid α-mannosidase, β-mannosidase, arylsulfatase B, arylsulfatase A, N-acetylgalactosamine-6-sulfate sulfatase, acid β-galactosidase, acid α-glucosidase, β-hexosaminidase B, heparan-N-sulfatase, alpha-N-acetylglucosaminidase, acetyl-CoA:α-glucosaminide N-acetyltransferase, N-acetylglucosamine-6-sulfate sulfatase, alpha-N-acetylgalactosaminidase, sialidase, β-glucuronidase, and β-hexosaminidase A.

In certain embodiments comprising delivery of an mRNA molecule encoding a functional protein, the mRNA encodes a secreted protein. In some variations, a secreted protein is a hormone, a cytokine, a growth factor, a clotting factor, an anti-protease protein, an angiogenic protein, an antiangiogenic protein, a chemokine, or an antibody. Exemplary secreted proteins include erythropoietin, thrombopoietin, granulocyte-colony stimulating factor, granulocyte macrophage-colony stimulating factor, leptin, platelet-derived growth factors (e.g., platelet-derived growth factor B), keratinocyte growth factor, bone morphogenic protein 2, bone morphogenic protein 7, insulin, glucagon-like peptide-1, human growth hormone, Factor VII, Factor VIII, Factor IX, relaxins (e.g., relaxin-2), interferons (e.g., interferon-α, interferon-β, interferon-γ), interleukins (e.g., interleukin-2, interleukin-4, interleukin-10, interleukin-11, interleukin-12, interleukin-18, interleukin-21), CC subfamily chemokines, CXC subfamily chemokines, C subfamily chemokines, and CX3C subfamily chemokines. Antibodies may be selected from various antibody embodiments described herein. Particularly suitable antibodies include genetically engineered antibodies such as, for example, chimeric antibodies, humanized antibodies, single-chain antibodies (e.g., a single-chain Fv (scFv)), and bispecific antibodies. In some variations, the mRNA encodes an antibody that specifically binds and antagonizes a protein selected from vascular endothelial growth factor A (VEGF-A), tumor necrosis factor α (TNFα), interleukin-6 (IL-6), interleukin-17A (IL-17A), interleukin-17F (IL-17F), interleukin-21 (IL-21), interleukin-23 (IL-23), cytotoxic T-lymphocyte-associated protein 4 (CTLA-4), and programmed cell death protein 1 (PD-1).

In certain embodiments, the mRNA encodes ornithine transcarbamylase (OTC). In particular variations, the mRNA molecule encodes an OTC protein comprising an amino acid sequence having at least 90% or at least 95% sequence identity with residues 35-354 of SEQ ID NO: 1 (e.g., at least 96%, at least 97%, at least 98%, at least 99%, at least 99.5%, or 100% sequence identity with residues 35-354 of SEQ ID NO: 1). To direct an encoded OTC protein to the mitochondria of the cell, an mRNA molecule encoding the OTC protein includes a sequence encoding a mitochondrial targeting signal peptide (also referred to herein as a "mitochondrial leader sequence"). The mitochondrial leader sequence may be that of a native OTC protein (e.g., residues 1-34 of SEQ ID NO: 1 (a native human mitochondrial leader sequence)), derived from another protein comprising a mitochondrial targeting signal peptide, or synthesized de novo. An engineered cleavage site may be included at the junction between the mitochondrial leader sequence and the remainder of the polypeptide to optimize proteolytic processing in the cell. The mitochondrial leader sequence is operably linked to the mRNA sequence encoding the mature OTC protein, i.e., the two sequences are joined in the correct reading frame and positioned to direct the newly synthesized polypeptide to the mitochondria of a cell. Mitochondrial leader sequences are commonly positioned at the amino terminus of the protein. In specific variations, the encoded OTC protein with a mitochondrial leader sequence has an amino acid sequence as set forth in SEQ ID NO: 1.

In other embodiments, the mRNA encodes argininosuccinate lyase (ASL) or argininosuccinate synthetase (ASS1). In particular variations, the mRNA molecule encodes an ASL protein comprising an amino acid sequence having at least 90% or at least 95% sequence identity with SEQ ID NO:2 (e.g., at least 96%, at least 97%, at least 98%, at least 99%, at least 99.5%, or 100% sequence identity with SEQ ID NO:2). In other variations, the mRNA molecule encodes an ASS1 protein comprising an amino acid sequence having at least 90% or at least 95% sequence identity with SEQ ID NO:3 (e.g., at least 96%, at least 97%, at least 98%, at least 99%, at least 99.5%, or 100% sequence identity with SEQ ID NO:3).

In yet other embodiments, the mRNA encodes methylmalonyl CoA mutase (MUT), propionyl CoA carboxylase subunit A (PCCA), propionyl CoA carboxylase subunit B (PCCB), or a subunit of branched-chain ketoacid dehydrogenase (BCKDH). In particular variations, the mRNA molecule encodes a MUT protein comprising an amino acid sequence having at least 90% or at least 95% sequence identity with residues 33-750 of SEQ ID NO:4 (e.g., at least 96%, at least 97%, at least 98%, at least 99%, at least 99.5%, or 100% sequence identity with residues 33-750 of SEQ ID NO:4). In other variations, the mRNA molecule encodes a PCCA protein comprising an amino acid sequence having at least 90% or at least 95% sequence identity with residues 53-728 of SEQ ID NO:5 (e.g., at least 96%, at least 97%, at least 98%, at least 99%, at least 99.5%, or 100% sequence identity with residues 53-728 of SEQ ID NO:5). In other variations, the mRNA molecule encodes a PCCB protein comprising an amino acid sequence having at least 90% or at least 95% sequence identity with residues 29-539 of SEQ ID NO:6 (e.g., at least 96%, at least 97%, at least 98%, at least 99%, at least 99.5%, or 100% sequence identity with residues 29-539 of SEQ ID NO:6). To direct an encoded MUT, PCCA, PCCB, or BCKDH subunit protein to the mitochondria of the cell, an mRNA molecule encoding the protein includes a sequence encoding a mitochondrial leader sequence. The mitochondrial leader sequence may be that of a native protein (e.g., residues 1-32 of SEQ ID NO:4 (a native human MUT mitochondrial leader sequence), residues 1-52 of SEQ ID NO:5 (a native human PCCA mitochondrial leader sequence), or residues 1-28 of SEQ ID NO:6 (a native human PCCB mitochondrial leader sequence)), derived from another protein comprising a mitochondrial targeting signal peptide, or synthesized de novo. An engineered cleavage site may be included at the junction between the mitochondrial leader sequence and the remainder of the polypeptide to optimize proteolytic processing in the cell. The mitochondrial leader sequence is operably linked to the mRNA sequence encoding the mature MUT, PCCA, PCCB, or BCKDH subunit protein, i.e., the two sequences are joined in the correct reading frame and positioned to direct the newly synthesized polypeptide to the mitochondria of a cell. In specific variations, the encoded MUT protein with a mitochondrial leader sequence has an amino acid sequence as set forth in SEQ ID NO:4, the encoded PCCA protein with a mitochondrial leader sequence has an amino acid sequence as set forth in SEQ ID NO:5, or the encoded PCCB protein with a mitochondrial leader sequence has an amino acid sequence as set forth in SEQ ID NO:6.

Thus, in certain embodiments of the present invention, an mRNA is formulated into a lipid nanoparticle comprising a branched PEG-lipid. In some embodiments of the present disclosure, the LNP comprises a cationic lipid, a branched PEG-lipid of Formula I as described herein, cholesterol, and an anionic lipid. The lipids are typically solubilized, e.g., in 100% ethanol, typically from 20 mg/mL to 200 mg/mL individually and then mixed together to obtain, for example, the following lipid ratio ranges: 20-60 mol % cationic lipid, 0-50 mol % anionic lipid, 0-40 mol % cholesterol, and 0.1-15 mol % branched PEG-lipid. A lipid mixture in ethanol is typically prepared in a range from 1 mg/mL to 40 mg/mL. The mRNA may be prepared using a standard in vitro transcription reaction according to well-known procedures. The mRNA solution is typically diluted in an aqueous/isotonic buffer at about normal physiological pH (e.g., pH 7.4) at a concentration from 0.01 mg/mL to 1 mg/mL. The lipid mixture in ethanol and mRNA aqueous solution may then be mixed together at a 1:3 ratio of lipid:mRNA using a microfluidic device. Lipid concentrations, mRNA concentrations, and mixing ratio can be adjusted to prepare lipid:mRNA formulations at N:P ratios (nitrogen to phosphorous ratio between the cationic lipid and the mRNA) from 0.5 to 40. After an incubation time, the mRNA/LNP is typically dialyzed overnight in an aqueous/isotonic buffer. The formulations may be used for delivery of the mRNA to target cells (e.g., the formulations may be contacted with cells in vitro or administered to a subject, such as mice, in vivo). In some variations comprising in vivo delivery, a membrane-destabilizing polymer is also administered to the subject, as disclosed further herein; membrane-destabilizing polymers and their use for enhancing delivery of therapeutic agents encapsulated in LNPs are also disclosed in International PCT Application Publication No. WO 2016/118697, incorporated by reference herein in its entirety. In some variations, the mRNA/LNP and membrane-destabilizing polymer are co-injected as a single composition; in other variations, a sequential injection of a membrane-destabilizing polymer is given, e.g., approximately 1 to 15 minutes following the mRNA/LNP. The polymer may be solubilized in an aqueous/isotonic buffer at about normal physiological pH (e.g., pH 7.4). Particularly suitable concentrations of solubilized polymer range from 1 mg/mL to 50 mg/mL.

In further variations where an mRNA is formulated into a lipid nanoparticle and delivered in accordance with the present disclosure, the mRNA/LNP is formulated so as to reduce or eliminate in a subject an undesired immune response against the mRNA. For example, RNA transcribed in vitro typically contains multiple contaminants, including short RNAs produced by abortive initiation events, and double-stranded (ds)RNAs generated by self-complementary 3' extension, RNA-primed transcription from RNA templates and RNA-dependent RNA polymerase activity.

See Karikó et al., *Nucleic Acids Research,* 2011, 1-10, doi:10.1093/nar/gkr695. These dsRNA contaminants can be immunostimulatory through binding and activating a number of innate immune receptors, including toll-like receptors TLR3, TLR7, TLR8, retinoic acid-inducible gene I (RIG-I), and RNA-dependent protein kinase (PKR).

To reduce or eliminate a potential immune response against mRNA encapsulated in an LNP, as well as to reduce or eliminate a potential rapid plasma clearance following repeat administrations of the mRNA/LNP, certain variations of the mRNA or mRNA/LNP formulation may be used. For example, the mRNA may be purified (e.g., using HPLC purification) to remove immunostimulatory dsRNA contaminants. HPLC-purified mRNA has been shown to avoid stimulating type I interferon cytokines (IFN-α, IFN-3 and TNF-α). See Karikó et al., supra. In some variations, one or more uridines in the mRNA sequence are substituted with pseudouridine or N1-methyl-pseudouridine, which has been shown to avoid activating innate immune receptors (see id.). In other embodiments, the mRNA sequence may be codon optimized to remove or reduce the number of uridines, which can activate the innate immune response. Any one or more of these variations may be used for in vivo delivery of mRNA and related methods of treatment in accordance with the present disclosure.

Methods for purifying mRNA are generally known in the art and may be used to prepare mRNA for formulation with a lipid nanoparticle in accordance with the present disclosure. For example, after isolation of in vitro-transcribed (IVT) mRNA constructs from transcription mixtures, further purification of the material may be performed using ion-pair/reversed-phase HPLC or anion-exchange HPLC. These techniques may remove length-based sequence variants and other nucleic acid impurities when performed under denaturing conditions. Ion-pair/reversed phase HPLC utilizes a traditional C8 or C18 stationary phase (alternatively, polymeric-based media may be used) and a mobile phase system containing a suitable ion-pairing agent such as triethylammonium acetate. The material is traditionally eluted using an acetonitrile gradient. The purification occurs under denaturing conditions (typically at temperatures >55° C.). Strong or weak anion-exchange HPLC may also be utilized. For example, a strong anion exchange column (utilizing a quaternary ammonium in the stationary phase) may be used with a mobile phase system buffered at neutral to basic pH (e.g., 20 mM sodium phosphate at pH 8.0), with elution modulated by gradient addition of a stronger salt solution (e.g., 1M sodium bromide) to displace interaction of the nucleic acid backbone with the column stationary phase. Because the strong ionic environment increases the stability of the mRNA conformation (and therefore confers a higher Tm relative to the Ion-pair/reversed phase separations), the purification may require a higher temperature and/or pH environment to fully melt out secondary or double-stranded structures.

In another aspect, the present invention provides a composition comprising (a) a lipid nanoparticle as described herein and (b) a membrane-destabilizing polymer. In a related aspect, the present invention provides a delivery system comprising (a) a lipid nanoparticle as described herein and (b) a membrane-destabilizing polymer. Such compositions and delivery systems are particularly useful in methods for in vivo delivery of therapeutic or diagnostic agents to the cytosol of a target cell in a subject (e.g., in vivo cytosolic delivery of the agent to a plurality of target cells within a target tissue). Methods, compositions, and delivery systems utilizing a combination of a membrane destabilizing polymer and a separate LNP "carrier" formulated with a therapeutic or diagnostic agent are also disclosed in International PCT Application Publication No. WO 2016/118697, incorporated by reference herein in its entirety.

Typically, where a membrane-destabilizing polymer is added to a lipid nanoparticle formulation in accordance with the present disclosure (e.g., for making a composition comprising (a) a lipid nanoparticle comprising a therapeutic or diagnostic agent and (b) a membrane-destabilizing polymer), the polymer is not contained within the lipid nanoparticle. In certain embodiments of the various aspects disclosed herein, the membrane-destabilizing polymer forms a nanoparticle that is compositionally distinct from the lipid nanoparticle. For example, where the membrane-destabilizing polymer is a polymer comprising hydrophilic and hydrophobic segments, the polymer may form a micelle or micelle-like particle in aqueous solution.

In accordance with aspects of the present invention comprising a combination of (a) a lipid nanoparticle comprising a branched PEG-lipid as described herein and (b) a membrane-destabilizing polymer, the membrane-destabilizing polymer is either co-formulated with the lipid nanoparticle containing the therapeutic or diagnostic agent, for co-injection into a subject, or is separately formulated for separate injection (e.g., sequential injection) of the LNP and membrane-destabilizing polymer. Typically, for co-injection variations, the lipid nanoparticle and membrane-destabilizing polymer are initially formulated as separate compositions and then mixed together into a single composition prior to administration (typically within one hour prior to administration, more typically within 30 minutes prior to administration, and preferably within 15 minutes or within five minutes prior to administration). The membrane-destabilizing polymer elicits a permeability change in a cellular membrane structure (e.g., an endosomal membrane) so as to permit macromolecules or biomolecules, or small molecules, to enter a cell or to exit a cellular vesicle (e.g., an endosome or lysosome). A variety of membrane-destabilizing polymers are generally known in the art and may be used in accordance with the present methods described herein. Known types of membrane-destabilizing polymers include, for example, copolymers such as amphipathic copolymers, polycationic or amphipathic peptides, membrane active toxins, and viral fusogenic peptides. Certain types of particularly suitable membrane-destabilizing polymers are described, e.g., in International PCT Application Publication Nos. WO 2009/140427, WO 2009/140429, and WO 2016/118697, each incorporated by reference herein in its entirety.

In some variations, a membrane-destabilizing polymer includes a targeting moiety that specifically binds to the surface of a target cell. Suitable targeting moieties include moieties disclosed herein in the context of branched PEG molecules; such moieties may also be readily incorporated in a membrane-destabilizing polymer for targeting of the polymer to a target cell. In particular variations, a targeting moiety includes an N-acetylgalactosamine (GalNAc) sugar residue.

In some embodiments, a membrane-destabilizing polymer is or comprises a membrane-destabilizing peptide. Exemplary membrane-destabilizing peptides are disclosed in International PCT Application Publication No. WO 2016/118697, incorporated by reference herein.

The membrane-destabilizing polymer can be a pH sensitive polymer having membrane-destabilizing activity at a desired pH. In some embodiments, membrane-destabilizing polymers (e.g., copolymers such as block copolymers) provided herein are membrane destabilizing (e.g., in an aqueous medium) at an endosomal pH. In some embodiments, the membrane-destabilizing polymers are membrane destabilizing (e.g., in an aqueous medium) at a pH of about 6.5 or lower, preferably at a pH ranging from about 5.0 to about 6.5, or at a pH of about 6.2 or lower, preferably at a pH ranging from about 5.0 to about 6.2, or at a pH of about 6.0 or lower, preferably at a pH ranging from about 5.0 to about 6.0.

Typically, in each case, the membrane-destabilizing polymer can have membrane destabilizing activity at a desired quantity (e.g., concentration) of polymer. A membrane-destabilizing characteristic of a polymer can be determined by suitable assays known in the art. For example, membrane-destabilizing activity of a polymer can be determined in an in vitro cell assay such as the red blood cell hemolysis assay or a liposomal leakage assay. An endosomolytic polymer activity can be determined in an in vitro cell assay.

In general, the membrane-destabilizing polymer is composed of monomeric residues with particular properties. For example, the polymer may have amines that are primary, secondary, tertiary, or quaternary and which drive interactions of the polymer with membranes. These amines may be permanently charged or have $pK_a$s ranging from 4 to 14. In particular, these $pK_a$s may be between 4.5 and 7.5 such that they can undergo acid-base reactions in endosome. The polymers may also have hydrophobic groups to further enhance interaction with membranes. The polymer may also have carboxylic functional groups with $pK_a$s in the range of 4.0 to 7.5.

In certain embodiments, a membrane-destabilizing polymer includes one or more monomeric species selected from anionic, cationic, hydrophobic, and hydrophilic monomeric residues. Anionic monomeric residues comprise a species charged or chargeable to an anion, including a protonatable anionic species. Anionic monomeric residues can be anionic at an approximately neutral pH of 7.2-7.4. Cationic monomeric residues comprise a species charged or chargeable to a cation, including a deprotonatable cationic species. Cationic monomeric residues can be cationic at an approximately neutral pH of 7.2-7.4. Hydrophobic monomeric residues comprise a hydrophobic species. Hydrophilic monomeric residues comprise a hydrophilic species.

In some variations, a membrane-destabilizing polymer is or comprises at least one polymer chain that is hydrophobic. In some such embodiments, the polymer is or comprises at least one polymer chain that includes a plurality of anionic monomeric residues. In this regard, for example, the polymer may be or comprise at least one polymer chain that includes (i) a plurality of hydrophobic monomeric residues having a hydrophobic species, and (ii) a plurality of anionic monomeric residues that are preferably anionic at approximately neutral pH, and substantially neutral or non-charged at an endosomal pH or weakly acidic pH.

In such aforementioned embodiments, the polymer can further include a plurality of cationic species. Accordingly, for example, the polymer can be or comprise at least one polymer chain that includes a plurality of anionic monomeric residues (e.g., having species that are anionic at about neutral pH), and a plurality of hydrophobic monomeric residues (e.g., having hydrophobic species), and optionally a plurality of cationic monomeric residues (e.g., having species that are cationic at about neutral pH). In such embodiments, and as discussed further below, the polymer can be or comprise at least one polymer chain that is charge modulated, and preferably charge balanced—being substantially overall neutral in charge.

In some embodiments, membrane-destabilizing polymer is a block copolymer comprising a membrane-destabilizing segment (e.g., as a block or region of the polymer). The membrane-destabilizing segment can comprise a plurality of anionic monomeric residues (e.g., having species that are anionic at about neutral pH), and a plurality of hydrophobic monomeric residues (e.g., having hydrophobic species), and optionally a plurality of cationic monomeric residues (e.g., having species that are cationic at about neutral pH). In such embodiments, the segment (e.g., block or region) can be hydrophobic considered in the aggregate. In such embodiments, the block copolymer may further comprise a hydrophilic segment.

In some embodiments of a block copolymer comprising a membrane-destabilizing block, the block copolymer includes a first polymer chain defining a first block A of the copolymer and a second, membrane-destabilizing polymer chain defining a second block B of the copolymer. For example, the block copolymer can comprise a first polymer chain defining a first block A of the copolymer, which is hydrophilic, and a second polymer chain defining a second block B of the copolymer that includes (i) a plurality of hydrophobic monomeric residues and (ii) a plurality of anionic monomeric residues being anionic at serum physiological pH and substantially neutral or non-charged at an endosomal pH.

In some embodiments, the membrane-destabilizing polymer is or comprises at least one polymer chain that includes a plurality of anionic monomeric residues, a plurality of hydrophobic monomeric residues, and optionally a plurality of cationic monomeric residues in ratios adapted to enhance membrane destabilizing or membrane destabilizing activity of the polymer chain. For example and without limitation, in such embodiments at pH 7.4, the ratio of hydrophobic:(anionic+cationic) species ranges from about 1:2 to about 3:1, and the ratio of anionic:cationic species ranges from about 1:0 to about 1:5. In other such embodiments, at pH 7.4, the ratio of hydrophobic:(anionic+cationic) species ranges from about 1:1 to about 2:1, and the ratio of anionic:cationic species ranges from about 4:1 to about 1:5.

In some embodiments, the membrane-destabilizing polymer is or comprises at least one polymer chain that includes a plurality of cationic monomeric residues, a plurality of hydrophobic monomeric residues, and optionally a plurality of anionic monomeric residues in ratios adapted to enhance membrane destabilizing or membrane destabilizing activity of the polymer chain. For example and without limitation, in such embodiments at pH 7.4, the ratio of hydrophobic:(cationic+anionic) species ranges from about 1:2 to about 3:1, and the ratio of cationic:anionic species ranges from about 1:0 to about 1:20. In other such embodiments, at pH 7.4, the ratio of hydrophobic:(cationic+anionic) species ranges from about 1:1 to about 2:1, and the ratio of cationic:anionic species ranges from about 1:0 to about 1:5.

In some embodiments, the membrane-destabilizing polymer is or comprises at least one polymer chain that includes a plurality of cationic monomeric residues, and optionally a plurality of hydrophobic monomeric residues in ratios adapted to enhance membrane destabilizing or membrane destabilizing activity of the polymer chain. For example and without limitation, in such embodiments at pH 7.4, the ratio of hydrophobic:cationic species ranges from about 0:1 to about 5:1. In other such embodiments, at pH 7.4, the ratio of hydrophobic:cationic species ranges from about 0:1 to about 2:1.

Generally, the membrane-destabilizing polymer can be or comprise at least one polymer chain that is charge modulated, for example including hydrophobic monomeric residues together with both anionic monomeric residues and cationic monomeric residues. The relative ratio of anionic monomeric residues and cationic monomeric residues can be controlled to achieve a desired overall charge characteristic. In typical embodiments, for example, such polymer or polymer chain can be charge balanced—having a substantially neutral overall charge in an aqueous medium at physiological pH (e.g., pH 7.2 to 7.4).

Embodiments comprising a block copolymer, in which at least one block is or comprises a membrane-destabilizing polymer, such as a hydrophobic membrane-destabilizing polymer, can comprise one or more further polymer chains as additional blocks of the block copolymer. Generally, such further polymer blocks are not narrowly critical, and can be or comprise a polymer chain which is hydrophilic, hydrophobic, amphiphilic, and in each case, which is neutral, anionic or cationic in overall charge characteristics.

In some embodiments, the membrane-destabilizing polymer is or comprises a polymer chain that is adapted to facilitate one or more additional constituent components and/or functional features. For example, such polymer chain can comprise an end functional group (e.g., on the alpha end or omega end of the polymer chain) adapted for covalently linking, directly or indirectly, to a targeting ligand (affinity reagent) or a shielding agent. Additionally or alternatively, such polymer chain can comprise one or more monomeric residues having a pendant functional group adapted for conjugating to an agent. Such conjugatable monomeric residues can be effected for covalently linking, directly or indirectly, to an affinity reagent, a shielding agent, or other biomolecular agent. Additionally or alternatively, such polymer chain can comprise one or more monomeric residues having a shielding species. For example, shielding monomeric residues can be derived directly from a polymerization reaction which includes polymerizable monomers comprising a shielding moiety. Shielding agents include poly ethylene glycol monomers and/or polymers. Additionally or alternatively, such polymer chain can comprise one or more monomeric residues having a two or more pendant functional groups suitable for cross-linking between polymer chains. Such cross-linking monomeric residues can be a constituent moiety of a cross-linked polymer or polymer chain, as derived directly from a polymerization reaction that includes one or more polymerizable monomers comprising a multi-functional (e.g., bis-functional) cross-linking monomer.

Generally, one or more blocks of a block copolymer can be a random copolymer block which comprises two or more compositionally distinct monomeric residues.

Generally, a single monomeric residue can include multiple moieties having different functionality—e.g., can comprise hydrophobic species as well as anionic species, can comprise hydrophobic species as well as cationic species, or can comprise anionic species as well as cationic species. Hence, in any embodiment, the polymer can be or can comprise a polymer comprising a monomeric residue such as an anionic hydrophobic monomeric residue—which includes hydrophobic species and anionic species (e.g., species that are anionic at about neutral pH).

In typical variations, anionic monomeric residues comprise a protonatable anionic species. Considered in the aggregate, as incorporated into a polymer chain, such anionic monomeric residues can be substantially anionic at a pH of or greater than 7.0 and substantially neutral (non-charged) at pH of or less than 6.0. Preferably, such anionic monomeric residues have a $pK_a$ ranging from about 4 to about 6.8, (e.g., from about 4 to about 6, from about 4 to about 5, from about 5 to about 6, from about 5 to about 6.8, or from about 5.5 to about 6.8). Anionic monomeric residues can independently comprise a plurality of monomeric residues having a protonatable anionic species selected from carboxylic acid, sulfonamide, boronic acid, sulfonic acid, sulfinic acid, sulfuric acid, phosphoric acid, phosphinic acid, and phosphorous acid groups, and combinations thereof. Particularly suitable anionic monomeric residues may be derived from polymerization of a ($C_2$-$C_8$) alkylacrylic acid.

Hydrophobic monomeric residues can be charged or noncharged, generally. Some embodiments include neutral (non-charged) hydrophobic monomeric residues. In some embodiments, polymer chains can independently comprise a plurality of monomeric residues having a hydrophobic species selected from ($C_1$-$C_{18}$) alkyl (e.g., ($C_2$-$C_8$) alkyl), ($C_1$-$C_{18}$) alkenyl (e.g., ($C_2$-$C_8$) alkenyl), ($C_1$-$C_{18}$) alkynyl (e.g., ($C_2$-$C_8$) alkynyl), aryl, heteroaryl, and cholesterol (each of which may be optionally substituted). In certain embodiments, the plurality of monomeric residues can be derived from polymerization of ($C_1$-$C_{18}$) alkyl-ethacrylate (e.g., ($C_2$-$C_8$) alkyl-ethacrylate), a ($C_1$-$C_{18}$) alkyl-methacrylate (e.g., ($C_2$-$C_8$) alkyl-methacrylate), or a ($C_1$-$C_{18}$) alkyl-acrylate (e.g., ($C_2$-$C_8$) alkyl-acrylate) (each of which may be optionally substituted).

Cationic monomeric residues can preferably comprise a deprotonatable cationic species. Considered in the aggregate, as incorporated into a polymer chain, such cationic monomeric residues can be substantially cationic at a pH of or greater than 7.0. Preferably, such cationic monomeric residues have a $pK_a$ ranging from about 5.5 to about 9.0 (e.g., from about 6.5 to about 9.0). Cationic monomeric residues can independently comprise a plurality of monomeric residues having a deprotonatable cationic species selected from the group consisting of acyclic amine, acyclic imine, cyclic amine, cyclic imine, and nitrogen-containing heteroaryl. Preferred cationic monomeric residues can be derived from polymerization of, in each case optionally substituted, (N,N-di($C_1$-$C_6$)alkyl-amino($C_1$-$C_5$)alkyl-ethacrylate, N,N-di($C_1$-$C_6$)alkyl-amino($C_1$-$C_6$)alkyl-methacrylate, or N,N-di($C_1$-$C_6$)alkyl-amino($C_1$-$C_6$)alkyl-acrylate.

In some embodiments, a pH-sensitive membrane-destabilizing polymer includes a random copolymer chain, such as, e.g., a random copolymer chain comprising two or more monomeric residue species as described above. For example, in particular variations, the random copolymer chain has monomeric residues derived from polymerization of propyl acrylic acid, N,N-dimethylaminoethylmethacrylate, and butyl methacrylate. In particular embodiments, the pH-sensitive polymer is a block copolymer comprising the random copolymer chain as a membrane-destabilizing polymer block, and further comprising one or more additional blocks (e.g., a hydrophilic block). For example, in some embodiments, the polymer is a diblock copolymer comprising a membrane-destabilizing random copolymer block and a second block, which can be represented by the schematic $[A]_v$-$[B]_w$, where [B] represents the membrane-destabilizing block, [A] represents the second block (e.g., a hydrophilic block or an amphiphilic block), and the letters v and w represent the molecular weight (number average) of the respective blocks in the copolymer. In certain variations of a block copolymer comprising a membrane-destabilizing polymer block and a hydrophilic block, the hydrophilic block is polymerized from both hydrophilic monomers and hydrophobic monomers such that there are more hydrophilic monomeric residues than hydrophobic monomeric residues in the hydrophilic block.

In some variations, a pH-sensitive membrane-destabilizing polymer is a diblock copolymer having a hydrophilic random copolymer block and a hydrophobic random copolymer block, where (i) the hydrophilic block is an amphiphilic block comprising both hydrophilic monomeric residues and hydrophobic monomeric residues, where the number of hydrophilic monomeric residues in the hydrophilic block is greater than the number of hydrophobic monomeric residues, (ii) the hydrophobic block is an amphiphilic, membrane-destabilizing block comprising both hydrophobic monomeric residues and hydrophilic monomeric residues and having an overall hydrophobic character at a pH of about 7.4, and (iii) each of the hydrophilic monomeric residues of the hydrophilic and hydrophobic blocks is independently selected from monomeric residues that are ionic at a pH of about 7.4, monomeric residues that are neutral at a pH of about 7.4, and monomeric residues that are zwitterionic at a pH of about 7.4. In some such embodiments, the monomers used to prepare the diblock copolymer comprise acrylate(s), methacrylate(s), acrylamide(s), and/or methacrylamide(s). In particular variations, the hydrophilic block comprises hydrophilic monomeric residues that are neutral at a pH of about 7.4, and/or the hydrophobic block comprises both hydrophilic monomeric residues that are cationic at a pH of about 7.4 and hydrophilic monomeric residues that are anionic at a pH of about 7.4. Suitable hydrophilic and hydrophobic monomeric residues for use in a diblock copolymer as above are further described herein. In some embodiments, a diblock copolymer as above is a random block copolymer of formula I as set forth herein.

In some variations, a pH-sensitive membrane-destabilizing polymer is a diblock copolymer having a hydrophilic random copolymer block and a hydrophobic random copolymer block, where (i) the hydrophilic block is an amphiphilic block comprising both hydrophilic monomeric residues and hydrophobic monomeric residues and having an overall hydrophilic character at a pH of about 7.4, (ii) the hydrophobic block is an amphiphilic, membrane-destabilizing block comprising both hydrophobic monomeric residues and hydrophilic monomeric residues and having an overall hydrophobic character at a pH of about 7.4, and (iii) each of the hydrophilic monomeric residues of the hydrophilic and hydrophobic blocks is independently selected from monomeric residues that are ionic at a pH of about 7.4, monomeric residues that are neutral at a pH of about 7.4, and monomeric residues that are zwitterionic at a pH of about 7.4. In some such embodiments, the monomers used to prepare the diblock copolymer comprise acrylate(s), methacrylate(s), acrylamide(s), and/or methacrylamide(s).

In certain embodiments, a pH-sensitive polymer is covalently linked to a membrane-destabilizing peptide. For example, the pH-sensitive polymer may include a plurality of pendant linking groups, and a plurality of membrane-destabilizing peptides may be linked to the pH-sensitive polymer via the plurality of pendant linking groups. In some variations, a peptide comprising a cysteine residue at either the amino or carboxyl terminus is conjugated to a monomer containing a disulfide moiety through the cysteine thiol to form a disulfide bridge. Exemplary membrane-destabilizing peptides that may be linked to a polymer are disclosed in International PCT Application Publication No. WO 2016/118697, incorporated by reference herein.

In some embodiments, a pH-sensitive polymer includes a random block copolymer of Formula VII:

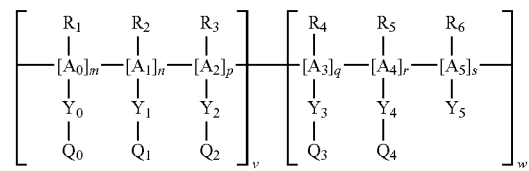

where $A_0$, $A_1$, $A_2$, $A_3$, $A_4$ and $A_5$ are each independently selected from the group consisting of —C—C—, —C(O)(C)$_a$C(O)O—, —O(C)$_a$C(O)—, —O(C)$_b$—, and —CR$_8$—CR$_9$; where tetravalent carbon atoms of $A_0$-$A_5$ that are not fully substituted with $R_1$-$R_6$ and $Y_0$-$Y_5$ are completed with an appropriate number of hydrogen atoms; wherein a and b are each independently 1-4; and where $R_8$ and $R_9$ are each independently selected from the group consisting of —C(O)OH, —C(O)Oalkyl, and —C(O)NR$_{10}$, where $R_8$ and $R_9$ are optionally covalently linked together to form a ring structure (e.g., a cyclic anhydride or cyclic imide);

$Y_5$ is hydrogen or is selected from the group consisting of -(1C-10C)alkyl, -(3C-6C)cycloalkyl, —O-(1C-10C)alkyl, —C(O)O(1C-10C)alkyl, —C(O)NR$_{11}$(1C-10C)alkyl, and -(6C-10C)aryl, any of which is optionally substituted with one or more fluorine atoms;

$Y_0$, $Y_3$, and $Y_4$ are each independently selected from the group consisting of a covalent bond, -(1C-10C)alkyl-, —C(O)O(2C-10C)alkyl-, —OC(O)(1C-10C)alkyl-, —O(2C-10C)alkyl-, —S(2C-10C)alkyl-, and —C(O)NR$_2$(2C-10C)alkyl-;

$Y_1$ and $Y_2$ are each independently selected from the group consisting of a covalent bond, -(1C-18C)alkyl-, -(3C-18C)branched alkyl, —C(O)O(2C-18C)alkyl-, —C(O)O(2C-18C)branched alkyl, —OC(OX)(1C-18C)alkyl-, —OC(OX)(1C-18C)branched alkyl-, —O(2C-18C)alkyl-, —O(2C-18C)branched alkyl-, —S(2C-18C)alkyl-, —S(2C-18C)branched alkyl-, —C(O)NR$_{12}$(2C-18C)alkyl-, and —C(O)NR$_{12}$(2C-18C)branched alkyl-, where any alkyl or branched alkyl group of $Y_1$ or $Y_2$ is optionally substituted with one or more fluorine atoms;

$R_1$, $R_2$, $R_3$, $R_4$, $R_5$, $R_6$, $R_8$, $R_9$, $R_{10}$, $R_{11}$, and $R_{12}$ are each independently hydrogen, —CN, or selected from the group consisting of alkyl, alkynyl, heteroalkyl, cycloalkyl, heterocycloalkyl, aryl and heteroaryl, any of which is optionally substituted with one or more fluorine atoms;

$Q_0$ is a residue selected from the group consisting of residues which are hydrophilic at physiologic pH; O—[(C)$_{2-3}$—O]$_x$—R$_7$; and O—[(C)$_{2-3}$—O]$_x$—C(O)—NR$_{13}$R$_{14}$; where x is 1-48; R$_7$ is —CH$_3$ or —CO$_2$H; and R$_{13}$ and R$_{14}$ are each independently hydrogen, —CN, or selected from the group consisting of alkyl, alkynyl, heteroalkyl, cycloalkyl, heterocycloalkyl, aryl and heteroaryl, any of which is optionally substituted with one or more fluorine atoms;

$Q_1$ and $Q_2$ are each independently absent or selected from a residue which is hydrophilic at normal physiological pH; a conjugatable or functionalizable residue; a residue which is hydrophobic at normal physiological pH; an alkyl group optionally substituted with one or more fluorine atoms; and a branched alkyl group optionally substituted with one or more fluorine atoms;

$Q_3$ is a residue which is positively charged at normal physiological pH;

$Q_4$ is a residue which is negatively charged at normal physiological pH, but undergoes protonation at lower pH;

m is a mole fraction of greater than 0 to 1.0;

n is a mole fraction of 0 to less than 1.0;

p is a mole fraction of 0 to less than 1.0; wherein m+n+p=1;

q is a mole fraction of 0.1 to 0.9;

r is a mole fraction of 0.05 to 0.9;

s is present up to a mole fraction of 0.85; wherein q+r+s=1;

v is from 1 to 25 kDa; and w is from 1 to 50 kDa.

In certain embodiments of a polymer of Formula VII as above, m is greater than n+p. In some such variations, p is 0.

In certain embodiments of a polymer of Formula VII as above, n is greater than 0. Particularly suitable polymers of Formula VII where n is greater than 0 include polymers where $R_2$-$A_1$-$Y_1$-$Q_1$ taken together is a monomeric residue having an overall hydrophobic character. In some such variations, the hydrophobic monomer contains an alkyl or branched alkyl group substituted with one or more fluorine atoms (e.g., at least one of $Y_1$ and $Q_1$ contains the alkyl or branched alkyl group as specified in Formula VII for $Y_1$ and $Q_1$, and where the alkyl or branched alkyl group is substituted with the one or more fluorine atoms).

In some variations of a polymer of Formula VII where n is greater than 0, p is 0. In some such embodiments, m is greater than n. For example, m is typically greater than n where $R_2$-$A_1$-$Y_1$-Q, taken together is a monomeric residue having an overall hydrophobic character.

In some specific embodiments of a polymer of Formula VII, the ratio of w:v ranges from about 1:1 to about 5:1, or from about 1:1 to about 2:1.

Exemplary membrane-destabilizing polymers can be or comprise a polymer chain which is a random copolymer represented as Formula VII, optionally with one or more counterions.

In certain embodiments, the constitutional units of the second block of Formula VII are derived from the polymerizable monomers N,N-dimethylaminoethylmethacrylate (DMAEMA), propylacrylic acid (PAA) and butyl methacrylate (BMA).

In certain embodiments comprising a pH-sensitive polymer of formula VII, the pH-sensitive polymer is a polymer of Formula VIII:

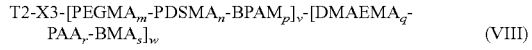
$$\text{T2-X3-[PEGMA}_m\text{-PDSMA}_n\text{-BPAM}_p]_v\text{-[DMAEMA}_q\text{-PAA}_r\text{-BMA}_s]_w \quad (VIII)$$

where

PEGMA is polyethyleneglycol methacrylate residue with 2-20 ethylene glycol units;

PDSMA is pyridyl disulfide methacrylate residue;

BPAM is 2-[2-Boc amino ethoxy] ethyl methacrylate residue;

BMA is butyl methacrylate residue;

PAA is propyl acrylic acid residue;

DMAEMA is dimethylaminoethyl methacrylate residue;

m is a mole fraction of 0.6 to 1;

n is a mole fraction of 0 to 0.4 (e.g., 0 to 0.2);

p is a mole fraction of 0 to 0.4 (e.g., 0 to 0.2); m+n+p=1;

q is a mole fraction of 0.2 to 0.75;

r is a mole fraction of 0.05 to 0.6;

s is a mole fraction of 0.2 to 0.75;

q+r+s=1;

v is 1 to 25 kDa;

w is 1 to 25 kDa;

T2 is absent or is a targeting moiety; and

X3 is absent or is a linking moiety.

In other embodiments comprising a pH-sensitive polymer of Formula I, the pH-sensitive polymer is a polymer of Formula IX:

$$\text{T2-X3-[PEGMA}_m\text{-M2}_n]_v\text{-[DMAEMA}_q\text{-PAA}_r\text{BMA}_s]_w \quad (IX)$$

where

PEGMA is polyethyleneglycol methacrylate residue with 2-20 ethylene glycol units;

M2 is a methacrylate residue selected from the group consisting of
a (C4-C18)alkyl-methacrylate residue;
a (C4-C18)branched alkyl-methacrylate residue;
a cholesteryl methacrylate residue;
a (C4-C18)alkyl-methacrylate residue substituted with one or more fluorine atoms; and
a (C4-C18)branched alkyl-methacrylate residue substituted with one or more fluorine atoms;

BMA is butyl methacrylate residue;

PAA is propyl acrylic acid residue;

DMAEMA is dimethylaminoethyl methacrylate residue;

m and n are each a mole fraction greater than 0, wherein m is greater than n and m+n=1;

q is a mole fraction of 0.2 to 0.75;

r is a mole fraction of 0.05 to 0.6;

s is a mole fraction of 0.2 to 0.75;

q+r+s=1;

v is 1 to 25 kDa;

w is 1 to 25 kDa;

T2 is absent or is a targeting moiety; and

X3 is absent or is a linking moiety.

Particularly suitable M2 methacrylate residues for use in a polymer of Formula IX include 2,2,3,3,4,4,4-heptafluorobutyl methacrylate residue; 3,3,4,4,5,6,6,6-octafluoro-5 (trifluoromethyl)hexyl methacrylate residue; 2,2,3,3,4,4,5,5, 6,6,7,7,8,8,8-pentadecafluorooctyl 2-methylacrylate residue; 3,3,4,4,5,5,6,6,6-nonafluorohexyl methacrylate residue (also referred to as 2-propenoic acid, 2-methyl-, 3,3,4,4,5,5,6,6,6-nonafluorohexyl ester residue); 3,3,4,4,5,5, 6,6,7,7,8,8,8-tridecafluorooctyl methacrylate residue; 1,1,1-trifluoro-2-(trifluoromethyl)-2-hydroxy-4-methyl-5-pentyl methacrylate residue; 2-[(1',1',1'-trifluoro-2'-(trifluoromethyl)-2'-hydroxy)propyl]-3-norbornyl methacrylate residue; 2-ethylhexyl methacrylate residue; butyl methacrylate residue; hexyl methacrylate residue; octyl methacrylate residue; n-decyl methacrylate residue; lauryl methacrylate residue; myristyl methacrylate residue; stearyl methacrylate residue; cholesteryl methacrylate residue; ethylene glycol phenyl ether methacrylate residue; 2-propenoic acid, 2-methyl-, 2-phenylethyl ester residue; 2-propenoic acid, 2-methyl-, 2-[[(1,1-dimethylethoxy)carbonyl]amino]ethyl ester residue; 2-propenoic acid, 2-methyl-, 2-(1H-imidazol-1-yl)ethyl ester residue; 2-propenoic acid, 2-methyl-, cyclohexyl ester residue; 2-propenoic acid, 2-methyl-, 2-[bis(1-methylethyl)amino]ethyl ester residue; 2-propenoic acid, 2-methyl-, 3-methylbutyl ester residue; neopentyl methacrylate residue; tert-butyl methacrylate residue; 3,3,5-trimethyl cyclohexyl methacrylate residue; 2-hydroxypropyl methacrylate residue; 5-nonyl methacrylate residue; 2-butyl-1-octyl methacrylate residue; 2-hexyl-1-decyl methacrylate residue; and 2-(tert-butyl amino)ethyl methacrylate residue.

In particular variations of a pH-sensitive polymer of Formula VIII or Formula IX, PEGMA has 4-5 ethylene glycol units or 7-8 ethylene glycol units. In some embodiments, T2 and X3 are present. T2 may include, for example, an N-acetylgalactosamine (GalNAc) residue, such as, e.g., a tri-GalNAc moiety as described herein. X3 may be a hydrophilic moiety such as, for example, a moiety comprising one or more PEG chains. In some embodiments, X3 is a hydrophilic moiety comprising from 2 to 240 ethylene glycol units (e.g., a polyethylene glycol (PEG) moiety having 2-20 ethylene glycol units).

In specific embodiments, a pH-sensitive polymer of Formula VIII is selected from the group consisting of

  (VIIIa)

  (VIIIb)

where "D" is DMAEMA as defined above for Formula VIII, "P" is PAA as defined above for Formula VIII, "B" is BMA as defined above for Formula VIII, "GalNAc" is an N-acetylgalactosamine residue, "PEG$_{12}$" is a linking moiety comprising a polyethylene glycol having 12 ethylene glycol units, "PEGMA," "PDSMA," and "BPAM" are as defined above for Formula VIII, and the values for m, n, p, q, r, s, v, and w are as defined above for Formula VIII. In particular variations of a polymer of Formula VIIIa, m is from 0.85 to 0.9, n is from 0.1 to 0.15, q is from 0.33 to 0.37, r is from 0.07 to 0.15, s is from 0.52 to 0.57, v is from 3 kDa to 4.5 kDa, and/or w is from 5.5 kDa to 7 kDa. In particular variations of a polymer of Formula VIIIb, m is from 0.75 to 0.8, n is from 0.1 to 0.13, p is from 0.1 to 0.12, q is from 0.25 to 0.37, r is from 0.07 to 0.25, s is from 0.5 to 0.57, v is from 3 kDa to 4.5 kDa, and w is from 5.5 kDa to 7 kDa. In some specific embodiments, the ratio of w:v ranges from about 1:1 to about 5:1, or from about 1:1 to about 2:1.

In specific embodiments, a pH-sensitive polymer of Formula IX is selected from the group consisting of

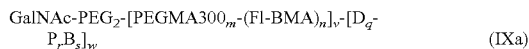  (IXa)

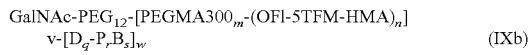  (IXb)

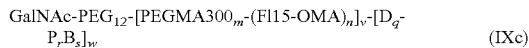  (IXc)

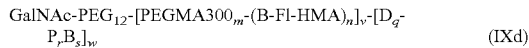  (IXd)

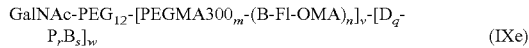  (IXe)

  (IXf)

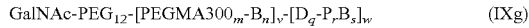  (IXg)

  (IXh)

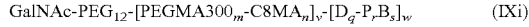  (IXi)

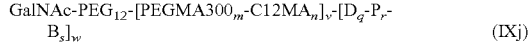  (IXj)

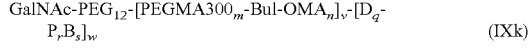  (IXk)

  (IXl)

where "D" is DMAEMA as defined above for Formula IX, "P" is PAA as defined above for Formula IX, "B" is BMA as defined above for Formula IX, "GalNAc" is an N-acetylgalactosamine residue, "PEG$_{12}$" is a linking moiety comprising a polyethylene glycol having 12 ethylene glycol units, "PEGMA" is as defined above for Formula IX, "Fl-BMA" is 2,2,3,3,4,4,4-heptafluorobutyl methacrylate residue, "OFl-5TFM-HMA" is 3,3,4,4,5,6,6,6-octafluoro-5-(trifluoromethyl)hexyl methacrylate residue, "F15-OMA" is 2,2,3,3,4,4,5,5,6,6,7,7,8,8,8-pentadecafluorooctyl 2-methylacrylate residue, "B—Fl-HMA" is 3,3,4,4,5,5,6,6,6-nonafluorohexyl methacrylate residue, "B—Fl-OMA" is 3,3,4,4,5,5,6,6,7,7,8,8,8-tridecafluorooctyl methacrylate residue, "EHMA" is 2-ethylhexyl methacrylate residue, "HMA" is hexyl methacrylate residue, "C8MA" is octyl methacrylate residue, "C12MA" is lauryl methacrylate residue, "2-Bul-OMA" is 2-butyl-1-octyl methacrylate residue, "5-NMA" is 5-nonyl methacrylate residue, and the values for m, n, q, r, s, v, and w are as defined above for Formula IX.

In particular variations of a polymer of Formula IX or any of Formulae IXa-IXl, m is from 0.55 to 0.9 (e.g., from 0.65 to 0.9 or from 0.7 to 0.85), n is from 0.1 to 0.45 (e.g., from 0.1 to 0.35 or from 0.15 to 0.3), q is from 0.25 to 0.4 (e.g., 0.28 to 0.37), r is from 0.07 to 0.15 (e.g., 0.9 to 0.15), s is from 0.5 to 0.65 (e.g., 0.5 to 0.6), v is from 2.5 kDa to 10 kDa (e.g., from 2.5 kDa to 7 kDa, from 2.5 kDa to 5 kDa, from 2.5 kDa to 4.5 kDa, or from 0.29 to 4 kDa), and/or w is from 4 kDa to 9 kDa (e.g., from 4 kDa to 7 kDa, from 4 kDa to 6 kDa, or from 5 kDa to 7 kDa). In some specific embodiments, the ratio of w:v ranges from about 1:0.8 to about 5:1, or from about 1:1 to about 2:1.

In some embodiments, the pH-sensitive, membrane-destabilizing polymer is a diblock copolymer having a hydrophilic random copolymer block and a hydrophobic random copolymer block, where the hydrophilic random copolymer block contains one or more fluorinated monomeric residues. Exemplary random block copolymers containing fluorinated monomers in a hydrophilic block are disclosed in International PCT Application Publication No. WO 2016/118697 (see. e.g., copolymers of formula Ia or Va), incorporated by reference herein.

Generally, a membrane-destabilizing polymer (or polymer chains included as constituent moieties such as blocks of a block copolymer) can include a shielding agent or solubilizing agent. The shielding agent can be effective for improving solubility of the polymer chain. The shielding agent can also be effective for reducing toxicity of the certain compositions. In some embodiments, the shielding agent can be a polymer comprising a plurality of neutral hydrophilic monomeric residues. The shielding polymer can be covalently coupled to a membrane destabilizing polymer, directly or indirectly, through an end group of the polymer or through a pendant functional group of one or more monomeric residues of the polymer. In some embodiments, a plurality of monomeric residues of the polymer chain can have a shielding species; preferably, such shielding species is a pendant moiety from a polymerizable monomer (from which the shielding monomeric residues are derived). For example, the polymer can comprise a plurality of monomeric residues having a pendant group comprising a shielding oligomer. A shielding/solubilizing species may be conjugated to a polymer via a labile linkage such as, for example, a pH-sensitive bond or linker. Particularly suitable pH-sensitive bonds and linkers include hydrazone, acetal, ketal, imine, orthoester, carbonate, and maleamic acid linkages. Labile linkages may be utilized, e.g., for linkage via a plurality of monomeric residues having pendant linking groups or for linkage of a polymer block comprising the shielding species to another polymer block (e.g., linkage of a shielding block to a membrane-destabilizing block).

A preferred shielding/solubilizing polymer can be a polyethylene glycol (PEG) oligomer (e.g., having 20 or less repeat units) or polymer (e.g., having more than 20 repeat units). In certain embodiments, one block of a block copolymer can be or comprises a polyethylene glycol (PEG) oligomer or polymer—for example, covalently coupled to the alpha end or the omega end of the membrane destabilizing block of the copolymer. In another embodiment, a polyethylene glycol (PEG) oligomer or polymer can be covalently coupled to the polymer through a conjugating monomeric residue having a species which includes a functional group suitable for linking, directly or indirectly, to the polyethylene glycol oligomer or polymer. In another embodiment, the monomeric residue can be derived from a polymerizable monomer which includes a polyethylene glycol oligomer pendant to the monomer (e.g., PEGMA).

Exemplary shielding polymers and monomeric residues comprising pendant shielding polymers for coupling to or incorporation in membrane-destabilizing polymers are also disclosed in International PCT Application Publication No. WO 2016/118697, incorporated by reference herein.

Generally, a polymer of a branched PEG-lipid of Formula I or of a branched PEG-protein of Formula IV, or a membrane-destabilizing polymer as discussed herein, can be prepared in any suitable manner. Suitable synthetic methods include, by way of non-limiting example, well-known "living polymerization" methods such as, e.g., cationic, anionic and free radical polymerization.

Using living polymerization, polymers of very low polydispersity or differences in chain length can be obtained. Polydispersity is usually measured by dividing the weight average molecular weight of the polymer chains by their number average molecular weight. The number average molecule weight is sum of individual chain molecular weights divided by the number of chains. The weight average molecular weight is proportional to the square of the molecular weight divided by the number of molecules of that molecular weight. Since the weight average molecular weight is always greater than the number average molecular weight, polydispersity is always greater than or equal to one. As the numbers come closer and closer to being the same, i.e., as the polydispersity approaches a value of one, the polymer becomes closer to being monodisperse in which every chain has exactly the same number of constitutional units. Polydispersity values approaching one are achievable using radical living polymerization. Methods of determining polydispersity such as, without limitation, size exclusion chromatography, dynamic light scattering, matrix-assisted laser desorption/ionization mass spectrometry, and electrospray mass spectrometry are well-known in the art.

Reversible addition-fragmentation chain transfer or RAFT is an exemplary living polymerization technique for use in synthesizing ethylenic backbone polymers. RAFT is well-known to those skilled in the art. RAFT comprises a free radical degenerative chain transfer process. Most RAFT procedures employ thiocarbonylthio compounds such as, without limitation, dithioesters, dithiocarbamates, trithiocarbonates and xanthates to mediate polymerization by a reversible chain transfer mechanism. Reaction of a polymeric radical with the C=S group of any of the preceding compounds leads to the formation of stabilized radical intermediates. These stabilized radical intermediates do not undergo the termination reactions typical of standard radical polymerization but, rather, reintroduce a radical capable of re-initiation or propagation with monomer, reforming the C=S bond in the process. This cycle of addition to the C=S bond followed by fragmentation of the ensuing radical continues until all monomer has been consumed or the reaction is quenched. The low concentration of active radicals at any particular time limits normal termination reactions. In other embodiments, polymers are synthesized by Macromolecular design via reversible addition-fragmentation chain transfer of Xanthates (MADIX) (Direct Synthesis of Double Hydrophilic Statistical Di- and Triblock Copolymers Comprised of Acrylamide and Acrylic Acid Units via the MADIX Process", Daniel Taton et al., *Macromolecular Rapid Communications,* 22:1497-1503, 2001.)

To prepare a branched PEG-lipid or branched PEG-proteins of the present disclosure, a polymer of a branched PEG-lipid of Formula I or a polymer of a branched PEG-protein of Formula IV (e.g., a polymer prepared by "living polymerization" such as, for example, RAFT polymerization), is linked to a lipid or therapeutic protein, respectively, using any suitable means. For example, in some variations, an end of the polymer (e.g., the α end of the polymer) includes a coupling group, and the polymer is conjugated to the lipid or therapeutic protein utilizing the coupling group. Conjugation chemistry approaches are generally well-known in the art and may be adapted for use by the skilled artisan for linking a branched PEG polymer to a lipid or therapeutic protein. Suitable conjugation chemistry approaches include, e.g., amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. A large variety of conjugation chemistries are optionally utilized (see, e.g., Bioconjugation. Aslam and Dent, Eds, Macmillan, 1998 and chapters therein; Hermanson, G. T. (2008). Bioconjugate Techniques: $2^{nd}$ Edition. New York: Academic Press). In particular variations for conjugating a branched PEG polymer to a lipid to make a branched PEG-lipid of Formula I, a coupling group is selected from an activated ester (e.g., an NHS ester or a pentafluorophenyl ester), an acid halide, a carbodiimide, a maleimide, an acetyl halide (α-haloacyl), an epoxide, an aziridine, an aldehyde, a ketone, an activated disulfide (e.g., a pyridyl disulfide), a sulfhydryl, an amine, an alcohol, a hydrazide, a carbonate, a thiocarbonate, an anhydride, an isocyanate, a photo-reactive group (e.g., an aryl azide, a diazirine, or a nitrene), and a hapten. In particular variations for conjugating a branched PEG polymer to a therapeutic protein to make a branched PEG-protein of Formula IV, a coupling group is selected from an amine-reactive group, a thiol-reactive group, a maleimide group, a thiol group, an aldehyde group, an NHS-ester group, an NHS-maleimide group, a haloacetyl group, an iodoacetyl group, a bromoacetyl group, a succinimidyl 4-(N-maleimidomethyl)cyclohexane-1-carboxylate (SMCC) group, a sulfosuccinimidyl 4-(N-maleimidomethyl)cyclohexane-1-carboxylate (Sulfo-SMCC) group, and a carbodiimide group.

In some embodiments of a method of making a branched PEG-lipid or branched PEG-protein where a branched PEG polymer is conjugated to a lipid or therapeutic protein, respectively, utilizing a coupling group, the method includes (a) synthesizing the polymer, where the polymer synthesis step comprises contacting a compound of Formula VIa, VIb, VIc, or VId (VIa)

$$C-X1-S-\underset{S}{\overset{S}{C}}-S-R^1,$$

(VIb)

$$C-X1-S-\underset{S}{\overset{S}{C}}-O-R^2,$$

(VIc)

$$C-X1-S-\underset{S}{\overset{S}{C}}-N\underset{R^4}{\overset{R^3}{\diagdown}},$$

(VId)

$$C-X1-S-\underset{S}{\overset{S}{C}}-\text{Ph},$$

where
C is the coupling group,
X1 is absent or a linking moiety,
$R^1$ is $C_1$-$C_{12}$ alkyl,
$R^2$ is $C_1$-$C_{12}$ alkyl, and
$R^3$ and $R^4$ are each independently H, alkyl, aryl, or heteroaryl,
with a plurality of ethylenic monomers comprising monomers of the formula A1

(A1)

$$\text{CH}_2=C(R^5)-C(O)-R^6-R^7-R^8,$$

where
$R^5$ is H or C1-C6alkyl, $R^6$ is O, S, $NR^9$, OC1-C6alkyl, OC1-C6alkyl-O, OC1-C6alkyl-OC(O)C1-C6alkyl, OC1-C6alkyl-OC(O)C1-C6alkyl-O, OC1-C6alkyl-OC(O)C1-C6alkyl-NH, OC1-C6alkyl-NH, OC1-C6alkyl-NHC(O)C1-C6alkyl, OC1-C6alkyl-NHC(O)C1-C6alkyl-O, OC1-C6alkyl-NHC(O)C1-C6alkyl-NH, $NR^9$(C1-C6alkyl), $NR^9$(C1-C6alkyl)-O, $NR^9$(C1-C6alkyl)-OC(O)C1-C6alkyl, $NR^9$(C1-C6alkyl)-OC(O)C1-C6alkyl-O, $NR^9$(C1-C6alkyl)-OC(O)C1-C6alkyl-NH, $NR^9$(C1-C6alkyl)-NH, $NR^9$(C1-C6alkyl)-NHC(O)C1-C6alkyl, $NR^9$(C1-C6alkyl)-NHC(O)C1-C6alkyl-O, $NR^9$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6alkyl-O, or C1-C6alkyl-NHC(O)C1-C6alkyl-NH,
$R^7$ is $(CH_2CH_2O)_{2\text{-}50}$ (e.g., $(CH_2CH_2O)_{2\text{-}40}$, $(CH_2CH_2O)_{2\text{-}25}$, or $(CH_2CH_2O)_{2\text{-}20}$),
$R^8$ is H or C1-C6alkyl-$R^{10}$,
$R^9$ is H or C1-C6alkyl, and
$R^{10}$ is H, $CO_2H$, $NH_2$, NH(C1-C6alkyl), N(C1-C6alkyl)$_2$, or N(C1-C6alkyl)$_3$, in the presence of a free radical; and (b) conjugating the product of step (a) to a lipid or a therapeutic protein utilizing the coupling group. Suitable A1 monomers include poly (ethylene glycol) methyl ether methacrylates (PEGMAs), poly(ethylene glycol) methyl ether acrylate (PEGAs), poly (ethylene glycol) methyl ether methacrylamides, and poly (ethylene glycol) methyl ether acrylamides. In some embodiments, the plurality of ethylenic monomers further includes a monomer of formula A2

(A2)

$$\text{CH}_2=C(R^{11})-C(O)-R^{12}-R^{13}-R^{14},$$

where
$R^{11}$ is H or C1-C6alkyl,
$R^{12}$ is O, S, $NR^{15}$, O(C1-C6alkyl), O(C1-C6alkyl)-O, O(C1-C6alkyl)-OC(O)C1-C6alkyl, O(C1-C6alkyl)-OC(O)C1-C6alkyl-O, O(C1-C6 alkyl)-OC(O)C1-C6alkyl-NH, O(C1-C6alkyl)-NH, O(C1-C6alkyl)-NHC(O)C1-C6alkyl, O(C1-C6alkyl)-NHC(O)C1-C6alkyl-O, O(C1-C6alkyl)-NHC(O)C1-C6alkyl-NH, $NR^{15}$(C1-C6alkyl), $NR^{15}$(C1-C6alkyl)-O, $NR^{15}$(C1-C6alkyl)-OC(O)C1-C6alkyl, $NR^5$(C1-C6 alkyl)-OC(O)C1-C6alkyl-O, $NR^{15}$(C1-C6alkyl)-OC(O)C1-C6alkyl-NH, $NR^{15}$(C1-C6alkyl)-NH, $NR^{15}$(C1-C6alkyl)-NHC(O)C1-C6alkyl, $NR^{15}$(C1-C6alkyl)-NHC(O)C1-C6alkyl-O, $NR^{15}$(C1-C6alkyl)-NHC(O) C1-C6alkyl-NH, C1-C6alkyl, C1-C6alkyl-O, C1-C6alkyl-OC(O)C1-C6alkyl, C1-C6alkyl-OC(O) C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6 alkyl-O, or C1-C6alkyl-NHC(O)C1-C6alkyl-NH,
$R^{13}$ is H, $(CH_2CH_2O)_{1\text{-}4}$, or C1-C6alkyl
$R^{14}$ is H or C1-C6alkyl-$R^6$,
$R^{15}$ is H or C1-C6alkyl, and
$R^{16}$ is H, $CO_2H$, $NH_2$, NH(C1-C6alkyl), N(C1-C6alkyl)$_2$, or N(C1-C6alkyl)$_3$.

In certain embodiments of a method as above, the plurality of ethylenic monomers consists of the monomers of formula A1. In some variations, the method further includes (c) removing the thio-carbonyl end group of the polymer synthesis step and (d) contacting the product of step (c) with a targeting moiety (e.g., a N-acetyl galactosamine (GalNAc) residue) comprising a thiol-reactive group or free radical.

In other variations of a method of making a branched PEG-lipid or branched PEG-protein, a branched PEG polymer is synthesized directly on a derivative of the lipid or therapeutic protein. For example, in the case of a living polymerization method such as, for example, RAFT polymerization, the lipid or protein derivative may be a chain transfer agent comprising the lipid or therapeutic protein (i.e., a lipid or therapeutic protein derivative that includes a reactive functionality for the polymerization). In some embodiments, a method of making a branched PEG-lipid includes (a) contacting a compound of Formula IIIa, IIIb, IIIc, or IIId

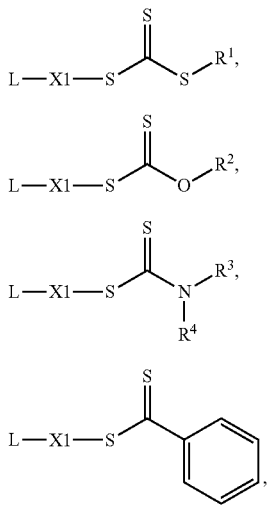

(IIIa)

(IIIb)

(IIIc)

(IIId)

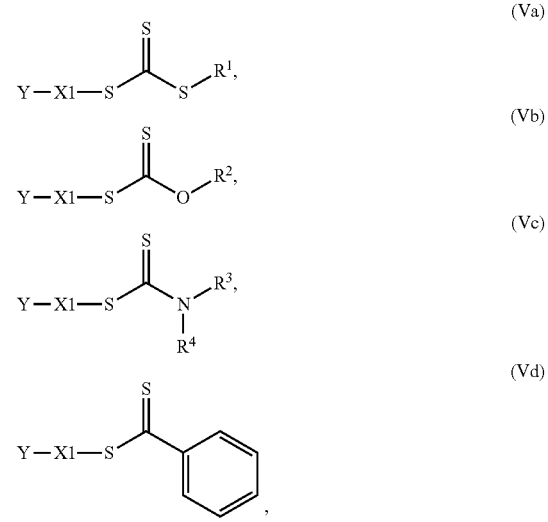

(Va)

(Vb)

(Vc)

(Vd)

where
L is a lipid, X1 is absent or a linking moiety,
$R^1$ is $C_1$-$C_{12}$ alkyl, $R^2$ is $C_1$-$C_{12}$ alkyl, and
$R^3$ and $R^4$ are each independently H, alkyl, aryl, or heteroaryl,
with a plurality of ethylenic monomers comprising monomers of the formula A1

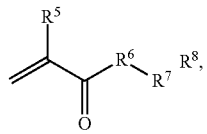

(A1)

where
$R^5$ is H or C1-C6alkyl,
$R^6$ is O, S, $NR^9$, OC1-C6alkyl, OC1-C6alkyl-O, OC1-C6alkyl-OC(O)C1-C6alkyl, OC1-C6alkyl-OC(O)C1-C6alkyl-O, OC1-C6alkyl-OC(O)C1-C6alkyl-NH, OC1-C6alkyl-NH, OC1-C6alkyl-NHC(O)C1-C6alkyl, OC1-C6alkyl-NHC(O)C1-C6alkyl-O, OC1-C6alkyl-NHC(O)C1-C6alkyl-NH, $NR^9$(C1-C6alkyl), $NR^9$(C1-C6alkyl)-O, $NR^9$(C1-C6alkyl)-OC(O)C1-C6alkyl, $NR^9$(C1-C6alkyl)-OC(O)C1-C6alkyl-O, $NR^9$(C1-C6alkyl)-OC(O)C1-C6alkyl-NH, $NR^9$(C1-C6alkyl)-NH, $NR^9$(C1-C6alkyl)-NHC(O)C1-C6alkyl, $NR^9$(C1-C6alkyl)-NHC(O)C1-C6alkyl-O, $NR^9$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6alkyl-O, or C1-C6alkyl-NHC(O)C1-C6alkyl-NH,
$R^7$ is $(CH_2CH_2O)_{2-50}$ (e.g., $(CH_2CH_2O)_{2-40}$, $(CH_2CH_2O)_{2-25}$, or $(CH_2CH_2O)_{2-20}$),
$R^8$ is H or C1-C6alkyl-$R^{10}$,
$R^9$ is H or C1-C6alkyl, and
$R^{10}$ is H, $CO_2H$, $NH_2$, NH(C1-C6alkyl), N(C1-C6alkyl)$_2$, or N(C1-C6alkyl)$_3$,
in the presence of a free radical. In other embodiments, a method of making a branched PEG-protein includes (a) contacting a compound of Formula Va, Vb, Vc, or Vd where
Y is a therapeutic protein,
X1 is absent or a linking moiety,
$R^1$ is $C_1$-$C_{12}$ alkyl,
$R^2$ is $C_1$-$C_{12}$ alkyl, and
$R^3$ and $R^4$ are each independently H, alkyl, aryl, or heteroaryl, with a plurality of ethylenic monomers comprising monomers of the formula A1

(A1)

wherein
$R^5$ is H or C1-C6alkyl,
$R^6$ is O, S, $NR^9$, OC1-C6alkyl, OC1-C6alkyl-O, OC1-C6alkyl-OC(O)C1-C6alkyl, OC1-C6alkyl-OC(O)C1-C6alkyl-O, OC1-C6alkyl-OC(O)C1-C6alkyl-NH, OC1-C6alkyl-NH, OC1-C6alkyl-NHC(O)C1-C6alkyl, OC1-C6alkyl-NHC(O)C1-C6alkyl-O, OC1-C6alkyl-NHC(O)C1-C6alkyl-NH, $NR^9$(C1l-C6alkyl), $NR^9$(C1-C6alkyl)-O, $NR^9$(C1-C6alkyl)-OC(O)C1-C6alkyl, $NR^9$(C1-C6alkyl)-OC(O)C1-C6alkyl-O, $NR^9$(C1-C6alkyl)-OC(O)C1-C6alkyl-NH, $NR^9$(C1-C6alkyl)-NH, $NR^9$(C1-C6alkyl)-NHC(O)C1-C6alkyl, $NR^9$(C1-C6alkyl)-NHC(O)C1-C6alkyl-O, $NR^9$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6alkyl-O, or C1-C6alkyl-NHC(O)C1-C6alkyl-NH,
$R^7$ is $(CH_2CH_2O)_{2-25}$,
$R^8$ is H or C1-C6alkyl-$R^{10}$,
$R^9$ is H or C1-C6alkyl, and
$R^{10}$ is H, $CO_2H$, $NH_2$, NH(C1-C6alkyl), N(C1-C6alkyl)$_2$, or N(C1-C6alkyl)$_3$,
in the presence of a free radical. Suitable A1 monomers, for either method as above for making a branched PEG-lipid or branched PEG-protein, include poly(ethylene glycol)

methyl ether methacrylates (PEGMAs), poly(ethylene glycol) methyl ether acrylate (PEGAs), poly(ethylene glycol) methyl ether methacrylamides, and poly(ethylene glycol) methyl ether acrylamides. In some embodiments of a method as above for making a branched PEG-lipid or branched PEG-protein, the plurality of ethylenic monomers further includes a monomer of formula A2

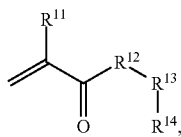
(A2)

where $R^{11}$ is H or C1-C6alkyl, $R^{12}$ is O, S, $NR^{15}$, O(C1-C6alkyl), O(C1-C6alkyl)-O, O(C1-C6alkyl)-OC(O)C1-C6alkyl, O(C1-C6alkyl)-OC(O)C1-C6alkyl-O, O(C1-C6 alkyl)-OC(O)C1-C6alkyl-NH, O(C1-C6alkyl)-NH, O(C1-C6alkyl)-NHC(O)C1-C6alkyl, O(C1-C6alkyl)-NHC(O)C1-C6alkyl-O, O(C1-C6alkyl)-NHC(O)C1-C6alkyl-NH, $NR^{15}$(C1-C6alkyl), $NR^{15}$(C1-C6alkyl)-O, $NR^{15}$(C1-C6alkyl)-OC(O)C1-C6alkyl, $NR^{15}$(C1-C6 alkyl)-OC(O)C1-C6alkyl-O, $NR^{15}$(C1-C6alkyl)-OC(O)C1-C6alkyl-NH, $NR^{15}$(C1-C6alkyl)-NH, $NR^{15}$(C1-C6alkyl)-NHC(O)C1-C6alkyl, $NR^{15}$(C1-C6alkyl)-NHC(O)C1-C6alkyl-O, $NR^{15}$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6 alkyl-O, or C1-C6alkyl-NHC(O)C1-C6alkyl-NH, $R^{13}$ is H, $(CH_2CH_2O)_{1-4}$, or C1-C6alkyl $R^{14}$ is H or C1-C6alkyl-$R^6$, $R^{15}$ is H or C1-C6alkyl, and $R^{16}$ is H, $CO_2H$, $NH_2$, NH(C1-C6alkyl), N(C1-C6alkyl)$_2$, or N(C1-C6alkyl)$_3$.

In certain embodiments of a method as above for making a branched PEG-lipid or branched PEG-protein, the plurality of ethylenic monomers consists of the monomers of formula A1. In some variations, the method further includes (b) removing the thio-carbonyl end group of the product of step (a), and (c) contacting the product of step (b) with a targeting moiety comprising a thiol-reactive group or free radical. In some such variations, the targeting moiety comprises a N-acetyl galactosamine (GalNAc) residue.

In other embodiments of a method of making a branched PEG-lipid or branched PEG-protein as described herein and in which a branched PEG polymer is synthesized directly on a derivative of the lipid or therapeutic protein, the method includes (a) conjugating a lipid or therapeutic protein to a first chain transfer agent comprising a coupling group, where the conjugation step utilizes the coupling group, to produce a second chain transfer agent comprising the lipid or therapeutic protein; and (b) synthesizing the polymer by a living polymerization method that utilizes the second transfer agent. In some such embodiments, the method includes (a) conjugating a lipid or a therapeutic protein to a compound of Formula VIa, VIb, VIc, or VId

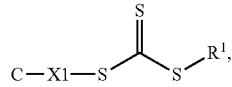
(VIa)

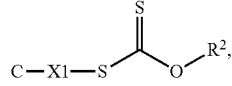
(VIb)

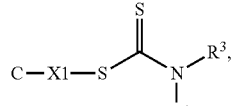
(VIc)

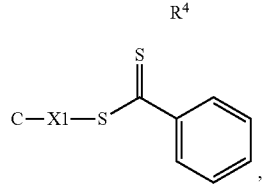
(VId)

where C is a coupling group,
X1 is absent or a linking moiety,
$R^1$ is $C_1$-$C_{12}$ alkyl,
$R^2$ is $C_1$-$C_{12}$ alkyl, and
$R^3$ and $R^4$ are each independently H, alkyl, aryl, or heteroaryl, where the conjugating of the lipid to the compound of Formula VIa, VIb, VIc, or VId utilizes the coupling group, and (b) contacting the product of step (a) with a plurality of ethylenic monomers comprising monomers of the formula A1

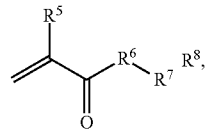
(A1)

where $R^5$ is H or C1-C6alkyl, $R^6$ is O, S, $NR^9$, OC1-C6alkyl, OC1-C6alkyl-O, OC1-C6alkyl-OC(O)C1-C6alkyl, OC1-C6alkyl-OC(O)C1-C6alkyl-O, OC1-C6alkyl-OC(O)C1-C6alkyl-NH, OC1-C6alkyl-NH, OC1-C6alkyl-NHC(O)C1-C6alkyl, OC1-C6alkyl-NHC(O)C1-C6alkyl-O, OC1-C6alkyl-NHC(O)C1-C6alkyl-NH, $NR^9$(C1-C6alkyl), $NR^9$(C1-C6alkyl)-O, $NR^9$(C1-C6alkyl)-OC(O)C1-C6alkyl, $NR^9$(C1-C6alkyl)-OC(O)C1-C6alkyl-O, $NR^9$(C1-C6alkyl)-OC(O)C1-C6alkyl-NH, $NR^9$(C1-C6alkyl)-NH, $NR^9$(C1-C6alkyl)-NHC(O)C1-C6alkyl, $NR^9$(C1-C6alkyl)-NHC(O)C1-C6alkyl-O, $NR^9$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6alkyl-O, or C1-C6alkyl-NHC(O)C1-C6alkyl-NH, $R^7$ is $(CH_2CH_2O)_{2-50}$ (e.g., $(CH_2CH_2O)_{2-40}$, $(CH_2CH_2O)_{2-25}$, or $(CH_2CH_2O)_{2-20}$), $R^8$ is H or C1-C6alkyl-$R^{10}$, $R^9$ is H or C1-C6alkyl, and $R^{10}$ is H, CO$_2$H, NH$_2$, NH(C1-C6alkyl), N(C1-C6alkyl)$_2$, or N(C1-C6alkyl)$_3$, in the presence of a free radical. In particular variations for conjugating a lipid to a compound of Formula VIa, VIb, VIc, or VId, a coupling group is selected from an activated ester (e.g., an NHS ester or a pentafluorophenyl ester), an acid halide, a carbodiimide, a maleimide, an acetyl halide (α-haloacyl), an epoxide, an aziridine, an aldehyde, a ketone, an activated disulfide (e.g., a pyridyl disulfide), a sulfhydryl, an amine, an alcohol, a hydrazide, a carbonate, a thiocarbonate, an anhydride, an isocyanate, a photo-reactive group (e.g., an aryl azide, a diazirine, or a nitrene), and a hapten. In particular variations for coupling a therapeutic protein to a compound of Formula VIa, VIb, VIc, or VId, the coupling group is selected from an amine-reactive group, a thiol-reactive group, a maleimide group, a thiol group, an aldehyde group, an NHS-ester group, an NHS-maleimide group, a haloacetyl group, an iodoacetyl group, a bromoacetyl group, a succinimidyl 4-(N-maleimidomethyl)cyclohexane-1-carboxylate (SMCC) group, a sulfosuccinimidyl 4-(N-maleimidomethyl)cyclohexane-1-carboxylate (Sulfo-SMCC) group, and a carbodiimide group. Suitable A1 monomers include poly(ethylene glycol) methyl ether methacrylates (PEGMAs), poly(ethylene glycol) methyl ether acrylate (PEGAs), poly(ethylene glycol) methyl ether methacrylamides, and poly(ethylene glycol) methyl ether acrylamides. In some embodiments, the plurality of ethylenic monomers further includes a monomer of formula A2

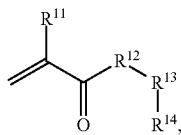

(A2)

where
$R^{11}$ is H or C1-C6alkyl,
$R^{12}$ is O, S, NR$^{15}$, O(C1-C6alkyl), O(C1-C6alkyl)-O, O(C1-C6alkyl)-OC(O)C1-C6alkyl, O(C1-C6alkyl)-OC(O)C1-C6alkyl-O, O(C1-C6 alkyl)-OC(O)C1-C6alkyl-NH, O(C1-C6alkyl)-NH, O(C1-C6alkyl)-NHC(O)C1-C6alkyl, O(C1-C6alkyl)-NHC(O)C1-C6alkyl-O, O(C1-C6alkyl)-NHC(O)C1-C6alkyl-NH, NR$^{15}$(C1-C6alkyl), NR$^{15}$(C1-C6alkyl)-O, NR$^{15}$(C1-C6alkyl)-OC(O)C1-C6alkyl, NR$^{15}$(C1-C6 alkyl)-OC(O)C1-C6alkyl-O, NR$^{15}$(C1-C6alkyl)-OC(O)C1-C6alkyl-NH, NR$^{15}$(C1-C6alkyl)-NH, NR$^{15}$(C1-C6alkyl)-NHC(O)C1-C6alkyl, NR$^{15}$(C1-C6alkyl)-NHC(O)C1-C6alkyl-O, NR$^{15}$(C1-C6alkyl)-NHC(O)C1-C6alkyl-NH, C1-C6alkyl, C1-C6alkyl-O, C1-C6alkyl-OC(O)C1-C6alkyl, C1-C6alkyl-OC(O)C1-C6alkyl-O, C1-C6alkyl-OC(O)C1-C6alkyl-NH, C1-C6alkyl-NH, C1-C6alkyl-NHC(O)C1-C6alkyl, C1-C6alkyl-NHC(O)C1-C6 alkyl-O, or C1-C6alkyl-NHC(O)C1-C6alkyl-NH,
$R^{13}$ is H, (CH$_2$CH$_2$O)$_{1-4}$, or C1-C6alkyl
$R^{14}$ is H or C1-C6alkyl-R$^6$,
$R^{15}$ is H or C1-C6alkyl, and
$R^{16}$ is H, CO$_2$H, NH$_2$, NH(C1-C6alkyl), N(C1-C6alkyl)$_2$, or N(C1-C6alkyl)$_3$.

In certain embodiments of a method as above, the plurality of ethylenic monomers consists of the monomers of formula A1. In some variations, the method further includes (c) removing the thio-carbonyl end group of the product of step (b), and (d) contacting the product of step (c) with a targeting moiety (e.g., a N-acetyl galactosamine (GalNAc) residue) comprising a thiol-reactive group or free radical.

In related aspects, the present invention provides compositions for making a branched PEG-lipid or branched PEG-protein as described herein. For example, in some embodiments of a composition for making a branched PEG-lipid, the composition comprises a compound of Formula IIIa, IIIb, IIIc, or IIId

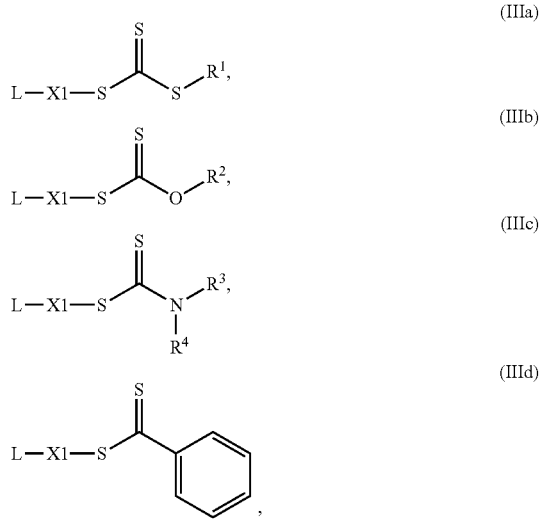

where L is a lipid, X1 is absent or a linking moiety, $R^1$ is $C_1$-$C_{12}$ alkyl, $R^2$ is $C_1$-$C_{12}$ alkyl, and $R^3$ and $R^4$ are each independently H, alkyl, aryl, or heteroaryl; in some such embodiments, L is a lipid selected from (i) a lipid comprising two $C_8$-$C_{24}$ hydrocarbon chains (e.g., two $C_{10}$-$C_{18}$ hydrocarbon chains), (ii) a sterol lipid, and (iii) a sphingolipid. In some embodiments of a composition for making a branched PEG-protein, the composition comprises a compound of Formula Va, Vb, Vc, or Vd

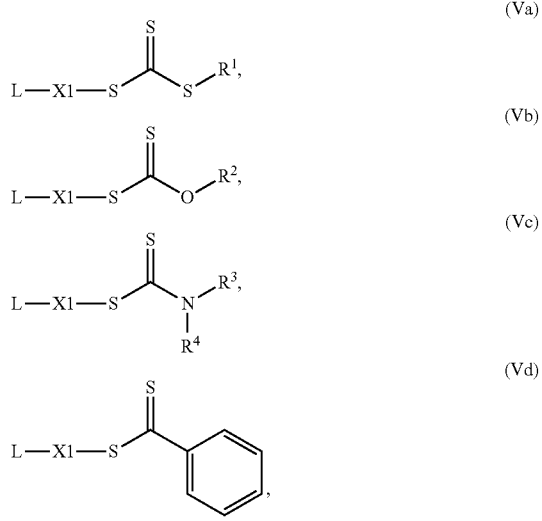

where Y is a therapeutic protein, X1 is absent or a linking moiety, $R^1$ is $C_1$-$C_{12}$ alkyl, $R^2$ is $C_1$-$C_{12}$ alkyl, and $R^3$ and $R^4$ are each independently H, alkyl, aryl, or heteroaryl.

In some embodiments of a method for making a branched PEG-lipid, a linear PEG methacrylate is polymerized onto a lipid tail via RAFT polymerization. In particular variations, a RAFT chain transfer agent is synthesized from 1,2-Distearoyl-sn-glycero-3-phosphoethanolamine (DSPE) or 1,2-dimyristoyl-sn-glycero-3-phosphoethanolamine (DMPE), and the resulting DSPE-CTA or DMPE-CTA is reacted with poly(ethylene glycol) methyl ether methacrylate (avg Mn=300; PEGMA$_{300}$) or poly(ethylene glycol) methyl ether methacrylate (avg Mn=500; PEGMA$_{500}$) together with a radical initiator (AIBN), to produce a highly branched PEG lipid (a DSPE-PEGMA or a DMPE-PEGMA). An embodiment of the formation of a branched PEG-lipid by RAFT polymerization is detailed in Scheme 1 below. In the schematic, $R_1$ and $R_2$ are alkyl chains of the lipid; $R_3$ is an alkyl chain containing a functional group that can be coupled to a polymerizable group containing a functional group on $R_4$; $R_4$ is an alkyl group containing a functional group that can be coupled to a functional group on $R_3$; Z is the end group of a thiocarbonylthio compound (RAFT chain transfer agent); x is the number of ethylene glycol repeat units in the PEG methacrylate monomer (or PEG acrylate monomer); and n is the number of PEG methacrylate monomers (or PEG acrylate monomers). Exemplary synthetic schemes for synthesis of a DSPE-PEGMA lipid (Scheme 2) and a DMPE-PEGMA lipid (Scheme 3) are also shown below. In more specific variations for synthesis of a DSPE-PEGMA lipid as shown in Scheme 2, x=4-5 and n=16-20, or x=7-9 and n=22-25 (e.g., n=23). In more specific variations for synthesis of a DMPE-PEGMA lipid as shown in Scheme 3, x=4-5 and n=16-20, or x=7-9 and n=22-25.

Scheme 1: Exemplary Reaction Scheme for Preparation of a Branched PEG-lipid

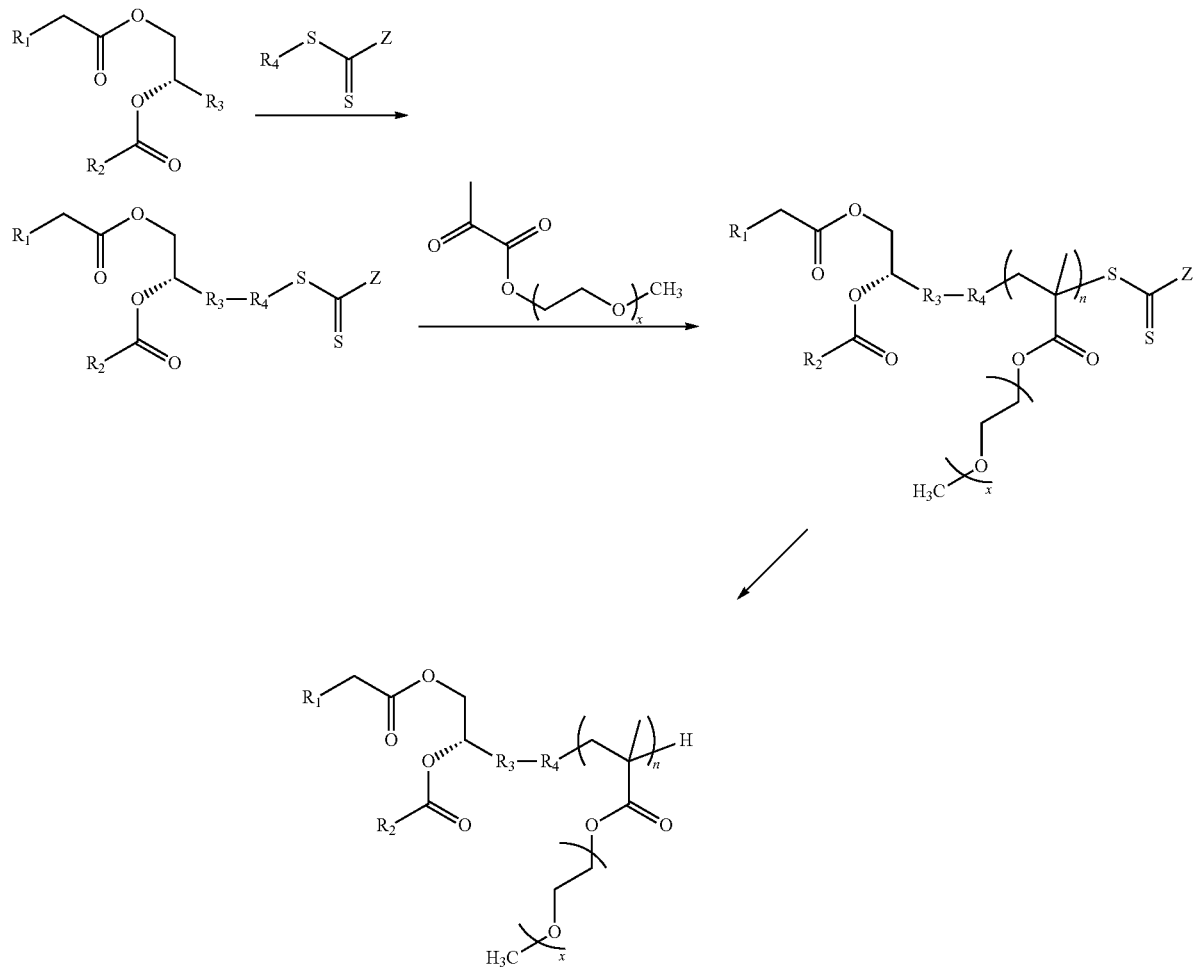

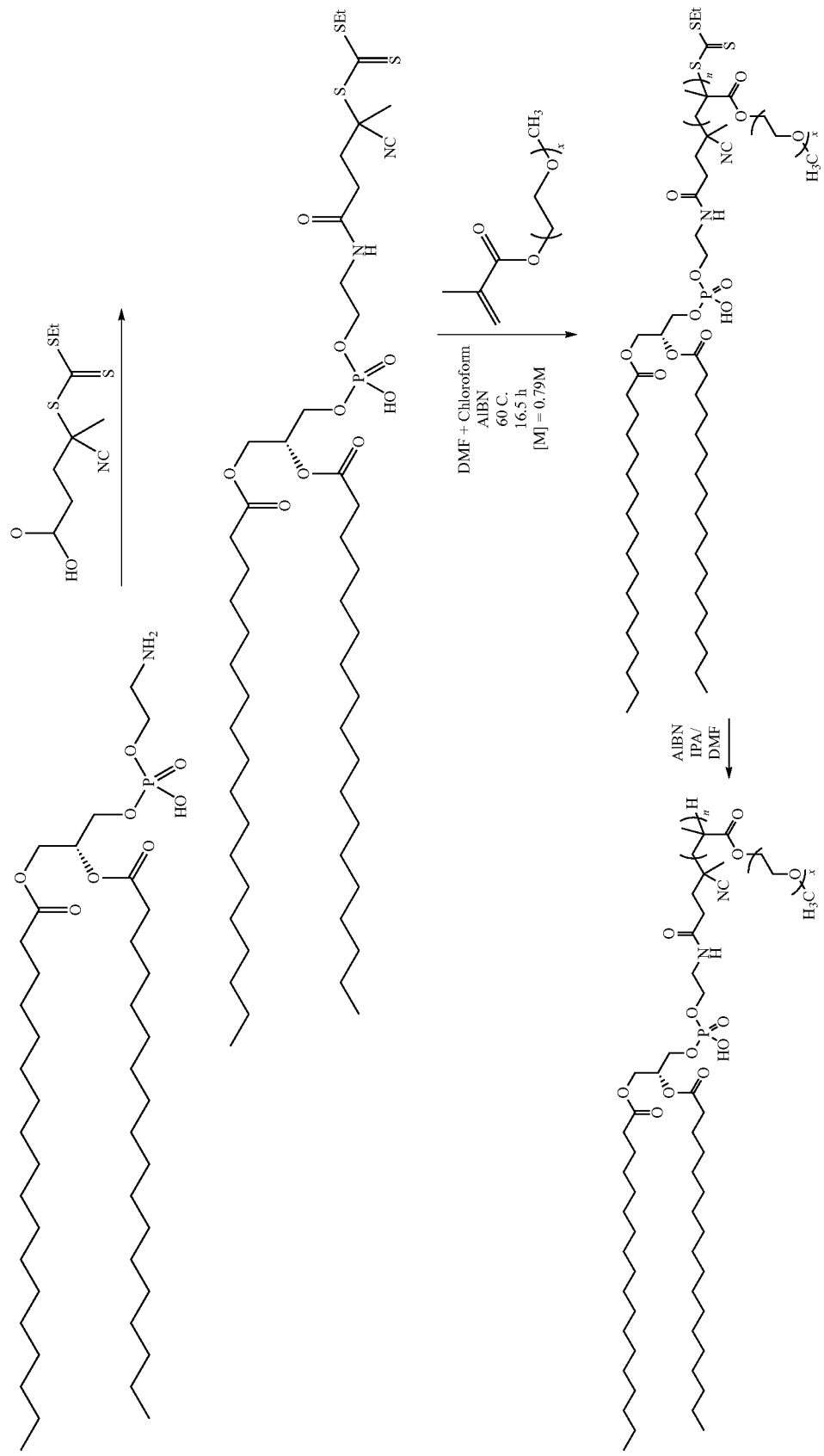
Scheme 2: Exemplary Reaction Scheme for Preparation of a DSPE-PEGMA

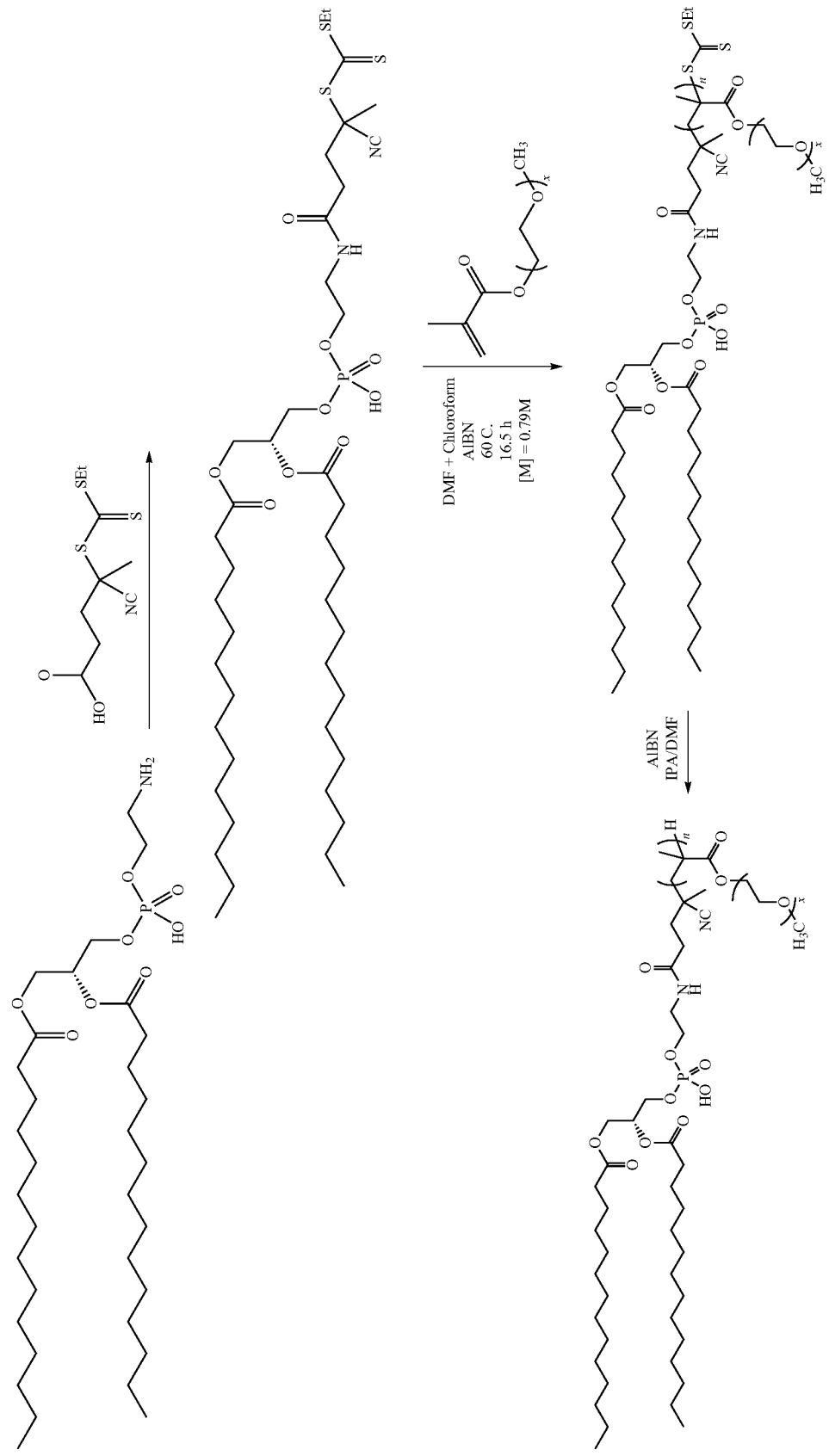

In another aspect, the present invention provides a method for in vivo delivery of a therapeutic or diagnostic agent to a subject. The method generally includes administering to the subject an effective amount of a lipid nanoparticle comprising a branched PEG-lipid as described herein. In some embodiments, the therapeutic or diagnostic agent is delivered to a target cell in the subject; for example, in some variations, a branched PEG-lipid of Formula I includes targeting moiety T, where T specifically binds to a molecule on the surface of the target cell. In some embodiments, the lipid nanoparticle is administered in a repeat dosage regime (e.g., a weekly or bi-weekly repeated administration protocol). In certain variations, the method delivers the therapeutic or diagnostic agent to the cytosol of the target cell in the subject; in some such variations, the method further includes administering to the subject an effective amount of a membrane-destabilizing polymer as described herein. For embodiments comprising delivery of a lipid nanoparticle and membrane-destabilizing polymer, the LNP and polymer can be administered separately (e.g., the membrane-destabilizing polymer administered after administration of the lipid nanoparticle) or, alternatively, together within a single composition. A membrane-destabilizing polymer may also be administered in a repeat dosage regime (e.g., a weekly or bi-weekly repeated administration protocol) together with a repeat dosing of a lipid nanoparticle. Typically, for separate administration, the lipid nanoparticle and membrane-destabilizing polymer are administered sequentially. For example, in particular embodiments, the membrane-destabilizing polymer is administered after administration of the lipid nanoparticle. In specific variations, the timing between administration of LNP and polymer is about two hours or less, typically about one hour or less, and more typically about 30 minutes or less, about 10 minutes or less, about five minutes or less, or about one minute or less. In some embodiments, the timing between administration of LNP and polymer is about 30 minutes, about 15 minutes, about 10 minutes, about five minutes, or about one minute. Typically, in variations comprising co-injection of the lipid nanoparticle and membrane-destabilizing polymer, the LNP and polymer are initially formulated as separate compositions and then mixed together into a single composition prior to administration. Methods for intracellular delivery of therapeutic or diagnostic agents comprising administration of both an LNP carrier and a membrane-destabilizing polymer are further disclosed in International PCT Application Publication No. WO 2016/118697, incorporated by reference herein.

In some embodiments of a method for in vivo delivery of a therapeutic agent to a subject and comprising administering an effective amount of a lipid nanoparticle comprising a branched PEG-lipid as described herein, the method is for treating a disease amenable to treatment with the therapeutic agent. In certain embodiments, the therapeutic agent is delivered intracellularly to cells of a target tissue for said treatment; in some such embodiments, the therapeutic agent is delivered to the target tissue via combined administration of the LNP and a membrane-destabilizing polymer. Typically, the therapeutic agent is delivered in a manner otherwise consistent with conventional methodologies associated with management of the disease or disorder for which treatment is sought. In accordance with the disclosure herein, a therapeutically effective amount of the lipid nanoparticle comprising the therapeutic agent is administered to a subject in need of such treatment for a time and under conditions sufficient to prevent or treat the disease.

In yet another aspect, the present invention provides a method for in vivo delivery of a therapeutic protein to a subject. The method generally includes administering to the subject an effective amount of a branched PEG-protein as described herein, where the branched PEG-protein comprises the therapeutic protein to be delivered in vivo. In some embodiments, the branched PEG-protein is administered in a repeat dosage regime (e.g., a weekly or bi-weekly repeated administration protocol). In some embodiments, the therapeutic protein is delivered to a target cell in the subject. For example, in some variations, a branched PEG-protein of Formula IV includes targeting moiety T, where T specifically binds to a molecule on the surface of the target cell.

In some embodiments of a method for in vivo delivery of a therapeutic protein to a subject and comprising administering an effective amount of a branched PEG-protein as described herein, the method is for treating a disease amenable to treatment with the therapeutic protein. Typically, the therapeutic protein is delivered in a manner otherwise consistent with conventional methodologies associated with management of the disease or disorder for which treatment is sought. In accordance with the disclosure herein, a therapeutically effective amount of the branched PEG-protein is administered to a subject in need of such treatment for a time and under conditions sufficient to prevent or treat the disease.

Any cell type or corresponding tissue may be targeted for agent delivery using the present methods. Suitable target cells include, e.g., chondrocytes, epithelial cells, nerve cells, muscle cells, blood cells (e.g., lymphocytes or myeloid leukocytes), endothelial cells, pericytes, fibroblasts, glial cells, and dendritic cells. Other suitable target cells include cancer cells, immune cells, bacterially-infected cells, virally-infected cells, or cells having an abnormal metabolic activity. In a particular variation where the target cell is a secretory cell, the target secretory cell is a hepatocyte. In some such embodiments, an LNP (and optionally a membrane-destabilizing polymer, for LNP embodiments further comprising administration of the membrane-destabilizing polymer) includes a targeting moiety that specifically binds to the asialoglycoprotein receptor (ASGPR). For example, if present, a targeting moiety T of a PEG-lipid of Formula I may be a moiety that binds to the ASGPR. In particular variations targeting the ASGPR, a targeting moiety includes an N-acetylgalactosamine (GalNAc) residue (e.g., a monovalent GalNAc moiety or a tri-GalNAc structure). In some embodiments comprising administration of both an lipid nanoparticle and a membrane-destabilizing polymer, both the LNP and the polymer comprise a targeting moiety, which may be the same or different (e.g., different targeting moiety species that bind to the same target cell); for example, in some embodiments, the targeting moiety T of a branched PEG-lipid of Formula I is present, and the membrane-destabilizing polymer includes a second targeting moiety, which may be the same as or different from T. Target cells further include those where the cell is in a mammalian animal, including, for example, a human, rodent, murine, bovine, canine, feline, sheep, equine, and simian mammal.

In various embodiments, a targeting moiety is attached to a lipid or polymeric component of a lipid nanoparticle, attached to either end of a membrane-destabilizing polymer (e.g., block copolymer), attached to a side chain of a monomeric unit of a polymer, or incorporated into a polymer block. Attachment of a targeting moiety to an LNP or a membrane-destabilizing polymer is achieved in any suitable manner, e.g., by any one of a number of conjugation chemistry approaches including, but not limited to, amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. In specific embodiments, "click" chemistry is used to attach the targeting moiety to a polymer (for example of "click" reactions, see. e.g., Wu and Fokin, "Catalytic Azide-Alkyne Cycloaddition: Reactivity and Applications," *Aldrichim. Acta* 40:7-17, 2007). A large variety of conjugation chemistries are optionally utilized (see, e.g., *Bioconjugation*, Aslam and Dent, Eds, Macmillan, 1998 and chapters therein). In some embodiments, targeting moieties are attached to a monomer and the resulting compound is then used in the polymerization synthesis of a polymer.

Targeting of lipid particles using a variety of targeting moieties has been previously described. See. e.g., U.S. Pat. Nos. 4,957,773 and 4,603,044. Targeting mechanisms generally require that the targeting moiety be positioned on the surface of the lipid particle in such a manner that the targeting moiety is available for interaction with the target, for example, a cell surface receptor. A variety of different targeting moieties and methods are known and available in the art, including those described above as well as, e.g., in Sapra and Allen, *Prog. Lipid Res.* 42:439-62, 2003, and Abra et al., *J. Liposome Res.* 12:1-3, 2002. Various targeting counter-receptors can be bound to the surface of the liposome, such as antibodies, antibody fragments, carbohydrates, vitamins, and transport proteins. For example, for targeting to the liver, liposomes can be modified with branched type galactosyllipid derivatives to target asialoglycoprotein receptors. See Kato and Sugiyama, *Crit. Rev. Ther. Drug Carrier Syst.* 14:287, 1997; Murahashi et al., *Biol. Pharm. Bull.* 20:259, 1997. In a more general approach to tissue targeting, target cells are prelabeled with biotinylated antibodies specific for a molecule expressed by the target cell. See Harasym et al., *Adv. Drug Deliv. Rev.* 32:99, 1998. After plasma elimination of free antibody, streptavidin-conjugated liposomes are administered. In another approach, targeting antibodies are directly attached to liposomes. See Harasym et al., supra.

Subjects for administration of a therapeutic agent as described herein include patients at high risk for developing a particular disease as well as patients presenting with an existing disease. In certain embodiments, the subject has been diagnosed as having the disease for which treatment is sought. Further, subjects can be monitored during the course of treatment for any change in the disease (e.g., for an increase or decrease in clinical symptoms of the disease).

In prophylactic applications, pharmaceutical compositions are administered to a patient susceptible to, or otherwise at risk of, a particular disease in an amount sufficient to eliminate or reduce the risk or delay the onset of the disease. In therapeutic applications, compositions are administered to a patient suspected of, or already suffering from, such a disease in an amount sufficient to cure, or at least partially arrest, the symptoms of the disease and its complications. An amount adequate to accomplish this is referred to as a therapeutically- or pharmaceutically-effective dose or amount. In both prophylactic and therapeutic regimes, agents are usually administered in several dosages until a sufficient response has been achieved. Typically, the response is monitored and repeated dosages are given if the desired response starts to fade.

To identify subject patients for treatment according to the methods of the invention, accepted screening methods may be employed to determine risk factors associated with specific diseases or to determine the status of an existing disease identified in a subject. Such methods can include, for example, determining whether an individual has relatives who have been diagnosed with a particular disease. Screening methods can also include, for example, blood tests to assay for buildups of metabolites caused by missing or mutated proteins in the liver (for certain liver diseases) or conventional work-ups to determine familial status for a particular disease known to have a heritable component (for example, various cancers and protein deficiency diseases are known to have certain inheritable components). Inheritable components of cancers include, for example, mutations in multiple genes that are transforming (e.g., Ras, Raf, EGFR, cMet and others), the presence or absence of certain HLA and killer inhibitory receptor (KIR) molecules, or mechanisms by which cancer cells are able to modulate immune suppression of cells like NK cells and T cells, either directly or indirectly (see. e.g., Ljunggren and Malmberg, *Nature Rev. Immunol.* 7:329-339, 2007; Boyton and Altmann, *Clin. Exp. Immunol.* 149:1-8, 2007). Toward this end, nucleotide probes can be routinely employed to identify individuals carrying genetic markers associated with a particular disease of interest. In addition, a wide variety of immunological methods are known in the art that are useful to identify markers for specific diseases. For example, various ELISA immunoassay methods are available and well-known in the art that employ monoclonal antibody probes to detect antigens associated with specific tumors. Screening may be implemented as indicated by known patient symptomology, age factors, related risk factors, etc. These methods allow the clinician to routinely select patients in need of the methods described herein for treatment.

A pharmaceutical composition comprising a lipid nanoparticle or a branched PEG-protein of the present disclosure can be formulated according to known methods to prepare pharmaceutically useful compositions. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See. e.g., Gennaro (ed.), Remington's Pharmaceutical Sciences (Mack Publishing Company, 19th ed. 1995).) Formulations may further include one or more excipients, preservatives, solubilizers, buffering agents, etc.

For embodiments comprising combined administration of a lipid nanoparticle and a membrane-destabilizing polymer, the LNP and polymer are formulated as a single pharmaceutical composition (for co-injection embodiments; typically mixed together just prior to administration) or as separate pharmaceutical compositions (for separate administration embodiments). A pharmaceutical composition comprising an LNP and/or membrane-destabilizing polymer can be formulated according to known methods to prepare pharmaceutically useful compositions, whereby the LNP and/or polymer component(s) are combined in a mixture with a pharmaceutically acceptable carrier.

For disease treatment, a pharmaceutical composition is administered to a subject in a therapeutically effective amount. According to the methods of the present invention, a pharmaceutical composition (e.g., a single composition comprising a lipid nanoparticle and a membrane-destabilizing polymer or separate compositions comprising the lipid nanoparticle and membrane-destabilizing polymer as separate formulations) may be administered to subjects by a variety of administration modes, including, for example, by intramuscular, subcutaneous, intravenous, intra-atrial, intra-articular, parenteral, intranasal, intrapulmonary, transdermal, intrapleural, intrathecal, and oral routes of administration. For prevention and treatment purposes, the compositions may be administered to a subject in a single bolus delivery, via continuous delivery (e.g., continuous transdermal delivery) over an extended time period, or in a repeated administration protocol (e.g., on an hourly, daily, weekly, or bi-weekly basis).

Determination of the proper dosage for a particular situation is within the skill in the art. Determination of effective dosages in this context is typically based on animal model studies followed up by human clinical trials and is guided by determining effective dosages and administration protocols that significantly reduce the occurrence or severity of the subject disease in model subjects. Effective doses of the compositions of the present invention vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy. Accordingly, a therapeutically or prophylactically effective amount is also one in which any undesired collateral effects are outweighed by beneficial effects. For administration of a therapeutic agent, a dosage typically ranges from about 0.1 μg to about 100 mg/kg or about 1 μg/kg to about 50 mg/kg, and more usually about 1 μg/kg to about 10 mg/kg or about 10 μg to about 5 mg/kg of the subject's body weight, exclusive of other components (e.g., for agents formulated within a lipid nanoparticle, exclusive of other LNP components, or for therapeutic proteins administered as a branched PEG-protein, exclusive of the branched PEG polymer component). In more specific embodiments, an effective amount of the agent is between about 1 μg/kg and about 20 mg/kg, between about 10 μg/kg and about 10 mg/kg, or between about 0.1 mg/kg and about 5 mg/kg, exclusive of other components. For embodiments comprising administration of a membrane-destabilizing polymer, the quantity of the membrane-destabilizing polymer may be varied or adjusted, for example, from about 10 μg to about 200 mg/kg, about 10 μg to about 100 mg/kg, about 0.1 mg/kg to about 100 mg/kg, about 0.1 mg/kg to about 50 mg/kg, or about 0.5 mg/kg to about 50 mg/kg. Dosages within this range can be achieved by single or multiple administrations, including, e.g., multiple administrations per day or daily, weekly, bi-weekly, or monthly administrations. For example, in certain variations, a regimen consists of an initial administration followed by multiple, subsequent administrations at weekly or bi-weekly intervals. Another regimen consists of an initial administration followed by multiple, subsequent administrations at monthly or bi-monthly intervals. Alternatively, administrations can be on an irregular basis as indicated by monitoring of physiological correlates of the disease and/or clinical symptoms of the disease.

With respect to delivery of a lipid nanoparticle, LNPs can adsorb to virtually any type of cell and then slowly release the encapsulated agent. Alternatively, an absorbed lipid nanoparticle may be endocytosed by cells (e.g., cells that are phagocytic). Endocytosis is typically followed by intralysosomal degradation of LNP lipids and release of the encapsulated agents (see Scherphof et al., Ann. N.Y. Acad. Sci. 446:368, 1985). After intravenous administration, lipid nanoparticles (e.g., liposomes of about 0.1 to 1.0 μm) are typically taken up by cells of the reticuloendothelial system, located principally in the liver and spleen. This preferential uptake of smaller liposomes by the cells of the reticuloendothelial system has been used to deliver chemotherapeutic agents to macrophages and to tumors of the liver. It is believed the combining administration of a lipid nanoparticle together with administration of a membrane-destabilizing polymer enhances efficiency of delivery of the LNP-associated therapeutic agent to the cytosol of a cell.

The reticuloendothelial system can be circumvented by several methods including saturation with large doses of lipid nanoparticles, or selective macrophage inactivation by pharmacological means (see Claassen et al., Biochim. Biophys. Acta 802:428, 1984). In addition, incorporation of glycolipid- or polyethelene glycol-derivatized phospholipids into liposome membranes has been shown to result in a significantly reduced uptake by the reticuloendothelial system (see Allen et al., Biochim. Biophys. Acta 1068:133, 1991; Allen et al., Biochim. Biophys. Acta 1150:9, 1993).

Lipid nanoparticles can also be prepared to target particular cells or tissues by varying phospholipid composition of the lipid nanoparticles. For example, liposomes prepared with a high content of a nonionic surfactant have been used to target the liver. (See. e.g., Japanese Patent 04-244,018 to Hayakawa et al.; Kato et al., Biol. Pharm. Bull. 16:960, 1993.) These formulations were prepared by mixing soybean phosphatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver. (See Shimizu et al., Biol. Pharm. Bull. 20:881, 1997.)

Compositions of the present disclosure (e.g., lipid nanoparticles and/or membrane-destabilizing polymers) can also be prepared to target particular cells or tissues by using a targeting moiety as discussed herein.

In some embodiments, a lipid nanoparticle and membrane-destabilizing polymer as described herein are used in a method for treating a disease associated with defective gene expression and/or activity in a subject. Such methods of treatment include administering to a subject having the disease associated with defective gene expression and/or activity (a) an effective amount of a lipid nanoparticle comprising a polynucleotide that is homologous to and can silence, for example by cleavage, a gene or that specifies the amino acid sequence of a protein and is translated during protein synthesis, and (b) an effective amount of a membrane-destabilizing polymer, where the polynucleotide is delivered into the cytosol of target cells of a target tissue associated with the disease, thereby treating the disease. In some embodiments, at least one of the lipid nanoparticle and membrane-destabilizing polymer includes a targeting ligand that specifically binds to a molecule on the surface of the target cells of the target tissue within the subject. Examples of a disease associated with defective gene expression and/or activity in a subject treatable by the methods disclosed herein include liver cancer (e.g., hepatocellular carcinoma), hepatitis, hypercholesterolemia, liver fibrosis, and haemochromatosis. In other variations, a disease or condition associated with defective gene expression and/or activity in a subject treatable by the methods disclosed herein is a cancer of the breast, ovaries, pancreas, endometrium, lungs, kidneys, colon, brain (e.g., glioblastoma), or myeloid cells of hematopoietic origin.

In certain embodiments, the disease associated with defective gene expression is a disease characterized by a deficiency in a functional polypeptide (also referred to herein as a "disease associated with a protein deficiency" or a "protein deficiency disease"). Such methods of treatment include administering to a subject having the protein deficiency disease (a) an effective amount of a lipid nanoparticle comprising an mRNA that encodes the functional protein or a protein having the same biological activity as the functional protein and (b) an effective amount of a membrane-destabilizing polymer, where the mRNA is delivered into the cytosol of target cells of a target tissue associated with the protein deficiency, and where the mRNA is translated during protein synthesis so as to produce the encoded protein within the target tissue in an amount sufficient to treat the disease. In some embodiments, at least one of the lipid nanoparticle and membrane-destabilizing polymer comprises a targeting ligand that specifically binds to a molecule on the surface of the target cells of the target tissue. In specific variations, the mRNA encodes a functional erythropoietin, alpha-galactosidase A, LDL receptor, Factor VII, Factor VIII, Factor IX, alpha-L-iduronidase, iduronate-2-sulfatase, heparan-N-sulfatase, alpha-N-acetylglucosaminidase, galactose 6-sulfatase, acid β-galactosidase, lysosomal acid lipase, ornithine transcarbamylase (OTC), alpha-1-antitrypsin, arylsulfatase A, arylsulfatase B, acid ceramidase, acid α-L-fucosidsase, acid β-glucosidase (also known as glucocerebrosidase), galactocerebrosidase, acid α-mannosidase, acid β-mannosidase, N-acetylgalactosamine-6-sulfate sulfatase, acid sphingomyelinase, acid α-glucosidase, β-hexosaminidase B, acetyl-CoA:α-glucosaminide N-acetyltransferase, N-acetylglucosamine-6-sulfate sulfatase, alpha-N-acetylgalactosaminidase, sialidase, β-glucuronidase, or β-hexosaminidase A. In other embodiments, the mRNA encodes a functional Retinoblastoma protein (pRb), p53 tumor-suppressor protein, Phosphatase and tensin homolog (PTEN), Von Hippel-Lindau tumor suppressor (pVHL), Adenomatous polyposis coli (APC), FAS receptor (FasR), Suppression of tumorigenicity 5 (ST5), YPEL3, Suppressor of tumorigenicity protein 7 (ST7), or Suppressor of tumorigenicity 14 protein (ST14). In yet other embodiments, the mRNA encodes a functional Galactose-1-phosphate uridylyltransferase, Galactokinase, UDP-galactose 4-epimerase, Transthyretin, complement regulatory protein (e.g., factor H, factor I, or membrane cofactor protein), phenylalanine hydroxylase (PAH), homogentisate 1,2-dioxygenase, Porphobilinogen deaminase, hypoxanthine-guanine phosphoribosyltransferase (HGPRT), argininosuccinate lyase (ASL), argininosuccinate synthetase (ASS1), or P-type ATPase protein, FIC-1.

Further examples of a disease or condition associated with defective gene expression and/or activity in a subject treatable by the methods disclosed herein include protein deficiency diseases associated with single-gene metabolic defects in the liver. Exemplary protein deficiency diseases of the liver include diseases associated with urea cycle defects (e.g., ornithine transcarbamylase (OTC) deficiency, carbamoyl phosphate synthetase I (CPS1) deficiency, argininosuccinic aciduria (argininosuccinate lyase (ASL) deficiency), and citrullinemia (argininosuccinate synthetase (ASS1) deficiency)); tyrosinemia type 1 (fumarylacetoacetase (FAH) enzyme deficiency); primary hyper-oxaluria type 1 (alanine: glyoxylate-aminotransferase (AGT) deficiency); organic acidemia (e.g., methylmalonic acidemia (MMA; deficiency in, for example, methylmalonyl CoA mutase), propionic acidemia (PA; propionyl CoA carboxylase (PCC) deficiency), and maple syrup urine disease (MSUD; branched-chain ketoacid dehydrogenase (BCKDH) deficiency)); Wilson's Disease (deficiency in copper-transporting ATPase, Atp7B); Crigler-Najjar Syndrome Type 1 (bilirubin uridinediphosphate glucuronyltransferase (BGT) enzyme deficiency); hemochromatosis (hepcidin deficiency); glycogen storage disease (GSD) type 1a (glucose-6-phosphatase (G6Pase) deficiency); glycogen storage disease (GSD) type 1b (glucose 6-phosphate translocase deficiency); lysosomal storage diseases (LSDs; deficiencies in lysosomal enzymes) such as, e.g., Gaucher's Disease types 1, 2, and 3 (lysosomal glucocerebrosidase (GB) deficiency), Niemann-Pick Disease Type C (mutation in either the NPC1 or NPC2 gene), and Niemann-Pick Disease Types A and B (acid sphingomyelinase (ASM) deficiency); alpha-1 antitrypsin (A1AT) deficiency; hemophilia B (Factor IX deficiency); galactosemia types 1, 2, and 3 (galactose-1-phosphate uridylyltransferase, galactokinase, and UDP-galactose 4-epimerase deficiencies, respectively); transthyretin-related hereditary amyloidosis (TTR-familial amyloid polyneuropathy; transthyretin deficiency); atypical haemolytic uremic syndrome-1 (deficiencies in complement regulatory proteins, e.g., factor H, factor I, or membrane cofactor protein); phenylketonuria (phenylalanine hydroxylase (PAH) deficiency); alcaptonuria (homogentisate 1,2-dioxygenase deficiency); acute intermittent porphyria (porphobilinogen deaminase deficiency); Lesch-Nyhan syndrome (hypoxanthine-guanine phosphoribosyltransferase (HGPRT) deficiency; and progressive familial intrahepatic cholestasis (PFIC) (P-type ATPase protein, FIC-1 deficiency). Additional examples of protein deficiency diseases that are lysosomal storage diseases (LSDs) include Fabry disease (alpha-galactosidase A deficiency); Farber disease (acid ceramidase deficiency); fucosidosis (acid α-L-fucosidsase deficiency); GMI gangliosidosis (acid β-galactosidase deficiency); Hunter syndrome (mucopolysaccharidosis type II (MPS II); iduronate-2-sulfatase deficiency); Hurler-Scheie, Hurler, and Scheie syndromes (mucopolysaccharidosis type I (MPS I); alpha-L-iduronidase deficiency); Krabbe disease (galactocerebrosidase deficiency); α-mannosidosis (acid α-mannosidase deficiency); β-mannosidosis (acid β-mannosidase deficiency); Maroteaux-Lamy syndrome (mucopolysaccharidosis type VI (MPS VI); arylsulfatase B deficiency); metachromatic leukodystrophy (arylsulfatase A deficiency); Morquio syndrome type A (mucopolysaccharidosis type IVA (MPS IVA); N-acetylgalactosamine-6-sulfate sulfatase deficiency); Morquio syndrome type B (mucopolysaccharidosis type IVB (MPS IVB); acid β-galactosidase deficiency); Pompe disease (acid α-glucosidase deficiency); Sandhoff disease (β-hexosaminidase B deficiency); Sanfilippo syndrome type A (mucopolysaccharidosis type IIIA (MPS IIIA); heparan-N-sulfatase deficiency); Sanfilippo syndrome type B (mucopolysaccharidosis type IIIB (MPS IIIB); alpha-N-acetylglucosaminidase deficiency); Sanfilippo syndrome type C (mucopolysaccharidosis type IIIC (MPS IIIC); acetyl-CoA:α-glucosaminide N-acetyltransferase deficiency); Sanfilippo syndrome type D (mucopolysaccharidosis type IIID (MPS IIID); N-acetylglucosamine-6-sulfate sulfatase deficiency); Schindler/Kanzaki disease (alpha-N-acetylgalactosaminidase deficiency); sialidosis (sialidase deficiency); Sly syndrome (mucopolysaccharidosis type VII (MPS VII); β-glucuronidase deficiency); and Tay-Sachs disease (β-hexosaminidase A deficiency).

In particular variations, an mRNA encoding an ornithine transcarbamylase (OTC) protein is delivered in accordance with the present methods to treat ornithine transcarbamylase deficiency (OTCD). OTCD is a urea cycle disorder that can trigger hyperammonemia, a life-threatening illness that leads to brain damage, coma or even death. This is due to deficiency in the activity of OTC, a key enzyme in the urea cycle, which primarily takes place in the liver and is responsible for removal of excess nitrogen in the body. Ammonium nitrogen is produced from protein intake as well as protein breakdown in the body. In the liver, this ammonium nitrogen is converted into urea by enzymes in the urea cycle. Urea is non-toxic and cleared easily through the kidneys in urine, normally. However, when the OTC enzyme is deficient, ammonia levels rise in blood and cause severe brain damage. Patients with severe OTC deficiency are most often identified 2-3 days after birth where the patient has significantly elevated blood ammonia levels and ends up in a coma. Patients with milder OTC deficiency can have crises during times of stress resulting in elevated ammonia levels that can also lead to coma. Current therapies include ammonia scavenger drugs (BUPHENYL®, RAVICTI®) for use in patients with hyperammonemia.

The OTC gene is X-linked. The disease is present in males with one mutant allele and in females either homozygous or heterozygous with mutant alleles. Male patients are typically those with the severest OTC deficiency found right after birth. In addition to elevation in blood ammonia levels, urinary orotic acid levels are also elevated. In patients with severe OTC deficiency, OTC enzyme activity is <20% of normal levels. In patients with milder OTC deficiency, OTC enzyme activity is up to 30% of normal levels.

A method for treating OTCD with a lipid nanoparticle comprising an OTC-encoding mRNA and a membrane-destabilizing polymer generally includes administering to a subject having OTCD an effective amount of the lipid nanoparticle and an effective amount of the membrane-destabilizing polymer, where at least one of the lipid nanoparticle and membrane-destabilizing polymer includes a targeting ligand that specifically binds to a molecule on the surface of liver cells within the subject, and whereby the OTC-encoding mRNA is delivered to liver cells and translated during protein synthesis to produce the OTC protein. The OTC-encoding mRNA may be an mRNA as set forth above with respect to a method for increasing OTC protein in a cell.

The efficacy of a composition or method for treating a disease can be evaluated in vivo in animal models of disease. Particularly suitable animal models for evaluating efficacy of a [lipid nanoparticle]/[membrane-destabilizing polymer] composition (or combination of LNP composition and polymer composition) for treatment of OTCD includes known mouse models having deficiencies of the OTC enzyme in the liver. One such mouse model, OTC-spf$^{ash}$ (sparse fur and abnormal skin and hair) mice, contain an R129H mutation resulting in reduced levels of OTC protein and have only 5-10% of the normal level of enzyme activity in liver (see Hodges et al., *Proc. Natl. Acad. Sci. USA* 86:4142-4146, 1989). Another model, OTC-spf mice, contain an H117N mutation which results in reduced levels of enzyme activity to 5-10% of normal levels (see Rosenberg et al., *Science* 222:426-428, 1983). Both of these mouse models have elevated urine orotic acid levels compared to their wild-type littermate mice. A third model for OTC deficiency is inducing hyperammonemia in OTC-spf or OTC-spf$^{ash}$ mice (Cunningham et al., *Mol Ther* 19: 854-859, 2011). These mice are treated with OTC siRNA or AAV2/8 vector/OTC shRNA to knockdown residual endogenous OTC expression and activity. Plasma ammonia levels are elevated and mice die within approximately 7-28 days.

In additional variations, an mRNA encoding an enzyme deficient in an organic acidemia is delivered in accordance with the present methods to treat the organic acidemia. Organic acidemia (also known as aciduria) (OA) is a group of disorders characterized by the excretion of non-amino organic acids in the urine. Most organic acidemias result from dysfunction of a specific step in amino acid catabolism, usually the result of deficient enzyme activity. The majority of organic acid disorders are caused by abnormal amino acid catabolism of branched-chain amino acids or lysine. They include propionic acidemia (PA), methylmalonic acidemia (MMA), maple syrup urine disease (MSUD), and others. These organic acidemias are inherited in an autosomal recessive manner. A neonate affected with an OA is usually well at birth and for the first few days of life. The usual clinical presentation is that of toxic encephalopathy and includes vomiting, poor feeding, neurologic symptoms such as seizures and abnormal tone, and lethargy progressing to coma. Outcome can be improved by diagnosis and treatment in the first ten days of life. In the older child or adolescent, variant forms of the OAs can present as loss of intellectual function, ataxia or other focal neurologic signs, Reye syndrome, recurrent ketoacidosis, or psychiatric symptoms.

Clinical laboratory findings indicate that organic acidemias include acidosis, ketosis, hyperammonemia, abnormal liver function, hypoglycemia, and neutropenia. First-line diagnosis in the organic acidemias is urine organic acid analysis using gas chromatography with mass spectrometry (GC/MS). The urinary organic acid profile is nearly always abnormal in the face of acute illness. Confirmatory testing involves assay of the activity of the deficient enzyme in lymphocytes or cultured fibroblasts and/or molecular genetic testing. Characteristics of the three primary disorders are summarized in Table 1.

TABLE 1

Metabolic Findings in Organic Acidemias Caused by Abnormal Amino Acid Catabolism

| Disorder | Amino Acid Pathway(s) Affected | Enzyme | Diagnostic Analytes by GC/MS and Quantitative Amino Acid Analysis |
| --- | --- | --- | --- |
| Propionic acidemia (PA) | Isoleucine, valine, methionine, threonine | Propionyl CoA carboxylase (PCC) (composed of three PCCA subunits and three PCCB subunits) | Propionic acid, 3-OH propionic acid, methyl citric acid, propionyl glycine in urine Propionyl carnitine, increased glycine in blood |

TABLE 1-continued

Metabolic Findings in Organic Acidemias Caused by Abnormal Amino Acid Catabolism

| Disorder | Amino Acid Pathway(s) Affected | Enzyme | Diagnostic Analytes by GC/MS and Quantitative Amino Acid Analysis |
|---|---|---|---|
| Methylmalonic acidemia (MMA) | Isoleucine, valine, methionine, threonine | Methylmalonyl CoA mutase (MUT) | Methylmalonic acid in blood and urine Propionic acid, 3-OH propionic acid, methyl citrate in urine Acyl carnitines, increased glycine in blood |
| Maple syrup urine disease (MSUD) | Leucine, isoleucine, valine | Branched-chain ketoacid dehydrogenase (BCKDH) (composed of four different subunits) | Branched-chain ketoacids and hydroxyacids in urine Alloisoleucine in plasma |

Once the detection of specific analytes narrows the diagnostic possibilities, the activity of the deficient enzyme is assayed in lymphocytes or cultured fibroblasts as a confirmatory test. For many pathways, no single enzyme assay can establish the diagnosis. For others, tests such as complementation studies need to be done.

The goal of therapy is to restore biochemical and physiologic homeostasis. Neonates require emergency diagnosis and treatment depending on the specific biochemical lesion, the position of the metabolic block, and the effects of the toxic compounds. Treatment strategies include: (1) dietary restriction of the precursor amino acids and (2) use of adjunctive compounds to (a) dispose of toxic metabolites or (b) increase activity of deficient enzymes. Liver transplantation has been successful in a small number of affected individuals. Even with current clinical management approaches, individuals with organic acidemias have a greater risk of infection and a higher incidence of pancreatitis, which can be fatal.

Enzyme replacement therapy via specific mRNA delivery to the liver offers the most effective treatment of the organic acidemias. In certain embodiments of a method for treating an organic acidemia, an mRNA encoding a methylmalonyl CoA mutase (MUT) is delivered to a subject in accordance with the present methods to treat methylmalonic acidemia MMA. In other embodiments, an mRNA encoding a PCC subunit (PCCA or PCCB) is delivered to a subject in accordance with the present methods to treat propionic acidemia (PA). In yet other embodiments, an mRNA encoding a BCKDH subunit is delivered to a subject in accordance with the present methods to treat maple syrup urine disease (MSUD). A method for treating MMA, PA, or MSUD with a lipid nanoparticle comprising an Mut, Pcca/b, or BCKDH subunit mRNA and a membrane-destabilizing polymer generally includes administering to a subject having an organic acidemia of the specified type an effective amount of the lipid nanoparticle and an effective amount of the membrane-destabilizing polymer, where at least one of the lipid nanoparticle and membrane-destabilizing polymer includes a targeting ligand that specifically binds to a molecule on the surface of liver cells within the subject, and whereby the Mut, Pcca/b, or BCKDH subunit mRNA is delivered to liver cells and translated during protein synthesis to produce the respective protein. A Mut or Pcca/b mRNA may be an mRNA as set forth above with respect to a method for increasing the respective protein in a cell.

The efficacy of a composition or method for treating an organic acidemia disease can be evaluated in vivo in animal models of disease. For example, particularly suitable animal models for evaluating efficacy of a mRNA/LNP and polymer composition (or combination of mRNA/LNP composition and polymer composition) for treatment of MMA and PA are as follows. $Mut^{-/-}$ neonatal mice with a severe form of MMA, which normally die within the first 21 days of life, have been successfully treated with hepatocyte-directed delivery of the methylmalonyl-CoA mutase (Mut) gene. Following an intrahepatic injection of adeno-associated virus expressing the murine Mut gene, $Mut^{-/-}$ mice were rescued and lived beyond 1 year of age (Carrillo-Carrasco et al., Hum. Gene Ther. 21:1147-1154, 2010). Another MMA disease model where mice survive into adulthood is $Mut^{-/-}$ mice with Mut cDNA expressed under the control of an insulated, muscle-specific promoter ($Mut^{-/-}$;$Tg^{INS-MCK-Mut}$) (Manoli et al., 2011, SIMD Abstract). These mice have elevated plasma methylmalonic acid levels and decreased oxidative capacity as measured by a $^{13}C$ propionate oxidation/breathe assay. A mouse model of PA ($Pcca^{-/-}$ mice) succumbs to death 24-36 h after birth and is associated with fatal ketoacidosis (Miyazaki et al., J. Biol. Chem. 276: 35995-35999, 2001). Pcca gene transfer that provides a postnatal PCC activity of 10-20% in the liver of a transgenic mouse strain attenuates the fatal ketoacidosis in newborn mice (Miyazaki et al., 2001, supra). Recently, an intrahepatic adeno-associated virus mediated gene transfer for human Pcca was tested in neonatal $Pcca^{-/-}$ mice (Chandler et al., Hum. Gene Ther. 22:477-481, 2010). The authors found a sustained therapeutic effect as demonstrated in a survival rate of approximately 64% and reduction of disease-related metabolites (Chandler et al., 2010, supra). Another mouse disease model of PA is a hypomorphic model where $Pcca^{-/-}$ mice express a transgene bearing an A138T mutant of the PCCA protein. These mice have 2% of wild-type PCC activity, survive to adulthood and have elevations in disease-related metabolites (Guenzel et al., Mol. Ther. 21:1316-1323, 2013). Treatment of these mice with adeno-virus or AAV vector expressing human PCCA cDNA resulted in increased PCC enzyme activity and correction of disease marker levels (Guenzel et al., 2013, supra). Taken together, in murine models of MMA and PA gene transfer approaches rescue neonatal mice or restore enzyme activity and correct disease metabolite levels in adult disease models thereby permitting evaluation of mRNA delivery for restoration of the defective enzymes.

In additional variations, an mRNA encoding arginosuccinate lyase (ASL) or argininosuccinate synthetase (ASS1) is delivered in accordance with the present methods to treat argininosuccinate aciduria (ASA) or citrullinemia type I (CTLN I), respectively. Suitable animal models for evaluating efficacy of a mRNA/LNP and polymer for treatment of ASA and CTLN I are as follows. ASL hypomorphic mice have a neomycin gene inserted into intron 9 which leads to deficiency in the ASL enzyme (~10% of wild type levels of mRNA and protein) and elevations in argininosuccinate and citrulline plasma levels (Erez et al., Nat Med. 17:1619-1626, 2011) which is the signature of ASA. These mice if left untreated will die on their own starting around 3 weeks of age. Treatment of these mice with helper dependent adenoviral vector expressing mouse ASL at 4 weeks of age led to improved survival, normalized ASL protein expression, and reduction in argininosuccinate and citrulline plasma levels (Nagamani et al., *Am J Hum Genet.* 90:836-846, 2012). ASS1 hypomorphic mice result from a spontaneous recessive mutation (T389I substitution) known as follicular dystrophy (fold). This mutation leads to unstable ASS1 protein structure and ~5-10% of normal enzyme activity. Homozygous fold/fold mice have elevated plasma citrulline and ammonia levels. These mice will also die on their own if untreated (Perez et al., *Am J Pathol.* 177:1958-1968, 2010). Treatment of these mice with AAV8 vector expressing human ASS1 led to improved survival and decreased plasma citrulline and ammonia levels (Chandler et al., *Gene Ther.* 20:1188-1191, 2013). Thus, in murine models of ASA and CTLN I hepatic gene transfer methods restore enzyme activity and correct the disease thereby permitting evaluation of mRNA delivery for restoration of the defective enzymes.

In certain other embodiments of a method of treating a disease associated with defective gene expression and/or activity, the gene is selected from a growth factor gene, a growth factor receptor gene, a gene encoding an enzyme (for example, a phosphatase or a kinase, e.g., a protein tyrosine, serine, or threonine kinase), an adaptor protein gene, a gene encoding a G protein superfamily molecule, or a gene encoding a transcription factor.

Further examples of suitable gene targets useful in the methods of treating a disease associated with defective gene expression and/or activity as described herein include the following genes or genes encoding the following proteins: MEX3, MMP2, ApoB, ERBB2, Vascular Endothelial Growth Factor (VEGF), Vascular Endothelial Growth Factor Receptor (VEGFR), Platelet Derived Growth Factor Receptor (PDGF), ABL, KITT, FMS-like tyrosine kinase 3 (FLT3), Cav-1, Epidermal Growth Factor Receptor (EGFR), H-Ras, K-Ras, N-Ras, Bc 1-2, Survivin, FAK, STAT-3, HER-3, Beta-Catenin, ornithine transcarbamylase, alpha-1-antitrypsin, and Src.

Other examples of suitable gene targets useful in the methods of treating a disease associated with defective gene expression and/or activity as described herein include tumor suppressors, where loss of function of the mutated gene can be corrected by delivery of mRNA encoding the functional protein to treat cancer. Suitable tumor suppressor targets include Retinoblastoma protein (pRb), p53 tumor-suppressor protein, Phosphatase and tensin homolog (PTEN), Von Hippel-Lindau tumor suppressor (pVHL), Adenomatous polyposis *coli* (APC), FAS receptor (FasR), Suppression of tumorigenicity 5 (ST5), YPEL3, Suppressor of tumorigenicity protein 7 (ST7), and Suppressor of tumorigenicity 14 protein (ST14).

In certain embodiments, lipid nanoparticle comprising a branched PEG-lipid and further comprising a therapeutic agent as described herein is used in the preparation of a medicament for the treatment of a disease amenable to treatment with the therapeutic agent. In some such embodiments, the disease is a disease associated with defective gene expression and/or activity in a subject.

In certain embodiments, a membrane-destabilizing polymer and a lipid nanoparticle comprising a branched PEG-lipid and further comprising a therapeutic agent as described herein are used in the preparation of a medicament or combination of medicaments for the treatment of a disease amenable to treatment with the therapeutic agent. In some such embodiments, the disease is a disease associated with defective gene expression and/or activity in a subject.

In some embodiments, a membrane-destabilizing polymer and a lipid nanoparticle comprising a branched PEG-lipid and further comprising an mRNA encoding a functional protein as described herein is used in the preparation of a medicament or combination of medicaments for the treatment of a disease associated with deficiency in a functional protein.

The invention is further illustrated by the following non-limiting examples.

EXAMPLES

Example 1: Synthesis of (R)-1,2-Di-stearoyl-sn-glycero-3-phosohoethanolamine-ECT (DSPE-ECT)

This Example describes the synthesis of (R)-1,2-Di-stearoyl-sn-glycero-3-phosphoethanolamine-ECT (DSPE-ECT), having the structure shown below.

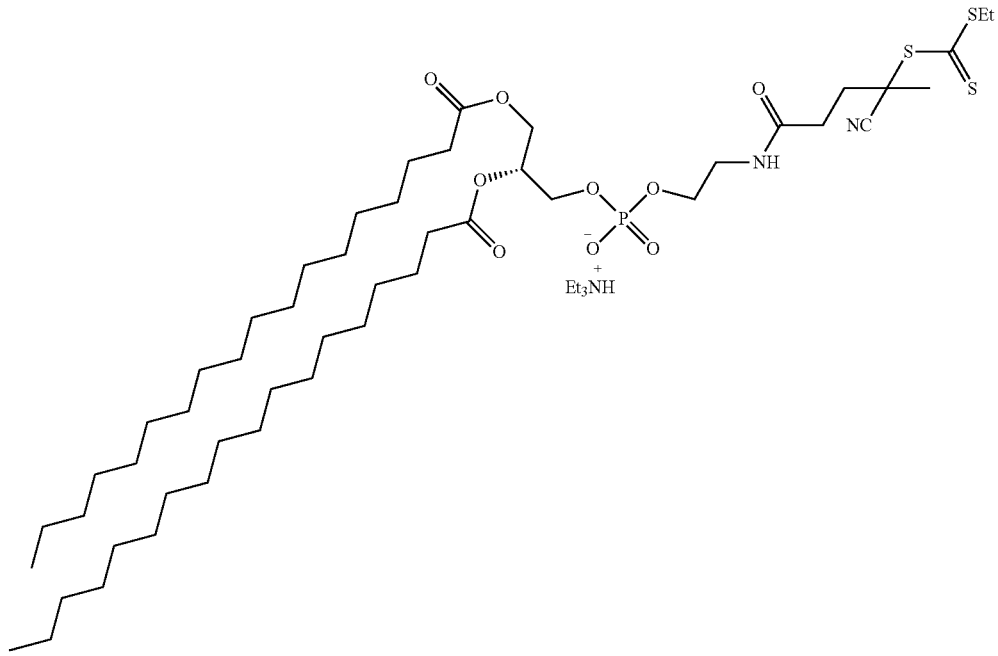

(R)-1,2-Di-stearoyl-sn-glycero-3-phosphoethanolamine (4.73 g, 6.32 mmol) was placed into a 500 mL round bottom flask and dissolved in anhydrous dichloromethane (50.0 mL) at RT. Triethylamine (2.20 mL, 15.8 mmol) was added to the mixture and the solution was cooled to 0° C. in an ice bath. In a separate 100 mL round bottom flask, ECT-pentafluorophenylacetate (4.05 g, 9.43 mmol) was dissolved in dichloromethane (20.0 mL) at RT and this mixture was added into the previously cooled DSPE solution via syringe over 10 min. The combined solution was allowed to warm to RT overnight and then diluted with dichloromethane (300 mL). The organic phase was washed with saturated sodium bicarbonate (2×50.0 mL) and brine (1×50.0 mL). The organic solution was dried over sodium sulfate overnight. The solid salts were filtered out and the organic solution was evaporated in vacuo. The yellow residue was dissolved in anhydrous diethyl ether and cooled to −20° C. for 60 h. The yellow precipitate was filtered on a Buchner funnel and washed with cold ether, then immediately purified via silica gel chromatography using a gradient of dichloromethane and methanol (0 to 20%). The combined pure fractions were concentrated on the rotovap and the resulting yellow oil was dissolved in anhydrous diethyl ether then cooled to −20° C. for 24 h. The yellow precipitate was filtered on a Buchner funnel, washed with ether and dried under high vacuum overnight. The pure product (yellow powder) was obtained as a triethylaminium salt (5.67 g, 5.70 mmol). Yield: 90% ($^1$H-NMR was taken in $CDCl_3$ on a Varian 400 MHz).

Example 2: Synthesis of (R)-1,2-Di-myristoyl-sn-glycero-3-phosohoethanolamine-ECT (DMPE-ECT)

This Example describes the synthesis of (R)-1,2-Di-myristoyl-sn-glycero-3-phosphoethanolamine-ECT (DMPE-ECT), having the structure shown below.

(R)-1,2-Di-myristoyl-sn-glycero-3-phosphoethanolamine (1.50 g, 2.36 mmol) was placed into a 500 mL round bottom flask and dissolved in anhydrous chloroform (220.0 mL) at RT. Triethylamine (0.822 mL, 5.74 mmol) was added to the mixture and the solution was cooled to 0° C. in an ice bath. In a separate 100 mL round bottom flask, ECT-pentafluorophenylacetate (1.52 g, 3.54 mmol) was dissolved in dichloromethane (20.0 mL) at RT and this mixture was added into the previously cooled DMPE solution via syringe over 10 min. The combined solution was allowed to warm to RT overnight and then diluted with chloroform (100 mL). The organic phase was washed with saturated sodium bicarbonate (2×50.0 mL) and brine (1×50.0 mL). The organic solution was dried over sodium sulfate overnight. The solid salts were filtered out and the organic solution was evaporated in vacuo. The yellow residue was dissolved in anhydrous diethyl ether and cooled to −20° C. overnight. The yellow precipitate was filtered on a Buchner funnel and washed with cold ether, then immediately purified via silica gel chromatography using a gradient of dichloromethane and methanol (0 to 15%). The combined pure fractions were concentrated on the rotovap and the resulting yellow oil was dissolved in anhydrous diethyl ether then cooled to −20° C. for 24 h. The yellow precipitate was filtered on a Buchner funnel, washed with ether and dried under high vacuum overnight. The pure product (yellow powder) was obtained as a triethylaminium salt (1.80 g, 2.04 mmol). Yield: 86% ($^1$H-NMR was taken in $CDCl_3$ on a Varian 400 MHz).

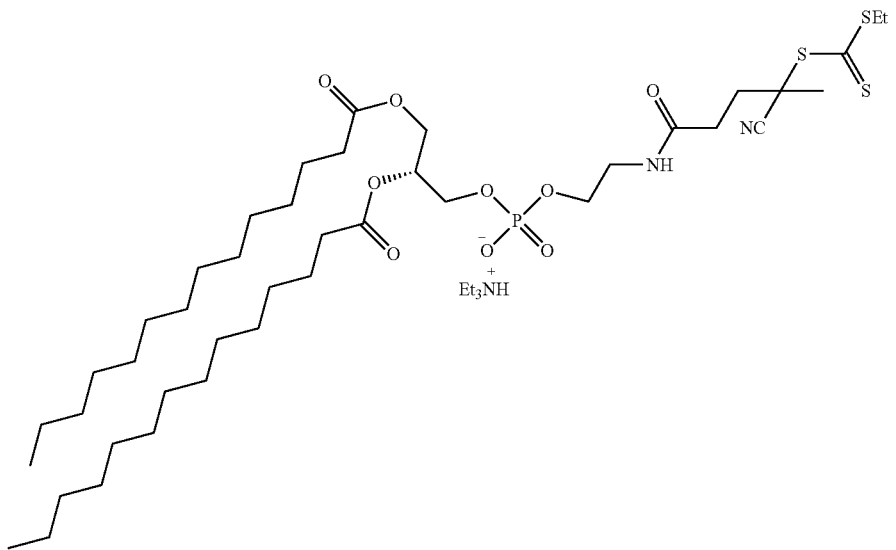

Example 3: Synthesis of
1,2-Di-stearoyl-sn-glycero-3-ECT Ester (DSG-ECT)

This Example describes the synthesis of 1,2-Di-stearoyl-sn-glycero-3-ECT Ester (DSG-ECT), having the structure shown below.

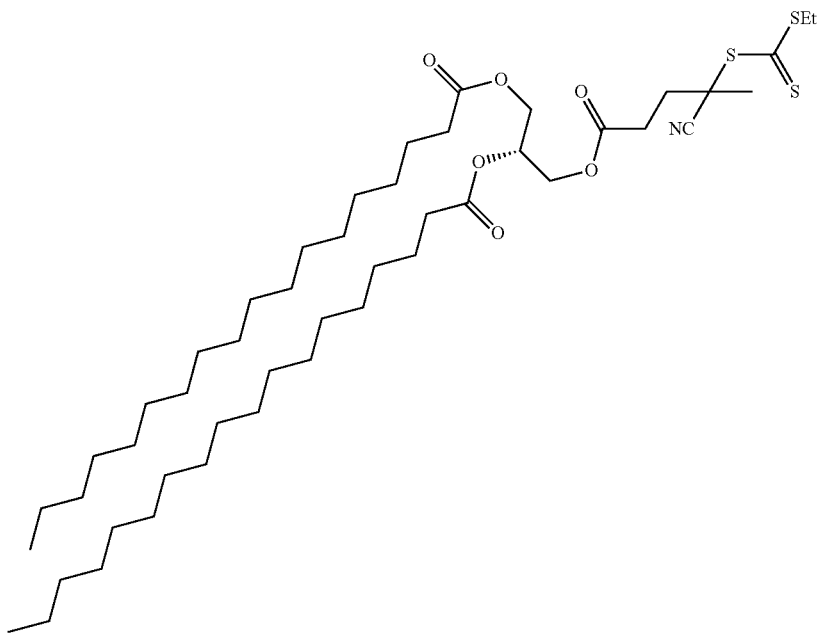

1,2-Di-stearoyl-sn-glycerol (2.50 g, 4.02 mmol) was placed into a 250 mL round bottom flask and dissolved in anhydrous dichloromethane (50.0 mL) at RT. Diisopropylethylamine (1.75 mL, 10.0 mmol) was added to the mixture and the solution was cooled to 0° C. in an ice bath. In a separate 100 mL round bottom flask, ECT-pentafluorophenylacetate (2.59 g, 6.03 mmol) was dissolved in dichloromethane (20.0 mL) at RT and this mixture was added into the previously cooled DSG solution via syringe over 10 min. The combined solution was allowed to warm to RT overnight and then diluted with dichloromethane (150 mL). The organic phase was washed with saturated sodium bicarbonate (2×100 mL) and brine (1×100 mL). The organic solution was dried over sodium sulfate overnight. The solid salts were filtered out and the organic solution was evaporated in vacuo. The yellow residue was dissolved in anhydrous diethyl ether and cooled to −20° C. for 20 h. The yellow precipitate was filtered on a Buchner funnel and washed with cold ether, then purified via silica gel chromatography using a gradient of hexane and ethyl acetate (0 to 5%). The combined pure fractions were concentrated on the rotovap and the resulting yellow oil was dissolved in anhydrous diethyl ether then cooled to −20° C. for 48 h. The yellow precipitate was filtered on a Buchner funnel, washed with ether and dried under high vacuum overnight. The pure product was obtained as a yellow powder (1.21 g, 1.39 mmol). Yield: 35%. ($^1$H-NMR was taken in $CDCl_3$ on a Varian 400 MHz).

Example 4: Synthesis of 1,2-Di-myristoyl-sn-glycero-3-ECT Ester (DMG-ECT)

This Example describes the synthesis of 1,2-Di-myristoyl-sn-glycero-3-ECT Ester (DMG-ECT), having the structure shown below.

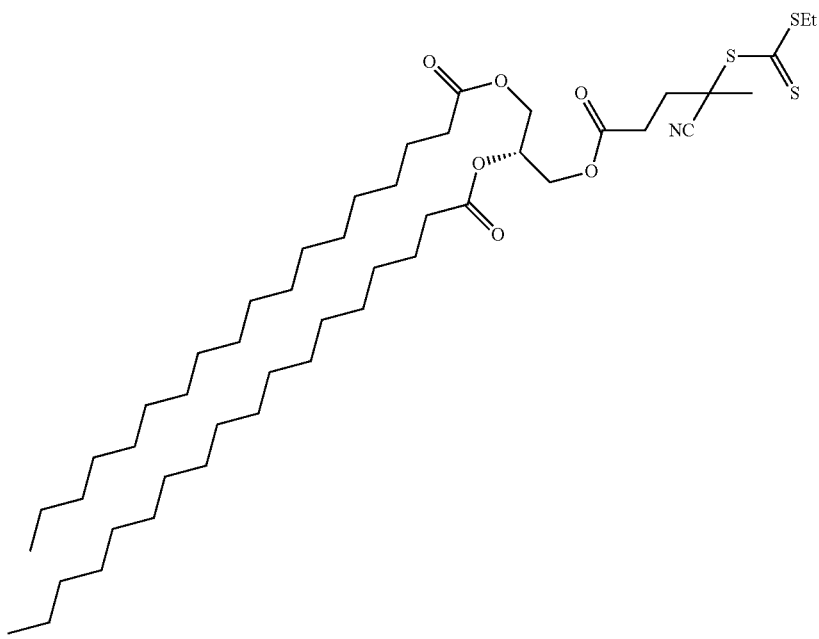

1,2-Di-myristoyl-sn-glycerol (2.56 g, 4.99 mmol) was placed into a 250 mL round bottom flask and dissolved in anhydrous dichloromethane (50.0 mL) at RT. Diisopropylethylamine (2.17 mL, 12.5 mmol) was added to the mixture and the solution was cooled to 0° C. in an ice bath. In a separate 100 mL round bottom flask, ECT-pentafluorophenylacetate (3.22 g, 7.50 mmol) was dissolved in dichloromethane (20.0 mL) at RT and this mixture was added into the previously cooled DMG solution via syringe over 10 min. The combined solution was allowed to warm to RT overnight and then diluted with dichloromethane (150 mL). The organic phase was washed with saturated sodium bicarbonate (2×100 mL) and brine (1×100 mL). The organic solution was dried over sodium sulfate overnight. The solid salts were filtered out and the organic solution was evaporated in vacuo. The yellow residue was dissolved in anhydrous diethyl ether and cooled to −20° C. overnight. The yellow precipitate was filtered on a Buchner funnel and washed with cold ether, then purified via silica gel chromatography using a gradient of hexane and ethyl acetate (0 to 5%). The combined pure fractions were concentrated on the rotovap and the resulting yellow oil was dissolved in anhydrous diethyl ether then cooled to −20° C. for 48 h. The yellow precipitate was filtered on a Buchner funnel, washed with ether and dried under high vacuum overnight. The pure product was obtained as a yellow powder (1.50 g, 1.39 mmol). Yield: 40%. ($^1$H-NMR was taken in CDCl$_3$ on a Varian 400 MHz).

Example 5: Synthesis of 1,2-Di-palmitoyl-sn-glycero-3-ECT Ester (DPG-ECT)

This Example describes the synthesis of 1,2-Di-palmitoyl-sn-glycero-3-ECT Ester (DPG-ECT), having the structure shown below.

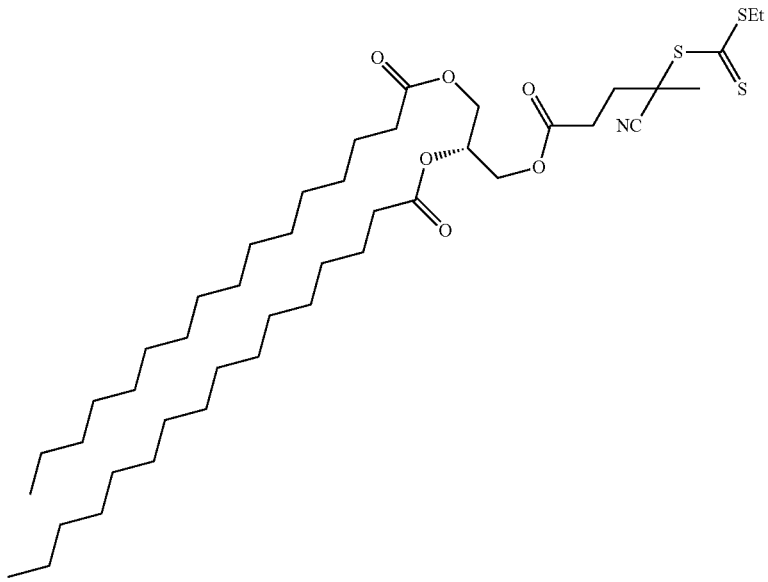

1,2-Di-palmitoyl-sn-glycerol (4.00 g, 7.03 mmol) was placed into a 500 mL round bottom flask and dissolved in anhydrous dichloromethane (50.0 mL) at RT. Triethylamine (2.50 mL, 17.9 mmol) was added to the mixture and the solution was cooled to 0° C. in an ice bath. In a separate 100 mL round bottom flask, ECT-pentafluorophenylacetate (4.53 g, 10.5 mmol) was dissolved in dichloromethane (20.0 mL) at RT and this mixture was added into the previously cooled DPG solution via syringe over 10 min. The combined solution was allowed to warm to RT overnight and then diluted with dichloromethane (150 mL). The organic phase was washed with saturated sodium bicarbonate (2×50 mL) and brine (1×50 mL). The organic solution was dried over sodium sulfate overnight. The solid salts were filtered out and the organic solution was evaporated in vacuo. The obtained yellow solid was purified via silica gel chromatography using a gradient of hexane and ethyl acetate (0 to 5%). The combined pure fractions were concentrated on the rotovap and the resulting yellow oil was dissolved in anhydrous diethyl ether then cooled to −20° C. for 48 h. The yellow precipitate was filtered on a Buchner funnel, washed with ether and dried under high vacuum overnight. The pure product was obtained as a yellow powder (3.00 g, 3.70 mmol). Yield: 52%. ($^1$H-NMR was taken in $CDCl_3$ on a Varian 400 MHz).

Example 6: Synthesis of DSPE-[PEGMA$_{600}$]6.2K

PEGMA$_{300}$ (1.594 g, 5.2720 mmol), DSPE-ECT (see Example 1, supra) (0.21 g, 0.2113 mmol; 1:25 CTA:Monomer), AIBN (2.08 mg, 0.0126 mmol; CTA:AIBN 16.7:1), DMF (2.83 g) and chloroform (3.0 g) were introduced in a sealed vial. The mixture was degassed by bubbling argon for 36 minutes, and the reaction was allowed to proceed at 60° C. with rapid stirring for 16 hours and 30 minutes. The reaction was stopped by placing the vial in ice-water bath and exposing the mixture to air. The resulting DSPE-PEGMA$_{300}$ was initially purified by precipitation into hexane/ether 75/25 (four times). The product was further purified by dialysis against DCM for 24 hours and then methanol for an additional 48 hours (Spectrum Labs, Spectra/Por Dialysis Membrane MWCO: 2000), followed by dialysis against water for four hours. The resulting dialyzed solution was lyophilized for four days in a lyophilizer. The structure and composition of the purified DSPE-PEGMA$_{300}$ were verified by $^1$H NMR, which also confirmed the absence of signals corresponding to vinyl groups of un-incorporated monomers. The number of PEGMA units calculated from NMR: 16. The molecular weight and molecular weight distribution were determined by GPC analysis. Mn,GPC=7,200 kDa, dn/dc=0.0489, PDI=1.24.

Example 7: Synthesis of DSPE-[PEGMA$_{500}$]12.3K

PEGMA$_{500}$ (2.11 g, 4.2277 mmol), DSPE-ECT (see Example 1, supra) (210 g, 0.2114 mmol; 1:20 CTA:Monomer), AIBN (2.6 mg, 0.0158 mmol; CTA:AIBN 13.3:1), DMF (3.0 g) and chloroform (6.2 g) were introduced in a sealed vial. The mixture was degassed by bubbling argon for 44 minutes, and the reaction was allowed to proceed at 61° C. with rapid stirring for 40 hours. The reaction was stopped by placing the vial in ice-water bath and exposing the mixture to air. The resulting DSPE-PEGMA$_{500}$ was initially purified by precipitation into hexane/ether 75/25 (four times). The product was further purified by dialysis against DCM/methanol mixture for 48 hours and then methanol for an additional 72 hours (Spectrum Labs, Spectra/Por Dialysis Membrane MWCO: 2000), followed by dialysis against water for 5 hour. The resulting dialyzed solution was lyophilized for four days in a lyophilizer. The structure and composition of the purified DSPE-PEGMA$_{500}$ were verified by $^1$H NMR, which also confirmed the absence of signals corresponding to vinyl groups of un-incorporated monomers. The number of PEGMA units calculated from NMR: 23. The molecular weight and molecular weight distribution were determined by GPC analysis. Mn,GPC=13.25 kDa, dn/dc=0.0481, PDI=1.27.

For removal of the trithiocarbonate end group, the purified DSPE-PEGMA$_{500}$ (0.77 g, 0.0581 mmol), AIBN (565 mg, mmol; CTA:AIBN=1:59), DMF (2.0 g) and 2-propanol (4.0 g) were introduced in a vial. The mixture was degassed by bubbling argon into the mixture for 26 minutes, and then allowed to react for 4 hour at 80° C. The reaction was stopped by placing the vial in ice-water bath and exposing the mixture to air. The colorless product was purified by precipitation into hexane/ether 75/25 (two times). The DSPE-PEGMA$_{500}$ was further purified by dialysis against DCM/methanol (2:3) mixture for 24 hours and then methanol for 72 hours, followed by dialysis against water for 5 hours (Spectrum Labs, Spectra/Por Dialysis Membrane MWCO: 2000). The resulting solution was lyophilized for four days. The structure and composition of the purified product were verified by $^1$H NMR. The removal of trithiocarbonate end groups from the DSPE-PEGMA$_{500}$ was confirmed by UV-Visible spectroscopy at 310 nm.

Example 8: Synthesis of DSPE-[PEGMA$_{500}$]11.5K

PEGMA$_{500}$ (2.56 g, 5.1296 mmol), DSPE-ECT (see Example 1, supra) (254.8 g, 0.2565 mmol; 1:20 CTA: Monomer), AIBN (3.16 mg, 0.01924 mmol; CTA:AIBN 13.3:1), DMF (3.1 g) and chloroform (6.23 g) were introduced in a sealed vial. The mixture was degassed by bubbling argon for 42 minutes, and the reaction was allowed to proceed at 61° C. with rapid stirring for 17 hours. The reaction was stopped by placing the vial in ice-water bath and exposing the mixture to air. The resulting DSPE-PEGMA$_{500}$ was purified by precipitation into hexane/ether 75/25 (five times). The structure and composition of the purified DSPE-PEGMA$_m$ were verified by $^1$H NMR, which also confirmed the absence of signals corresponding to vinyl groups of un-incorporated monomers. The molecular weight and molecular weight distribution were determined by GPC analysis. Mn,GPC=12.54 kDa, dn/dc=0.492, PDI=1.23.

For removal of the trithiocarbonate end group, the purified DSPE-PEGMA$_{500}$ (0.654 g, 0.0735 mmol), AIBN (326 mg, 1.985 mmol; CTA:AIBN=1:27), DMF (1.8 g) and 2-propanol (3.6 g) were introduced in a vial. The mixture was degassed by bubbling argon into the mixture for 37 minutes, and then allowed to react for 4 hour at 80° C. The reaction was stopped by placing the vial in ice-water bath and exposing the mixture to air. The colorless product was purified by precipitation into hexane/ether 75/25 (three times). The DSPE-PEGMA$_{500}$ was further purified by dialysis against DCM/methanol (2:3) mixture for 24 hours and then methanol for 72 hours, followed by dialysis against water for 5 hours (Spectrum Labs, Spectra/Por Dialysis Membrane MWCO: 2000). The resulting solution was lyophilized for four days. The structure and composition of the purified product were verified by $^1$H NMR. The number of PEGMA units calculated from NMR: 24. The removal of trithiocarbonate end groups from the DSPE-PEGMA$_{500}$ was confirmed by UV-Visible spectroscopy at 310 nm.

Example 9: Synthesis of DMPE-[PEGMA$_{500}$]

PEGMA$_{500}$ (2.39 g, 4.7773 mmol), DMPE-ECT (see Example 2, supra) (0.21 g, 0.2389 mmol; 1:20 CTA:Monomer), AIBN (2.94 mg, 0.0179 mmol; CTA:AIBN 13.3:1), DMF (3.0 g) and chloroform (9 g) were introduced in a sealed vial. The mixture was degassed by bubbling argon for 45 minutes, and the reaction was allowed to proceed at 61° C. with rapid stirring for 21 hours. The reaction was stopped by placing the vial in ice-water bath and exposing the mixture to air. The resulting DMPE-PEGMA$_{500}$ was initially purified by precipitation into hexane/ether 75/25 (four times). The product was further purified by dialysis against DCM/methanol mixture for 48 hours and then methanol for an additional 72 hours (Spectrum Labs, Spectra/Por Dialysis Membrane MWCO: 3,500), followed by removal of solvent by rotary evaporator and further dried under vacuum for 16 hours. The structure and composition of the purified DMPE-PEGMA$_{500}$ were verified by $^1$H NMR, which also confirmed the absence of signals corresponding to vinyl groups of un-incorporated monomers. The number of PEGMA units calculated from NMR: 23. Theoretical molecular weight would be 12,380 g/mol (by NMR). This value was used for the calculation of number of moles of DMPE-PEGMA$_{500}$ for the next step.

For removal of the trithiocarbonate end group, the purified DMPE-PEGMA$_{500}$ (0.3977 g, 0.0321 mmol), AIBN (192 mg, 1.1717 mmol; CTA:AIBN=1:36.5), toluene (1.0 g) and 2-propanol (1.44 g) were introduced in a vial. The mixture was degassed by bubbling argon into the mixture for 26 minutes, and then allowed to react for 3 hours and 10 minutes at 80° C. The reaction was stopped by placing the vial in ice-water bath and exposing the mixture to air. The product was purified by precipitation into hexane/ether 75/25 (two times). The DMPE-PEGMA$_{500}$ was further purified by dialysis against DCM/methanol (1:1) mixture for 24 hours and then methanol for 72 hours, followed by dialysis against water for five hours (Spectrum Labs, Spectra/Por Dialysis Membrane MWCO: 2000). The resulting solution was lyophilized for four days. The structure and composition of the purified product were verified by $^1$H NMR. The removal of trithiocarbonate end groups from the DMPE-PEGMA$_{500}$ was confirmed by UV-Visible spectroscopy at 310 nm. The molecular weight and molecular weight distribution were determined by GPC analysis. Mn,GPC=12.4 kDa, dn/dc=0.0475, PDI=1.25.

Example 10: Synthesis of DSG-[PEGMA$_{500}$]11.73K

PEGMA$_{500}$ (1.195 g, 2.3897 mmol), DSG-ECT (see Example 3, supra) (0.104 g, 0.1195 mmol; 1:20 CTA: Monomer), AIBN (1.47 mg, 0.0089 mmol; CTA:AIBN 13.3:1), DMF (3.8 g) and chloroform (3 g) were introduced in a sealed vial. The mixture was degassed by bubbling argon for 30 minutes, and the reaction was allowed to proceed at 61° C. with rapid stirring for 45 hours. The reaction was stopped by placing the vial in ice-water bath and exposing the mixture to air. The resulting DSG-PEGMA$_{500}$ was purified by precipitation into hexane/ether 50/50 (two times) and three precipitations using hexane/ether 75/25. The product was then dried under vacuum for 16 hours.

For removal of the trithiocarbonate end group, the purified DSG-PEGMA$_{500}$ (1.036 g, 0.1178 mmol, calculated using the theoretical molecular weight (8,794 g/mol) if 100% CTA was converted), AIBN (657.7 mg, 4.00 mmol; CTA:AIBN=1:34), DMF (3.0 g) and 2-propanol (5.6 g) were introduced in a vial. The mixture was degassed by bubbling argon into the mixture for 20 minutes, and then allowed to react for 3 hours and 30 minutes at 80° C. The reaction was stopped by placing the vial in ice-water bath and exposing the mixture to air. The resulting yellow solution was further treated with excess AIBN (590 mg) and with added solvents (DMF=3.0 g and 2-propanol=1.0 g). The solution was purged with argon for 25 minutes before placing to a preheated oil bath at 80° C. for overnight. The colorless product was purified by precipitation into hexane/ether 75/25 (two times). The DSG-PEGMA$_{500}$ was further purified by dialysis against methanol for 48 hours, followed by dialysis against water for five hours (Spectrum Labs, Spectra/Por Dialysis Membrane MWCO: 2000). The resulting solution was lyophilized for three days. The structure and composition of the purified product were verified by $^1$H NMR. The number of PEGMA units calculated from NMR: 24. The removal of trithiocarbonate end groups from the branched PEG-lipid was confirmed by UV-Visible spectroscopy at 310 nm. The molecular weight and molecular weight distribution were determined by GPC analysis. Mn,GPC=12.6 kDa, dn/dc=0.457, PDI=1.12.

Example 11: DOTAP:CHEMS:Cholesterol:DSPE-PEGMA$_{500}$ mRNA Nanoparticle Formulation with Co-Injection of a Polymer Formulation Characteristics DOTAP (Corden Pharma, Boulder, Colo., USA; catalog number LP-R4-117) was solubilized at 50 mg/mL in 200 proof ethanol at room temperature for 15 minutes. The DSPE-PEGMA$_{500}$ (see Example 7, supra) was solubilized at 50 mg/mL in 200 proof ethanol at room temperature for 15 minutes. The cholesteryl hemisuccinate (CHEMS) (Avanti Polar Lipid Alabaster, Ala., USA; catalog number 850524P) and the Cholesterol (CHOL) (Corden Pharma, Boulder, Colo., USA; catalog number CH-0355) were individually solubilized at 25 mg/mL in 200 proof at 75° C. for 5 minutes.

For a 2 mL preparation of DOTAP:CHEMS:CHOL: DSPE-PEGMA$_{500}$ (50:32:16:2 mol %) LNP at a N:P ratio of 7, a lipid ethanolic mixture containing 178 µL of DOTAP at 50 mg/mL in 200 proof ethanol, 158 µL of CHEMS at 25 mg/mL in 200 proof ethanol, 63 µL of CHOL at 25 mg/mL in 200 proof ethanol, 88 µL of DSPE-PEGMA500 at 50 mg/mL in 200 proof ethanol and 180 µL of 200 proof ethanol was prepared for a final volume of 0.666 mL and a total lipid concentration of 31.4 mg/mL. The DSPE-PEGMA$_{500}$ ratios were varied from 1 to 10 mol % in the lipid nanoparticle (LNP) formulations. The CHOL mol % was adjusted to result in 100 mol % final lipid concentration.

Fluc (firefly luciferase) mRNA stock solution (TriLink BioTechnologies, San Diego, Calif.) at 1 mg/mL in 10 mM Tris-HCl (pH 7.5) was diluted to 0.45 mg/mL in 300 mM sucrose 20 mM phosphate, pH 7.4 buffer (SUP buffer). The mRNA/LNPs were assembled at a N:P ratio of 7 by mixing the ethanolic lipid solution with 0.45 mg/mL mRNA in SUP buffer at a 1:2 ratio (lipid ethanolic mixture:mRNA in SUP buffer) using the microfluidic device from Precision NanoSystems Inc (Vancouver BC, Canada) at a 12 mL/minute flow rate. The mRNA/LNPs in 33% ethanol were then incubated at room temperature for 60 minutes prior to dialysis for 18 hours against 100 volumes (200 mL) of SUP buffer.

Polymer P200 (GalNAc-C5-PEG12-[PEGMA (300, 75%)-HMA (25%)]4.2 KDa-b-[DMAEMA (36%)-BMA (51%)-PAA (13%)]4.93 KDa) was solubilized at 20 mg/mL in SUP buffer with agitation at 400 rpm for 1 hour. The polymer was diluted to 4-10 mg/mL in SUP buffer prior to injection.

The formulation particle size was measured by adding 10 µL of formulation to 90 µL of SUP buffer into a disposable micro-cuvette and analyzed using the Zetasizer Nano ZS (Malvern Instrument Ltd, Worcestershire, UK). The LNPs showed a particle size of 85 nm (Z-average). The formulation zeta-potential at pH 7.4 was measured by adding 10 µL of formulation to 740 µL of SUP buffer into a disposable 1 mL cuvette. The formulation zeta-potential at pH 4 was measured by adding 10 µL of formulation to 740 µL of sucrose acetate buffer (pH 4) into a disposable 1 mL cuvette. The zeta dip cell was inserted into the 1 mL cuvette and the formulation was analyzed using the Zetasizer Nano ZS (Malvern Instrument Ltd, Worcestershire, UK). The LNPs had a zeta potential of +1.3 mV at pH 7 and +8 mV at pH 4.0.

The ability of the LNP to compact the mRNA was measured in a 96 well plate using a Ribo Green dye accessibility assay. The mRNA dye accessibility was measured using 100 µL of nanoparticles at a dilution of 1:100 in SUP for free RNA, and at a dilution of 1:400 in SUP for total RNA in a 96-well plate. To this, 100 µL of a 1:200 dilution of RiboGreen reagent in SUP buffer or 0.2% Triton X-100/ SUP buffer, respectively, was added to each well. As a positive control, a previously measured reference standard was included on the same plate. The plate was incubated at room temperature in the dark for 5 minutes. The fluorescence was read using the Molecular Devices SpectraMax MS with excitation at 480 nm and emission at 520 nm. Finally, the percent dye accessibility was calculated by subtracting the µM concentration of dye accessible mRNA from the µM concentration of the total mRNA, dividing that value by the µM concentration of total mRNA, and then multiplying by 100. The DSPE-PEGMA LNPs showed ~2% dye accessibility when prepared in SUP buffer. Table 2 below shows characterization of an exemplary DSPE-PEGMA LNP formulation.

TABLE 2

| Lipid composition | Mol % | % Dye access SUP pH 7.4 | Z-Ave (nm) | PDI | Number (nm) | ZP pH 7.4 | ZP pH 4 |
|---|---|---|---|---|---|---|---|
| 0.5 mg/kg Fluc mRNA/ DOTAP:CHEMS:CHOL:DSPE-PEGMA 500 at 16 mg/kg total lipid dose | (50:32:16:2) | 5 | 47 | 0.22 | 28 | 1.3 | 8 |

In Vivo Luminescence Detection

Female CD-1 mice (7-10 weeks old) were used for evaluating the Fluc mRNA/LNP+polymer formulations. A 2× solution of both mRNA/LNP and polymer were prepared. Just prior to dosing, the solutions were mixed in equal volumes and injected immediately. The formulations were dosed intravenously at 0.5 mg/kg of mRNA, 14 to 30 mg/kg of lipid, and 25 mg/kg of P200 with 5 mice injected per group.

The in vivo expression of luciferase was evaluated by detecting luminescence in mice using the Xenogen IVIS Lumina II Imaging System (Caliper Life Sciences, now Perkin Elmer). The imaging was performed at 6 hours following dosing. 15 minutes prior to imaging, each mouse received 0.25 mL of D-luciferin (Regis Technologies, Inc.), a luciferase substrate, at 30 mg/mL (dissolved in PBS) by intra-peritoneal injection. A few minutes before imaging, mice were place in an isoflurane chamber to induce anesthesia (isoflurane concentration at ~3%). Subsequently, mice were moved into the IVIS imaging chamber, with the snout connected to an isoflurane-filled nose cone with the mouse's ventral side up. The luminescence images were acquired using Living Image software (Caliper Life Sciences) with the exposure time, binning and F/Stop remaining the same throughout the study. Mice were put back to the cage as soon as the imaging was finished and they recovered within 1-3 minutes.

After the image acquisition was finished for all mice, the luminescence results were analyzed using Living Image software. Briefly, the color scale of each image was first adjusted to display specific luminescence signal and eliminate background signal. Then a region of interest (ROI) for the liver was defined using the ROI tools, and ROI measure button was clicked to show the photon flux data. Total flux (photons/sec) of the ROI on each animal was used to represent the intensity of luminescence. Total flux was averaged from all 5 mice for each formulation group for comparison.

Table 3 displays luminescence values in the liver for animals treated with Fluc mRNA/DOTAP:CHEMS:CHOL:DSPE-PEGMA500 and co-injection of polymer P200. One to 10 mol % of DSPE-PEGMA lipid was varied in the LNP formulations. For comparison, a Fluc mRNA/DOTAP:CHEMS:CHOL:DSPE-PEG2k LNP formulation containing DSPE-PEG2k lipid was tested. Data was acquired at 6 hours post dose. Similar luminescence was observed between LNPs containing two to 10 mol % DSPE-PEGMA and 10 mol % DSPE-PEG2k. A two to three-fold drop in activity was observed with LNP formulation containing 1 mol % DSPE-PEGMA500.

TABLE 3

| Formulation Description | Mol % PEG-Lipid | Fluc mRNA Dose (mg/kg) | Lipid Dose (mg/kg) | P200 (polymer used for co-injection) (mg/kg) | Total Flux (photons/sec) Geomean | STDEV |
|---|---|---|---|---|---|---|
| SUP Buffer only | 0 | 0 | 0 | 0 | 2.37E+05 | |
| DOTAP:CHEMS:CHOL:DSPE-PEG2k (50:32:8:10) | 10 mol % | 0.5 | 18 | 25 | 1.67E+10 | 6.31E+09 |
| DOTAP:CHEMS:CHOL:DSPE-PEGMA 500 (1-10%) (50:32:X:Y mol %) where X = 18-mol % PEG-lipid | 1 mol % | 0.5 | 14 | 25 | 7.31E+09 | 2.59E+09 |
| | 2 mol % | 0.5 | 16 | 25 | 2.09E+10 | 1.04E+10 |
| | 5 mol % | 0.5 | 21 | 25 | 1.27E+10 | 9.92E+09 |
| | 10 mol % | 0.5 | 30 | 25 | 2.01E+10 | 1.03E+10 |

Example 12: In Vivo Expression of mRNA with Reseat Doses of DOTAP:CHEMS:Cholesterol:DSPE-PEGMA$_{500}$ mRNA Nanoparticle Formulation with Co-injection of a Polymer LNP formulations co-injected with polymer were tested for mRNA expression using a repeat dosing regime. Co-injections of mRNA/LNP+polymer and evaluation of in vivo luciferase expression were performed using the same methods as described in Example 11.

Table 4 displays luminescence values in the liver for animals treated with DOTAP:CHEMS:CHOL:DSPE-PEGMA 500+Fluc mRNA nanoparticles with co-injection of polymer P200. LNPs containing 2 or 10 mol % DSPE-PEGMA500 were compared. mRNA/LNP+polymer were mixed at a 1:1 ratio and injected immediately into mice. Data was acquired at 6 hours post each dose. Formulations were repeat dosed by intravenous administration once a week for 8 weeks in female CD-1 mice. Repeat administration with both LNPs resulted in similar luminescent signal at each weekly dose out to 8 weeks. In a previous study, repeat administration with Fluc mRNA/LNP (DOTAP:CHEMS:CHOL:DSPE-PEG2k (50:32:8:10)) containing a stably incorporated PEG lipid, DSPE-PEG2K, resulted in a two to 8-fold drop in activity starting at week 3. On average, luminescence was 5-fold higher with LNP containing 2 mol % of DSPE-PEGMA 500 compared to LNP containing 10 mol % DSPE-PEGMA 500.

TABLE 4

| Lipid-mRNA Nanoparticle | mRNA Dose | Lipid Dose (mg/kg) | Polymer used for co-injection | Repeat dosing time point | Total Flux (photons/sec) Geomean | STDEV |
|---|---|---|---|---|---|---|
| DOTAP:CHEMS:CHOL:DSPE-PEGMA 500 (50:32:16:2) N:P 7 | 0.5 mg/kg Fluc mRNA | 16 | 25 mg/kg P200 | Week 1 | 2.33E+10 | 1.70E+10 |
| | | | | Week 2 | 1.53E+10 | 2.02E+10 |
| | | | | Week 3 | 1.16E+10 | 2.40E+10 |
| | | | | Week 4 | 2.39E+10 | 3.35E+10 |
| | | | | Week 5 | 1.50E+10 | 2.00E+10 |

TABLE 4-continued

| Lipid-mRNA Nanoparticle | mRNA Dose | Lipid Dose (mg/kg) | Polymer used for co-injection | Repeat dosing time point | Total Flux (photons/sec) | |
|---|---|---|---|---|---|---|
| | | | | | Geomean | STDEV |
| | | | | Week 6 | 1.01E+10 | 1.66E+10 |
| | | | | Week 7 | 2.27E+10 | 1.66E+10 |
| | | | | Week 8 | 1.16E+10 | 1.55E+10 |
| DOTAP:CHEMS:CHOL:DSPE-PEGMA 500 (50:32:8:10) N:P 7 | 0.5 mg/kg Fluc mRNA | 30 | 25 mg/kg P200 | Week 1 | 1.92E+09 | 2.51E+09 |
| | | | | Week 2 | 3.03E+09 | 3.11E+09 |
| | | | | Week 3 | 2.91E+09 | 4.63E+09 |
| | | | | Week 4 | 4.53E+09 | 3.17E+09 |
| | | | | Week 5 | 3.26E+09 | 3.91E+09 |
| | | | | Week 6 | 1.45E+09 | 4.31E+09 |
| | | | | Week 7 | 6.03E+09 | 5.33E+09 |
| | | | | Week 8 | 2.58E+09 | 3.73E+09 |

Example 13: In Vivo Expression of EPO mRNA in Rats with Repeat Doses of DOTAP:CHEMS:Cholesterol:DSPE-PEGMA$_{500}$ mRNA Nanoparticle Formulation with Co-Injection of a Polymer Human Erythropoietin (EPO) mRNA (TriLink BioTechnologies, San Diego, Calif.) was formulated in LNPs described in Table X and co-injected with a polymer. The formulations were prepared using the same methods as described in Example 11.

Male Sprague Dawley rats (6-7 weeks old) were used for evaluating the hEPO mRNA/LNP+polymer formulations. A 2× solution of both mRNA/LNP and polymer were prepared. Just prior to dosing, the solutions were mixed in equal volumes and injected immediately. The formulations were dosed intravenously at 1 mg/kg of mRNA, 32-36 mg/kg of lipid, and 15 mg/kg of P201 (P200 with trithiocarbonate end group removed by radical-induced reduction) with 4 rats injected per group. Formulations were repeat dosed by intravenous administration once a week for 5 weeks.

To measure human EPO protein levels, blood was collected at 6 hours post each weekly dose into serum separator tubes. Serum was isolated by centrifugation and stored frozen at −20° C. until assayed. For ELISA the serum was diluted in PBS and then run using the Human EPO Quantikine IVD ELISA (R&D Systems # DEP00) according to the manufacturer's protocol. Briefly, 100 μL of diluted serum sample was mixed with 100 μL assay diluent in an ELISA plate and shaken at 500 rpm for 1 hour. The solution was removed and replaced with 200 μL of conjugate and shaken for an additional hour. The plate was then washed and developed using a two component HRP/TMB system and read at 450 nm. EPO protein levels were calculated based on a standard curve in the ELISA and multiplied by the dilution factor used. Units in mIU/mL were converted to ng/mL by multiplying by 0.0084 conversion factor.

To measure anti-PEG IgM or anti-PEG IgG antibody levels, blood was collected at 24 hours post each weekly dose into serum separator tubes. Serum was isolated by centrifugation and stored frozen at −20° C. until assayed. For ELISA serum was diluted at 1:100 or 1:500 and analyzed using the rat anti-PEG IgM ELISA or rat anti-PEG IgG ELISA (cat # for IgM: PEGM-2, cat # for IgG: PEGG-2, Life Diagnostics, West Chester, Pa.) according to the manufacturer's protocol. Briefly, 100 μL of diluted serum sample and standards were dispensed into the wells of the ELISA plate and shaken at 100 rpm for 1 hour at room temperature. The solution was removed and wells were washed 5 times, replaced with 100 μL of diluted HRP conjugate, and shaken for an additional hour. The plate was then washed and developed using TMB reagent and read at 450 nm. The concentration of anti-PEG IgM and IgG in each sample was derived from standard curves, multiplied by the dilution factor, and expressed as relative units per mL (U/mL).

Table 5 displays human EPO protein levels in serum collected at 6 hours post each weekly dose for rats treated with 1 mg/kg hEPO mRNA+DOTAP:CHEMS:CHOL:DSPE-PEGMA 500 LNP and co-injection of polymer P201. hEPO mRNA formulated in LNP composed of DOTAP:CHEMS:CHOL:DSPE-PEG2k and co-injection of polymer P201 was used for comparison. Repeat administration of formulation containing DOTAP:CHEMS:CHOL:DSPE-PEG2K LNP resulted in a two to three-fold drop in hEPO protein levels at week 2 and 3. At week 4 and 5, hEPO protein levels returned to the level seen at week 1. This decrease in hEPO levels correlated with an increase in anti-PEG IgM and IgG levels at week 2 as shown in Tables 6 and 7. At week 4 and 5 as anti-PEG IgM levels decreased hEPO protein levels increased. Repeat administration of formulation containing DOTAP:CHEMS:CHOL:DSPE-PEGMA 500 LNP resulted in similar hEPO protein levels at weeks 1-3. A two-fold drop in hEPO levels was detected at week 4 and 5 compared to levels at week 1 and the drop was statistically significant only at week 4. Anti-PEG IgM levels were significantly lower at week 2 and anti-PEG IgG levels were lower at all time points with the DSPE-PEGMA 500 LNP compared to the DSPE-PEG2K LNP.

TABLE 5

| Lipid-mRNA Nanoparticle | mRNA Dose | Polymer used for co-injection | Repeat dosing time point | Human EPO Levels (ng/mL) | | p value to Week 1 |
|---|---|---|---|---|---|---|
| | | | | Average | STDEV | |
| SUP Buffer | 0 | 0 | Week 1 | Not detected | | |
| | | | Week 2 | Not detected | | |
| | | | Week 3 | Not detected | | |
| | | | Week 4 | Not detected | | |
| | | | Week 5 | Not detected | | |

TABLE 5-continued

| Lipid-mRNA Nanoparticle or | mRNA Dose | Polymer used for co-injection | Repeat dosing time point | Human EPO Levels (ng/mL) Average | STDEV | p value to Week 1 |
|---|---|---|---|---|---|---|
| DOTAP:CHEMS:CHOL:DSPE-PEG2K (50:32:8:10) N:P 7, 36 mg/kg | 1 mg/kg EPO mRNA | 15 mg/kg P201 | Week 1 | 3.87E+03 | 1.56E+03 | |
| | | | Week 2 | 2.13E+03 | 1.23E+03 | 0.13 |
| | | | Week 3 | 1.53E+03 | 9.53E+02 | 0.04 |
| | | | Week 4 | 4.10E+03 | 7.96E+02 | 0.83 |
| | | | Week 5 | 4.82E+03 | 7.13E+01 | 0.35 |
| DOTAP:CHEMS:CHOL:DSPE-PEGMA 500 (50:32:16:2) N:P 7, 32 mg/kg | 1 mg/kg EPO mRNA | 15 mg/kg P201 | Week 1 | 5.70E+03 | 1.64E+03 | |
| | | | Week 2 | 3.69E+03 | 1.41E+03 | 0.09 |
| | | | Week 3 | 4.75E+03 | 2.87E+03 | 0.55 |
| | | | Week 4 | 2.73E+03 | 9.97E+02 | 0.02 |
| | | | Week 5 | 2.89E+03 | 2.03E+03 | 0.07 |

TABLE 6

| Lipid-mRNA Nanoparticle | mRNA Dose | Polymer used for co-injection | Repeat dosing time point | Anti-PEG IgM (U/mL) Average | STDEV |
|---|---|---|---|---|---|
| SUP Buffer | 0 | 0 | Week 1 | Not detected | |
| | | | Week 2 | Not detected | |
| | | | Week 3 | Not detected | |
| | | | Week 4 | Not detected | |
| | | | Week 5 | Not detected | |
| DOTAP:CHEMS:CHOL:DSPE-PEG2K (50:32:8:10) N: P 7, 36 mg/kg | 1 mg/kg EPO mRNA | 15 mg/kg P201 | Week 1 | 57.7 | 75.2 |
| | | | Week 2 | 8802.5 | 4357.3 |
| | | | Week 3 | 982.0 | 755.0 |
| | | | Week 4 | 206.7 | 72.6 |
| | | | Week 5 | 464.6 | 61.4 |
| DOTAP:CHEMS:CHOL:DSPE-PEGMA 500 (50:32:16:2) N: P 7 32 mg/kg | 1 mg/kg EPO mRNA | 15 mg/kg P201 | Week 1 | 91.7 | 57.2 |
| | | | Week 2 | 1105.2 | 455.8 |
| | | | Week 3 | 350.5 | 204.1 |
| | | | Week 4 | 533.6 | 183.9 |
| | | | Week 5 | 1135.7 | 383.9 |

TABLE 7

| Lipid-mRNA Nanoparticle | mRNA Dose | Polymer used for co-injection | Repeat dosing time point | Anti-PEG IgG (U/mL) Average | STDEV |
|---|---|---|---|---|---|
| SUP Buffer | 0 | 0 | Week 1 | Not detected | |
| | | | Week 2 | Not detected | |
| | | | Week 3 | Not detected | |
| | | | Week 4 | Not detected | |
| | | | Week 5 | Not detected | |
| DOTAP:CHEMS:CHOL:DSPE-PEG2K (50:32:8:10) N: P 7, 36 mg/kg | 1 mg/kg EPO mRNA | 15 mg/kg P201 | Week 1 | 0.0 | 0.0 |
| | | | Week 2 | 9065.3 | 11261.0 |
| | | | Week 3 | 5021.0 | 7315.4 |
| | | | Week 4 | 3804.3 | 6073.4 |
| | | | Week 5 | 4014.3 | 5898.8 |
| DOTAP:CHEMS:CHOL:DSPE-PEGMA 500 (50:32:16:2) N: P 7, 32 mg/kg | 1 mg/kg EPO mRNA | 15 mg/kg P201 | Week 1 | 54.2 | 105.1 |
| | | | Week 2 | 765.2 | 991.2 |
| | | | Week 3 | 2425.1 | 3808.3 |
| | | | Week 4 | 551.5 | 256.5 |
| | | | Week 5 | 553.4 | 134.1 |

Example 14: Branched PEGylation of Recombinant Interferon Alpha-2b (INF-$\alpha_{2b}$)

NHS-ECT-PEGMA500$_{20}$ is prepared from ECT-PEGMA500$_{20}$ and NHS.

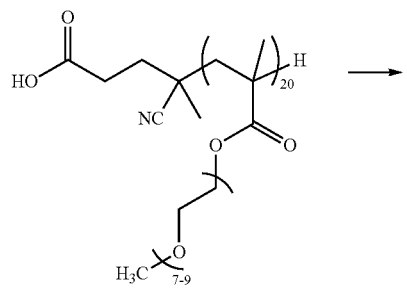

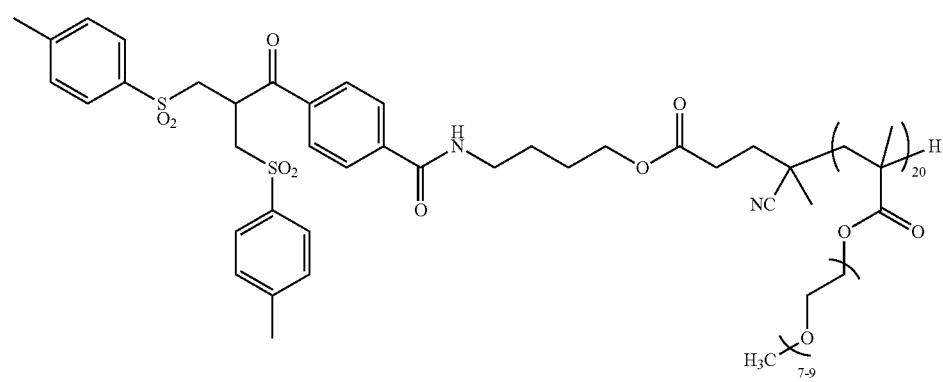

Compound 1

-continued

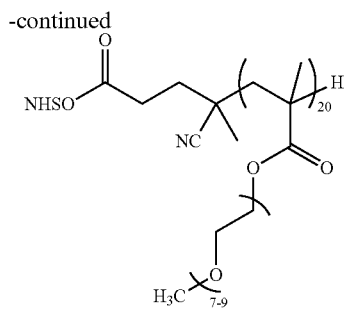

Purified recombinant INF-$\alpha_{2b}$ (interferon α-2b) is reacted with NHS-ECT-PEGMA500$_{20}$ in sodium phosphate buffer (100 mM, pH 6.5) in a method similar to that described by Wang et al. (*Advanced Drug Delivery Reviews* 54:547-570, 2002). The crude product is fractionated by ion-exchange chromatography to afford predominantly mono-PEGylated product.

Example 15: Preparation of His-Tag-Specific Branched PEG-dAb-His$_6$

To a solution of dAb-His$_6$ (a domain antibody having a 6-histidine His-tag on the C-terminus) in 50 mM sodium phosphate, 150 mM sodium chloride and 10 mM EDTA, pH 6.7, is added 1.5 mol equiv of Compound 1 in 5 mM sodium phosphate, 15 mM sodium chloride, and 1 mM EDTA, pH 8 (~20 mg/mL Compound 1) in a method similar to that described by Cong et al. (*Bioconjugate Chem.* 2012, dx.doi.org/10.1021/bc200530x). Compound 1 is incubated in the buffer for 3 h at ambient temperature prior to its addition to the dAb-His6 solution. The reaction solution is incubated at ambient temperature for a further 3 h. Purification is performed using either a HiTrap SP HP 5 mL or Resource S 1 mL column, depending on the scale of purification. The reaction mixture is first buffer exchanged into a loading buffer (20 mM sodium acetate, pH 4.5). A total of 10 column volumes of loading buffer are then used to wash the column to remove residual branched PEGylation reagent. A gradient elution from 0% to 100% elution buffer (20 mM sodium acetate, 0.7 M sodium chloride, pH 4.5) is carried out, typically over 30 min at 1 mL/min flow rate for 1 mL column, to separate the branched PEG-proteins. Eluates are fractionated and analyzed by SDS-PAGE.

Example 16: Preparation of Branched PEG-His8-INF

To a solution of His8-IFN (interferon α-2a having an 8-histidine His-tag on the N-terminus) in sodium acetate buffer, pH 5.3, containing 35 µM hydroquinone, is added 2.0 mol equiv of Compound 1 in 50 mM sodium phosphate, pH 7.4, in a method similar to that described by Cong et al. (*Bioconjugate Chem.* 2012, dx.doi.org/10.1021/bc200530x). Compound 1 is preincubated in the buffer for 8 h at 37° C. prior to its addition to the His8-IFN solution. The reaction solution is incubated for 17 h at 20° C. The reaction mixture is then treated with sodium triacetoxyborohydride (25 mM final concentration and added as a solid) and further incubated for 1 h at 4° C. Purification is performed using a HiTrap SP HP 5 mL cation exchange column, followed by polishing purification step using a Superdex 200 pep grade size exclusion column. The reaction mixture is first buffer exchanged into loading buffer (50 mM sodium acetate buffer, pH 4.0) using a PD-10 column. A total of 10 column volumes of loading buffer are then used to wash the column to remove residual branched PEGylation reagent. A gradient elution from 0% to 100% elution buffer (50 mM sodium acetate, 1.0 M sodium chloride, pH 4.0) is carried out, typically over 30 min at 1 mL/min flow rate, to separate the branched PEG-proteins. Eluates are fractionated and analyzed by SDS-PAGE. Fractions containing mono-PEGylated product are pooled and concentrated to ~2 mL using a Vivaspin concentrator (10,000 MWCO, 3000 g, 4° C.). The solution is then purified with a Superdex 200 pep grade column at a flow rate of 1 mL/min and 50 mM sodium phosphate buffer, 150 mM NaCl, pH 7.5, as a mobile phase.

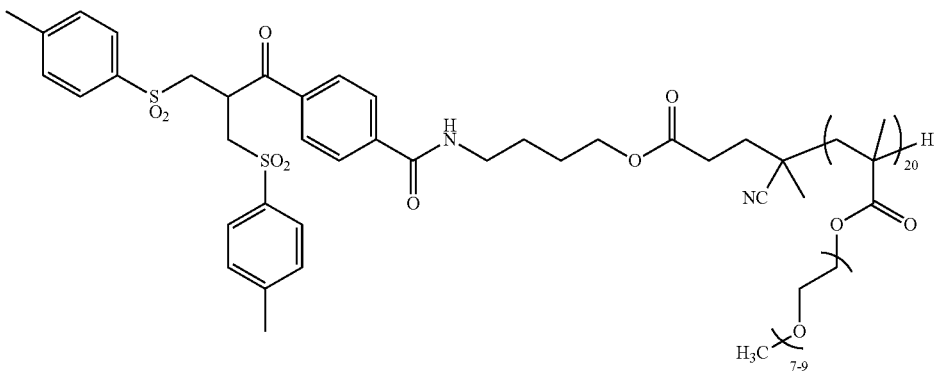

Compound 2

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. A pH-sensitive polymer of Formula IXh:
GalNAc-C5-PEG$_{12}$-[PEGMA300$_{0.75}$—HMA$_{0.25}$]$_{4.2KDa}$-[DMAEMA$_{0.36}$-PAA$_{0.13}$-BMA$_{0.51}$]4.93KDa, wherein
GalNAc is an N-acetylgalactosamine residue;
C5 is an alkylene group containing 5 carbon atoms;
PEG$_{12}$ is a link moiety comprising a polyethylene glycol having 12 ethylene glycol units;
PEGMA300 is polyethyleneglycol methacrylate residue having 4-5 ethylene glycol units;
HMA is hexyl methacrylate residue;
DAEMA is dimethylaminoethyl methacrylate residue;
PAA is propyl acrylic acid residue; and
BMA is butyl methacrylate residue.

2. A composition comprising a pH-sensitive polymer of Formula IXh:
GalNAc-C5-PEG$_{12}$- [PEGMA300$_{0.75}$—HMA$_{0.25}$]$_{4.2KDa}$-[DMAEMA$_{0.36}$-PAA$_{0.13}$-BMA$_{0.51}$]$_{4.93KDa}$; and
a therapeutic or diagnostic agent,
wherein
GalNAc is an N-acetylgalactosamine residue;
C5 is an alkylene group containing 5 carbon atoms;
PEG$_{12}$ is a link moiety comprising a polyethylene glycol having 12 ethylene glycol units;
PEGMA300 is polyethyleneglycol methacrylate residue having 4-5 ethylene glycol units;
HMA is hexyl methacrylate residue;

DAEMA is dimethylaminoethyl methacrylate residue;
PAA is propyl acrylic acid residue; and
BMA is butyl methacrylate residue.

3. The composition of claim 2, wherein the therapeutic agent is a polynucleotide, a protein, or a peptide.

4. The composition of claim 3, wherein the polynucleotide is an oligonucleotide.

5. The composition of claim 4, wherein the oligonucleotide is an siRNA, an antisense oligonucleotide, an anti-miR, a locked nucleic acid-based oligonucleotide, a dicer substrate, an miRNA, an aiRNA, an shRNA, a ribozyme, or a nucleic acid aptamer.

6. The composition of claim 4, wherein the oligonucleotide is an mRNA.

7. The composition of claim 6, wherein the mRNA encodes a secreted protein.

8. The composition of claim 7, wherein the secreted protein is a hormone, a cytokine, an growth factor, a clotting factor, an anti-protease protein, an angiogenic protein, an antiangiogenic protein, a chemokine, or an antibody.

9. A method for delivering a therapeutic or diagnostic agent to a subject, the method comprising: administering to a subject in need of thereof an effective amount of the composition of claim 2.

10. The method of claim 9, wherein the therapeutic agent is a polynucleotide, a protein, or a peptide.

\* \* \* \* \*

UNITED STATES PATENT AND TRADEMARK OFFICE
CERTIFICATE OF CORRECTION

Page 1 of 1

PATENT NO. : 11,684,584 B2
APPLICATION NO. : 16/475006
DATED : June 27, 2023
INVENTOR(S) : Roy et al.

It is certified that error appears in the above-identified patent and that said Letters Patent is hereby corrected as shown below:

In the Claims

In Claim 1, Column 157, Lines 56-58, the structure of Formula IXh should appear as follows:
GalNAc-C5-PEG$_{12}$-[PEGMA300$_{0.75}$–HMA$_{0.25}$]$_{4.2KDa}$-[DMAEMA$_{0.36}$-PAA$_{0.13}$-BMA$_{0.51}$]$_{4.93KDa}$ In Claim 8, Column 159, Line 18, "an growth factor" should read -- a growth factor --

In Claim 9, Column 159, Line 23, "in need of thereof" should read -- in need thereof --

Signed and Sealed this
Thirtieth Day of January, 2024

Katherine Kelly Vidal
*Director of the United States Patent and Trademark Office*